United States Patent
Nazdan et al.

(10) Patent No.: US 8,049,068 B2
(45) Date of Patent: Nov. 1, 2011

(54) NUCLEOTIDE SEQUENCES AND POLYPEPTIDES ENCODED THEREBY FOR ENHANCING PLANT DROUGHT TOLERANCE

(75) Inventors: Gregory Nazdan, Woodland Hills, CA (US); Kenneth A. Feldmann, Newbury Park, CA (US); Cory Christensen, Simi Valley, CA (US)

(73) Assignee: Ceres, Inc., Thousand Oaks, CA (US)

( * ) Notice: Subject to any disclaimer, the term of this patent is extended or adjusted under 35 U.S.C. 154(b) by 1499 days.

(21) Appl. No.: 11/305,666

(22) Filed: Dec. 16, 2005

(65) Prior Publication Data

US 2006/0150285 A1 Jul. 6, 2006

Related U.S. Application Data

(60) Provisional application No. 60/637,104, filed on Dec. 16, 2004.

(51) Int. Cl.
*A01H 5/00* (2006.01)
*C12N 15/82* (2006.01)

(52) U.S. Cl. ........ 800/295; 800/278; 800/298; 435/419; 435/468

(58) Field of Classification Search ............... None
See application file for complete search history.

(56) References Cited

U.S. PATENT DOCUMENTS

| | | |
|---|---|---|
| 2002/0040490 A1 | 4/2002 | Gorlach et al. |
| 2004/0025202 A1 | 2/2004 | Laurie et al. |
| 2004/0123343 A1 | 6/2004 | La Rosa et al. |
| 2004/0216182 A1 | 10/2004 | Federspiel et al. |
| 2004/0216190 A1 | 10/2004 | Kovalic |

FOREIGN PATENT DOCUMENTS

| | | |
|---|---|---|
| EP | 1033405 | 6/2000 |
| EP | 1033405 A2 * | 9/2000 |
| WO | WO97/13843 | 4/1997 |
| WO | WO02/16655 | 2/2002 |
| WO | WO02/052012 | 7/2002 |
| WO | WO2004/058963 | 7/2004 |
| WO | WO02/22675 | 3/2006 |

OTHER PUBLICATIONS

Ngo et al., The Protein Folding Problem and Tertiary Structure Prediction, K. Merz., and S. Le Grand (eds.) pp. 492-495,1994.*
Wells, Biochemistry 29:8509-8517, 1990.*
Thornton et al., Nature structural Biology, structural genomics supplement, Nov. 2000.*
Keskin et al., Protein Science, 13:1043-1055, 2004.*
XP002173128, Improving plant drought, salt, and freezing tolerance by gene transfer of a single stress-inducible transcription factor, Mie Kasuga, et al., *Nature Biotechnology*, vol. 17 Mar. 1999, pp. 287-291.
XP002378439, Physiological and molecular insights into drought tolerance, Mundree, et al., *African Journal of Biotechnology*, vol. 1(2) pp. 28-38, Dec. 2002.
XP002378470, Plant Responses to drought, salinity and extreme temperatures: towards genetic engineering for stress tolerance, Wang, et al., *Planta* 2003 218: pp. 1-14.
XP008025694, Genetics and genetic improvement of drought resistance in crop plants, Jason Mitre, Western Regional Research Station, Indian Grassland and Fodder Research Institute, Avikanagar 304, 501, India, *Current Science*, vol. 80, No. 6, Mar. 25, 2001, pp. 758-763.
Office Action issued by EPO on Dec. 8, 2010—EP Appl. No. 05 854 483.4.

* cited by examiner

*Primary Examiner* — Vinod Kumar
(74) *Attorney, Agent, or Firm* — Birch, Stewart, Kolasch and Birch, LLP

(57) ABSTRACT

Isolated polynucleotides and polypeptides encoded thereby are described, together with the use of those products for making transgenic plants with increased tolerance to abiotic stress (e.g., high or low temperature, drought, flood).

13 Claims, 6 Drawing Sheets

```
SEQ-ID-NO-4-CeresClone:760406   MLRS-FPQAR  ----------  ----------  -PLLRRMGF   DKRDAYFFKQ  GKGMLCTYA    37
SEQ-ID-NO-2-gi:50900870         MLRG-FPQAR  ----------  ----------  -RLLRRMGL   EKEDAYFWKQ  MGKGMLCTYA   37
SEQ-ID-NO-3-CeresClone:311568   MLRN-FPQAR  ----------  ----------  -RLLRRMGF   EKEDAYFWKQ  MGKAMLCTYT   37
SEQ-ID-NO-1-Lead-68-clone3086   MVRKQFQQAK  TGIEALKSMD  ANNYLKKVGL  GRDDMFFWKQ  VGKALLCTYT              50
SEQ-ID-NO-5-CeresGdna:1461694   MVRKRFQETK  TGIEYLKSVD  YDKYLRKVGI  GKEDHYFWKQ  LGKALLCTYT              50

Consensus                       MLR---FPQAR ---------- ---------- -RLLRRMGL   DKEDAYFWKQ  -GKAMLCTYT   50

SEQ-ID-NO-4-CeresClone:760406   LFGAAWLWNE  TSPLGWWTLK  PLPKEEKEMA  HLYERREFPY  PGDEEAVEEF   87
SEQ-ID-NO-2-gi:50900870         LFGAAWLWNE  TSPLGWWTLK  PRPKEEREMA  HLYERRMFPY  PGDEEAVEEF   87
SEQ-ID-NO-3-CeresClone:311568   LFGVVWLWNE  TSPLGWWTLK  PRPKEERELA  HLYERRKFPY  PGDDEAVEEF   87
SEQ-ID-NO-1-Lead-68-clone3086   FGMAWIYNE   TSPLGWWTLK  PRPKEERELA  HLYERREFPY  PGDTEAMEDF   100
SEQ-ID-NO-5-CeresGdna:1461694   LTGVVWYNE   TSPLGWWTLK  PKPKEEREFA  HLYERREFPY  PGDAEAMEEF   100

Consensus                       LFGVAWLWNE  TSPLGWWTLK  PRPKEEREMA  HLYERREFPY  PGDEEAVEEF   100

SEQ-ID-NO-4-CeresClone:760406   KSEGALGTT   IGPKGFADTN  VDSDKMQKQL  QSKKFDQEAQ  NLWFRMRNEV   137
SEQ-ID-NO-2-gi:50900870         IKSGGALGTT  IGPKGFADSN  MDSDNMQKQL  QSKKFDQEAQ  KLWFRMRNEV   137
SEQ-ID-NO-3-CeresClone:311568   VKSGGALGTT  IGPRGFADAN  MDSENMQKQL  QSK------   ----------   120
SEQ-ID-NO-1-Lead-68-clone3086   VAKGGMGTA   IGPKGIVESE  GEADNYQKEM  EKKKFDKEAQ  KLWLRMRNEV   150
SEQ-ID-NO-5-CeresGdna:1461694   VAKGGMGTT   IGPKGTVETD  KDSYNYQKQL  QDKKFEQEAQ  KMWFRMRNEV   150

Consensus                       VKSGGALGTT  IGPKGFAD-N  MDSDNMQKQL  QSKKFDQEAQ  KLWFRMRNEV   150

SEQ-ID-NO-4-CeresClone:760406   AHELQEKGFG  VE    149
SEQ-ID-NO-2-gi:50900870         VQELQEKGFD  VE    149
SEQ-ID-NO-3-CeresClone:311568   ----------  --    120
SEQ-ID-NO-1-Lead-68-clone3086   ITELQEKGHN  LE    162
SEQ-ID-NO-5-CeresGdna:1461694   QELQEKGYD   VE    162

Consensus                       V-ELQEKG-D  VE    162
```

| | |
|---|---|
| SEQ-ID-NO-48-CeresClone:569763 | ELITVMQ- 127 |
| SEQ-ID-NO-50-CeresGdna:1466677 | ELVNVAE- 120 |
| SEQ-ID-NO-44-CeresClone:127651 | ELVNVAE- 146 |
| SEQ-ID-NO-47-CeresClone:215916 | ELVNVEG- 146 |
| SEQ-ID-NO-45-gi|57900332 | ELVNVEE- 140 |
| SEQ-ID-NO-46-CeresClone:678019 | ELVSVEA- 139 |
| SEQ-ID-NO-42-CeresClone:967348 | ELVNVVE- 101 |
| SEQ-ID-NO-49-Lead94 | ELVNVVE 137 |
| SEQ-ID-NO-41-CeresClone:560149 | ELVNVVE 101 |
| SEQ-ID-NO-43-CeresClone:162655 | ELVNVAE 137 |

Consensus        ELVNV--E--   158

| | | | | | | | |
|---|---|---|---|---|---|---|---|
| SEQ-ID-NO-65-gi\|4689382 | MAT | ATAT | AAA | TSS- | FMGT | RL | LDAHS----GS | GRI | QARFGFG | S---- | KKAAP | 43 |
| SEQ-ID-NO-68-CeresCdna:1454179 | --- | ---- | --- | ---- | MGT | RL | PDLYS----NS | GRI | QARFGFG | ----- | GKKAP | 27 |
| SEQ-ID-NO-54-gi\|445116 | --- | MASSV | AAA | AST- | FLGT | RL | ADPRP----QN | GRI | VARFGFG | ----- | KKKAPP | 40 |
| SEQ-ID-NO-66-CeresClone:104796 | --- | MASSV | AAA | AST- | FLGT | RL | ADPAP----QN | GRI | VARFGFG | ----- | KKKAPP | 40 |
| SEQ-ID-NO-67-CeresClone:299035 | --- | MASSV | AAA | AST- | FLGT | RL | ADPAP----QS | GRI | VARFGFG | ----- | KKKAPP | 43 |
| SEQ-ID-NO-69-gi\|51978982 | --- | MATAT | AAA | ATSYF | FGT | RL | NNWNFTTLNN | GRF | HALLNFG | LGG- | KAKPA | 42 |
| SEQ-ID-NO-63-CeresClone:481415 | --- | MATTT | AAA | A-G- | FGTR | I | QDPRP----G- | GRV | QARFGFS | -GG- | KKAAAK | 48 |
| SEQ-ID-NO-61-Lead95-Clone26369 | --- | MATTT | AAA | ASG- | IFGI | RI | ODPSS----GA | GRV | QAKFNFS | KKKT | APPPPP | 43 |
| SEQ-ID-NO-62-CeresClone:963170 | --- | ---- | --- | ---- | ---- | -- | ----------- | --- | ------- | FGKKK | PAPPPP | 44 |
| Consensus | --- | MA-S- | AAA | AST- | FLGT | RL | -DP-P------ | GRI | -ARFGFG | ----- | -K-K-PP | 50 |

| | | | | | | | |
|---|---|---|---|---|---|---|---|
| SEQ-ID-NO-65-gi\|4689382 | KKV- | --SKGPS | TDRPLWYPGA | KAPEWLDGSL | VGDYGFDPFG | LGKPAEYLQF | 91 |
| SEQ-ID-NO-68-CeresCdna:1454179 | KKS- | -KPST | PDRPLWYPGA | KAPEYLDGSL | VGDYGFDPFG | LGKPAEYLQF | 75 |
| SEQ-ID-NO-54-gi\|445116 | KKA- | -KAPPT | DRPLWFPGA | QAPEYLDGTL | VGDYGFDPFG | LGKPAEYLQY | 88 |
| SEQ-ID-NO-66-CeresClone:104796 | KKA- | -KAPPT | DRPLWFPGA | QAPEYLDGTL | VGDYGFDPFG | LGKPAEYLQY | 88 |
| SEQ-ID-NO-67-CeresClone:299035 | KKVA | -KTSTS | DRPLWFPGA | VAPDYLDGSL | VGDYGFDPFG | LGKPAEYLQF | 92 |
| SEQ-ID-NO-69-gi\|51978982 | KAAR | -PSAPT | TDRPLWFPGA | VAPDYLDGSL | VGDYGFDPFG | LGKPAEYLQF | 91 |
| SEQ-ID-NO-63-CeresClone:481415 | KKEV | VKPS | GDRLVWFPNA | EPPEWLDGSM | CDRGFDPFG | FAKPAEYLQF | 98 |
| SEQ-ID-NO-61-Lead95-Clone26369 | KKSR | -QVODD | GDRLVWFPGA | NPPEWLDGSM | CDRGFDPFG | LGKPAEYLQF | 92 |
| SEQ-ID-NO-62-CeresClone:963170 | KKTK | -D-OND | GDRLVWFPGA | NPPEWLDGSM | CDRGFDPFG | LGKPAEYLQY | 93 |
| Consensus | KK-- | -K---PT | TDRPLWFPGA | -APEWLDGSL | VGDYGFDPFG | LGKPAEYLQY | 100 |

| | | | | | | | |
|---|---|---|---|---|---|---|---|
| SEQ-ID-NO-65-gi\|4689382 | ELDSLDQNLA | IGT | RTEVADVKST | PFQPYSEVFG | LQRFRECELI | 141 |
| SEQ-ID-NO-68-CeresCdna:1454179 | ELDSLDQNLA | KNLAGDI-GT | RTEFADVKST | PFQPYSEVFG | LQRFRECELI | 125 |
| SEQ-ID-NO-54-gi\|445116 | DVDSLDQNLA | QNLAGEI-GT | RFEDADVKST | PFQPYAEVFG | LQRFRECELI | 138 |
| SEQ-ID-NO-66-CeresClone:104796 | DVDSLDQNLA | KNEAGI-GT | RFESSEVKST | PLQPYSEVFG | LQRFRECELI | 138 |
| SEQ-ID-NO-67-CeresClone:299035 | ELDSLDQNLA | XNNAGEI-GT | RFET-GEVKST | PFQPYSEVFG | LQRFRECELI | 142 |
| SEQ-ID-NO-69-gi\|51978982 | ELDSLDQNLA | KNI AGDVI GT | BVEVAEVKPT | PFQPYSEVFG | QRFRECELI | 141 |
| SEQ-ID-NO-63-CeresClone:481415 | DLDSLDQNLA | KNVAGDI-GT | LOESSEI KPT | PFQPTEVFG | ORFRECELI | 148 |
| SEQ-ID-NO-61-Lead95-Clone26369 | DFDGLDQNLA | KNVAGLLGV | BQESKEI NPT | PFQPYTEMFG | ORF RECELI | 142 |
| SEQ-ID-NO-62-CeresClone:963170 | DFDGLDQNLA | | | | ERFRECELI | 143 |
| Consensus | DLDSLDQNLA | KNLAG-II GT | R-E-ADVKST | PFQPYSEVFG | LQRFRECELI | 150 |

NUCLEOTIDE SEQUENCES AND POLYPEPTIDES ENCODED THEREBY FOR ENHANCING PLANT DROUGHT TOLERANCE

CROSS-REFERENCE TO RELATED APPLICATION

This Non-provisional application claims priority under 35 U.S.C. §119(e) on U.S. Provisional Application No(s). 60/637,104 filed on Dec. 16, 2004, the entire contents of which are hereby incorporated by reference.

FIELD OF THE INVENTION

The present invention relates to isolated polynucleotides, polypeptides encoded thereby, and the use of those sequences for making transgenic plants with enhanced drought tolerance.

BACKGROUND OF THE INVENTION

Plants are constantly exposed to a variety of biotic (e.g., pathogen infection and insect herbivory) and abiotic (e.g., high or low temperature, drought, flood, anaerobic conditions and salinity) stresses. To survive these challenges, plants have developed elaborate mechanisms to perceive external signals and to manifest adaptive responses with proper physiological and morphological changes (Bohnert et al., 1995). Plants exposed to heat and/or low water or drought conditions typically have low yields of plant material, seeds, fruit and other edible products. Practically all agricultural regions are prone to drought due to climatic variation or socio-economic constraints on water resources. It would, therefore, be of great interest and importance to be able to identify genes that confer drought tolerance to thereby enable one to create transformed plants (such as crop plants) with improved ability to survive water limiting conditions.

In the field of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Availability and maintenance of a reproducible stream of food and feed has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed and energy for the population.

Great progress has been made in using molecular genetics approaches to manipulate plants to provide better crops. Through introduction and expression of recombinant nucleic acid molecules in plants, researchers are now poised to provide the community with plant species tailored to grow more efficiently and produce more product despite unique geographic and/or climatic environments. These new approaches have the additional advantage of not being limited to one plant species, but instead being applicable to multiple different plant species (1).

SUMMARY OF THE INVENTION

The present invention, therefore, relates to isolated polynucleotides, polypeptides encoded thereby, and the use of those sequences for making transgenic plants with enhanced drought tolerance.

The present invention also relates to processes for increasing the growth potential in plants under abnormal water conditions, recombinant nucleic acid molecules and polypeptides used for these processes and their uses, as well as to plants themselves.

Unless otherwise defined, all technical and scientific terms used herein have the same meaning as commonly understood by one of ordinary skill in the art to which this invention belongs.

BRIEF DESCRIPTION OF THE FIGURES

FIG. 1. Amino acid sequence alignment of homologues of Lead 68, SEQ ID NO. 1. Conserved regions are enclosed in a box. A consensus sequence (SEQ ID NO: 177) is shown below the alignment.

Figure 3A:
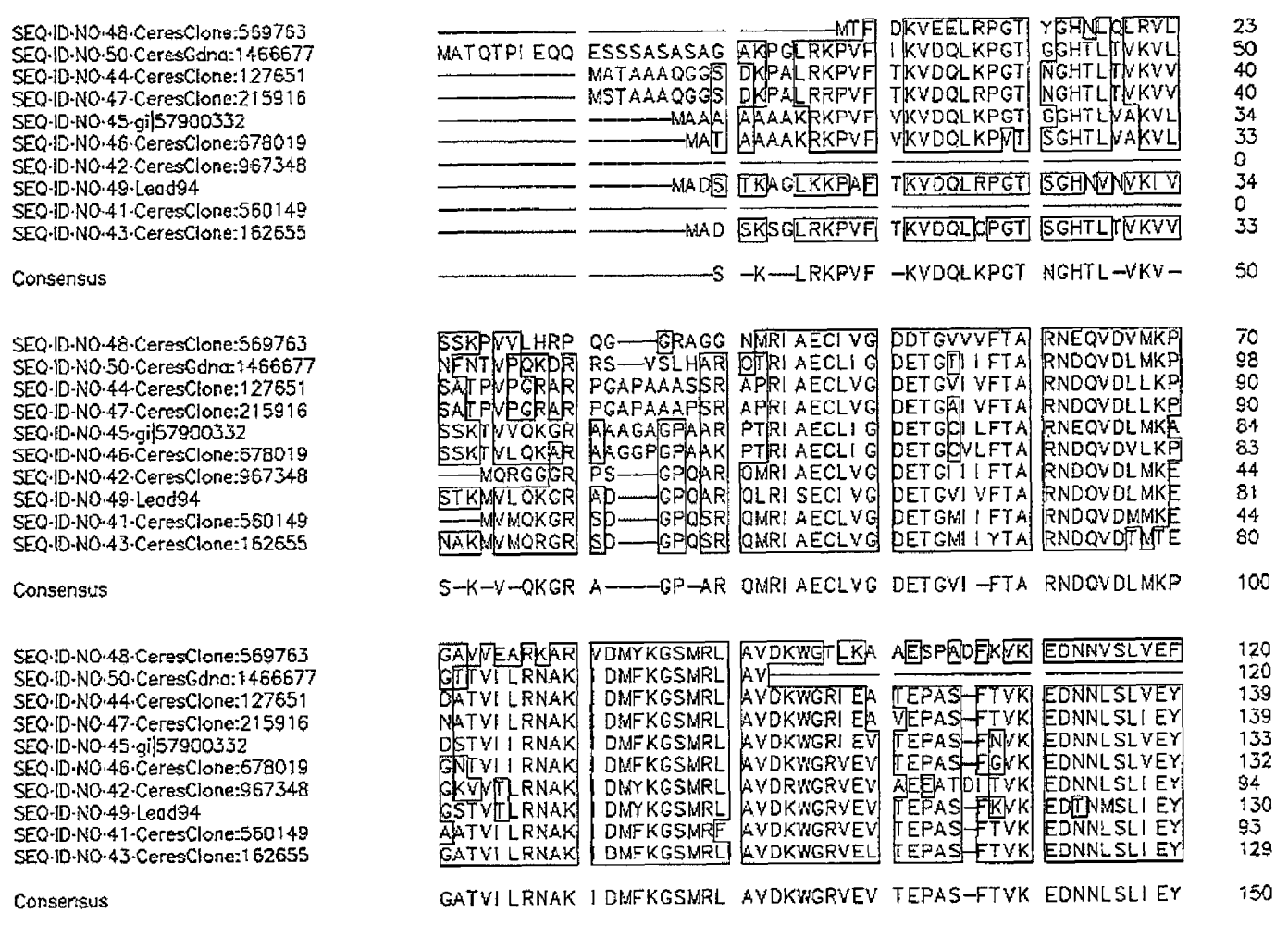

FIG. 3A and FIG. 3B. Amino acid sequence alignment of homologues of Lead 94, SEQ ID NO. 49. Conserved regions are enclosed in a box. A consensus sequence (SEQ ID NO: 179) is shown below the alignment.

FIG. 4A and FIG. 4B. Amino acid sequence alignment of homologues of Lead 95, SEQ ID NO. 61. Conserved regions are enclosed in a box. A consensus sequence (SEQ ID NO: 180) is shown below the alignment.

DETAILED DESCRIPTION OF THE INVENTION

1. The Invention

Figure 2:
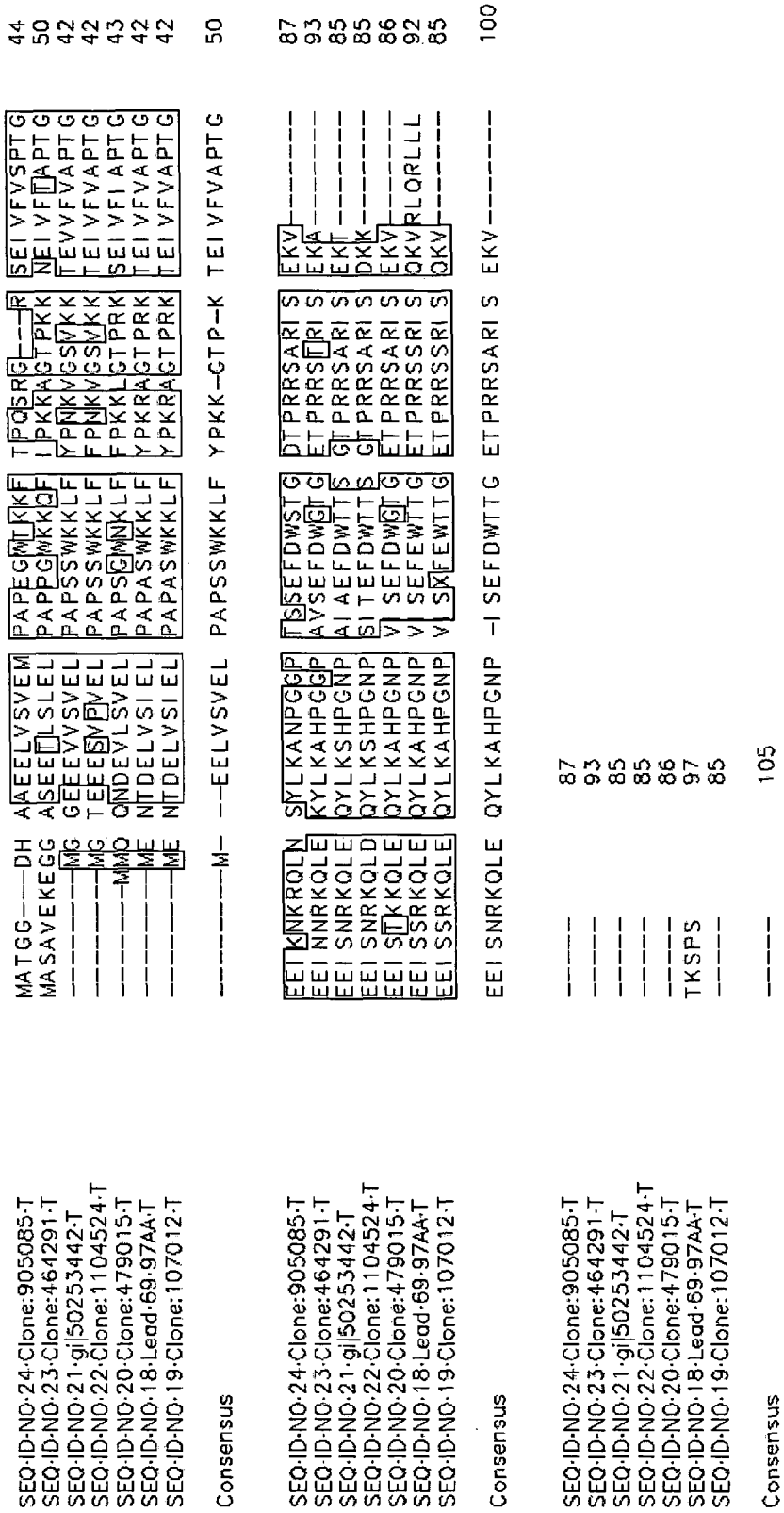
FIG. 2. Amino acid sequence alignment of homologues of Lead 69, SEQ ID NO. 18, Conserved regions are enclosed in a box. A consensus sequence (SEQ ID NO: 178) is shown below the alignment.

The invention of the present application may be described by, but not necessarily limited to, the following exemplary embodiments.

The present invention discloses novel isolated nucleic acid molecules, nucleic acid molecules that interfere with these nucleic acid molecules, nucleic acid molecules that hybridize to these nucleic acid molecules, and isolated nucleic acid molecules that encode the same protein due to the degeneracy of the DNA code. Additional embodiments of the present application further include the polypeptides encoded by the isolated nucleic acid molecules of the present invention.

More particularly, the nucleic acid molecules of the present invention comprise: (a) a nucleotide sequence encoding an amino acid sequence that is at least 85% identical to any one of Leads 68, 69, 94 and 95, corresponding to SEQ ID NO: 7, 26, 58 and 70 respectively, (b) a nucleotide sequence that is complementary to any one of the nucleotide sequences according to (a), (c) a nucleotide sequence according to any one of SEQ ID NO: 6, 14, 17, 25, 39, 57, 59, 71, 92, 173, 174, 175 and 176, (d) a nucleotide sequence that is in reverse order of any one of the nucleotide sequences according to (c) when read in the 5' to 3' direction, (e) a nucleotide sequence able to interfere with any one of the nucleotide sequences according to (a), (f) a nucleotide sequence able to form a hybridized nucleic acid duplex with the nucleic acid according to any one of paragraphs (a)-(e) at a temperature from about 40° C. to about 48° C. below a melting temperature of the hybridized nucleic acid duplex, and (g) a nucleotide sequence encoding any one of amino acid sequences of Leads 68, 69, 94 and 95, corresponding to SEQ ID NO: 7, 26, 58 and 70, respectively.

Additional embodiments of the present invention include those polypeptide and nucleic acid molecule sequences disclosed in SEQ ID NOS: 1-93 and 173-176.

The present invention further embodies a vector comprising a first nucleic acid having a nucleotide sequence encoding a plant transcription and/or translation signal, and a second nucleic acid having a nucleotide sequence according to the isolated nucleic acid molecules of the present invention. More particularly, the first and second nucleic acids may be operably linked. Even more particularly, the second nucleic acid may be endogenous to a first organism, and any other nucleic acid in the vector may be endogenous to a second organism. Most particularly, the first and second organisms may be different species.

In a further embodiment of the present invention, a host cell may comprise an isolated nucleic acid molecule according to the present invention. More particularly, the isolated nucleic acid molecule of the present invention found in the host cell of the present invention may be endogenous to a first organism and may be flanked by nucleotide sequences endogenous to a second organism. Further, the first and second organisms may be different species. Even more particularly, the host cell of the present invention may comprise a vector according to the present invention, which itself comprises nucleic acid molecules according to those of the present invention.

In another embodiment of the present invention, the isolated polypeptides of the present invention may additionally comprise amino acid sequences that are at least 85% identical to any one of Leads 68, 69, 94 and 95, corresponding to SEQ ID Nos. XX-XX 7, 26, 58 and 70, respectively.

Other embodiments of the present invention include methods of introducing an isolated nucleic acid of the present invention into a host cell. More particularly, an isolated nucleic acid molecule of the present invention may be contacted to a host cell under conditions allowing transport of the isolated nucleic acid into the host cell. Even more particularly, a vector as described in a previous embodiment of the present invention, may be introduced into a host cell by the same method.

Methods of detection are also available as embodiments of the present invention. Particularly, methods for detecting a nucleic acid molecule according to the present invention in a sample. More particularly, the isolated nucleic acid molecule according to the present invention may be contacted with a sample under conditions that permit a comparison of the nucleotide sequence of the isolated nucleic acid molecule with a nucleotide sequence of nucleic acid in the sample. The results of such an analysis may then be considered to determine whether the isolated nucleic acid molecule of the present invention is detectable and therefore present within the sample.

A further embodiment of the present invention comprises a plant, plant cell, plant material or seeds of plants comprising an isolated nucleic acid molecule and/or vector of the present invention. More particularly, the isolated nucleic acid molecule of the present invention may be exogenous to the plant, plant cell, plant material or seed of a plant.

A further embodiment of the present invention includes a plant regenerated from a plant cell or seed according to the present invention. More particularly, the plant, or plants derived from the plant, plant cell, plant material or seeds of a plant of the present invention preferably has enhanced drought tolerance as compared to a wild-type plant cultivated under identical conditions. Furthermore, the transgenic plant may comprise a first isolated nucleic acid molecule of the present invention, which encodes a protein involved in increased drought tolerance, and a second isolated nucleic acid molecule which encodes a promoter capable of driving expression in plants, wherein the increased drought tolerance component and the promoter are operably linked. More preferably, the gene conferring increased drought tolerance may be mis-expressed in the transgenic plant of the present invention, and the transgenic plant exhibits an increased drought tolerance as compared to a progenitor plant devoid of the gene, when the transgenic plant and the progenitor plant are cultivated under identical environmental conditions. In another embodiment of the present invention increased drought tolerance phenotype may be due to the inactivation of a particular sequence, using for example an interfering RNA.

A preferred embodiment consists of a plant, plant cell, plant material or seed of a plant according to the present invention which comprises an isolated nucleic acid molecule of the present invention, wherein the plant, or plants derived from the plant, plant cell, plant material or seed of a plant, has increased drought tolerance as compared to a wild-type plant cultivated under identical conditions.

Another embodiment of the present invention includes methods of enhancing drought tolerance in plants. More particularly, these methods comprise transforming a plant with an isolated nucleic acid molecule according to the present invention. Preferably, the method is a method of enhancing drought tolerance in the transformed plant, whereby the plant is transformed with a nucleic acid molecule encoding the polypeptide of the present invention.

Polypeptides of the present invention include consensus sequences. The consensus sequences are those as shown in FIGS. 1-4.

2. Definitions

The following terms are utilized throughout this application:

Drought: Plant species vary in their capacity to tolerate drought conditions. "Drought" can be defined as the set of environmental conditions under which a plant will begin to suffer the effects of water deprivation, such as decreased stomatal conductance and photosynthesis, decreased growth rate, loss of turgor (wilting), or ovule abortion. For these reasons, plants experiencing drought stress typically exhibit a significant reduction in biomass and yield. Water deprivation may be caused by lack of rainfall or limited irrigation. Alternatively, water deficit may also be caused by high temperatures, low humidity, saline soils, freezing temperatures or water-logged soils that damage roots and limit water uptake to the shoot. Since plant species vary in their capacity to tolerate water deficit, the precise environmental conditions that cause drought stress can not be generalized. However, drought tolerant plants produce higher biomass and yield than plants that are not drought tolerant under water limited conditions and may also exhibit enhanced survivability and/or delayed desiccation under severely water limited conditions. Differences in physical appearance, recovery and yield can be quantified and statistically analyzed using well known measurement and analysis methods.

Flood: Plant species vary in their capacity to tolerate flooding. Some plants, such as rice, are cultivated in water while plants such as corn do not tolerate flooding. "Flood," as referred to within, is the state of water saturation at which soils become hypoxic or anoxic, thus limiting respiration in the root. Reduced respiration damages roots and can limit the permeability of roots to water, resulting in decreased leaf water potential and wilting. Since plant species vary in their capacity to tolerate flooding, the precise environmental conditions that cause flood stress can not be generalized. However, flood tolerant plants are characterized by their ability to retain their normal appearance or recover quickly from flood. Such flood tolerant plants produce higher biomass and yield than plants that are not flood tolerant. Differences in physical appearance, recovery and yield can be quantified and statistically analyzed using well known measurement and analysis methods.

Functionally Comparable Proteins or Functional Homologs: This term describes those proteins that have at least one functional characteristic in common. Such characteristics include sequence similarity, biochemical activity, transcriptional pattern similarity and phenotypic activity. Typically, the functional homologs share some sequence similarity and at least one biochemical function. In addition, functional homologs generally share at least one biochemical and/or phenotypic activity.

Functional homologs will give rise to the same characteristic to a similar, but not necessarily to the same degree. Typically, functional homologs give the same characteristics where the quantitative measurement due to one of the comparables is at lest 20% of the other; more typically, between 30 to 40%; even more typically, between 50%-60%; even more typically 70% to 80%; even more typically between 90% to 100%.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

High Temperature: Plant species vary in their capacity to tolerate high temperatures. Very few plant species can survive temperatures higher than 45° C. The effects of high temperatures on plants, however, can begin at lower temperatures depending on the species and other environmental conditions such as humidity and soil moisture. "High temperature" can be defined as the temperature at which a given plant species will be adversely affected as evidenced by symptoms such as decreased photosynthesis. Since plant species vary in their capacity to tolerate high temperature, the precise environmental conditions that cause high temperature stress can not be generalized. However, high temperature tolerant plants are characterized by their ability to retain their normal appearance or recover quickly from high temperature conditions. Such high temperature tolerant plants produce higher biomass and yield than plants that are not high temperature tolerant. Differences in physical appearance, recovery and yield can be quantified and statistically analyzed using well known measurement and analysis methods.

Low Temperature: Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "low temperature" can be defined as the temperature at which a given plant species will be adversely affected as evidenced by symptoms such as decreased photosynthesis and membrane damage (measured by electrolyte leakage). Since plant species vary in their capacity to tolerate low temperature, the precise environmental conditions that cause low temperature stress can not be generalized. However, low temperature tolerant plants are characterized by their ability to retain their normal appearance or recover quickly from low temperature conditions. Such low temperature tolerant plants produce higher biomass and yield than plants that are not low temperature tolerant. Differences in physical appearance, recovery and yield can be quantified and statistically analyzed using well known measurement and analysis methods.

Plant seeds vary considerably in their ability to germinate under low temperature conditions. Seeds of most plant species will not germinate at temperatures less than 10° C. Once seeds have imbibed water they become very susceptible to disease, water and chemical damage. Seeds that are tolerant to low temperature stress during germination can survive for relatively long periods under which the temperature is too low to germinate. Since plant species vary in their capacity to tolerate low temperature during germination, the precise environmental conditions that cause low temperature stress during germination can not be generalized. However, plants that tolerate low temperature during germination are characterized by their ability to remain viable or recover quickly from low temperature conditions. Such low temperature tolerant plants produce, germinate, become established, grow more quickly and ultimately produce more biomass and yield than plants that are not low temperature tolerant. Differences in germination rate, appearance, recovery and yield can be quantified and statistically analyzed using well known measurement and analysis methods.

Misexpression: The term "misexpression" refers to an increase or a decrease in the transcription of a coding region into a complementary RNA sequence as compared to the wild-type. This term also encompasses expression and/or translation of a gene or coding region or inhibition of such transcription and/or translation for a different time period as compared to the wild-type and/or from a non-natural location within the plant genome, including a gene or coding region from a different plant species or from a non-plant organism.

Percentage of sequence identity: As used herein, the term "percent sequence identity" refers to the degree of identity between any given query sequence and a subject sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

In case of the functional homolog searches, to ensure a subject sequence having the same function as the query sequence, the alignment has to be along at least 80% of the length of the query sequence so that the majority of the query sequence is covered by the subject sequence.

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Regulatory regions can be classified in two categories, promoters and other regulatory regions.

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$-5° C. to $T_m$-110° C. Medium or moderate stringency conditions are those providing $T_m$-20° C. to $T_m$-29° C. Low stringency conditions are those providing a condition of $T_m$-40° C. to $T_m$-48° C. The relationship of hybridization conditions to $T_m$ (in ° C.) is expressed in the mathematical equation $$T_m = 81.5 - 16.6(\log_{10}[Na^+]) + 0.41(\% G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log\{[Na^+]/(1+0.7[Na^+])\} + 0.41(\% G+C) - 500/L \; 0.63(\% \text{ formamide}) \quad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" contains an equal amount of seed from 500 different events, representing 100 distinct exogenous nucleotide sequences. An event is a plant carrying a unique insertion of a distinct exogenous sequence which misexpresses that sequence. Transformation of a single nucleotide can result in multiple events because the sequence can insert in a different part of the genome with each transformation.

$T_0$: As used in the current application, the term "$T_0$" refers to the whole plant, explant or callus tissue inoculated with the transformation medium.

$T_1$: $T_1$ refers to a unique event which is either the progeny of the $T_0$ plant, in the case of whole-plant transformation, or the regenerated seedling in the case of explant or callous tissue transformation.

$T_2$: $T_2$ refers to the progeny of the $T_1$ plant. $T_2$ progeny are the result of self-fertilization or cross pollination of a $T_1$ plant.

$T_3$: $T_3$ refers to second generation progeny of the plant that is the direct result of a transformation experiment. $T_3$ progeny are the result of self-fertilization or cross pollination of a $T_2$ plant.

3. Important Characteristics of the Polynucleotides and Polypeptides of the Invention The polynucleotides and polypeptides of the present invention are of interest because when they are misexpressed (i.e.

when expressed at a non-natural location or in an increased or decreased amount) they produce plants with enhanced drought tolerance. "Drought tolerance" is a term that includes various responses to environmental conditions that affect the amount of water available to the plant. For example, under high heat conditions water is rapidly evaporated from both the soil and from the plant itself, resulting in a decrease of available water for maintaining or initiating physiological processes. Likewise, water availability is limited during cold or drought conditions or when there is low water content in the soil. Interestingly, flood conditions also affect the amount of water available to the plant because it damages the roots and thus limits the plant's ability to transport water to the shoot. As used herein, enhancing drought tolerance is intended to encompass all of these situations as well as other environmental situations that affect the plant's ability to use and/or maintain water effectively (e.g. osmotic stress, salinity, etc.).

Short term or prolonged drought is one of the major impediments to yield in most non-irrigated fields. Lack of inexpensive water is also one of the major environmental factors in limiting where a crop can be grown. Throughout the Midwestern United States, drought is the primary factor contributing to yield losses year to year. It is recognized that there are a number of times throughout the plant's life cycle where tolerance to drought would be advantageous. Tolerance to drought can be measured in a number of ways including increased leaf vigor at the seedling or whole plant level, recovery from severe drought, increased yield, reduced ovule abortion, increased photosynthetic capacity, relative water content, and increased water potential.

The polynucleotides and polypeptides of the invention, as discussed below and as evidenced by the results of various experiments, are useful for enhancing drought tolerance. These traits can be used to exploit or maximize plant products for agriculture, horticulture, biomass for bioconversion and/or forestry purposes in different environment conditions of water supply. Modulating the expression of the nucleotides and polypeptides of the present invention leads to transgenic plants that resist desiccation, require less water and result in better yield in high heat and/or drought conditions, or that have increased tolerance levels for an excess of water and result in better yield in wet conditions. Both categories of transgenic plants lead to reduced costs for the farmer and better yield in their respective environmental conditions.

Drought tolerance according to the invention can also be modulated by expressing these genes/polynucleotides under the control of a drought inducible promoter.

4. The Genes of the Invention

The polynucleotides of the present invention and the proteins expressed via translation of these polynucleotides are set forth in the Sequence Listing, specifically SEQ ID Nos: 6, 7, 14, 15, 16, 17, 25, 26, 39, 40, 57, 58, 59, 60, 70, 71, 76, 80, 92, 93, 173, 174, 175 and 176. The Sequence Listing consists of functionally comparable proteins. Polypeptides comprised of a sequence within and defined by one of the consensus sequences can be utilized for the purposes of the invention, namely to make transgenic plants with increased drought tolerance.

5. Use of the Genes to Make Transgenic Plants

To use the sequences of the present invention or a combination of them or parts and/or mutants and/or fusions and/or variants of them, recombinant DNA constructs are prepared that comprise the polynucleotide sequences of the invention inserted into a vector and that are suitable for transformation of plant cells. The construct can be made using standard recombinant DNA techniques (see, 16) and can be introduced into the plant species of interest by, for example, *Agrobacterium*-mediated transformation, or by other means of transformation, for example, as disclosed below.

The vector backbone may be any of those typically used in the field such as plasmids, viruses, artificial chromosomes, BACs, YACs, PACs and vectors such as, for instance, bacteria-yeast shuttle vectors, lamda phage vectors, T-DNA fusion vectors and plasmid vectors (see, 17-24).

Typically, the construct comprises a vector containing a nucleic acid molecule of the present invention with any desired transcriptional and/or translational regulatory sequences such as, for example, promoters, UTRs, and 3' end termination sequences. Vectors may also include, for example, origins of replication, scaffold attachment regions (SARs), markers, homologous sequences, and introns. The vector may also comprise a marker gene that confers a selectable phenotype on plant cells. The marker may preferably encode a biocide resistance trait, particularly antibiotic resistance, such as resistance to, for example, kanamycin, bleomycin, or hygromycin, or herbicide resistance, such as resistance to, for example, glyphosate, chlorosulfuron or phosphinotricin.

It will be understood that more than one regulatory region may be present in a recombinant polynucleotide, e.g., introns, enhancers, upstream activation regions, transcription terminators, and inducible elements. Thus, more than one regulatory region can be operably linked to said sequence.

To "operably link" a promoter sequence to a sequence, the translation initiation site of the translational reading frame of said sequence is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell* 1:977-984 (1989)).

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to said sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al., *Plant Cell*, 1:855-866 (1989); Bustos, et al., *Plant Cell,* 1:839-854 (1989); Green, et al., *EMBO J.* 7, 4035-4044 (1988); Meier, et al., *Plant Cell*, 3, 309-316 (1991); and Zhang, et al., *Plant Physiology* 110: 1069-1079 (1996).

Examples of various classes of promoters are described below. Some of the promoters indicated below are described in more detail in U.S. Patent Application Ser. Nos. 60/505, 689; 60/518,075; 60/544,771; 60/558,869; 60/583,691; 60/619,181; 60/637,140; Ser. Nos. 10/950,321; 10/957,569; 11/058,689; 11/172,703; 11/208,308; and PCT/US05/23639. It will be appreciated that a promoter may meet criteria for one classification based on its activity in one plant species, and yet meet criteria for a different classification based on its activity in another plant species.

Other Regulatory Regions: A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

Various promoters can be used to drive expression of the genes of the present invention. Nucleotide sequences of such promoters are set forth in SEQ ID NOs: 94-172. Some of them can be broadly expressing promoters, others may be more tissue preferential.

A promoter can be said to be "broadly expressing" when it promotes transcription in many, but not necessarily all, plant tissues or plant cells. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO: 169), YP0144 (SEQ ID NO: 148), YP0190 (SEQ ID NO: 152), p13879 (SEQ ID NO: 168), YP0050 (SEQ ID NO: 128), p32449 (SEQ ID NO: 170), 21876 (SEQ ID NO: 94), YP0158 (SEQ ID NO: 150), YP0214 (SEQ ID NO: 154), YP0380 (SEQ ID NO: 163), PT0848 (SEQ ID NO: 119), PT1026 and PT0633 (SEQ ID NO: 100). Additional examples include the cauliflower mosaic virus (CaMV) 35S promoter, the mannopine synthase (MAS) promoter, the 1' or 2' promoters derived from T-DNA of Agrobacterium tumefaciens, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root-active promoters drive transcription in root tissue, e.g., root endodermis, root epidermis, or root vascular tissues. In some embodiments, root-active promoters are root-preferential promoters, i.e., drive transcription only or predominantly in root tissue. Root-preferential promoters include the YP0128 (SEQ ID NO: 145), YP0275 (SEQ ID NO: 156), PT0625 (SEQ ID NO: 99), PT0660 (SEQ ID NO: 102), PT0683 (SEQ ID NO: 107), and PT0758 (SEQ ID NO: 115). Other root-preferential promoters include the PT0613 (SEQ ID NO: 98), PT0672 (SEQ ID NO: 104), PT0688 (SEQ ID NO: 108), and PT0837 (SEQ ID NO: 117), which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci.* USA 86:7890-7894 (1989)), root cell specific promoters reported by Conkling et al., *Plant Physiol*. 93:1203-1211 (1990), and the tobacco RD2 gene promoter.

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin gene promoter (Bustos et al., *Plant Cell* 1(9):839-853 (1989)), the soybean trypsin inhibitor promoter (Riggs et al., *Plant Cell* 1(6):609-621 (1989)), the ACP promoter (Baerson et al., *Plant Mol Biol,* 22(2):255-267 (1993)), the stearoyl-ACP desaturase gene (Slocombe et al., *Plant Physiol* 104(4):167-176 (1994)), the soybean α' subunit of β-conglycinin promoter (Chen et al., *Proc Natl Acad Sci* USA 83:8560-8564 (1986)), the oleosin promoter (Hong et al., *Plant Mol Biol* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.* 13:5829-5842 (1993)), the beta-amylase gene promoter, and the barley hordein gene promoter. Other maturing endosperm promoters include the YP0092 (SEQ ID NO: 131), PT0676 (SEQ ID NO: 105), and PT0708 (SEQ ID NO: 110).

Promoters that drive transcription in ovary tissues such as the ovule wall and mesocarp can also be useful, e.g., a polygalacturonidase promoter, the banana TRX promoter, and the melon actin promoter. Other such promoters that drive gene expression preferentially in ovules are YP0007 (SEQ ID NO: 123), YP0111 (SEQ ID NO: 139), YP0092 (SEQ ID NO: 131), YP0103 (SEQ ID NO: 136), YP0028 (SEQ ID NO: 126), YP0121 (SEQ ID NO: 144), YP0008 (SEQ ID NO: 124), YP0039 (SEQ ID NO: 127), YP0115 (SEQ ID NO: 140), YP0119 (SEQ ID NO: 142), YP0120 (SEQ ID NO: 143) and YP0374 (SEQ ID NO: 161).

In some other embodiments of the present invention, embryo sac/early endosperm promoters can be used in order drive transcription of the sequence of interest in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase.

Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao (1996) *Plant Mol. Biol.*, 32:571-57; Conceicao (1994) Plant, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142:1009-1020); maize Cat3 (see, GenBank No. L05934; Abler (1993) *Plant Mol. Biol.*, 22:10131-1038). Other promoters include the following *Arabidopsis* promoters: YP0039 (SEQ ID NO: 127), YP0101 (SEQ ID NO: 134), YP0102 (SEQ ID NO: 135), YP0110 (SEQ ID NO: 138), YP0117 (SEQ ID NO: 114), YP0119 (SEQ ID NO: 142), YP0137 (SEQ ID NO: 146), DME, YP0285 (SEQ ID NO: 157), and YP0212 (SEQ ID NO: 90). Other promoters that may be useful include the following rice promoters: p530c10, pOsFIE2-2, pOsMEA, pOsYp102, and pOsYp285.

Promoters that preferentially drive transcription in zygotic cells following fertilization can provide embryo-preferential expression and may be useful for the present invention. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654, YP0097 (SEQ ID NO: 133), YP0107 (SEQ ID NO: 137), YP0088 (SEQ ID NO: 130), YP0143 (SEQ ID NO: 147), YP0156 (SEQ ID NO: 149), PT0650 (SEQ ID NO: 101), PT0695 (SEQ ID NO: 109), PT0723 (SEQ ID NO: 112), PT0838 (SEQ ID NO: 118), PT0879 (SEQ ID NO: 121) and PT0740 (SEQ ID NO: 113).

Promoters active in photosynthetic tissue in order to drive transcription in green tissues such as leaves and stems are of particular interest for the present invention. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.* 35:773-778 (1994)), the Cab-1 gene promoter from wheat (Fejes et al., *Plant Mol. Biol.* 15:921-932 (1990)), the CAB-1 promoter from spinach (Lubberstedt et al., *Plant Physiol.* 104:997-1006 (1994)), the cabiR promoter from rice (Luan et al., *Plant Cell* 4:971-981 (1992)), the pyruvate orthophosphate dikinase (PPDK) promoter from corn (Matsuoka et al., *Proc Natl Acad. Sci* USA 90:9586-9590 (1993)), the tobacco Lhcb1 *2 promoter (Cerdan et al., *Plant Mol. Biol.* 33:245-255 (1997)), the *Arabidopsis thaliana* SUC2 sucrose-H+ symporter promoter (Truernit et al., *Planta* 196:564-570 (1995)), and thylakoid membrane protein promoters from spinach (psaD, psaF, psaE, PC, FNR, atpC, atpD, cab, rbcS. Other promoters that drive transcription in stems, leafs and green tissue are PT0535 (SEQ ID NO: 96), PT0668 (SEQ ID NO: 95), PT0886 (SEQ ID NO: 122), PR0924 (SEQ ID NO: 171), YP0144 (SEQ ID NO: 148), YP0380 (SEQ ID NO: 163) and PT0585 (SEQ ID NO: 97).

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought. Examples of drought inducible promoters are YP0380 (SEQ ID NO: 163), PT0848 (SEQ ID NO: 119), YP0381 (SEQ ID NO: 164), YP0337 (SEQ ID NO: 159), YP0337 (SEQ ID NO: 159), PT0633 (SEQ ID NO: 100), YP0374 (SEQ ID NO: 161), PT0710 (SEQ ID NO: 111), YP0356 (SEQ ID NO: 160), YP0385 (SEQ ID NO: 166), YP0396 (SEQ ID NO: 167), YP0384 (SEQ ID NO: 165), YP0384 (SEQ ID NO: 165), PT0688 (SEQ ID NO: 108), YP0286 (SEQ ID NO: 158), YP0377 (SEQ ID NO: 162), PD1367 (SEQ ID NO: 172), RD29a promoter (Kasuga et al., *Plant Cell Physiol.* 45:346 (2004) and Yamaguchi-Shinozaki and Shinozaki, *Mol Gen Genet.* 236: 331 (1993)), and other DRE-containing (dehydration-responsive elements) promoters, such as DREB1 (Liu et al, Cell 10: 1391 (1998)). Examples of promoters induced by nitrogen are PT0863 (SEQ ID NO: 120), PT0829 (SEQ ID NO: 116), PT0665 (SEQ ID NO: 103) and PT0886 (SEQ ID NO: 122). An example of a shade inducible promoter is PR0924.

Other Promoters: Other classes of promoters include, but are not limited to, leaf-preferential, stem/shoot-preferential, callus-preferential, guard cell-preferential, such as PT0678 (SEQ ID NO: 106), and senescence-preferential promoters. Promoters designated YP0086 (SEQ ID NO: 129), YP0188 (SEQ ID NO: 88), YP0263 (SEQ ID NO: 155), PT0758 (SEQ ID NO: 115), PT0743 (SEQ ID NO: 51), PT0829 (SEQ ID NO: 116), YP0119 (SEQ ID NO: 142), and YP0096 (SEQ ID NO: 132), as described in the above-referenced patent applications, may also be useful.

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant. In another alternative embodiment of the present invention, the misexpression can be accomplished by having the sequences of the two component system transformed in one transgenic plant line.

Another alternative consists in inhibiting expression of a drought-tolerance polypeptide in a plant species of interest. The term "expression" refers to the process of converting genetic information encoded in a polynucleotide into RNA through transcription of the polynucleotide (i.e., via the enzymatic action of an RNA polymerase), and into protein, through translation of mRNA. "Up-regulation" or "activation" refers to regulation that increases the production of expression products relative to basal or native states, while "down-regulation" or "repression" refers to regulation that decreases production relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a drought-tolerance polypeptide. A nucleic acid that decreases the level of a transcription or translation product of a gene encoding a drought-tolerance polypeptide is transcribed into an antisense nucleic acid similar or identical to the sense coding sequence of the drought-tolerance polypeptide. Alternatively, the transcription product of an isolated nucleic acid can be similar or identical to the sense coding sequence of a drought-tolerance polypeptide, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al., *Proc. Natl. Acad. Sci. USA*, 92(13): 6175-6179 (1995); de Feyter and Gaudron, Methods in Molecular Biology, Vol. 74, Chapter 43, "Expressing Ribozymes in Plants", Edited by Turner, P. C, Humana Press Inc., Totowa, N.J. RNA endoribonucleases such as the one that occurs naturally in *Tetrahymena Thermophila*, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the biomass-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997*Antisense Nucleic Acid Drug Dev.*, 7:187-195; Hyrup et al., 1996, *Bioorgan. Med. Chem.*, 4: 5-23. In addition, the deoxyphosphate backbone can be replaced with, for example, a phosphorothioate or phosphorodithioate backbone, a phosphoroamidite, or an alkyl phosphotriester backbone.

Transformation

Nucleic acid molecules of the present invention may be introduced into the genome or the cell of the appropriate host plant by a variety of techniques. These techniques, able to transform a wide variety of higher plant species, are well known and described in the technical and scientific literature (see, e.g., 28-29).

A variety of techniques known in the art are available for the introduction of DNA into a plant host cell. These techniques include transformation of plant cells by injection (30), microinjection (31), electroporation of DNA (32), PEG (33), use of biolistics (34), fusion of cells or protoplasts (35), and via T-DNA using *Agrobacterium tumefaciens* (36-37) or *Agrobacterium rhizogenes* (38) or other bacterial hosts (39), for example.

In addition, a number of non-stable transformation methods that are well known to those skilled in the art may be desirable for the present invention. Such methods include, but are not limited to, transient expression (40) and viral transfection (41).

Seeds are obtained from the transformed plants and used for testing stability and inheritance. Generally, two or more generations are cultivated to ensure that the phenotypic feature is stably maintained and transmitted.

A person of ordinary skill in the art recognizes that after the expression cassette is stably incorporated in transgenic plants and confirmed to be operable, it can be introduced into other plants by sexual crossing. Any of a number of standard breeding techniques can be used, depending upon the species to be crossed.

The nucleic acid molecules of the present invention may be used to confer the trait of increased drought-tolerance.

The nucleic acid molecules of the present invention encode appropriate proteins from any organism, but are preferably found in plants, fungi, bacteria or animals.

The methods according to the present invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belonging to the orders of the Magniolales, illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales, for example, are also suitable. Monocotyledonous plants belonging to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales also may be useful in embodiments of the present invention. Further examples include, but are not limited to, plants belonging to the class of the Gymnospermae are Pinales, Ginkgoales, Cycadales and Gnetales.

The methods of the present invention are preferably used in plants that are important or interesting for agriculture, horticulture, biomass for bioconversion and/or forestry. Non-limiting examples include, for instance, tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, *poinsettia, petunia*, guayule, cabbages, spinach, alfalfa, artichokes, sugarcane, mimosa, *Servicea lespedera*, corn, wheat, rice, rye, barley, sorghum and grasses such as switch grass, giant reed, Bermuda grass, Johnson grass or turf grasses, millet, hemp, bananas, poplars, *eucalyptus* trees and conifers.

Homologues Encompassed by the Invention

It is known in the art that one or more amino acids in a sequence can be substituted with other amino acid(s), the charge and polarity of which are similar to that of the substituted amino acid, i.e. a conservative amino acid substitution, resulting in a biologically/functionally silent change. Conservative substitutes for an amino acid within the polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

Nucleic acid molecules of the present invention can comprise sequences that differ from those encoding a protein or fragment thereof selected from the group consisting of [leads 68, 69, 94 and 95, nucleotides] due to the fact that the different nucleic acid sequence encodes a protein having one or more conservative amino acid changes.

Biologically functional equivalents of the polypeptides, or fragments thereof, of the present invention can have about 10 or fewer conservative amino acid changes, more preferably about 7 or fewer conservative amino acid changes, and most preferably about 5 or fewer conservative amino acid changes. In a preferred embodiment of the present invention, the polypeptide has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

6. Experiments Confirming the Usefulness of the Polynucleotides and Polypeptides of the Invention 6.1 General Protocols 6.1.1 *Agrobacterium*-Mediated Transformation of *Arabidopsis*

Wild-type *Arabidopsis thaliana Wassilewskija* (WS) plants are transformed with Ti plasmids containing clones in the sense orientation relative to the 35S promoter. A Ti plasmid vector useful for these constructs, CRS 338, contains the Ceres-constructed, plant selectable marker gene phosphinothricin acetyltransferase (PA 7), which confers herbicide resistance to transformed plants.

Ten independently transformed events are typically selected and evaluated for their qualitative phenotype in the $T_1$ generation.

Preparation of Soil Mixture: 24 L SunshineMix #5 soil (Sun Gro Horticulture, Ltd., Bellevue, Wash.) is mixed with 16 L Therm-O-Rock vermiculite (Therm-O-Rock West, Inc., Chandler, Ariz.) in a cement mixer to make a 60:40 soil mixture. To the soil mixture is added 2 Tbsp Marathon 1% granules (Hummert, Earth City, Mo.), 3 Tbsp OSMOCOTE® 14-14-14 (Hummert, Earth City, Mo.) and 1 Tbsp Peters fertilizer 20-20-20 (J. R. Peters, Inc., Allentown, Pa.), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of *Agrobacterium*: To 150 mL fresh YEB is added 0.1 mL each of carbenicillin, spectinomycin and rifampicin (each at 100 mg/ml stock concentration). *Agrobacterium* starter blocks are obtained (96-well block with *Agrobacterium* cultures grown to an $OD_{600}$ of approximately 1.0) and inoculated one culture vessel per construct by transferring 1 mL from appropriate well in the starter block. Cultures are then incubated with shaking at 27° C. Cultures are spun down after attaining an $OD_{600}$ of approximately 1.0 (about 24 hours). 200 mL infiltration media is added to resuspend *Agrobacterium* pellets. Infiltration media is prepared by adding 2.2 g MS salts, 50 g sucrose, and 5 µl 2 mg/ml benzylaminopurine to 900 ml water.

Dipping Infiltration: The pots are inverted and submerged for 5 minutes so that the aerial portion of the plants are in the *Agrobacterium* suspension. Plants are allowed to grow normally and seed is collected.

The nucleotide sequences of the invention are identified by use of a variety of screens that modify water conditions. These screens are recognized by those skilled in the art to be predictive of nucleotide sequences that provide plants with enhanced drought tolerance including improved tolerance to heat and/or low water conditions because they emulate the different environmental conditions that can result from increased heat and/or low water conditions. These screens generally fall into two categories (1) soil screens and (2) in vitro screens.

Soil screens have the advantage of assaying the response of the entire plant to particular conditions, such as drought or high heat. On the other hand, in vitro screens have the advantage of relying on defined media and so allow more defined manipulation of growth conditions. Some "surrogate" in vitro screens decrease the water available to the plant by adding particular chemicals to the growth media, such as mannitol or polyethylene glycol (PEG) (e.g., Quesada et al. (2000) *Genetics* 154:421-36; van der Weele et al. (2000) *J Exp. Bot.* 51:1555-1562). The decrease in the osmotic potential of the growth media minics conditions plants experience in dry soil.

Another type of surrogate in vitro screen is for abscisic acid (ABA) resistance. ABA is a plant hormone that is a key regulator of environmental stress responses. ABA-mediated signaling controls the expression of some stress-responsive genes and regulates the closing of stomata in response to water deficit. Screens in the presence of ABA can identify plants with altered stress responses and are useful for identifying plants with increased drought tolerance (Shinozaki et al. (2003) *Curr. Opin. Plant Biol.* 6:410-417).

The soil screens and in vitro screens used to identify the polynucleotides and polypeptides of the invention are described in more detail below. In general, these screens are conducted using superpools of *Arabidopsis* $T_2$ transformed plants. The $T_1$ plants are transformed with a Ti plasmid containing a particular nucleotide sequence in the sense orientation relative to a constitutive promoter and harboring the plant-selectable marker gene phosphinothricin acetyltransferase (PAT), which confers herbicide resistance to transformed plants, specifically to the herbicide Finale™ (Hoechst). Each superpool is comprised of $T_2$ seeds from approximately 5 independent transformation events for each of 100 different transgenes. For all screens, seeds from multiple superpools are tested. The results of the screens conducted for each polynucleotide can be found in the Examples below.

6.1.2 Mannitol

Superpool seeds are sterilized in 30% household bleach for 5 minutes then washed with water three times. Sterilized seed is stratified in the dark at 4° C. for a minimum of 3 days before use.

Mannitol media consists of 375 mM mannitol, 0.5% (w/v) sucrose, 0.025% (w/v) MES hydrate, 0.5× Murashige and Skoog (MS) salts, and 0.6% (w/v) phytagar. Approximately 1200 seeds per Superpool are evenly spread on a mannitol plate and then grown at 22° C. for 14 days.

Putative mannitol-resistant seedlings are transferred to mannitol-free media for recovery. Approximately one week later, these seedlings are transferred to soil and sprayed with Finale™ to select for transgenic plants. The transgene present in the Finale™-resistant plants is determined by PCR. Unpooled $T_2$ seeds and $T_3$ seeds from the original transgenic line are retested on 375 mM mannitol media.

6.1.3 Polyethylene Glycol (PEG)

Superpool seeds are sterilized in 30% household bleach for 5 minutes then washed with water three times. Sterilized seed is stratified in the dark at 4° C. for a minimum of 3 days before use.

PEG media consists of 20% PEG 8000, 0.5% (w/v) sucrose, 0.025% (w/v) MES hydrate, 0.5×MS salts and 0.3% (w/v) gelrite. Approximately 1200 seeds per Superpool are evenly spread on a PEG plate and then grown at 22° C. for 14 days.

Putative PEG-resistant seedlings are transferred to PEG-free media with 0.01% (v/v) Finale™. One week later, resistant seedlings are transferred to soil. The transgene present in the Finale™-resistant plants is determined by PCR. Unpooled $T_2$ seeds and $T_3$ seeds from the original transgenic line are retested on 20% PEG media.

6.1.4 ABA

Superpool seeds are sterilized in 30% household bleach for 5 minutes then washed with water three times. Sterilized seed is stratified in the dark at 4° C. for a minimum of 3 days before use.

ABA media consists of 1.5 µM ABA, 0.5% (w/v) sucrose, 0.05% (w/v) MES hydrate, 1.0×MS salt and 0.6% (w/v) phytagar. Approximately 1200 seeds per Superpool are evenly distributed on a PEG plate and then grown at 22° C. for 14 days.

Putative ABA-resistant seedlings are transferred to ABA-free media with 0.01% (v/v) Finale™. One week later, resistant seedlings are transferred to soil. The transgene present in the Finale™-resistant plants is determined by PCR. Unpooled $T_2$ seeds and $T_3$ seeds from the original transgenic line are retested on 20% PEG media.

6.1.5 Soil Drought

Soil drought screens identify plants with enhanced tolerance to drought (desiccation tolerance) and enhanced recovery after drought.

(a) Soil Drought Superpool Screen

Six-pot flats are filled with a soil mixture of 3:2 Sunshine Mix #5 (Sun Gro Horticulture):Vermiculite and then saturated with water by sub-irrigation. Approximately 1700 superpool seeds are sown evenly across five of the six pots. The sixth pot is reserved for wild-type and positive control seeds. After sowing, the flats are covered with humidity domes and stratified for at least 3 days at 4° C., then transferred to the green house (16:8 hour light: dark cycle; 150µ Einstein; 70% relative humidity; 22° C.).

The humidity dome is removed after approximately 4 days in the greenhouse and flats are watered as needed. At 10 days, plants are sprayed with Finale™ to eliminate any that are non-transgenic. When 90% of the plants boltd, water is withheld and pots are removed from the flat to promote uniform drying. After approximately 5 days of drying, plants are assessed for desiccation tolerance. Subsequently the flats are rewatered and plants are allowed to recover for several days and then assessed for recovery from desiccation. Tissue from plants exhibiting desiccation tolerance or enhanced recovery is harvested and subjected to PCR to determine the identity of the transgene. $T_2$ seeds from the original transgenic line are retested in the Soil Drought Pre-Validation Assay.

(b) Soil Drought Pre-Validation Assay

Seeds are planted in 72-pot flats using 12 pots for each transgenic event to be evaluated and 12 pots of wild-type control. Flats are watered and covered with a plastic humidity dome then placed in the dark at 4° C. for 3 days. After cold treatment, the flats are moved to the growth chamber (16:8 hour light: dark cycle; 150 µl Einstein; 70% relative humidity; 22° C.).

The humidity domes are removed after approximately 3 days at 22° C. or when the cotyledens are fully expanded. Seedlings are thinned such that only one seedling remained in each pot. Flats are irrigated alternatively with 0.5× Hoagland's Solution and filtered water as needed. Twelve days after sowing, the flats are watered for the last time. Plants are scored as drought-tolerant or non-drought-tolerant after approximately 12-16 days of drying. Events showing a significant number of tolerant plants are advanced to the Soil Drought Assay—Desiccation Tolerance.

(c) Soil Drought Assay-Desiccation Tolerance

Seeds are planted in 24-pot flats containing prepared soil. Flats are watered and covered with a plastic humidity dome then placed in the dark at 4° C. for 3 days. After cold treatment, the flats removed to the growth chamber (16:8 hour light: dark cycle; 150μ Einstein; 70% relative humidity; 22° C.).

The humidity domes are removed after 5 days at 22° C. or when the cotyledens are fully expanded. On the $5^{th}$ day, seedlings are thinned such that only one seedling remained in each pot. Flats are irrigated alternatively with 0.5× Hoagland's Solution and filtered water as needed.

Five days post-bolting, a cauline leaf is harvested onto solid medium containing Finale™ (Hoescht) in order to identify transgenic (Finale™ resistant) and non-transgenic (Finale™ sensitive) segregants. Drought treatment is begun approximately 16 days after transfer to 22° C. Plants are observed regularly for wilting, which occurs about 12 days after the last watering. When approximately 90% of the control plants have wilted to a score of 3, all samples are scored according to the scale: (1) no visible changes, (2) leaf color changes, (3) some leaves wilted, (4) all leaves wilted, and (5) all eaves severely wilted and loss of color.

(d) Soil Drought Assay-Recovery from Drought

To assess plants for enhanced recovery after drought, the above procedures are followed. Then 48 hours after about 90% of the control plants have wilted, the flat is filled ¾ full with water, and one hour later excess water is removed. Approximately two to four days after re-watering, plants are assessed for recovery from wilting using the scale: (1) all leaves recovered, (2) most mature leaves recovered, (3) some mature leaves recovered (4) only young leaves recovered, and (5) no leaves recovered.

6.3 Results

The results of the above experiments are set forth below wherein each individual example relates to all of the experimental results for a particular polynucleotide/polypeptide of the invention.

EXAMPLE 1

Lead 94-ME04218-Clone 15450-cDNA 14297769

ME04218 was Identified from a Superpool Screen for Desiccation Tolerance.

Superpool 29 was screened for plants that resisted wilting by testing them for drought tolerance as described above. Twelve candidates were chosen from Superpool 29. All were successfully sequenced. ME04218 was represented once in this set. The gene corresponding to Clone 15450 is upregulated in germinating seeds and reproductive tissues including: flowers, pollen and siliques.

Three Events of ME04218 Showed Desiccation Tolerance in a Pre-Validation Assay.

Seeds from all four events of ME04218 were sown according to the Soil Drought Pre-Validation Assay. Events -01, -02 and -04 segregated for desiccation tolerant seedlings and were advanced to the validation assay where they were scored 1-5 as described above. Event-03 failed to germinate. Three events of ME04218 showed significant desiccation tolerance.

Seeds from three $T_2$ events of ME04218 were tested for dessication tolerance in the Soil Drought Assay—Desiccation Tolerance. Subsequently, two of these Events were re-evaluated in both the $T_2$ and $T_3$ generations. The $T_3$ lines are indicated as −99 meaning the seeds are the bulked progeny from several $T_2$ plants. Transgenic plants show better recovery after drought than non-transgenic plants. Table 1-1 shows the tolerance of both $T_2$ and $T_3$ generation plants.

TABLE 1-1

Chi-square test of desiccation tolerance.

| Assay | Events | Transgene Status[a] | Tolerant | Non-tolerant | Tol_Exp[b] | NT_Exp[c] | Chi-Test p-value[d] |
|---|---|---|---|---|---|---|---|
| $1^{st}$ Assay | ME04218-01 | T | 3 | 7 | 0.5 | 9.5 | 0.0001 |
| | ME04218-01 | N | 2 | 5 | | | |
| | ME04218-02 | T | 12 | 17 | 1.3 | 27.7 | 1.69E−21 |
| | ME04218-02 | N | 1 | 12 | | | |
| | ME04218-02-99 | T | 12 | 11 | 1.0 | 22.0 | 5.58E−28 |
| | ME04218-04 | T | 4 | 9 | 0.6 | 12.4 | 5.65E−06 |
| | ME04218-04 | N | 1 | 3 | | | |
| | ME04218-04-99 | T | 0 | 19 | 0.9 | 18.1 | 0.3415 |
| | ME04218-04-99 | N | 0 | 8 | | | |
| | WS | N | 0 | 56 | | | |
| | Combined N | N | 4 | 84 | | | |
| $2^{nd}$ Assay[e] | ME04218-01-99 | T | 5 | 8 | 1.5 | 11.5 | 0.0028 |
| | ME04218-01-99 | N | 1 | 4 | | | |
| | ME04218-02 | T | 5 | 11 | 1.9 | 14.1 | 0.0156 |
| | ME04218-02 | N | 0 | 2 | | | |
| | ME04218-04 | T | 3 | 6 | 1.1 | 7.9 | 0.0446 |
| | ME04218-04 | N | 2 | 1 | | | |
| | WS | N | 1 | 23 | | | |
| | Combined N | N | 4 | 30 | | | |

[a] T is transgenic and N is non-transgenic
[b] Expected number of tolerant plants for the null hypothesis is calculated by multiplying the total number of plants (tolerant plus non-tolerant) with the frequency of tolerant plants among the combined non-transgenics
[c] Expected number of non-tolerant plants for the null hypothesis is calculated by multiplying the total number of plants (tolerant plus non-tolerant) with the frequency of non-tolerant plants among the combined non-transgenics
[d] P-value resulting from a chi-square test comparing the tolerant to non-tolerant ratio for each event to the expected tolerant to non-tolerant ratio. Significant p-values are in bold type.
[e] The second assay was performed because the $T_3$ seeds for Event-01 were not available when the first assay was run. Events-02 and -04 were repeated for controls.

Three Events of ME04218 Show 3:1 Segregation for Finale™ Resistance.

Events -01, -02 and -04 segregated 3:1 (R:S) for Finale™ resistance in the $T_2$ generation.

Qualitative Analysis of the $T_1$ Plants:

The physical appearance of the four $T_1$ plants was identical to the controls.

Functional Homologs: Functional homologs of ME 04218 were identified by the procedure described above, and are shown in FIG. 3.

EXAMPLE 2

Lead 95-ME01466-Clone 26369-cDNA 14298505

ME01466 was Identified from Superpool Screens for PEG and Mannitol Tolerance.

1200 seeds from Superpool 01 were screened for seedlings with increased vigor and growth on 20% PEG plates or on 375 mM Mannitol plates. In follow-up experiments, $T_2$ seeds from Events -01 and -02 were observed to segregate in approximately a 3:1 ratio of tolerant to non-tolerant seedlings on PEG and Mannitol. Event-04 also segregated tolerant plants on PEG, but not in a 3:1 ratio. These observations indicate that ME01466 confers tolerance to osmotic stress. These Events were subsequently tested for desiccation tolerance in soil.

Three Events of ME01466 Showed Significant Desiccation Tolerance.

Three experiments were completed to test events of ME01466 for dessication tolerance. Table 2-1 shows the combined results from all three experiments.

In the third experiment, it was observed that the drought tolerant plants were slightly shorter than the non-tolerant plants. The results are shown below in Table 2-2 and indicate that shorter plants show delayed desiccation. Reduced plant height in plants with a wilt score of 4 or 5 is likely to result from the tip of the inflorescence withering or an earlier cessation of inflorescence elongation.

Comparison of Soil Moisture and Wilt Score Among Transgenic Me01466 Plants.

The degree of wilting exhibited by transgenic plants was significantly correlated to the amount of moisture remaining in the soil (50% is saturated soil). Table 2-2 shows a correlation between wilt score and plant height indicating that the shorter plants resist desiccation better than the taller plants. In addition, wilt score is also correlated to the amount of moisture remaining in the soil. Taken together, these observations suggest the mode-of-action for desiccation tolerance in ME01466 is desiccation postponement occasioned by decreased water usage in the shorter plants.

TABLE 2-2

Comparison of plant height and wilt score among transgenic ME01466 plants.

| Wilt Score | Avg. Height | SE Height | Avg. % Soil Moisture | SE % Soil Moisture | n |
|---|---|---|---|---|---|
| 1 | 15.26 | 0.87 | 1.95% | 0.22% | 12 |
| 2 | 16.66 | 0.35 | 1.64% | 0.08% | 40 |
| 3 | 17.89 | 0.30 | 1.06% | 0.04% | 60 |

TABLE 2-1

Chi-square test of desiccation tolerance

| Events | Event-Generation | TS[a] | Tolerant | Non-tolerant | Tol_Exp[b] | NT_Exp[c] | Chi-Test p-value[d] |
|---|---|---|---|---|---|---|---|
| ME01466-01-01 | 01-$T_3$ | T | 11 | 11 | 1.8 | 20.2 | 1.24E−12 |
| ME01466-01-01 | 01-$T_3$ | N | 1 | 10 | 0.9 | 10.1 | 0.9223 |
| ME01466-01$T_4$-01 | 01-$T_4$ | T | 19 | 14 | 2.7 | 30.3 | 9.07E−25 |
| ME01466-01$T_4$-01 | 01-$T_4$ | N | 2 | 5 | 0.6 | 6.4 | 0.0514 |
| ME01466-01$T_4$-01-766658[e] | 01-$T_5$ | T | 8 | 5 | 1.1 | 11.9 | 3.22E−12 |
| ME01466-01$T_4$-01-766658[e] | 01-$T_5$ | N | 2 | 3 | 0.4 | 4.6 | 0.0101 |
| ME01466-02-01 | 02-$T_3$ | T | 27 | 10 | 3.1 | 33.9 | 2.95E−46 |
| ME01466-02-01 | 02-$T_3$ | N | 0 | 9 | 0.7 | 8.3 | 0.3674 |
| ME01466-02-01-762925[e] | 02-$T_4$ | T | 5 | 13 | 1.5 | 16.5 | 0.0027 |
| ME01466-02-01-762987[e] | 02-$T_4$ | T | 4 | 14 | 1.5 | 16.5 | 0.0318 |
| ME01466-04 | 04-$T_2$ | T | 3 | 12 | 1.2 | 13.8 | 0.0995 |
| ME01466-04 | 04-$T_2$ | N | 0 | 3 | 0.2 | 2.8 | 0.6028 |
| ME01466-04$T_3$ | 04-$T_3$ | T | 6 | 10 | 1.3 | 14.7 | 2.22E−05 |
| ME01466-04$T_3$ | 04-$T_3$ | N | 0 | 2 | 0.2 | 1.8 | 0.6709 |
| WS | | N | 8 | 112 | 9.9 | 110.1 | 0.5213 |
| Combined N | | N | 13 | 144 | | | |

[a] Transgene Status, T is transgenic and N is non-transgenic
[b] Expected number of tolerant plants for the null hypothesis is calculated by multiplying the total number of plants (tolerant plus non-tolerant) with the frequency of tolerant plants among the combined non-transgenics
[c] Expected number of non-tolerant plants for the null hypothesis is calculated by multiplying the total number of plants (tolerant plus non-tolerant) with the frequency of non-tolerant plants among the combined non-transgenics
[d] P-value resulting from a chi-squared test comparing the tolerant to non-tolerant ratio for each event to the expected tolerant to non-tolerant ratio. Significant p-values are in bold type.

TABLE 2-2-continued

Comparison of plant height and wilt score among transgenic ME01466 plants.

| Wilt Score | Avg. Height | SE Height | Avg. % Soil Moisture | SE % Soil Moisture | n |
|---|---|---|---|---|---|
| 4 | 17.71 | 0.38 | 0.61% | 0.04% | 42 |
| 5 | 17.09 | 1.06 | 0.23% | 0.07% | 9 |

Three Events of ME01466 Show 3:1 Segregation for Finale™ Resistance.

Events -01 and -02 segregated 3:1 (R:S) for Finale™ resistance in the $T_3$ generation. Event-04 also segregated 3:1 (R:S) for Finale™ resistance in the $T_2$ generation.

Qualitative Analysis of the $T_1$ Plants:

Event-03, not included in this study, exhibited a larger rosette, increased branches and lanceolate shaped leaves. The physical appearance of the remaining 19 $T_1$ plants was identical to the controls; there are 20 Events because the construct was introduced into the ME pipeline on two different occasions.

Table 2-3 summarizes the results of the above experiments from ME 01466/clone 26365, showing enhanced dessication tolerance on soil, and improved seeding vigor and growth in PEG and mannitol.

TABLE 2-3

Summary of Results for ME 01466

| Construct | Event/Generation | Plant Stage | Assay | Result |
|---|---|---|---|---|
| 35S::26369 | -01/$T_3$ Finale resistant plants | Flowering | Desiccation Tolerance | Significant at p ≦ .05 |
| 35S::26369 | -02/$T_3$ Finale resistant plants | Flowering | Desiccation Tolerance | Significant at p ≦ .05 |
| 35S::26369 | -04/$T_3$ Finale resistant plants | Flowering | Desiccation Tolerance | Significant at p ≦ .05 |
| 35S::26369 | -01/$T_4$ Finale resistant plants | Flowering | Desiccation Tolerance | Significant at p ≦ .05 |
| 35S::26369 | -02/$T_4$ Finale resistant plants | Flowering | Desiccation Tolerance | Significant at p ≦ .05 |
| 35S::26369 | -01/$T_5$ Finale resistant plants | Flowering | Desiccation Tolerance | Significant at p ≦ .05 |
| 35S::26369 | -01/$T_2$ | Seedling | Mannitol Tolerance | 3:1 segregation |
| 35S::26369 | -02/$T_2$ | Seedling | Mannitol Tolerance | 3:1 segregation |
| 35S::26369 | -01/$T_2$ | Seedling | PEG Tolerance | 3:1 segregation |
| 35S::26369 | -02/$T_2$ | Seedling | PEG Tolerance | 3:1 segregation |
| 35S::26369 | -03/$T_2$ | Seedling | PEG Tolerance | 3:1 segregation |
| 35S::26369 | -04/$T_2$ | Seedling | PEG Tolerance | 1:1 segregation |

Functional Homolog: Functional homologs of ME 014661/clone 26369 were identified by the procedure described above, and are shown in FIG. 4.

EXAMPLE 3

Lead 69-ME01854-Clone 16209-cDNA 23462374

ME01854 was Identified from a Superpool Screen for Mannitol Tolerance as a Line to Assay Under Soil Drought.

Superpool 4 yielded ME01854 as a Mannitol-tolerant plant line. Individual events -01 through -04 and -08 were tested for ABA, Mannitol, and PEG tolerance. Events -03 and -08 showed definitive ABA tolerance in two generations.

Two Events of ME01854 show 3:1 Segregation for Finale™.

Events -03 and -08 segregated 3:1 (R:S) for Finale™ in the $T_2$ generation.

Two Generations of Two Events of ME01854 Show a Delay in Desiccation in Response to Water Deprivation in Comparison to Controls.

Events ME01854-03 and -08 were selected for testing on soil drought based on their surrogate drought screen results. Aspects of drought resistance such as desiccation delay and drought recovery were used to evaluate overall drought performance. In both the $T_2$ and $T_3$ of the two events, the transgenics showed a significantly improved performance in delay in desiccation in response to drought, as determined by a Chi-square comparison test at p=0.05. (See Table 3-1) For recovery after drought, the events trended toward enhanced recovery, but were not significant via Chi-square comparison test in both events in both generation to a level of p=0.05. Event-03 was significant in the $T_3$ but not the $T_2$ generation, whereas Event-08 was significant in the $T_2$ but not the $T_3$ generation.

TABLE 3-1

Analysis of delay in desiccation in response to drought in two generations ($T_2$ and $T_3$) for two events of ME01854 after 11 days of water deprivation.

| | Tolerant | | Non-tolerant | | |
|---|---|---|---|---|---|
| | observed | expected | observed | expected | Total |
| Wildtype | 60 | 65 | 308 | 303 | 368 |
| ME01854-03 ($T_2$) | 8 | 3 | 9 | 14 | 17 |
| Total | 68 | | 317 | | 385 |
| Chi-sq. = 10.57 | | | | | |

TABLE 3-1-continued

Analysis of delay in desiccation in response to drought in two generations ($T_2$ and $T_3$) for two events of ME01854 after 11 days of water deprivation.

| | Tolerant | | Non-tolerant | | |
|---|---|---|---|---|---|
| | observed | expected | observed | expected | Total |
| Wildtype | 60 | 65.3 | 308 | 302.7 | 368 |
| ME01854-03 ($T_3$) | 8 | 2.7 | 7 | 12.3 | 15 |
| Total | 68 | | 315 | | 383 |
| Chi-sq. = 13.53 | | | | | |
| Wildtype | 60 | 64.2 | 308 | 303.8 | 368 |
| ME01854-08 ($T_2$) | 7 | 2.8 | 9 | 13.2 | 16 |
| Total | 67 | | 317 | | 384 |
| Chi-sq. = 8.02 | | | | | |
| Wildtype | 60 | 63.4 | 308 | 304.6 | 368 |
| ME01854-08 ($T_3$) | 6 | 2.6 | 9 | 12.4 | 15 |
| Total | 66 | | 317 | | 383 |
| Chi-sq. = 5.67 | | | | | |

Qualitative Analysis of the $T_1$ Plants:

The physical appearance of 9 of 10 $T_1$ plants was identical to the controls. Event-01 was noted as tall with reduced fertility, but this phenotype may have been environmentally influenced, as it was not shared by any of the other events.

Functional Homolog: Functional homologs of ME 01854/clone 16209 were identified by the procedure described above, and are shown in FIG. 2.

EXAMPLE 4

Lead 68-ME00270-Clone3086-cDNA 23650508

ME00270 was Identified from a Superpool Screen for ABA Tolerance as a Line to Assay Under Soil Drought.

Superpool 10 yielded ME00270 as an ABA-tolerant plant line. Individual events -01 through -06 were tested for ABA, Mannitol, and PEG tolerance. Event-04 showed putative, but not definitive Mannitol tolerance, and Event-05 showed definitive ABA tolerance in two generations (data not shown). These two events were selected for soil drought assays.

Two Events of ME00270 Show 3:1 Segregation for Finale™.

Events -04 and -05 segregated 3:1 (R:S) for Finale™ in the $T_2$ generation (data not shown).

Two Generations of Two Events of ME00270 Show a Delay in Desiccation in Response to Water Deprivation, and Enhanced Recovery Following Drought in Comparison to Controls.

Events ME00270-04 and -05 were selected for testing on soil drought based on their surrogate drought screen results. Aspects of drought resistance such as desiccation delay and drought recovery were used to evaluate overall drought performance. In both the $T_2$ and $T_3$ of the two events, the transgenics showed a significant delay in desiccation in response to drought, and recovery from drought, as determined by a Chi-square comparison test at p=0.05.

TABLE 4-1

Analysis of delay in desiccation in response to drought in two generations ($T_2$ and $T_3$) for two events of ME00270 11 days after the last watering.

|  | Tolerant | | Non-tolerant | | |
| --- | --- | --- | --- | --- | --- |
|  | observed | expected | observed | expected | Total |
| Wildtype | 60 | 66.9 | 308 | 301.1 | 368 |
| ME00270-04 ($T_2$) | 10 | 3.1 | 7 | 13.9 | 17 |
| Total | 70 | | 315 | | 385 |
| chi-sq. = 19.75 | | | | | |
| Wildtype | 60 | 64.8 | 308 | 303.2 | 368 |
| ME00270-04-09 ($T_3$) | 8 | 3.2 | 10 | 14.8 | 18 |
| Total | 68 | | 318 | | 386 |
| chi-sq. = 9.36 | | | | | |
| Wildtype | 60 | 66.0 | 308 | 302.0 | 368 |
| ME00270-05 ($T_2$) | 8 | 2.0 | 3 | 9.0 | 11 |
| Total | 68 | | 311 | | 379 |
| chi-sq. = 23.10 | | | | | |
| Wildtype | 60 | 63.1 | 308 | 304.9 | 368 |
| ME00270-05-18 ($T_3$) | 5 | 1.9 | 6 | 9.1 | 11 |
| Total | 65 | | 314 | | 379 |
| chi-sq. = 6.39 | | | | | |

TABLE 4-2

Analysis of recovery from soil drought in two generations ($T_2$ and $T_3$) for two events of ME00270 3 days after recovery following re-watering.

|  | Recovery | | Non-recovery | | |
| --- | --- | --- | --- | --- | --- |
|  | observed | expected | observed | expected | Total |
| Wildtype | 127 | 132.9 | 241 | 235.1 | 368 |
| ME00270-04 ($T_2$) | 12 | 6.1 | 5 | 10.9 | 17 |
| Total | 139 | | 246 | | 385 |
| chi-sq. = 9.17 | | | | | |
| Wildtype | 127 | 131.6 | 241 | 236.4 | 368 |
| ME00270-04-09 ($T_3$) | 11 | 6.4 | 7 | 11.6 | 18 |
| Total | 138 | | 248 | | 386 |
| chi-sq. = 5.29 | | | | | |
| Wildtype | 127 | 132.1 | 241 | 235.9 | 368 |
| ME00270-05 ($T_2$) | 9 | 3.9 | 2 | 7.1 | 11 |
| Total | 136 | | 243 | | 379 |
| chi-sq. = 10.39 | | | | | |
| Wildtype | 127 | 132.1 | 241 | 235.9 | 368 |
| ME00270-05-18 ($T_3$) | 9 | 3.9 | 2 | 7.1 | 11 |
| Total | 136 | | 243 | | 379 |
| chi-sq. = 6.39 | | | | | |

Functional Homolog: Functional homologs of ME00270/clone 3086 were identified by the procedure described above, and are shown in FIG. 1.

Plants transformed with the polynucleotides of the invention (specifically Lead Nos. 94, 95, 68 and 69) were also evaluated for any deleterious, negative or undesirable characteristics. Such characteristics include reduction in germination rate, modification of general morphology/architecture, changes in days to flowering, changes in the size of the plant rosette area after bolting, and changes in fertility (based, for example, on silique number of seed fill). For the observed plants, no statistically significant differences were noted between the transformed plants of the invention as compared to controls.

EXAMPLE 5

Determination of Functional Homolog Sequences

The "Lead" sequences described in above Examples 1-4 are utilized to identify functional homologs of the lead sequences and, together with those sequences, are utilized to determine a consensus sequence for a given group of lead and functional homolog sequences.

A subject sequence is considered a functional homolog of a query sequence if the subject and query sequences encode proteins having a similar function and/or activity. A process known as Reciprocal BLAST (Rivera et al, *Proc. Natl Acad. Sci USA*, 1998, 95:6239-6244) is used to identify potential functional homolog sequences from databases consisting of all available public and proprietary peptide sequences, including NR from NCBI and peptide translations from Ceres clones.

Before starting a Reciprocal BLAST process, a specific query polypeptide is searched against all peptides from its source species using BLAST in order to identify polypeptides having sequence identity of 80% or greater to the query polypeptide and an alignment length of 85% or greater along the shorter sequence in the alignment. The query polypeptide and any of the aforementioned identified polypeptides are designated as a cluster.

The main Reciprocal BLAST process consists of two rounds of BLAST searches; forward search and reverse search. In the forward search step, a query polypeptide sequence, "polypeptide A," from source species $S^A$ is BLASTed against all protein sequences from a species of interest. Top hits are determined using an E-value cutoff of $10^{-5}$ and an identity cutoff of 35%. Among the top hits, the sequence having the lowest E-value is designated as the best hit, and considered a potential functional homolog. Any other top hit that had a sequence identity of 80% or greater to the best hit or to the original query polypeptide is considered a potential functional homolog as well. This process is repeated for all species of interest.

In the reverse search round, the top hits identified in the forward search from all species are used to perform a BLAST search against all protein or polypeptide sequences from the source species $S^A$. A top hit from the forward search that returned a polypeptide from the aforementioned cluster as its best hit is also considered as a potential functional homolog.

Functional homologs are identified by manual inspection of potential functional homolog sequences. Representative functional homologs are shown in FIGS. 1-4. Each Figure represents a grouping of a lead/query sequence aligned with the corresponding identified functional homolog subject sequences. Lead sequences and their corresponding functional homolog sequences are aligned to identify conserved amino acids and to determine a consensus sequence that contains a frequently occurring amino acid residue at particular positions in the aligned sequences, as shown in FIGS. 1-4.

Each consensus sequence then is comprised of the identified and numbered conserved regions or domains, with some of the conserved regions being separated by one or more amino acid residues, represented by a dash (-), between conserved regions.

Useful polypeptides of the inventions, therefore, include each of the lead and functional homolog sequences shown in FIGS. 1-4, as well as the consensus sequences shown in those Figures. The invention also encompasses other useful polypeptides constructed based upon the consensus sequence and the identified conserved regions. Thus, useful polypeptides include those which comprise one or more of the numbered conserved regions in each alignment table in an individual Figure depicted in FIGS. 1-4, wherein the conserved regions may be separated by dashes. Useful polypeptides also include those which comprise all of the numbered conserved regions in an individual alignment table selected from FIGS. 1-4, alternatively comprising all of the numbered conserved regions in an individual alignment table and in the order as depicted in an individual alignment table selected from FIGS. 1-4. Useful polypeptides also include those which comprise all of the numbered conserved regions in an individual alignment table and in the order as depicted in an individual alignment table selected from FIGS. 1-4, wherein the conserved regions are separated by dashes, wherein each dash between two adjacent conserved regions is comprised of the amino acids depicted in the alignment table for lead and/or functional homolog sequences at the positions which define the particular dash. Such dashes in the consensus sequence can be of a length ranging from length of the smallest number of dashes in one of the aligned sequences up to the length of the highest number of dashes in one of the aligned sequences.

Such useful polypeptides can also have a length (a total number of amino acid residues) equal to the length identified for a consensus sequence or of a length ranging from the shortest to the longest sequence in any given family of lead and functional homolog sequences identified in an individual alignment table selected from FIGS. 1-4.

The present invention further encompasses nucleotides that encode the above described polypeptides, as well as the complements thereof, and including alternatives thereof based upon the degeneracy of the genetic code.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

REFERENCES (1) Zhang et al. (2004) *Plant Physiol.* 135:615.
(2) Salomon et al. (1984) *EMBO J.* 3:141.
(3) Herrera-Estrella et al. (1983) *EMBO J.* 2:987.
(4) Escudero et al. (1996) *Plant J.* 10:355.
(5) Ishida et al. (1996) *Nature Biotechnology* 14:745.
(6) May et al. (1995) *Bio/Technology* 13:486)
(7) Armaleo et al. (1990) *Current Genetics* 17:97.
(8) Smith. T. F. and Waterman, M. S. (1981) *Adv. App. Math.* 2:482.
(9) Needleman and Wunsch (1970) *J. Mol. Biol.* 48:443.
(10) Pearson and Lipman (1988) *Proc. Natl. Acad. Sci. (USA)* 85: 2444.
(11) Yamauchi et al. (1996) *Plant Mol. Biol.* 30:321-9.
(12) Xu et al. (1995) *Plant Mol. Biol.* 27:237.
(13) Yamamoto et al. (1991) *Plant Cell* 3:371.
(14) P. Tijessen, "Hybridization with Nucleic Acid Probes" In Laboratory Techniques in Biochemistry and Molecular Biology, P. C. vand der Vliet, ed., c. 1993 by Elsevier, Amsterdam.
(15) Bonner et al., (1973) *J. Mol. Biol.* 81:123.
(16) Sambrook et al., Molecular Cloning: A Laboratory Manual, Second Edition, Cold Spring Harbor Laboratory Press, 1989, New York.
(17) Shizuya et al. (1992) *Proc. Natl. Acad. Sci. USA,* 89: 8794-8797.
(18) Hamilton et al. (1996) *Proc. Natl. Acad. Sci USA,* 93: 9975-9979.
(19) Burke et al. (1987) *Science,* 236:806-812.
(20) Sternberg N. et al. (1990) *Proc Natl Acad Sci USA.,* 87:103-7.
(21) Bradshaw et al. (1995) *Nucl Acids Res,* 23: 4850-4856.
(22) Frischauf et al. (1983) *J. Mol Biol,* 170: 827-842.
(23) Huynh et al., Glover N M (ed) DNA Cloning: A practical Approach, Vol. 1 Oxford: IRL Press (1985).
(24) Walden et al. (1990) *Mol Cell Biol* 1: 175-194.
(25) Vissenberg et al. (2005) *Plant Cell Physiol* 46:192.
(26) Husebye et al. (2002) *Plant Physiol* 128:1180.
(27) Plesch et al. (2001) *Plant J* 28:455.
(28) Weising et al. (1988) Ann. Rev. Genet., 22:421.
(29) Christou (1995) *Euphytica, v.* 85, n.1-3:13-27.
(30) Newell (2000)
(31) Griesbach (1987) *Plant Sci.* 50:69-77.
(32) Fromm et al. (1985) *Proc. Natl. Acad. Sci. USA* 82:5824.
(33) Paszkowski et al. (1984) *EMBO J.* 3:2717.
(34) Klein et al. (1987) *Nature* 327:773.
(35) Wilmitzer, L. (1993) Transgenic Plants. In: iotechnology, A Multi-Volume Comprehensive treatise (H. J. Rehm, G. Reed, A. Püler, P. Stadler, eds., Vol. 2, 627-659, VCH Weinheim-New York-Basel-Cambridge).

(36) *Crit. Rev. Plant. Sci.* 4:1-46.
(37) Fromm et al. (1990) *Biotechnology* 8:833-844.
(38) Cho et al. (2000) *Planta* 210:195-204.
(39) Brootghaerts et al. (2005) *Nature* 433:629-633.
(40) Lincoln et al. (1998) *Plant Mol. Biol. Rep.* 16:1-4.
(41) Lacomme et al. (2001), "Genetically Engineered Viruses" (C. J. A. Ring and E. D. Blair, Eds). Pp. 59-99, BIOS Scientific Publishers, Ltd. Oxford, UK.

What is claimed is:

1. A transgenic plant cell transformed with a recombinant DNA construct comprising a polynucleotide sequence which comprises a nucleotide sequence encoding an amino acid sequence that is at least 95% identical to SEQ ID NO: 58, and wherein the nucleotide sequence is operably linked to a promoter, and wherein said plant cell exhibits increased drought tolerance upon overexpression of said polypeptide in said transformed plant cell as compared to a control plant cell of the same species lacking said DNA construct.

2. A transgenic plant cell according to claim 1, wherein said nucleotide sequence encodes the amino acid sequence as set forth in SEQ ID NO: 58.

3. A transformed plant regenerated from the transgenic plant cell of claim 1 or 2, and wherein the regenerated transformed plant has increased drought tolerance as compared to a control plant of the same species lacking said DNA construct.

4. A progeny obtained from the transformed plant of claim 3, and wherein the progeny comprises said DNA construct.

5. A seed obtained from the transformed plant of claim 3, and wherein the seed comprises said DNA construct.

6. A vegetative tissue obtained from the transformed plant of claim 3, and wherein the vegetative tissue comprises said DNA construct.

7. A method for increasing drought tolerance in a plant, said method comprising the steps of:
   (a) transforming plant cells with a recombinant DNA construct comprising a polynucleotide sequence which comprises a nucleotide sequence encoding an amino acid sequence that is at least 95% identical to SEQ ID NO: 58, and wherein the nucleotide sequence is operably linked to a promoter;
   (b) regenerating transgenic plants from said transformed plant cells; and
   (c) selecting a transformed plant from said transgenic plants which exhibits increase in tolerance to drought stress as compared to an untransformed plant of the same species, and wherein said increase in drought tolerance is due to the overexpression of said polypeptide in said selected transformed plant.

8. The method according to claim 7, wherein said nucleotide sequence encodes the amino acid sequence as set forth in SEQ ID NO: 58.

9. The method of claim 7 or 8, wherein said promoter is selected from the group consisting of YP0380 (SEQ ID NO: 163), PT0848 (SEQ ID NO: 119), YP0381 (SEQ ID NO: 164), YP0337 (SEQ ID NO: 159), YP0337 (SEQ ID NO: 159), PT0633 (SEQ ID NO: 100), YP0374 (SEQ ID NO: 161), PT0710 (SEQ ID NO: 111), YP0356 (SEQ ID NO: 160), YP0385 (SEQ ID NO: 166), YP0396 (SEQ ID NO: 167), YP0384 (SEQ ID NO: 165), YP0384 (SEQ ID NO: 165), PT0688 (SEQ ID NO: 108), YP0286 (SEQ ID NO: 158), YP0377 (SEQ ID NO: 162), and PD1367 (SEQ ID NO: 172), a RD29a promoter and a DREB1 promoter.

10. The method of claim 7 or 8, wherein said promoter is selected from the group consisting of p326 (SEQ ID NO: 169), YP0144 (SEQ ID NO: 148), YP0190 (SEQ ID NO: 152), p13879 (SEQ ID NO: 168), YP0050 (SEQ ID NO: 128), p32449 (SEQ ID NO: 170), 21876 (SEQ ID NO: 94), YP0158 (SEQ ID NO: 150), YP0214 (SEQ ID NO: 154), YP0380 (SEQ ID NO: 163), PT0848 (SEQ ID NO: 119), PTO633 (SEQ ID NO: 100), a cauliflower mosaic virus (CaMV) 35S promoter, a mannopine synthase (MAS) promoter, 1' or 2' promoters derived from T-DNA of *Agrobacterium tumefaciens*, a figwort mosaic virus 34S promoter, a rice actin promoter, and a maize ubiquitin-1 promoter.

11. The method of claim 7 or 8, wherein said promoter is selected from the group consisting of ribulose-1,5-bisphosphate carboxylase (RbcS) promoters, a pine cab6 promoter, a Cab-1 gene promoter from wheat, a CAB-1 promoter from spinach, a cab 1R promoter from rice, a pyruvate orthophosphate dikinase (PPDK) promoter from corn, a tobacco Lhcb1*2 promoter, an *Arabidopsis thaliana* SUC2 sucrose-H+symporter promoter, thylakoid membrane protein promoters from spinach, PT0535 (SEQ ID NO: 96), PT0668 (SEQ ID NO: 95), PT0886 (SEQ ID NO: 122), PR0924 (SEQ ID NO: 171), YP0144 (SEQ ID NO: 148), YP0380 (SEQ ID NO: 163) and PT0585 (SEQ ID NO: 97).

12. The method of claim 7 or 8, wherein said promoter is selected from the group consisting of PT0678 (SEQ ID NO: 106), YP0086 (SEQ ID NO: 129), YP0188 (SEQ ID NO: 88), YP0263 (SEQ ID NO: 155), PT0758 (SEQ ID NO: 115), PT0743 (SEQ ID NO: 51), PT0829 (SEQ ID NO: 116), YP0119 (SEQ ID NO: 142), and YP0096 (SEQ ID NO: 132).

13. The method of claim 7 or 8, wherein said promoter is selected from the group consisting of YP0128 (SEQ ID NO: 145), YP0275 (SEQ ID NO: 156), PT0625 (SEQ ID NO: 99), PT0660 (SEQ ID NO: 102), PT0683 (SEQ ID NO: 107), PT0758 (SEQ ID NO: 115), PT0613 (SEQ ID NO: 98), PT0672 (SEQ ID NO: 104), PT0688 (SEQ ID NO: 108) and PT0837 (SEQ ID NO: 117).

* * * * *

SEQUENCE LISTING

```
<160> NUMBER OF SEQ ID NOS: 180

<210> SEQ ID NO 1
<211> LENGTH: 162
<212> TYPE: PRT
<213> ORGANISM: Arabidopsis thaliana
<220> FEATURE:
<221> NAME/KEY: misc_feature
<222> LOCATION: (1)..(162)
<223> OTHER INFORMATION: Ceres CLONE ID no. 3086
<220> FEATURE:
<221> NAME/KEY: misc_feature
<222> LOCATION: (1)..(162)
<223> OTHER INFORMATION: Also Known As Ceres CDNA ID no. 36575759
<220> FEATURE:
<221> NAME/KEY: misc_feature
<222> LOCATION: (1)..(162)
<223> OTHER INFORMATION: Also Known as Lead 68

<400> SEQUENCE: 1

Met Val Arg Lys Gln Phe Gln Gln Ala Lys Thr Gly Ile Glu Ala Leu
1               5                   10                  15

Lys Ser Met Asp Ala Asn Asn Tyr Leu Lys Lys Val Gly Leu Gly Arg
            20                  25                  30

Asp Asp Met Phe Phe Trp Lys Gln Val Gly Lys Ala Leu Leu Cys Thr
        35                  40                  45

Tyr Thr Ile Phe Gly Met Ala Trp Ile Tyr Asn Glu Thr Ser Pro Leu
    50                  55                  60

Gly Trp Trp Thr Leu Lys Pro Arg Pro Lys Glu Glu Arg Glu Leu Ala
65                  70                  75                  80

His Leu Tyr Glu Arg Arg Glu Phe Pro Tyr Pro Gly Asp Thr Glu Ala
                85                  90                  95

Met Glu Asp Phe Val Ala Lys Gly Gly Met Ile Gly Thr Ala Ile Gly
            100                 105                 110

Pro Lys Gly Ile Val Glu Ser Gly Gly Glu Ala Asp Asn Tyr Gln Lys
        115                 120                 125

Glu Met Glu Lys Lys Phe Asp Lys Glu Ala Gln Lys Leu Trp Leu
    130                 135                 140

Arg Met Arg Asn Glu Val Ile Thr Glu Leu Gln Glu Lys Gly His Asn
145                 150                 155                 160

Leu Glu

<210> SEQ ID NO 2
<211> LENGTH: 149
<212> TYPE: PRT
<213> ORGANISM: Oryza sativa subsp. japonica
<220> FEATURE:
<221> NAME/KEY: misc_feature
<222> LOCATION: (1)..(149)
<223> OTHER INFORMATION: Public GI no. 50900870

<400> SEQUENCE: 2

Met Leu Arg Gly Phe Pro Gln Ala Arg Arg Leu Leu Arg Arg Met Gly
1               5                   10                  15

Leu Glu Lys Glu Asp Ala Tyr Phe Trp Lys Gln Met Gly Lys Gly Met
            20                  25                  30
```

```
Leu Cys Thr Tyr Ala Leu Phe Gly Ala Ala Trp Leu Trp Asn Glu Thr
            35                  40                  45

Ser Pro Leu Gly Trp Trp Thr Leu Lys Pro Arg Pro Lys Glu Glu Arg
 50                          55                  60

Glu Met Ala His Leu Tyr Glu Arg Arg Met Phe Pro Tyr Pro Gly Asp
 65                  70                  75                  80

Glu Glu Ala Val Glu Glu Phe Ile Lys Ser Gly Gly Ala Leu Gly Thr
                    85                  90                  95

Thr Ile Gly Pro Lys Gly Phe Ala Asp Ser Asn Met Asp Ser Asp Asn
                100                 105                 110

Met Gln Lys Gln Leu Gln Ser Lys Lys Phe Asp Gln Glu Ala Gln Lys
                115                 120                 125

Leu Trp Phe Arg Met Arg Asn Glu Val Val Gln Glu Leu Gln Glu Lys
                130                 135                 140

Gly Phe Asp Val Glu
145

<210> SEQ ID NO 3
<211> LENGTH: 149
<212> TYPE: PRT
<213> ORGANISM: Zea mays
<220> FEATURE:
<221> NAME/KEY: misc_feature
<222> LOCATION: (1)..(149)
<223> OTHER INFORMATION: Ceres CLONE ID no. 311568

<400> SEQUENCE: 3

Met Leu Arg Asn Phe Pro Gln Ala Arg Arg Leu Leu Arg Arg Met Gly
 1               5                  10                  15

Phe Glu Lys Glu Asp Ala Tyr Phe Trp Lys Gln Met Gly Lys Ala Met
                20                  25                  30

Leu Cys Thr Tyr Thr Leu Phe Gly Val Val Trp Leu Trp Asn Glu Thr
            35                  40                  45

Ser Pro Leu Gly Trp Trp Thr Leu Lys Pro Arg Pro Lys Glu Glu Arg
 50                          55                  60

Glu Met Ala His Leu Tyr Glu Arg Arg Lys Phe Pro Tyr Pro Gly Asp
 65                  70                  75                  80

Asp Glu Ala Val Glu Glu Phe Val Lys Ser Gly Gly Ala Leu Gly Thr
                    85                  90                  95

Thr Ile Gly Pro Arg Gly Phe Ala Asp Ala Asn Met Asp Ser Glu Asn
                100                 105                 110

Met Gln Lys Gln Leu Gln Ser Lys Lys Phe Glu Gln Glu Ala Gln Lys
                115                 120                 125

Leu Trp Ile Arg Met Arg Asn Glu Val Val Gln Glu Leu Gln Glu Lys
                130                 135                 140

Gly Phe Asp Ile Glu
145

<210> SEQ ID NO 4
<211> LENGTH: 149
<212> TYPE: PRT
<213> ORGANISM: Triticum aestivum
<220> FEATURE:
<221> NAME/KEY: misc_feature
<222> LOCATION: (1)..(149)
<223> OTHER INFORMATION: Ceres CLONE ID no. 760406

<400> SEQUENCE: 4

Met Leu Arg Ser Phe Pro Gln Ala Arg Pro Leu Leu Arg Arg Met Gly
 1               5                  10                  15
```

-continued

Phe Asp Lys Arg Asp Ala Tyr Phe Lys Gln Ile Gly Lys Gly Met
            20                  25                  30

Leu Cys Thr Tyr Ala Leu Phe Gly Ala Ala Trp Leu Trp Asn Glu Thr
        35                  40                  45

Ser Pro Leu Gly Trp Trp Thr Leu Lys Pro Leu Pro Lys Glu Glu Lys
50                  55                  60

Glu Met Ala His Leu Tyr Glu Arg Arg Glu Phe Pro Tyr Pro Gly Asp
65                  70                  75                  80

Glu Glu Ala Val Glu Glu Phe Ile Lys Ser Glu Gly Ala Leu Gly Thr
                85                  90                  95

Thr Ile Gly Pro Lys Gly Phe Ala Asp Thr Asn Val Asp Ser Asp Lys
            100                 105                 110

Met Gln Lys Gln Leu Gln Ser Lys Lys Phe Asp Gln Glu Ala Gln Asn
        115                 120                 125

Leu Trp Phe Arg Met Arg Asn Glu Val Ala His Glu Leu Gln Glu Lys
    130                 135                 140

Gly Phe Gly Val Glu
145

<210> SEQ ID NO 5
<211> LENGTH: 162
<212> TYPE: PRT
<213> ORGANISM: Populus balsamifera subsp. trichocarpa
<220> FEATURE:
<221> NAME/KEY: misc_feature
<222> LOCATION: (1)..(162)
<223> OTHER INFORMATION: Ceres GDNA ANNOT ID no. 1461694
<220> FEATURE:
<221> NAME/KEY: misc_feature
<222> LOCATION: (1)..(162)
<223> OTHER INFORMATION: REFERENCED BY SEQ ID NO: 15

<400> SEQUENCE: 5

Met Val Arg Lys Arg Phe Gln Glu Thr Lys Thr Gly Ile Glu Tyr Leu
1               5                   10                  15

Lys Ser Val Asp Tyr Asp Lys Tyr Leu Arg Lys Val Gly Ile Gly Lys
            20                  25                  30

Glu Asp His Tyr Phe Trp Lys Gln Ile Gly Lys Ala Leu Leu Cys Thr
        35                  40                  45

Tyr Thr Leu Ile Gly Val Val Trp Val Tyr Asn Glu Thr Ser Pro Leu
50                  55                  60

Gly Trp Trp Thr Leu Lys Pro Lys Pro Lys Glu Glu Arg Glu Leu Ala
65                  70                  75                  80

His Leu Tyr Glu Arg Arg Glu Phe Pro Tyr Pro Gly Asp Ala Glu Ala
                85                  90                  95

Met Glu Glu Phe Val Ala Lys Gly Gly Met Ile Gly Thr Thr Ile Gly
            100                 105                 110

Pro Lys Gly Thr Val Glu Thr Asp Lys Asp Ser Tyr Asn Tyr Gln Lys
        115                 120                 125

Gln Leu Gln Asp Lys Lys Phe Glu Gln Glu Ala Gln Lys Met Trp Phe
    130                 135                 140

Arg Met Arg Asn Glu Val Ile Gln Glu Leu Gln Glu Lys Gly Tyr Asp
145                 150                 155                 160

Val Glu

<210> SEQ ID NO 6
<211> LENGTH: 801
<212> TYPE: DNA

-continued

<213> ORGANISM: Arabidopsis thaliana
<220> FEATURE:
<221> NAME/KEY: misc_feature
<222> LOCATION: (1)..(801)
<223> OTHER INFORMATION: Ceres CLONE ID no. 3086
<220> FEATURE:
<221> NAME/KEY: misc_feature
<222> LOCATION: (1)..(801)
<223> OTHER INFORMATION: Also Known As Ceres CDNA ID no. 36575759
<220> FEATURE:
<221> NAME/KEY: misc_feature
<222> LOCATION: (1)..(801)
<223> OTHER INFORMATION: Also Known as Lead 68
<220> FEATURE:
<221> NAME/KEY: misc_feature
<222> LOCATION: (82)..(570)
<223> OTHER INFORMATION: CDS - REFERENCED BY SEQ ID NO: 7

<400> SEQUENCE: 6

```
aggctccaat gtcgctggac ttagctcgtt gatcatcgta caaaaagctt gctcgtagct    60
atcagctccc cggagaagaa gatggtgcgg aaacagtttc aacaggctaa aactggaata   120
gaggcattga agtcaatgga tgctaacaac tacttgaaga aggttggatt agggcgtgac   180
gatatgttct tttggaaaca gtgggaaaa gcattgctat gcacttacac aatctttggt   240
atggcttgga tttacaatga aacgtctcct ttaggttggt ggacgctgaa gccaagacca   300
aaggaagaga gagaattggc tcatttgtat gagcggcgtg agtttcctta tcctggtgat   360
acagaggcta tggaggattt tgttgcaaag gggggaatga ttggtactgc aattggaccg   420
aaaggaattg ttgagtccga aggtgaggct gataattacc agaaggaaat ggagaagaag   480
aagtttgata agaggctca gaaactgtgg ttgagaatga ggaatgaggt tattactgaa   540
cttcaagaga aagggcataa tcttgaataa ggaagtgcaa tagggttttg ataaataaaa   600
aagctgtgtg taatttaggg tgtgtatcag ttagactaag gattcaacca ctcgtacaag   660
tgtttctgtc tacgtatagc tgaaagtact atactggttg atgttcttgc tcttggggaa   720
gtagctcttg tcctttattg gtggcttgat tcatgttttg gcttaaaccc tttggaatat   780
aacttgatgc gttttgctcc c                                            801
```

<210> SEQ ID NO 7
<211> LENGTH: 162
<212> TYPE: PRT
<213> ORGANISM: Arabidopsis thaliana
<220> FEATURE:
<221> NAME/KEY: misc_feature
<222> LOCATION: (1)..(162)
<223> OTHER INFORMATION: Ceres CLONE ID no. 3086
<220> FEATURE:
<221> NAME/KEY: misc_feature
<222> LOCATION: (1)..(162)
<223> OTHER INFORMATION: Also Known As Ceres CDNA ID no. 36575759
<220> FEATURE:
<221> NAME/KEY: misc_feature
<222> LOCATION: (1)..(162)
<223> OTHER INFORMATION: Also Known as Lead 68

<400> SEQUENCE: 7

```
Met Val Arg Lys Gln Phe Gln Gln Ala Lys Thr Gly Ile Glu Ala Leu
 1               5                  10                  15

Lys Ser Met Asp Ala Asn Asn Tyr Leu Lys Lys Val Gly Leu Gly Arg
            20                  25                  30

Asp Asp Met Phe Phe Trp Lys Gln Val Gly Lys Ala Leu Leu Cys Thr
        35                  40                  45

Tyr Thr Ile Phe Gly Met Ala Trp Ile Tyr Asn Glu Thr Ser Pro Leu
    50                  55                  60
```

```
Gly Trp Trp Thr Leu Lys Pro Arg Pro Lys Glu Arg Glu Leu Ala
 65                  70                  75                  80

His Leu Tyr Glu Arg Glu Phe Pro Tyr Pro Gly Asp Thr Glu Ala
             85                  90                  95

Met Glu Asp Phe Val Ala Lys Gly Gly Met Ile Gly Thr Ala Ile Gly
            100                 105                 110

Pro Lys Gly Ile Val Glu Ser Glu Gly Glu Ala Asp Asn Tyr Gln Lys
        115                 120                 125

Glu Met Glu Lys Lys Lys Phe Asp Lys Glu Ala Gln Lys Leu Trp Leu
    130                 135                 140

Arg Met Arg Asn Glu Val Ile Thr Glu Leu Gln Glu Lys Gly His Asn
145                 150                 155                 160

Leu Glu

<210> SEQ ID NO 8
<211> LENGTH: 149
<212> TYPE: PRT
<213> ORGANISM: Oryza sativa subsp. japonica
<220> FEATURE:
<221> NAME/KEY: misc_feature
<222> LOCATION: (1)..(149)
<223> OTHER INFORMATION: Public GI no. 50900870

<400> SEQUENCE: 8

Met Leu Arg Gly Phe Pro Gln Ala Arg Arg Leu Leu Arg Met Gly
 1               5                  10                  15

Leu Glu Lys Glu Asp Ala Tyr Phe Trp Lys Gln Met Gly Lys Gly Met
             20                  25                  30

Leu Cys Thr Tyr Ala Leu Phe Gly Ala Ala Trp Leu Trp Asn Glu Thr
        35                  40                  45

Ser Pro Leu Gly Trp Trp Thr Leu Lys Pro Arg Pro Lys Glu Glu Arg
 50                  55                  60

Glu Met Ala His Leu Tyr Glu Arg Arg Met Phe Pro Tyr Pro Gly Asp
 65                  70                  75                  80

Glu Glu Ala Val Glu Glu Phe Ile Lys Ser Gly Gly Ala Leu Gly Thr
             85                  90                  95

Thr Ile Gly Pro Lys Gly Phe Ala Asp Ser Asn Met Asp Ser Asp Asn
            100                 105                 110

Met Gln Lys Gln Leu Gln Ser Lys Phe Asp Gln Ala Gln Lys
        115                 120                 125

Leu Trp Phe Arg Met Arg Asn Glu Val Val Glu Leu Gln Glu Lys
    130                 135                 140

Gly Phe Asp Val Glu
145

<210> SEQ ID NO 9
<211> LENGTH: 128
<212> TYPE: PRT
<213> ORGANISM: Glycine max
<220> FEATURE:
<221> NAME/KEY: misc_feature
<222> LOCATION: (1)..(128)
<223> OTHER INFORMATION: Ceres CLONE ID no. 707476
<220> FEATURE:
<221> NAME/KEY: misc_feature
<222> LOCATION: (98)..(98)
<223> OTHER INFORMATION: Xaa is any aa, unknown, or other

<400> SEQUENCE: 9

Met Pro Arg Lys Arg Phe Gln Glu Pro Gln Pro Lys Thr Gly Leu Gln
 1               5                  10                  15
```

His Thr Gln Asp Phe Leu Arg Lys Ile Gly Leu Gly Lys Glu Asn Tyr
              20                  25                  30

Tyr Phe Trp Lys Gln Ile Gly Lys Ala Leu Leu Cys Thr Tyr Ala Val
          35                  40                  45

Ile Gly Ala Val Trp Val Tyr Asn Glu Thr Ser Pro Leu Gly Trp Trp
 50                  55                  60

Thr Leu Lys Pro Lys Pro Lys Glu Glu Leu Glu Leu Ala His Leu Tyr
 65                  70                  75                  80

Glu Arg Arg Gln Phe Pro Tyr Pro Gly Asp Glu Glu Ala Met Gln Glu
                 85                  90                  95

Phe Xaa Ala Arg Gly Gly Met Ile Gly Thr Thr Ile Gly Pro Lys Gly
            100                 105                 110

Met Val Glu Gly Asp Lys Asp Glu Ser Asp Tyr Lys Lys Glu Leu Lys
            115                 120                 125

<210> SEQ ID NO 10
<211> LENGTH: 149
<212> TYPE: PRT
<213> ORGANISM: Zea mays
<220> FEATURE:
<221> NAME/KEY: misc_feature
<222> LOCATION: (1)..(149)
<223> OTHER INFORMATION: Ceres CLONE ID no. 311568

<400> SEQUENCE: 10

Met Leu Arg Asn Phe Pro Gln Ala Arg Arg Leu Leu Arg Arg Met Gly
 1               5                  10                  15

Phe Glu Lys Glu Asp Ala Tyr Phe Trp Lys Gln Met Gly Lys Ala Met
             20                  25                  30

Leu Cys Thr Tyr Thr Leu Phe Gly Val Val Trp Leu Trp Asn Glu Thr
         35                  40                  45

Ser Pro Leu Gly Trp Trp Thr Leu Lys Pro Arg Pro Lys Glu Glu Arg
 50                  55                  60

Glu Met Ala His Leu Tyr Glu Arg Arg Lys Phe Pro Tyr Pro Gly Asp
 65                  70                  75                  80

Asp Glu Ala Val Glu Glu Phe Val Lys Ser Gly Gly Ala Leu Gly Thr
                 85                  90                  95

Thr Ile Gly Pro Arg Gly Phe Ala Asp Ala Asn Met Ser Glu Asn
            100                 105                 110

Met Gln Lys Gln Leu Gln Ser Lys Lys Phe Glu Gln Glu Ala Gln Lys
            115                 120                 125

Leu Trp Ile Arg Met Arg Asn Glu Val Val Gln Glu Leu Gln Glu Lys
            130                 135                 140

Gly Phe Asp Ile Glu
145

<210> SEQ ID NO 11
<211> LENGTH: 149
<212> TYPE: PRT
<213> ORGANISM: Triticum aestivum
<220> FEATURE:
<221> NAME/KEY: misc_feature
<222> LOCATION: (1)..(149)
<223> OTHER INFORMATION: Ceres CLONE ID no. 760406

<400> SEQUENCE: 11

Met Leu Arg Ser Phe Pro Gln Ala Arg Pro Leu Leu Arg Arg Met Gly
 1               5                  10                  15

Phe Asp Lys Arg Asp Ala Tyr Phe Phe Lys Gln Ile Gly Lys Gly Met

-continued

```
                20                  25                  30
Leu Cys Thr Tyr Ala Leu Phe Gly Ala Ala Trp Leu Trp Asn Glu Thr
         35                  40                  45

Ser Pro Leu Gly Trp Trp Thr Leu Lys Pro Leu Pro Lys Glu Glu Lys
 50                  55                  60

Glu Met Ala His Leu Tyr Glu Arg Arg Glu Phe Pro Tyr Pro Gly Asp
 65                  70                  75                  80

Glu Glu Ala Val Glu Phe Ile Lys Ser Gly Ala Leu Gly Thr
                 85                  90                  95

Thr Ile Gly Pro Lys Gly Phe Asp Thr Asn Val Asp Ser Asp Lys
             100                 105                 110

Met Gln Lys Gln Leu Gln Ser Lys Lys Phe Asp Gln Glu Ala Gln Asn
         115                 120                 125

Leu Trp Phe Arg Met Arg Asn Glu Val Ala His Glu Leu Gln Glu Lys
 130                 135                 140

Gly Phe Gly Val Glu
145
```

<210> SEQ ID NO 12
<211> LENGTH: 46
<212> TYPE: PRT
<213> ORGANISM: Glycine max
<220> FEATURE:
<221> NAME/KEY: misc_feature
<222> LOCATION: (1)..(46)
<223> OTHER INFORMATION: Ceres CLONE ID no. 692689

<400> SEQUENCE: 12

```
Met Gln Glu Phe Ile Ala Arg Gly Gly Met Ile Gly Thr Thr Ile Gly
 1               5                  10                  15

Pro Lys Gly Val Phe Glu Asp Asp Lys Asp Lys Ser Asp Tyr Lys Lys
             20                  25                  30

Glu Leu Lys Asp Lys Lys Phe Gly Gln Glu Ala Gln Lys Leu
         35                  40                  45
```

<210> SEQ ID NO 13
<211> LENGTH: 48
<212> TYPE: PRT
<213> ORGANISM: Triticum aestivum
<220> FEATURE:
<221> NAME/KEY: misc_feature
<222> LOCATION: (1)..(48)
<223> OTHER INFORMATION: Ceres CLONE ID no. 747294

<400> SEQUENCE: 13

```
Met Leu Arg Ser Phe Pro Gln Ala Arg Arg Leu Leu Lys Arg Leu Gly
 1               5                  10                  15

Phe Glu Lys Gly Asp Ala Tyr Phe Phe Lys Gln Met Gly Lys Gly Met
             20                  25                  30

Leu Cys Thr Tyr Ala Leu Phe Gly Ala Ala Trp Phe Trp Asn Glu Thr
         35                  40                  45
```

<210> SEQ ID NO 14
<211> LENGTH: 489
<212> TYPE: DNA
<213> ORGANISM: Populus balsamifera subsp. trichocarpa
<220> FEATURE:
<221> NAME/KEY: misc_feature
<222> LOCATION: (1)..(489)
<223> OTHER INFORMATION: Ceres GDNA ANNOT ID no. 1461694
<220> FEATURE:
<221> NAME/KEY: misc_feature
<222> LOCATION: (1)..(489)

<223> OTHER INFORMATION: CDS - Referenced by SEQ ID NO: 15

<400> SEQUENCE: 14

```
atggttcgca aacgttttca agagaccaaa acaggtattg aatatctgaa atcagtggat      60
tacgataagt atctgaggaa agtaggaata ggaaaagaag accattactt ctggaagcaa     120
ataggcaagg cgcttctctg cacatacact ctcatcggtg ttgtgtgggt ttacaacgaa     180
acatcaccac ttggttggtg gacactgaaa ccaaaaccaa aggaggaaag agagcttgcc     240
catttgtatg agaggcgaga atttccatat ccaggcgatg cagaagcaat ggaagagttt     300
gttgcgaagg gaggaatgat tggcacgaca attgggccga agggaccgt ggagactgat      360
aaggattcgt ataattatca gaaacagttg caggataaga agtttgagca agaagcacag     420
aagatgtggt ttaggatgag gaatgaggtt attcaggagc ttcaagagaa agggtatgat     480
gttgagtga                                                             489
```

<210> SEQ ID NO 15
<211> LENGTH: 162
<212> TYPE: PRT
<213> ORGANISM: Populus balsamifera subsp. trichocarpa
<220> FEATURE:
<221> NAME/KEY: misc_feature
<222> LOCATION: (1)..(162)
<223> OTHER INFORMATION: Ceres GDNA ANNOT ID no. 1461694

<400> SEQUENCE: 15

Met Val Arg Lys Arg Phe Gln Glu Thr Lys Thr Gly Ile Glu Tyr Leu
1               5                   10                  15

Lys Ser Val Asp Tyr Asp Lys Tyr Leu Arg Lys Val Gly Ile Gly Lys
            20                  25                  30

Glu Asp His Tyr Phe Trp Lys Gln Ile Gly Lys Ala Leu Leu Cys Thr
        35                  40                  45

Tyr Thr Leu Ile Gly Val Val Trp Val Tyr Asn Glu Thr Ser Pro Leu
    50                  55                  60

Gly Trp Trp Thr Leu Lys Pro Lys Pro Lys Glu Glu Arg Glu Leu Ala
65                  70                  75                  80

His Leu Tyr Glu Arg Arg Glu Phe Pro Tyr Pro Gly Asp Ala Glu Ala
                85                  90                  95

Met Glu Glu Phe Val Ala Lys Gly Gly Met Ile Gly Thr Thr Ile Gly
            100                 105                 110

Pro Lys Gly Thr Val Glu Thr Asp Lys Asp Ser Tyr Asn Tyr Gln Lys
        115                 120                 125

Gln Leu Gln Asp Lys Lys Phe Glu Gln Glu Ala Gln Lys Met Trp Phe
    130                 135                 140

Arg Met Arg Asn Glu Val Ile Gln Glu Leu Gln Glu Lys Gly Tyr Asp
145                 150                 155                 160

Val Glu

<210> SEQ ID NO 16
<211> LENGTH: 57
<212> TYPE: PRT
<213> ORGANISM: Populus balsamifera subsp. trichocarpa
<220> FEATURE:
<221> NAME/KEY: misc_feature
<222> LOCATION: (1)..(57)
<223> OTHER INFORMATION: Ceres GDNA ANNOT ID no. 1492703

<400> SEQUENCE: 16

Met Ile Gly Thr Thr Ile Gly Pro Lys Gly Thr Val Glu Asn Asp Lys
1               5                   10                  15

```
Asp Ser Tyr Asn Tyr Gln Lys Gln Leu Gln Asp Lys Lys Phe Asp Gln
         20                  25                  30

Glu Ala Gln Lys Leu Trp Phe Arg Met Arg Asn Glu Val Ile Gln Glu
     35                  40                  45

Leu Gln Glu Lys Gly Cys Gly Val Glu
 50                  55
```

```
<210> SEQ ID NO 17
<211> LENGTH: 201
<212> TYPE: DNA
<213> ORGANISM: Populus balsamifera subsp. trichocarpa
<220> FEATURE:
<221> NAME/KEY: misc_feature
<222> LOCATION: (1)..(201)
<223> OTHER INFORMATION: Ceres GDNA ANNOT ID no. 1492703
<220> FEATURE:
<221> NAME/KEY: misc_feature
<222> LOCATION: (1)..(201)
<223> OTHER INFORMATION: CDS - Referenced by SEQ ID NO: 16

<400> SEQUENCE: 17
atggaagagt tgttgcaagg gggaggaatg attggcacga caattgggcc gaaagggact      60
gtggagaatg ataaagattc ttataattat cagaaacagt tgcaggataa aaagtttgat     120
caagaagcac agaaactgtg gtttaggatg aggaatgagg ttattcagga gcttcaagag     180
aaagggtgtg gtgttgagtg a                                               201
```

```
<210> SEQ ID NO 18
<211> LENGTH: 97
<212> TYPE: PRT
<213> ORGANISM: Arabidopsis thaliana
<220> FEATURE:
<221> NAME/KEY: misc_feature
<222> LOCATION: (1)..(97)
<223> OTHER INFORMATION: Ceres CLONE ID no. 16209_T
<220> FEATURE:
<221> NAME/KEY: misc_feature
<222> LOCATION: (1)..(97)
<223> OTHER INFORMATION: Also Known As Ceres CDNA ID no. 23462374_T
<220> FEATURE:
<221> NAME/KEY: misc_feature
<222> LOCATION: (1)..(97)
<223> OTHER INFORMATION: Also Known as Lead 69
<220> FEATURE:
<221> NAME/KEY: misc_feature
<222> LOCATION: (4)..(77)
<223> OTHER INFORMATION: Pfam Name: MBD; Pfam Description: Methyl-CpG
      binding domain

<400> SEQUENCE: 18

Met Glu Asn Thr Asp Glu Leu Val Ser Ile Glu Leu Pro Ala Pro Ala
1               5                   10                  15

Ser Trp Lys Lys Leu Phe Tyr Pro Lys Arg Ala Gly Thr Pro Arg Lys
             20                  25                  30

Thr Glu Ile Val Phe Val Ala Pro Thr Gly Glu Glu Ile Ser Ser Arg
         35                  40                  45

Lys Gln Leu Glu Gln Tyr Leu Lys Ala His Pro Gly Asn Pro Val Ile
     50                  55                  60

Ser Glu Phe Glu Trp Thr Thr Gly Glu Thr Pro Arg Arg Ser Ser Arg
65                  70                  75                  80

Ile Ser Gln Lys Val Arg Leu Gln Arg Leu Leu Thr Lys Ser Pro
                 85                  90                  95

Ser
```

```
<210> SEQ ID NO 19
<211> LENGTH: 96
<212> TYPE: PRT
<213> ORGANISM: Artificial Sequence
<220> FEATURE:
<223> OTHER INFORMATION: Synthetic peptide: Ceres CLONE ID no. 107012_T
<220> FEATURE:
<221> NAME/KEY: misc_feature
<222> LOCATION: (66)..(66)
<223> OTHER INFORMATION: Xaa is any aa, unknown, or other

<400> SEQUENCE: 19

Met Glu Asn Thr Asp Glu Leu Val Ser Ile Glu Leu Pro Ala Pro Ala
1               5                   10                  15

Ser Trp Lys Lys Leu Phe Tyr Pro Lys Arg Ala Gly Thr Pro Arg Lys
            20                  25                  30

Thr Glu Ile Val Phe Val Ala Pro Thr Gly Glu Glu Ile Ser Ser Arg
        35                  40                  45

Lys Gln Leu Glu Gln Tyr Leu Lys Ala His Pro Gly Asn Pro Val Ile
    50                  55                  60

Ser Xaa Phe Glu Trp Thr Thr Gly Glu Thr Pro Arg Arg Ser Ser Arg
65                  70                  75                  80

Ile Ser Gln Lys Val Lys Ala Thr Thr Pro Thr Pro Asp Lys Glu Pro
                85                  90                  95

<210> SEQ ID NO 20
<211> LENGTH: 97
<212> TYPE: PRT
<213> ORGANISM: Artificial Sequence
<220> FEATURE:
<223> OTHER INFORMATION: Synthetic peptide: Ceres CLONE ID no. 479015_T

<400> SEQUENCE: 20

Met Met Gln Gln Asn Asp Glu Val Leu Ser Val Glu Leu Pro Ala Pro
1               5                   10                  15

Ser Gly Trp Asn Lys Leu Phe Phe Pro Lys Lys Leu Gly Thr Pro Arg
            20                  25                  30

Lys Ser Glu Ile Val Phe Ile Ala Pro Thr Gly Glu Glu Ile Ser Thr
        35                  40                  45

Lys Lys Gln Leu Glu Gln Tyr Leu Lys Ala His Pro Gly Asn Pro Val
    50                  55                  60

Ile Ser Glu Phe Asp Trp Gly Thr Gly Glu Thr Pro Arg Arg Ser Ala
65                  70                  75                  80

Arg Ile Ser Glu Lys Val Lys Ser Thr Pro Pro Ala Asp Ser Asp Thr
                85                  90                  95

Pro

<210> SEQ ID NO 21
<211> LENGTH: 96
<212> TYPE: PRT
<213> ORGANISM: Arabidopsis thaliana
<220> FEATURE:
<221> NAME/KEY: misc_feature
<222> LOCATION: (1)..(96)
<223> OTHER INFORMATION: Public GI no. 50253442_T

<400> SEQUENCE: 21

Met Gly Gly Glu Glu Glu Val Ser Val Glu Leu Pro Ala Pro Ser
1               5                   10                  15

Ser Trp Lys Lys Leu Phe Tyr Pro Asn Lys Val Gly Ser Val Lys Lys
            20                  25                  30

Thr Glu Val Val Phe Val Ala Pro Thr Gly Glu Glu Ile Ser Asn Arg
```

```
                       35                  40                  45
Lys Gln Leu Glu Gln Tyr Leu Lys Ser His Pro Gly Asn Pro Ala Ile
 50                  55                  60

Ala Glu Phe Asp Trp Thr Thr Ser Gly Thr Pro Arg Arg Ser Ala Arg
 65                  70                  75                  80

Ile Ser Glu Lys Thr Lys Ala Thr Pro Ser Pro Asp Lys Glu Pro Pro
                 85                  90                  95

<210> SEQ ID NO 22
<211> LENGTH: 99
<212> TYPE: PRT
<213> ORGANISM: Artificial Sequence
<220> FEATURE:
<223> OTHER INFORMATION: Synthetic peptide: Ceres CLONE ID no. 1104524_T

<400> SEQUENCE: 22

Met Gly Thr Glu Glu Glu Ser Val Pro Val Glu Leu Pro Ala Pro Ser
 1               5                  10                  15

Ser Trp Lys Lys Leu Phe Phe Pro Asn Lys Val Gly Ser Val Lys Lys
                 20                  25                  30

Thr Glu Ile Val Phe Val Ala Pro Thr Gly Glu Glu Ile Ser Asn Arg
             35                  40                  45

Lys Gln Leu Asp Gln Tyr Leu Lys Ser His Pro Gly Asn Pro Ser Ile
 50                  55                  60

Thr Glu Phe Asp Trp Thr Thr Ser Gly Thr Pro Arg Arg Ser Ala Arg
 65                  70                  75                  80

Ile Ser Asp Lys Lys Thr Lys Ser Thr Pro Ser Pro Asp Lys Glu Pro
                 85                  90                  95

Pro Lys Lys

<210> SEQ ID NO 23
<211> LENGTH: 104
<212> TYPE: PRT
<213> ORGANISM: Artificial Sequence
<220> FEATURE:
<223> OTHER INFORMATION: Synthetic peptide: Ceres CLONE ID no. 464291_T

<400> SEQUENCE: 23

Met Ala Ser Ala Val Glu Lys Glu Gly Gly Ala Ser Glu Glu Thr Leu
 1               5                  10                  15

Ser Leu Glu Leu Pro Ala Pro Pro Gly Trp Lys Lys Gln Phe Ile Pro
                 20                  25                  30

Lys Lys Ala Gly Thr Pro Lys Lys Asn Glu Ile Val Phe Thr Ala Pro
             35                  40                  45

Thr Gly Glu Glu Ile Asn Asn Arg Lys Gln Leu Glu Lys Tyr Leu Lys
 50                  55                  60

Ala His Pro Gly Gly Pro Ala Val Ser Glu Phe Asp Trp Gly Thr Gly
 65                  70                  75                  80

Glu Thr Pro Arg Arg Ser Thr Arg Ile Ser Glu Lys Ala Lys Ala Ala
                 85                  90                  95

Pro Pro Thr Gln Arg Glu Pro Pro
            100

<210> SEQ ID NO 24
<211> LENGTH: 103
<212> TYPE: PRT
<213> ORGANISM: Artificial Sequence
<220> FEATURE:
<223> OTHER INFORMATION: Synthetic peptide: Ceres CLONE ID no. 905085_T
```

-continued

```
<400> SEQUENCE: 24

Met Ala Thr Gly Gly Asp His Ala Ala Glu Glu Leu Val Ser Val Glu
1               5                   10                  15

Met Pro Ala Pro Glu Gly Trp Thr Lys Lys Phe Thr Pro Gln Ser Arg
            20                  25                  30

Gly Arg Ser Glu Ile Val Phe Val Ser Pro Thr Gly Glu Glu Ile Lys
        35                  40                  45

Asn Lys Arg Gln Leu Asn Ser Tyr Leu Lys Ala Asn Pro Gly Gly Pro
    50                  55                  60

Thr Ser Ser Glu Phe Asp Trp Ser Thr Gly Asp Thr Pro Arg Arg Ser
65              70                  75                  80

Ala Arg Ile Ser Glu Lys Val Lys Val Phe Asp Ser Pro Gln Gly Glu
                85                  90                  95

Lys Ile Pro Lys Arg Ser Arg
            100

<210> SEQ ID NO 25
<211> LENGTH: 1435
<212> TYPE: DNA
<213> ORGANISM: Arabidopsis thalia
<220> FEATURE:
<221> NAME/KEY: misc_feature
<222> LOCATION: (1)..(1435)
<223> OTHER INFORMATION: Ceres CLONE ID no. 16209
<220> FEATURE:
<221> NAME/KEY: misc_feature
<222> LOCATION: (1)..(1435)
<223> OTHER INFORMATION: Also Known As Ceres CDNA ID no. 23462374
<220> FEATURE:
<221> NAME/KEY: misc_feature
<222> LOCATION: (1)..(1435)
<223> OTHER INFORMATION: Also Known as Lead 69
<220> FEATURE:
<221> NAME/KEY: misc_feature
<222> LOCATION: (523)..(1302)
<223> OTHER INFORMATION: CDS - Referenced by SEQ ID NO: 26

<400> SEQUENCE: 25
acgcaaacat atccattagg gtcacaacgg ttcttacagc ttctattacc agaaaggaaa      60
gaaagccgaa atttgtttca agataaagta atttaagttg gagcttgttt cttggtcgta     120
cagtgtcagg tgaatagaga agaagaagat ggaaaacaca gacgagcttg tctccattga     180
gctaccagct ccagcttcat ggaagaaact gttttatccg aaaagagccg gtactccgag     240
aaagacggag attgtgtttg tggctccaac gggtgaagag attagctcgc ggaagcagtt     300
ggagcagtac ctgaaggccc atcctggcaa tcctgtcatc tctgagtttg agtggacaac     360
tggggaaact ccaaggaggt cttcaaggat cagccaaaag gtaaggctac aacgcctact     420
cctgacaaag agcccctcct gaagaagaga cgatcttctc tcacgaagaa ggacaataag     480
gaggctgctg agaaaaatga agaggctgct gtgaaggaga acatggatgt tgataaggat     540
gggaagacgg aaaacgcaga ggctgagaag gagaaagaga aggagggagt gacagaaatt     600
gcagaggcgg agaaggagaa caacgagggt gagaagactg aggctgagaa ggtgaacaaa     660
gagggtgaga aaactgaggc tgggaaggag ggtcaaacgg aaattgcaga ggctgagaag     720
gagaaggagg gtgaaaaggc tgaggctgag aacaaagagg cagaagttgt gagagacaag     780
aaagagtcca tggaagtgga tacctctgag ttggagaaga aggctgggag tggagaagga     840
gctgaagaac cttccaaagt tgaaggcctc aaggacactg aaatgaaaga ggcgcaggaa     900
gttgttactg aggctgatgt agagaagaag cctgcagagg aaaagactga gaacaagggc     960
agcgtgacaa ccgaagctaa cggagaacag aatgtaaccc tgggtgagcc taaccttgat    1020
```

-continued

```
gcagatgctg aagcagataa gggaaaagaa tccaaagaat atgatgagaa gacgacagaa    1080
gctgaggcga ataaggaaaa tgacactcaa gaatctgatg agaagaagac agaagctgca    1140
gcaaataagg agaacgaaac ccaagagtct gatgtcaaga agaccgaagc tgcagtagca    1200
gaggagaaga gtaacgacat gaaggcagaa gacacaaaca gaagcttgga ggcgaatcaa    1260
gttcaacagc agcagggagc tgcagcttcc gtgagctgtt aaaacctata tcgttctgta    1320
cagagcacag agcgtgaaga gtttgttgtg atttcaggtg tagcattaac attatgagtg    1380
gttgttgtat gtgttggtag aactaatgtc tctctatgtt gtagttcagt ccatt         1435
```

<210> SEQ ID NO 26
<211> LENGTH: 97
<212> TYPE: PRT
<213> ORGANISM: Arabidopsis thalia
<220> FEATURE:
<221> NAME/KEY: misc_feature
<222> LOCATION: (1)..(97)
<223> OTHER INFORMATION: Ceres CLONE ID no. 16209
<220> FEATURE:
<221> NAME/KEY: misc_feature
<222> LOCATION: (1)..(97)
<223> OTHER INFORMATION: Also Known As Ceres CDNA ID no. 23462374
<220> FEATURE:
<221> NAME/KEY: misc_feature
<222> LOCATION: (1)..(162)
<223> OTHER INFORMATION: Also Known as Lead 69
<220> FEATURE:
<221> NAME/KEY: misc_feature
<222> LOCATION: (4)..(77)
<223> OTHER INFORMATION: Pfam Name: MBD; Pfam Description: Methyl-CpG
      binding domain

<400> SEQUENCE: 26

Met Glu Asn Thr Asp Glu Leu Val Ser Ile Glu Leu Pro Ala Pro Ala
1               5                   10                  15

Ser Trp Lys Lys Leu Phe Tyr Pro Lys Arg Ala Gly Thr Pro Arg Lys
            20                  25                  30

Thr Glu Ile Val Phe Val Ala Pro Thr Gly Glu Glu Ile Ser Ser Arg
        35                  40                  45

Lys Gln Leu Glu Gln Tyr Leu Lys Ala His Pro Gly Asn Pro Val Ile
    50                  55                  60

Ser Glu Phe Glu Trp Thr Thr Gly Glu Thr Pro Arg Arg Ser Ser Arg
65                  70                  75                  80

Ile Ser Gln Lys Val Arg Leu Gln Arg Leu Leu Leu Thr Lys Ser Pro
                85                  90                  95

Ser

<210> SEQ ID NO 27
<211> LENGTH: 346
<212> TYPE: PRT
<213> ORGANISM: Arabidopsis thaliana
<220> FEATURE:
<221> NAME/KEY: misc_feature
<222> LOCATION: (1)..(346)
<223> OTHER INFORMATION: Public GI no. 24417370

<400> SEQUENCE: 27

Met Glu Asn Thr Asp Glu Leu Val Ser Ile Glu Leu Pro Ala Pro Ala
1               5                   10                  15

Ser Trp Lys Lys Leu Phe Tyr Pro Lys Arg Ala Gly Thr Pro Arg Lys
            20                  25                  30

Thr Glu Ile Val Phe Val Ala Pro Thr Gly Glu Glu Ile Ser Ser Arg
        35                  40                  45

-continued

```
Lys Gln Leu Glu Gln Tyr Leu Lys Ala His Pro Gly Asn Pro Val Ile
         50                  55                  60

Ser Glu Phe Glu Trp Thr Thr Gly Glu Thr Pro Arg Arg Ser Ser Arg
 65                  70                  75                  80

Ile Ser Gln Lys Val Lys Ala Thr Pro Asp Lys Glu Pro Leu Leu Lys
                 85                  90                  95

Lys Arg Arg Ser Ser Leu Thr Lys Asp Asn Lys Glu Ala Ala Glu
            100                 105                 110

Lys Asn Glu Glu Ala Ala Val Lys Glu Asn Met Asp Val Asp Lys Asp
            115                 120                 125

Gly Lys Thr Glu Asn Ala Glu Ala Glu Lys Glu Lys Glu Lys Glu Gly
        130                 135                 140

Val Thr Glu Ile Ala Glu Ala Glu Lys Glu Asn Asn Glu Gly Glu Lys
145                 150                 155                 160

Thr Glu Ala Glu Lys Val Asn Lys Glu Gly Glu Lys Thr Glu Ala Gly
                165                 170                 175

Lys Glu Gly Gln Thr Glu Ile Ala Ala Glu Lys Glu Lys Glu Gly
            180                 185                 190

Glu Lys Ala Glu Ala Glu Asn Lys Glu Ala Glu Val Val Arg Asp Lys
            195                 200                 205

Lys Glu Ser Met Glu Val Asp Thr Ser Glu Leu Glu Lys Lys Ala Gly
210                 215                 220

Ser Gly Glu Gly Ala Glu Glu Pro Ser Lys Val Glu Gly Leu Lys Asp
225                 230                 235                 240

Thr Glu Met Lys Glu Ala Gln Glu Val Val Thr Glu Ala Asp Val Glu
                245                 250                 255

Lys Lys Pro Ala Glu Glu Lys Thr Glu Asn Lys Gly Ser Val Thr Thr
            260                 265                 270

Glu Ala Asn Gly Glu Gln Asn Val Thr Leu Gly Glu Pro Asn Leu Asp
        275                 280                 285

Ser Asp Ala Glu Gln Ile Arg Glu Lys Asn Pro Lys Asn Met Met Arg
290                 295                 300

Arg Arg Gln Lys Leu Arg Arg Ile Arg Lys Met Thr Leu Lys Asn Leu
305                 310                 315                 320

Met Arg Arg Arg Gln Lys Leu Gln Gln Ile Arg Arg Thr Lys Pro Lys
                325                 330                 335

Ser Leu Met Ser Arg Arg Pro Lys Leu Gln
            340                 345

<210> SEQ ID NO 28
<211> LENGTH: 384
<212> TYPE: PRT
<213> ORGANISM: Arabidopsis thaliana
<220> FEATURE:
<221> NAME/KEY: misc_feature
<222> LOCATION: (1)..(384)
<223> OTHER INFORMATION: Ceres CLONE ID no. 107012
<220> FEATURE:
<221> NAME/KEY: misc_feature
<222> LOCATION: (66)..(66)
<223> OTHER INFORMATION: Xaa is any aa, unknown, or other
<220> FEATURE:
<221> NAME/KEY: misc_feature
<222> LOCATION: (220)..(220)
<223> OTHER INFORMATION: Xaa is any aa, unknown, or other
<220> FEATURE:
<221> NAME/KEY: misc_feature
<222> LOCATION: (293)..(293)
<223> OTHER INFORMATION: Xaa is any aa, unknown, or other
<220> FEATURE:
```

<221> NAME/KEY: misc_feature
<222> LOCATION: (320)..(320)
<223> OTHER INFORMATION: Xaa is any aa, unknown, or other
<220> FEATURE:
<221> NAME/KEY: misc_feature
<222> LOCATION: (322)..(322)
<223> OTHER INFORMATION: Xaa is any aa, unknown, or other

<400> SEQUENCE: 28

```
Met Glu Asn Thr Asp Glu Leu Val Ser Ile Glu Leu Pro Ala Pro Ala
1               5                   10                  15

Ser Trp Lys Lys Leu Phe Tyr Pro Lys Arg Ala Gly Thr Pro Arg Lys
                20                  25                  30

Thr Glu Ile Val Phe Val Ala Pro Thr Gly Glu Glu Ile Ser Ser Arg
            35                  40                  45

Lys Gln Leu Glu Gln Tyr Leu Lys Ala His Pro Gly Asn Pro Val Ile
    50                  55                  60

Ser Xaa Phe Glu Trp Thr Thr Gly Glu Thr Pro Arg Arg Ser Ser Arg
65                  70                  75                  80

Ile Ser Gln Lys Val Lys Ala Thr Thr Pro Thr Pro Asp Lys Glu Pro
                85                  90                  95

Leu Leu Lys Lys Arg Arg Ser Ser Leu Thr Lys Lys Asp Asn Lys Glu
            100                 105                 110

Ala Ala Glu Lys Asn Glu Glu Ala Ala Val Lys Glu Asn Met Asp Val
        115                 120                 125

Asp Lys Asp Gly Lys Thr Glu Asn Ala Glu Ala Glu Lys Glu Lys Glu
    130                 135                 140

Lys Glu Gly Val Thr Glu Ile Ala Glu Ala Glu Lys Glu Asn Asn Glu
145                 150                 155                 160

Gly Glu Lys Thr Glu Ala Glu Lys Val Asn Lys Glu Gly Glu Lys Thr
                165                 170                 175

Glu Ala Gly Lys Glu Gly Gln Thr Glu Ile Ala Glu Ala Glu Lys Glu
            180                 185                 190

Lys Glu Gly Glu Lys Ala Glu Ala Glu Asn Lys Glu Ala Glu Val Val
        195                 200                 205

Arg Asp Lys Lys Glu Ser Met Glu Val Asp Thr Xaa Glu Leu Glu Lys
    210                 215                 220

Lys Ala Gly Ser Gly Glu Gly Ala Glu Glu Pro Ser Lys Val Glu Gly
225                 230                 235                 240

Leu Lys Asp Thr Glu Met Lys Glu Ala Gln Glu Val Val Thr Glu Ala
                245                 250                 255

Asp Val Glu Lys Lys Pro Ala Glu Glu Lys Thr Glu Asn Lys Gly Ser
            260                 265                 270

Val Thr Thr Glu Ala Asn Gly Gln Asn Val Thr Leu Gly Glu Pro
    275                 280                 285

Asn Leu Asp Ala Xaa Ala Glu Ala Asp Lys Gly Lys Glu Ser Lys Glu
290                 295                 300

Tyr Asp Glu Lys Thr Thr Glu Ala Glu Ala Asn Lys Glu Asn Asp Xaa
305                 310                 315                 320

Gln Xaa Ser Asp Glu Lys Lys Thr Glu Ala Ala Asn Lys Glu Asn
                325                 330                 335

Glu Thr Gln Glu Ser Asp Val Lys Lys Thr Glu Ala Ala Val Ala Glu
            340                 345                 350

Glu Lys Ser Asn Asp Met Lys Ala Glu Asp Thr Asn Arg Ser Leu Glu
        355                 360                 365

Ala Asn Gln Val Gln Gln Gln Gly Ala Ala Ala Ser Val Ser Cys
```

-continued

<210> SEQ ID NO 29
<211> LENGTH: 269
<212> TYPE: PRT
<213> ORGANISM: Glycine max
<220> FEATURE:
<221> NAME/KEY: misc_feature
<222> LOCATION: (1)..(269)
<223> OTHER INFORMATION: Ceres CLONE ID no. 479015

<400> SEQUENCE: 29

Met Met Gln Gln Asn Asp Glu Val Leu Ser Val Glu Leu Pro Ala Pro
1               5                   10                  15

Ser Gly Trp Asn Lys Leu Phe Phe Pro Lys Lys Leu Gly Thr Pro Arg
            20                  25                  30

Lys Ser Glu Ile Val Phe Ile Ala Pro Thr Gly Glu Ile Ser Thr
        35                  40                  45

Lys Lys Gln Leu Glu Gln Tyr Leu Lys Ala His Pro Gly Asn Pro Val
    50                  55                  60

Ile Ser Glu Phe Asp Trp Gly Thr Gly Glu Thr Pro Arg Arg Ser Ala
65                  70                  75                  80

Arg Ile Ser Glu Lys Val Lys Ser Thr Pro Pro Ala Asp Ser Asp Thr
                85                  90                  95

Pro Lys Lys Arg Ala Arg Lys Ser Ser Gly Ser Lys Lys Asp Asn Lys
            100                 105                 110

Glu Thr Glu Ser Ala Ser Glu Glu Gly Lys Ala Lys Ser Asp Thr Glu
        115                 120                 125

Asp Pro Lys Ala Ala Glu Glu Glu Lys Asn Glu Gly Asn Asp Asn Ser
    130                 135                 140

Asn Ser Gly Gly Lys Gln Leu Glu Asn Gly Asp Lys Thr Glu Gln Ile
145                 150                 155                 160

Asp Glu Gln Ala Lys Lys Pro Asp Val Asp Met Glu Glu Asn Asp Leu
                165                 170                 175

Asn Asp Thr Asn Asn Lys Leu Glu Asn Asp Ser Asp Glu Ile Lys Asn
            180                 185                 190

Ser His Val Asn Gly Glu Asn Val Ile Ala Glu Arg Pro Glu Gly Glu
        195                 200                 205

Glu Ala Gln Lys Gln Val Glu Pro Ala Glu Lys Val Ala Glu Glu
    210                 215                 220

Ala Ala Asn Thr Ala Glu Thr Glu Lys Ser Leu Leu Thr Glu Leu Glu
225                 230                 235                 240

Lys Glu Lys Asn Glu Glu Lys Thr Asp Thr Ala Thr Leu Glu Ala Asn
                245                 250                 255

Gly Gly Gly Glu Lys Glu Asn Pro Asn Ala Ala Gln Met
            260                 265

<210> SEQ ID NO 30
<211> LENGTH: 254
<212> TYPE: PRT
<213> ORGANISM: Arabidopsis thaliana
<220> FEATURE:
<221> NAME/KEY: misc_feature
<222> LOCATION: (1)..(254)
<223> OTHER INFORMATION: Public GI no. 50253442

<400> SEQUENCE: 30

Met Gly Gly Glu Glu Val Val Ser Val Glu Leu Pro Ala Pro Ser
1               5                   10                  15

```
Ser Trp Lys Lys Leu Phe Tyr Pro Asn Lys Val Gly Ser Val Lys Lys
         20                  25                  30

Thr Glu Val Val Phe Val Ala Pro Thr Gly Glu Glu Ile Ser Asn Arg
             35                  40                  45

Lys Gln Leu Glu Gln Tyr Leu Lys Ser His Pro Gly Asn Pro Ala Ile
 50                  55                  60

Ala Glu Phe Asp Trp Thr Thr Ser Gly Thr Pro Arg Arg Ser Ala Arg
 65                  70                  75                  80

Ile Ser Glu Lys Thr Lys Ala Thr Pro Ser Pro Asp Lys Glu Pro Pro
             85                  90                  95

Lys Lys Arg Gly Arg Thr Lys Ser Pro Val Ser Lys Lys Asp Ala Glu
            100                 105                 110

Gly Glu Lys Ser Glu Gly Gly Glu Glu Asn Ser His Val Lys Asp
            115                 120                 125

Thr Glu Met Asn Pro Pro Glu Gly Ile Ala Glu Asn Glu Asn Val Thr
            130                 135                 140

Asp Lys Asn Gly Ser Gly Glu Thr Glu Arg Val Asn Asp Ala Lys Glu
145                 150                 155                 160

Asn Ile Val Ala Glu Glu Thr Pro Asn Ala Ala Pro Val Gln Glu Glu
                165                 170                 175

Gly Glu Ser Met Lys Glu Lys Ala Leu Asp Ser Val Asp Asp Lys Ser
            180                 185                 190

Lys Glu Thr Asp Lys Glu Lys Asp Thr Gly Ser Ile Glu Lys Asn Ser
            195                 200                 205

Val Asp Val Glu Lys Lys Thr Val Glu Ala Ser Asp Glu Lys Lys Asn
            210                 215                 220

Ser Glu Ala Glu Thr Arg Asn His Glu Glu Asn Gly Leu Thr Thr Glu
225                 230                 235                 240

Ala Glu Gly Lys Glu Lys Thr Ala Glu Gly Glu Ala Thr Gly
                245                 250

<210> SEQ ID NO 31
<211> LENGTH: 99
<212> TYPE: PRT
<213> ORGANISM: Brassica napus
<220> FEATURE:
<221> NAME/KEY: misc_feature
<222> LOCATION: (1)..(99)
<223> OTHER INFORMATION: Ceres CLONE ID no. 1104524

<400> SEQUENCE: 31

Met Gly Thr Glu Glu Ser Val Pro Val Glu Leu Pro Ala Pro Ser
1               5                   10                  15

Ser Trp Lys Lys Leu Phe Phe Pro Asn Lys Val Gly Ser Val Lys Lys
         20                  25                  30

Thr Glu Ile Val Phe Val Ala Pro Thr Gly Glu Glu Ile Ser Asn Arg
             35                  40                  45

Lys Gln Leu Asp Gln Tyr Leu Lys Ser His Pro Gly Asn Pro Ser Ile
 50                  55                  60

Thr Glu Phe Asp Trp Thr Thr Ser Gly Thr Pro Arg Arg Ser Ala Arg
 65                  70                  75                  80

Ile Ser Asp Lys Lys Thr Lys Ser Thr Pro Ser Pro Asp Lys Glu Pro
             85                  90                  95

Pro Lys Lys

<210> SEQ ID NO 32
<211> LENGTH: 305
```

```
<212> TYPE: PRT
<213> ORGANISM: Glycine max
<220> FEATURE:
<221> NAME/KEY: misc_feature
<222> LOCATION: (1)..(305)
<223> OTHER INFORMATION: Ceres CLONE ID no. 464291

<400> SEQUENCE: 32

Met Ala Ser Ala Val Glu Lys Glu Gly Gly Ala Ser Glu Glu Thr Leu
1               5                   10                  15

Ser Leu Glu Leu Pro Ala Pro Pro Gly Trp Lys Lys Gln Phe Ile Pro
            20                  25                  30

Lys Lys Ala Gly Thr Pro Lys Lys Asn Glu Ile Val Phe Thr Ala Pro
        35                  40                  45

Thr Gly Glu Glu Ile Asn Asn Arg Lys Gln Leu Glu Lys Tyr Leu Lys
    50                  55                  60

Ala His Pro Gly Gly Pro Ala Val Ser Glu Phe Asp Trp Gly Thr Gly
65                  70                  75                  80

Glu Thr Pro Arg Arg Ser Thr Arg Ile Ser Glu Lys Ala Lys Ala Ala
                85                  90                  95

Pro Pro Thr Gln Arg Glu Pro Pro Lys Lys Arg Thr Lys Arg Ser Ser
            100                 105                 110

Ala Ser Gln Lys Glu Ile Ser Gln Glu Glu Lys Glu Glu Glu Thr Lys
        115                 120                 125

Glu Ala Glu Met Gln Glu Ala Asp Asp Thr Thr Lys Gly Asp Asn Asp
    130                 135                 140

Ile Glu Lys Glu Lys Val Val Asn Glu Asn His Asp Lys Ser Val
145                 150                 155                 160

Glu Asp Thr Asp Val Asn Lys Ser Thr Arg Tyr Gly Glu Glu Ala Lys
                165                 170                 175

Ala Gly Glu Asn Val Glu Val Pro Ile Glu Glu Lys Ser Asn Ala
            180                 185                 190

Ala Asp Gly Glu Leu Pro Ala Leu Lys Asp Lys Ala Asp Lys Val
        195                 200                 205

Thr Glu Gly Ser Glu Val Phe Leu Arg Lys Asp Glu Glu Lys Ile Glu
    210                 215                 220

Gln Pro Gln Glu Glu Thr Lys Glu Tyr Ser Gly Phe Gly Pro Glu
225                 230                 235                 240

Lys Leu Glu Thr Cys Thr Thr Ala Asp Lys Thr Val Glu Val Glu Gly
                245                 250                 255

Val Asn Lys Glu Asp His Val Lys Ser Thr His Glu Phe Val Gly
            260                 265                 270

Glu Ile Glu Gly Thr Lys Val Asn Gly Glu Glu His His Lys Leu Asp
        275                 280                 285

Glu Ile Asn Lys Ala Glu Ala Glu Leu Thr Val Asn Gly Thr His Glu
    290                 295                 300

Ser
305

<210> SEQ ID NO 33
<211> LENGTH: 166
<212> TYPE: PRT
<213> ORGANISM: Glycine max
<220> FEATURE:
<221> NAME/KEY: misc_feature
<222> LOCATION: (1)..(166)
<223> OTHER INFORMATION: Ceres CLONE ID no. 1345786

<400> SEQUENCE: 33
```

```
Met Ala Ser Ala Val Glu Lys Glu Gly Gly Ala Arg Glu Thr Phe
1               5                   10                  15

Ser Leu Glu Leu Pro Ala Pro Pro Gly Trp Lys Lys Gln Phe Ile Pro
            20                  25                  30

Lys Lys Ala Gly Thr Pro Lys Lys Asn Glu Ile Val Phe Thr Ala Ala
                35                  40                  45

Thr Gly Glu Glu Ile His Asn Arg Lys Gln Leu Glu Lys Tyr Leu Lys
50                      55                  60

Ala His Pro Gly Gly Pro Ala Val Ser Glu Phe Asp Trp Gly Thr Gly
65                  70                  75                  80

Glu Thr Pro Arg Arg Ser Thr Arg Ile Ser Glu Lys Ala Lys Ala Ala
                85                  90                  95

Pro Pro Ser Val Ser Glu Pro Lys Lys Arg Thr Lys Arg Ser Ser
                100                 105                 110

Ala Ser Gln Lys Glu Thr Ser Gln Glu Glu Lys Glu Gln Glu Ile Lys
            115                 120                 125

Glu Ala Glu Met Gln Glu Ala Asp Asp Thr Thr Lys Asp Asp Asn Asp
130                 135                 140

Ile Gly Lys Glu Lys Asp Val Val Lys Glu Asn Gln Asp Lys Cys
145                 150                 155                 160

Val Glu Asp Thr Asp Val
                165
```

<210> SEQ ID NO 34
<211> LENGTH: 433
<212> TYPE: PRT
<213> ORGANISM: Zea mays
<220> FEATURE:
<221> NAME/KEY: misc_feature
<222> LOCATION: (1)..(433)
<223> OTHER INFORMATION: Ceres CLONE ID no. 304949

<400> SEQUENCE: 34

```
Met Pro Ala Pro Asp Gly Trp Thr Lys Lys Phe Thr Pro Leu Arg Gly
1               5                   10                  15

Gly Arg Ser Glu Ile Val Phe Val Ser Pro Thr Gly Glu Glu Ile Lys
            20                  25                  30

Asn Lys Arg Gln Leu Ser Gln Tyr Leu Lys Ala His Pro Gly Gly Pro
                35                  40                  45

Ala Val Ser Glu Phe Asp Trp Gly Thr Gly Thr Pro Arg Arg Ser
50                      55                  60

Ala Arg Ile Ser Glu Lys Val Lys Val Phe Asp Ser Pro Glu Gly Glu
65                  70                  75                  80

Lys Ile Pro Lys Arg Ser Arg Asn Ser Ser Gly Arg Lys Gly Lys Gln
                85                  90                  95

Gly Lys Lys Glu Thr Pro Glu Thr Glu Glu Ala Lys Asp Ala Glu Thr
            100                 105                 110

Gly Lys Glu Ala Glu Glu Ala Pro Ser Glu Asp Ala Ala Lys Glu Thr
            115                 120                 125

Asp Val Glu Met Lys Pro Ala Glu Glu Val Lys Gly Ala Ser Ala Glu
130                 135                 140

Thr Glu Asp Ala Asp Met Ala Asp Ala Pro Ala Pro Ala Pro Met Glu
145                 150                 155                 160

Glu Asp Lys Lys Gln Thr Glu Glu Leu Ala Glu Ala Ile Ala Ala Pro
                165                 170                 175

Pro Val Pro Ser Glu Glu Lys Lys Asp Val Lys Pro Ala Glu Pro Glu
```

```
                    180                 185                 190
Ala Ala Ala Ser Asn Pro Thr Glu Asp Ser Pro Ala Pro Ala Glu
            195                 200                 205

Pro Ala Asp Val Ala Ala Pro Ala Ala Glu Pro Lys Ser Asp Ala Lys
210                 215                 220

Pro Ala Ala Val Ala Ala Pro Val Pro Glu Thr Lys Ser Asp Ala Glu
225                 230                 235                 240

Pro Ala Ala Val Ala Ala Pro Ala Pro Glu Thr Lys Ser Asp Ala Glu
            245                 250                 255

Pro Ala Ala Val Ala Ala Pro Ala Pro Glu Thr Lys Ser Val Ala Glu
            260                 265                 270

Pro Ala Ala Val Ala Ala Pro Ala Pro Glu Thr Lys Ser Asp Ala Glu
            275                 280                 285

Pro Ala Ala Val Ala Ala Pro Val Pro Glu Thr Lys Ser Asp Ala Glu
            290                 295                 300

Pro Ala Ala Val Ala Ala Pro Val Pro Glu Thr Lys Ser Asp Ala Glu
305                 310                 315                 320

Pro Ala Ala Asp Ala Ala Pro Val Pro Glu Met Lys Ser Glu Ser Glu
            325                 330                 335

Pro Ala Ala Val Ala Ala Pro Ala Ser Glu Thr Lys Ser Asp Ala Glu
            340                 345                 350

Pro Ala Ala Val Ala Ala Pro Ala Pro Glu Thr Lys Ser Asp Ala Glu
            355                 360                 365

Pro Ala Ala Ala Ala Ala Pro Val Pro Gly Thr Asn Ser Asp Ala Ala
            370                 375                 380

Ala Thr Asp Pro Ala Pro Gly Thr Lys Ala Thr Ala Ala Asp Pro Ala
385                 390                 395                 400

Pro Gly Ala Pro Ala Glu Asn Ser Thr Asp Lys Asp Gly Ser Gln Glu
            405                 410                 415

Ser Gln Pro Val Asn Asn Gly Gln Leu Pro His Ser Thr Val Lys Cys
            420                 425                 430

Thr

<210> SEQ ID NO 35
<211> LENGTH: 108
<212> TYPE: PRT
<213> ORGANISM: Glycine max
<220> FEATURE:
<221> NAME/KEY: misc_feature
<222> LOCATION: (1)..(108)
<223> OTHER INFORMATION: Ceres CLONE ID no. 601907

<400> SEQUENCE: 35

Met Ala Ser Ser Xaa Xaa Lys Glu Gly Xaa Ala Ser Glu Glu Thr Phe
1               5                   10                  15

Ser Leu Glu Leu Pro Ala Pro Pro Gly Trp Lys Lys Xaa Phe Ile Pro
            20                  25                  30

Lys Lys Ala Gly Thr Pro Lys Lys Asn Glu Ile Val Phe Thr Ser Pro
        35                  40                  45

Thr Gly Glu Xaa Ile Asn Ser Arg Lys Gln Leu Glu Lys Xaa Xaa Lys
    50                  55                  60

Ala His Pro Gly Gly Pro Ala Val Xaa Glu Phe Asp Xaa Gly Thr Gly
65                  70                  75                  80

Glu Thr Pro Arg Arg Ser Thr Arg Ile Ser Glu Lys Ala Lys Val Ala
                85                  90                  95

Pro Pro Ala Glu Ser Glu Xaa Pro Lys Glu Ala Tyr
            100                 105
```

-continued

```
                    100                 105
```

<210> SEQ ID NO 36
<211> LENGTH: 428
<212> TYPE: PRT
<213> ORGANISM: Zea mays
<220> FEATURE:
<221> NAME/KEY: misc_feature
<222> LOCATION: (1)..(428)
<223> OTHER INFORMATION: Ceres CLONE ID no. 222489

<400> SEQUENCE: 36

```
Met Pro Ala Pro Asp Gly Trp Thr Lys Lys Phe Thr Pro Gln Arg Gly
1               5                   10                  15

Gly Arg Ser Glu Ile Val Phe Val Ser Pro Thr Gly Glu Glu Ile Lys
            20                  25                  30

Asn Lys Arg Gln Leu Ser Gln Tyr Leu Lys Ala His Pro Gly Gly Pro
        35                  40                  45

Ala Ala Ser Asp Phe Asp Trp Gly Thr Gly Asp Thr Pro Arg Arg Ser
    50                  55                  60

Ala Arg Ile Ser Glu Lys Val Lys Val Phe Asp Ser Pro Glu Gly Glu
65                  70                  75                  80

Lys Ile Pro Lys Arg Ser Arg Asn Ser Ser Gly Arg Lys Gly Arg Gln
                85                  90                  95

Gly Lys Lys Glu Ala Pro Glu Thr Glu Glu Ala Lys Asp Ala Glu Thr
            100                 105                 110

Gly Gln Asp Ala Pro Ser Glu Asp Gly Thr Lys Glu Thr Asp Val Glu
        115                 120                 125

Met Lys Pro Ala Glu Glu Ala Lys Glu Ala Pro Thr Glu Thr Asp Asp
    130                 135                 140

Ala Glu Lys Ala Ala Asp Lys Ala Asp Asp Thr Pro Ala Pro Ala Pro
145                 150                 155                 160

Met Glu Glu Asp Glu Lys Glu Thr Glu Lys Pro Ala Glu Ala Val Val
                165                 170                 175

Ala Pro Leu Ala Gln Ser Glu Glu Lys Lys Glu Asp Ala Lys Pro Asp
            180                 185                 190

Glu Pro Glu Ala Val Ala Pro Ala Pro Val Ser Asn Pro Thr Glu Asn
        195                 200                 205

Ser Ala Pro Ala Pro Ala Glu Pro Ala Ala Val Pro Ala Pro Val Pro
    210                 215                 220

Glu Thr Glu Ser Val Ala Glu Pro Ala Ala Val Leu Ala Pro Ala Pro
225                 230                 235                 240

Glu Thr Lys Pro Asp Ala Lys Pro Ala Ala Val Pro Ala Pro Ala Pro
                245                 250                 255

Glu Asn Lys Pro Asp Ala Glu Pro Ala Ala Ala Ala Pro Ala Pro Val Pro
            260                 265                 270

Asp Thr Lys Ser Val Ala Glu Pro Ala Ala Ala Pro Ala Pro Asp Thr
        275                 280                 285

Lys Ser Val Ala Glu Pro Ala Ala Ala Pro Val Pro Glu Thr Lys
    290                 295                 300

Leu Val Ala Glu Ser Ala Ala Asp Ala Val Ala Ala Pro Ala Pro Glu
305                 310                 315                 320

Thr Lys Ser Asp Ala Glu Pro Ala Ala Pro Val Pro Glu Thr Lys
                325                 330                 335

Pro Val Ala Glu Ser Ala Ala Asp Ala Val Ala Ala Pro Ala Pro Glu
            340                 345                 350
```

Thr Lys Ser Asp Ala Glu Pro Ala Ala Ala Asp Pro Ala Pro Glu
        355                 360                 365

Ile Lys Ser Asp Ala Ala Ala Ala Asp Pro Ala Pro Gly Thr Lys Ala
    370                 375                 380

Asp Ala Ala Thr Asp Ala Pro Gly Ala Glu Pro Asp Ala Ala
385                 390                 395                 400

Pro Leu Glu Asn Thr Ala Ala Asp Lys Gly Gly Ser Glu Ser Ser
                405                 410                 415

Gln Pro Val Asn Asn Val Asn Asn Gly His Ser Thr
            420                 425

<210> SEQ ID NO 37
<211> LENGTH: 113
<212> TYPE: PRT
<213> ORGANISM: Triticum aestivum
<220> FEATURE:
<221> NAME/KEY: misc_feature
<222> LOCATION: (1)..(113)
<223> OTHER INFORMATION: Ceres CLONE ID no. 905085

<400> SEQUENCE: 37

Met Ala Thr Gly Gly Asp His Ala Ala Glu Glu Leu Val Ser Val Glu
1               5                   10                  15

Met Pro Ala Pro Glu Gly Trp Thr Lys Lys Phe Thr Pro Gln Ser Arg
            20                  25                  30

Gly Arg Ser Glu Ile Val Phe Val Ser Pro Thr Gly Glu Glu Ile Lys
        35                  40                  45

Asn Lys Arg Gln Leu Asn Ser Tyr Leu Lys Ala Asn Pro Gly Gly Pro
    50                  55                  60

Thr Ser Ser Glu Phe Asp Trp Ser Thr Gly Asp Thr Pro Arg Arg Ser
65                  70                  75                  80

Ala Arg Ile Ser Glu Lys Val Lys Val Phe Asp Ser Pro Gln Gly Glu
                85                  90                  95

Lys Ile Pro Lys Arg Ser Arg Asn Ser Ser Gly Arg Lys Gly Lys Gln
            100                 105                 110

Glu

<210> SEQ ID NO 38
<211> LENGTH: 221
<212> TYPE: PRT
<213> ORGANISM: Triticum aestivum
<220> FEATURE:
<221> NAME/KEY: misc_feature
<222> LOCATION: (1)..(221)
<223> OTHER INFORMATION: Ceres CLONE ID no. 570851

<400> SEQUENCE: 38

Met Ala Ser Glu Gly Glu His Ala Ala Ala Gly Glu Gln Thr Pro Leu
1               5                   10                  15

Lys Lys Ala Gly Glu Ala Glu Gln Gly Glu Glu Leu Gln Ala Pro Ser
            20                  25                  30

Gly Trp Thr Lys Lys Leu Asn Pro Thr Arg Gly Gly Lys Phe Glu Val
        35                  40                  45

Val Phe Val Ala Pro Thr Gly Glu Glu Val Lys Thr Lys Arg Ala Leu
    50                  55                  60

Thr Thr Tyr Leu Lys Ala His Pro Gly Gly Pro Ala Leu Ser Glu Phe
65                  70                  75                  80

Val Trp Ala Thr Gly Asn Thr Pro Arg Arg Ser Ser Arg Leu Ser Ala
                85                  90                  95

```
Lys Pro Lys Ala Thr Glu Ser Pro Glu Asp Glu Lys Pro Ser Arg Arg
            100                 105                 110
Ser Gly Lys Ser Lys Ala Thr Glu Ser Pro Glu Asp Glu Lys Pro Ala
            115                 120                 125
Lys Arg Gly Arg Pro Ser Ser Lys Lys Gly Lys Lys Gly Lys Gln
        130                 135                 140
Glu Asp Ala Glu Asp Ala Glu Ala Glu Ser Gly Asp His Ala Asp Ala
145                 150                 155                 160
Glu Glu Ala Lys Gly Thr Glu Val Glu Met Lys Asp Ala Glu Glu Ala
                165                 170                 175
Lys Val Thr Asp Leu Asp Leu Glu Met Lys Glu Ala Asp Ser Ala Xaa
            180                 185                 190
Gly Arg Glu Glu Arg Gly Arg Gly Trp Lys Phe Gly Trp Arg Glu Glu
        195                 200                 205
Arg Asp Arg His Cys Cys Ser Gly Arg Glu Glu Ser Gly
210                 215                 220
```

<210> SEQ ID NO 39
<211> LENGTH: 669
<212> TYPE: DNA
<213> ORGANISM: Populus balsamifera subsp. trichocarpa
<220> FEATURE:
<221> NAME/KEY: misc_feature
<222> LOCATION: (1)..(669)
<223> OTHER INFORMATION: Ceres GDNA ANNOT ID no. 1487125
<220> FEATURE:
<221> NAME/KEY: misc_feature
<222> LOCATION: (1)..(669)
<223> OTHER INFORMATION: CDS - REFERENCED BY SEQ ID NO: 40

<400> SEQUENCE: 39

```
atggagcaca gacaggtttt aaattcctcg attacaattc cttcttttg tatggcttac      60
tgtcttggtt ccttgcagta tttccccaag agtatagaca caccaaggaa gaatgaaatc    120
ctgctcatag ctccaactgg ggaagagact aacaacagga agcaagtgga gcagtacctg    180
aagggcactg gtgagacccc aagaagatct gcaagaatca gcgagaaggc caaggcaact    240
cctcctgaga aggagcaccc aaagaagcga ggccgaaaat catctggttc aagaaagat    300
gaaacgggaa ctattaccga agaaaatgag ggtgagaatg aggttcaaat gcaagatgaa    360
gagaatggca gtgaaggaaa tgctaaggga ttccagcaag cattggaagt taagagaaa    420
gaaaacgcag gggaagcagt gaaggacaaa gctgctgaag aagctggttc cagtgaagtg    480
gctgaagata gagccgataa ggttgaagac ttggcagaaa aggtgccacg aactgaggca    540
gagaaagaga atgccccagg ccacaaggac atcccagata gttttctgat gaaagcaaat    600
gatggagcac aaaaagagaa gactaatggg actgaccgat gccccccagc atccaccccc    660
aatgtctga                                                            669
```

<210> SEQ ID NO 40
<211> LENGTH: 222
<212> TYPE: PRT
<213> ORGANISM: Populus balsamifera subsp. trichocarpa
<220> FEATURE:
<221> NAME/KEY: misc_feature
<222> LOCATION: (1)..(222)
<223> OTHER INFORMATION: Ceres GDNA ANNOT ID no. 1487125

<400> SEQUENCE: 40

```
Met Glu His Arg Gln Val Leu Asn Ser Ser Ile Thr Ile Pro Ser Phe
1               5                   10                  15
Cys Met Ala Tyr Cys Leu Gly Ser Leu Gln Tyr Phe Pro Lys Ser Ile
```

```
                    20                  25                  30
Asp Thr Pro Arg Lys Asn Glu Ile Leu Leu Ile Ala Pro Thr Gly Glu
            35                  40                  45

Glu Thr Asn Asn Arg Lys Gln Val Glu Gln Tyr Leu Lys Gly Thr Gly
     50                  55                  60

Glu Thr Pro Arg Arg Ser Ala Arg Ile Ser Glu Lys Ala Lys Ala Thr
 65                  70                  75                  80

Pro Pro Glu Lys Glu His Pro Lys Lys Arg Gly Arg Lys Ser Ser Gly
                 85                  90                  95

Ser Lys Lys Asp Glu Thr Gly Thr Ile Thr Glu Glu Asn Glu Gly Glu
             100                 105                 110

Asn Glu Val Gln Met Gln Asp Glu Glu Asn Gly Ser Glu Gly Asn Ala
         115                 120                 125

Lys Gly Phe Gln Gln Ala Leu Glu Val Lys Glu Lys Glu Asn Ala Gly
     130                 135                 140

Glu Ala Val Lys Asp Lys Ala Ala Glu Glu Ala Gly Ser Ser Glu Val
145                 150                 155                 160

Ala Glu Asp Arg Ala Asp Lys Val Glu Asp Leu Ala Glu Lys Val Pro
                 165                 170                 175

Arg Thr Glu Ala Glu Lys Glu Asn Ala Pro Gly His Lys Asp Ile Pro
             180                 185                 190

Asp Ser Phe Leu Met Lys Ala Asn Asp Gly Ala Gln Lys Glu Lys Thr
         195                 200                 205

Asn Gly Thr Asp Arg Cys Pro Pro Ala Ser Thr Pro Asn Val
     210                 215                 220

<210> SEQ ID NO 41
<211> LENGTH: 101
<212> TYPE: PRT
<213> ORGANISM: Glycine max
<220> FEATURE:
<221> NAME/KEY: misc_feature
<222> LOCATION: (1)..(101)
<223> OTHER INFORMATION: Ceres CLONE ID no. 560149

<400> SEQUENCE: 41

Met Val Met Gln Lys Gly Arg Ser Asp Gly Pro Gln Ser Arg Gln Met
 1               5                  10                  15

Arg Ile Ala Glu Cys Leu Val Gly Asp Glu Thr Gly Met Ile Ile Phe
             20                  25                  30

Thr Ala Arg Asn Asp Gln Val Asp Met Met Lys Glu Ala Ala Thr Val
         35                  40                  45

Ile Leu Arg Asn Ala Lys Ile Asp Met Phe Lys Gly Ser Met Arg Phe
     50                  55                  60

Ala Val Asp Lys Trp Gly Arg Val Glu Val Thr Glu Pro Ala Ser Phe
 65                  70                  75                  80

Thr Val Lys Glu Asp Asn Asn Leu Ser Leu Ile Glu Tyr Glu Leu Val
                 85                  90                  95

Asn Val Val Val Glu
         100

<210> SEQ ID NO 42
<211> LENGTH: 101
<212> TYPE: PRT
<213> ORGANISM: Brassica napus
<220> FEATURE:
<221> NAME/KEY: misc_feature
<222> LOCATION: (1)..(101)
<223> OTHER INFORMATION: Ceres CLONE ID no. 967348
```

-continued

```
<400> SEQUENCE: 42

Met Gln Arg Gly Gly Gly Arg Pro Ser Gly Pro Gln Ala Arg Gln Met
1               5                   10                  15

Arg Ile Ala Glu Cys Leu Val Gly Asp Glu Thr Gly Ile Ile Ile Phe
            20                  25                  30

Thr Ala Arg Asn Asp Gln Val Asp Leu Met Lys Glu Gly Lys Val Val
        35                  40                  45

Thr Leu Arg Asn Ala Lys Ile Asp Met Tyr Lys Gly Ser Met Arg Leu
    50                  55                  60

Ala Val Asp Arg Trp Gly Arg Val Glu Val Ala Glu Glu Ala Thr Asp
65                  70                  75                  80

Ile Thr Val Lys Glu Asp Asn Asn Leu Ser Leu Ile Glu Tyr Glu Leu
                85                  90                  95

Val Ser Val Glu Ala
            100

<210> SEQ ID NO 43
<211> LENGTH: 137
<212> TYPE: PRT
<213> ORGANISM: Glycine max
<220> FEATURE:
<221> NAME/KEY: misc_feature
<222> LOCATION: (1)..(137)
<223> OTHER INFORMATION: Ceres CLONE ID no. 1626553

<400> SEQUENCE: 43

Met Ala Asp Ser Lys Ser Gly Leu Arg Lys Pro Val Phe Thr Lys Val
1               5                   10                  15

Asp Gln Leu Cys Pro Gly Thr Ser Gly His Thr Leu Thr Val Lys Val
            20                  25                  30

Val Asn Ala Lys Met Val Met Gln Arg Gly Arg Ser Asp Gly Pro Gln
        35                  40                  45

Ser Arg Gln Met Arg Ile Ala Glu Cys Leu Val Gly Asp Glu Thr Gly
    50                  55                  60

Met Ile Ile Tyr Thr Ala Arg Asn Asp Gln Val Asp Thr Met Thr Glu
65                  70                  75                  80

Gly Ala Thr Val Ile Leu Arg Asn Ala Lys Ile Asp Met Phe Lys Gly
                85                  90                  95

Ser Met Arg Leu Ala Val Asp Lys Trp Gly Arg Val Glu Leu Thr Glu
                100                 105                 110

Pro Ala Ser Phe Thr Val Lys Glu Asp Asn Asn Leu Ser Leu Ile Glu
            115                 120                 125

Tyr Glu Leu Val Asn Val Val Ala Glu
        130                 135

<210> SEQ ID NO 44
<211> LENGTH: 146
<212> TYPE: PRT
<213> ORGANISM: Zea mays
<220> FEATURE:
<221> NAME/KEY: misc_feature
<222> LOCATION: (1)..(146)
<223> OTHER INFORMATION: Ceres CLONE ID no. 1276512

<400> SEQUENCE: 44

Met Ala Thr Ala Ala Ala Gln Gly Gly Ser Asp Lys Pro Ala Leu Arg
1               5                   10                  15

Lys Pro Val Phe Thr Lys Val Asp Gln Leu Lys Pro Gly Thr Asn Gly
            20                  25                  30
```

```
His Thr Leu Thr Val Lys Val Val Ser Ala Thr Pro Val Pro Gly Arg
        35                  40                  45

Ala Arg Pro Gly Ala Pro Ala Ala Ser Ser Arg Ala Pro Arg Ile
 50                  55                  60

Ala Glu Cys Leu Val Gly Asp Glu Thr Gly Val Ile Val Phe Thr Ala
 65                  70                  75                  80

Arg Asn Asp Gln Val Asp Leu Leu Lys Pro Asp Ala Thr Val Ile Leu
                 85                  90                  95

Arg Asn Ala Lys Ile Asp Met Phe Lys Gly Ser Met Arg Leu Ala Val
                100                 105                 110

Asp Lys Trp Gly Arg Ile Glu Ala Thr Glu Pro Ala Ser Phe Thr Val
            115                 120                 125

Lys Glu Asp Asn Asn Leu Ser Leu Val Glu Tyr Glu Leu Val Asn Val
130                 135                 140

Ala Glu
145

<210> SEQ ID NO 45
<211> LENGTH: 140
<212> TYPE: PRT
<213> ORGANISM: Oryza sativa subsp. japonica
<220> FEATURE:
<221> NAME/KEY: misc_feature
<222> LOCATION: (1)..(140)
<223> OTHER INFORMATION: Public GI no. 57900332

<400> SEQUENCE: 45

Met Ala Ala Ala Ala Ala Ala Lys Arg Lys Pro Val Phe Val Lys
1               5                   10                  15

Val Asp Gln Leu Lys Pro Gly Thr Gly Gly His Thr Leu Val Ala Lys
            20                  25                  30

Val Leu Ser Ser Lys Thr Val Val Gln Lys Gly Arg Ala Ala Ala Gly
        35                  40                  45

Ala Gly Pro Ala Ala Arg Pro Thr Arg Ile Ala Glu Cys Leu Ile Gly
 50                  55                  60

Asp Glu Thr Gly Cys Ile Leu Phe Thr Ala Arg Asn Glu Gln Val Asp
65                  70                  75                  80

Leu Met Lys Ala Asp Ser Thr Val Ile Arg Asn Ala Lys Ile Asp
                 85                  90                  95

Met Phe Lys Gly Ser Met Arg Leu Ala Val Asp Lys Trp Gly Arg Ile
                100                 105                 110

Glu Val Thr Glu Pro Ala Ser Phe Asn Val Lys Glu Asp Asn Asn Leu
            115                 120                 125

Ser Leu Val Glu Tyr Glu Leu Val Asn Val Glu Gly
130                 135                 140

<210> SEQ ID NO 46
<211> LENGTH: 139
<212> TYPE: PRT
<213> ORGANISM: Triticum aestivum
<220> FEATURE:
<221> NAME/KEY: misc_feature
<222> LOCATION: (1)..(139)
<223> OTHER INFORMATION: Ceres CLONE ID no. 678019

<400> SEQUENCE: 46

Met Ala Thr Ala Ala Ala Ala Lys Arg Lys Pro Val Phe Val Lys Val
1               5                   10                  15

Asp Gln Leu Lys Pro Val Thr Ser Gly His Thr Leu Val Ala Lys Val
```

-continued

```
                20                  25                  30
Leu Ser Ser Lys Thr Val Leu Gln Lys Ala Arg Ala Ala Gly Gly Pro
         35                  40                  45

Gly Pro Ala Ala Lys Pro Thr Arg Ile Ala Glu Cys Leu Ile Gly Asp
     50                  55                  60

Glu Thr Gly Cys Val Leu Phe Thr Ala Arg Asn Asp Gln Val Asp Val
 65                  70                  75                  80

Leu Lys Pro Gly Asn Thr Val Ile Ile Arg Asn Ala Lys Ile Asp Met
                 85                  90                  95

Phe Lys Gly Ser Met Arg Leu Ala Val Asp Lys Trp Gly Arg Val Glu
            100                 105                 110

Val Thr Glu Pro Ala Ser Phe Gly Val Lys Glu Asp Asn Asn Leu Ser
        115                 120                 125

Leu Val Glu Tyr Glu Leu Val Asn Val Glu Glu
    130                 135
```

<210> SEQ ID NO 47
<211> LENGTH: 146
<212> TYPE: PRT
<213> ORGANISM: Zea mays
<220> FEATURE:
<221> NAME/KEY: misc_feature
<222> LOCATION: (1)..(146)
<223> OTHER INFORMATION: Ceres CLONE ID no. 215916

<400> SEQUENCE: 47

```
Met Ser Thr Ala Ala Ala Gln Gly Gly Ser Asp Lys Pro Ala Leu Arg
 1               5                  10                  15

Arg Pro Val Phe Thr Lys Val Asp Gln Leu Arg Pro Gly Thr Asn Gly
                20                  25                  30

His Thr Leu Thr Val Lys Val Val Ser Ala Thr Pro Val Pro Gly Arg
            35                  40                  45

Ala Arg Pro Gly Ala Pro Ala Ala Pro Ser Arg Ala Pro Arg Ile
        50                  55                  60

Ala Glu Cys Leu Val Gly Asp Glu Thr Gly Ala Ile Val Phe Thr Ala
 65                  70                  75                  80

Arg Asn Asp Gln Val Asp Leu Leu Lys Pro Asn Ala Thr Val Ile Leu
                 85                  90                  95

Arg Asn Ala Lys Ile Asp Met Phe Lys Gly Ser Met Arg Leu Ala Val
            100                 105                 110

Asp Lys Trp Gly Arg Ile Glu Ala Val Glu Pro Ala Ser Phe Thr Val
        115                 120                 125

Lys Glu Asp Asn Asn Leu Ser Leu Ile Glu Tyr Glu Leu Val Asn Val
    130                 135                 140

Ala Glu
145
```

<210> SEQ ID NO 48
<211> LENGTH: 127
<212> TYPE: PRT
<213> ORGANISM: Triticum aestivum
<220> FEATURE:
<221> NAME/KEY: misc_feature
<222> LOCATION: (1)..(127)
<223> OTHER INFORMATION: Ceres CLONE ID no. 569763

<400> SEQUENCE: 48

```
Met Thr Phe Asp Lys Val Glu Glu Leu Arg Pro Gly Thr Tyr Gly His
 1               5                  10                  15
```

```
Asn Leu Gln Leu Arg Val Leu Ser Ser Lys Pro Val Val Leu His Arg
             20                  25                  30

Pro Gln Gly Gly Arg Ala Gly Asn Met Arg Ile Ala Glu Cys Ile
         35                  40                  45

Val Gly Asp Asp Thr Gly Val Val Phe Thr Ala Arg Asn Glu Gln
 50                  55                  60

Val Asp Val Met Lys Pro Gly Ala Val Glu Ala Arg Lys Ala Arg
 65                  70                  75                  80

Val Asp Met Tyr Lys Gly Ser Met Arg Leu Ala Val Asp Lys Trp Gly
                 85                  90                  95

Thr Leu Lys Ala Ala Glu Ser Pro Ala Asp Phe Lys Val Lys Glu Asp
            100                 105                 110

Asn Asn Val Ser Leu Val Glu Phe Glu Leu Ile Thr Val Met Gln
        115                 120                 125

<210> SEQ ID NO 49
<211> LENGTH: 137
<212> TYPE: PRT
<213> ORGANISM: Arabidopsis thalia
<220> FEATURE:
<221> NAME/KEY: misc_feature
<222> LOCATION: (1)..(137)
<223> OTHER INFORMATION: Ceres CLONE ID no. 15450
<220> FEATURE:
<221> NAME/KEY: misc_feature
<222> LOCATION: (1)..(137)
<223> OTHER INFORMATION: Also Known As Ceres CDNA ID no. 23368182
<220> FEATURE:
<221> NAME/KEY: misc_feature
<222> LOCATION: (1)..(162)
<223> OTHER INFORMATION: Also Known as Lead 94

<400> SEQUENCE: 49

Met Ala Asp Ser Thr Lys Ala Gly Leu Lys Lys Pro Ala Phe Thr Lys
 1               5                  10                  15

Val Asp Gln Leu Arg Pro Gly Thr Ser Gly His Asn Val Asn Val Lys
             20                  25                  30

Ile Val Ser Thr Lys Met Val Leu Gln Lys Gly Arg Ala Asp Gly Pro
         35                  40                  45

Gln Ala Arg Gln Leu Arg Ile Ser Glu Cys Ile Val Gly Asp Glu Thr
     50                  55                  60

Gly Val Ile Val Phe Thr Ala Arg Asn Asp Gln Val Asp Leu Met Lys
 65                  70                  75                  80

Glu Gly Ser Thr Val Thr Leu Arg Asn Ala Lys Ile Asp Met Tyr Lys
                 85                  90                  95

Gly Ser Met Arg Leu Ala Val Asp Lys Trp Gly Arg Val Glu Val Thr
            100                 105                 110

Glu Pro Ala Ser Phe Lys Val Lys Glu Asp Thr Asn Met Ser Leu Ile
        115                 120                 125

Glu Tyr Glu Leu Val Asn Val Val Glu
    130                 135

<210> SEQ ID NO 50
<211> LENGTH: 155
<212> TYPE: PRT
<213> ORGANISM: Populus balsamifera subsp. trichocarpa
<220> FEATURE:
<221> NAME/KEY: misc_feature
<222> LOCATION: (1)..(155)
<223> OTHER INFORMATION: Ceres GDNA ANNOT ID no. 1466677

<400> SEQUENCE: 50
```

```
Met Ala Thr Gln Thr Pro Ile Glu Gln Gln Glu Ser Ser Ala Ser
1               5                   10                  15

Ala Ser Ala Gly Ala Lys Pro Gly Leu Arg Lys Pro Val Phe Ile Lys
            20                  25                  30

Val Asp Gln Leu Lys Pro Gly Thr Gly His Thr Leu Thr Val Lys
            35                  40                  45

Val Leu Asn Phe Asn Thr Val Pro Gln Lys Asp Arg Arg Ser Val Ser
        50                  55                  60

Leu His Ala Arg Gln Thr Arg Ile Ala Glu Cys Leu Ile Gly Asp Glu
65                  70                  75                  80

Thr Gly Thr Ile Ile Phe Thr Ala Arg Asn Asp Gln Val Asp Leu Met
                85                  90                  95

Lys Pro Gly Thr Thr Val Ile Leu Arg Asn Ala Lys Ile Asp Met Phe
            100                 105                 110

Lys Gly Ser Met Arg Leu Ala Val Asp Lys Trp Gly Arg Val Glu Val
            115                 120                 125

Thr Glu Pro Ala Glu Phe Val Val Lys Glu Asp Asn Asn Leu Ser Leu
            130                 135                 140

Val Glu Tyr Glu Leu Val Asn Val Ala Glu Glu
145                 150                 155

<210> SEQ ID NO 51
<211> LENGTH: 101
<212> TYPE: PRT
<213> ORGANISM: Brassica napus
<220> FEATURE:
<221> NAME/KEY: misc_feature
<222> LOCATION: (1)..(101)
<223> OTHER INFORMATION: Ceres CLONE ID no. 967348

<400> SEQUENCE: 51

Met Gln Arg Gly Gly Gly Arg Pro Ser Gly Pro Gln Ala Arg Gln Met
1               5                   10                  15

Arg Ile Ala Glu Cys Leu Val Gly Asp Glu Thr Gly Ile Ile Ile Phe
            20                  25                  30

Thr Ala Arg Asn Asp Gln Val Asp Leu Met Lys Glu Gly Lys Val Val
            35                  40                  45

Thr Leu Arg Asn Ala Lys Ile Asp Met Tyr Lys Gly Ser Met Arg Leu
        50                  55                  60

Ala Val Asp Arg Trp Gly Arg Val Glu Val Glu Glu Ala Thr Asp
65                  70                  75                  80

Ile Thr Val Lys Glu Asp Asn Asn Leu Ser Leu Ile Glu Tyr Glu Leu
            85                  90                  95

Val Ser Val Glu Ala
            100

<210> SEQ ID NO 52
<211> LENGTH: 137
<212> TYPE: PRT
<213> ORGANISM: Glycine max
<220> FEATURE:
<221> NAME/KEY: misc_feature
<222> LOCATION: (1)..(137)
<223> OTHER INFORMATION: Ceres CLONE ID no. 1626553

<400> SEQUENCE: 52

Met Ala Asp Ser Lys Ser Gly Leu Arg Lys Pro Val Phe Thr Lys Val
1               5                   10                  15

Asp Gln Leu Cys Pro Gly Thr Ser Gly His Thr Leu Thr Val Lys Val
            20                  25                  30
```

-continued

Val Asn Ala Lys Met Val Met Gln Arg Gly Arg Ser Asp Gly Pro Gln
            35                  40                  45

Ser Arg Gln Met Arg Ile Ala Glu Cys Leu Val Gly Asp Glu Thr Gly
     50                  55                  60

Met Ile Ile Tyr Thr Ala Arg Asn Asp Gln Val Asp Thr Met Thr Glu
 65                  70                  75                  80

Gly Ala Thr Val Ile Leu Arg Asn Ala Lys Ile Asp Met Phe Lys Gly
                 85                  90                  95

Ser Met Arg Leu Ala Val Asp Lys Trp Gly Arg Val Glu Leu Thr Glu
            100                 105                 110

Pro Ala Ser Phe Thr Val Lys Glu Asp Asn Asn Leu Ser Leu Ile Glu
        115                 120                 125

Tyr Glu Leu Val Asn Val Val Ala Glu
    130                 135

<210> SEQ ID NO 53
<211> LENGTH: 146
<212> TYPE: PRT
<213> ORGANISM: Zea mays
<220> FEATURE:
<221> NAME/KEY: misc_feature
<222> LOCATION: (1)..(146)
<223> OTHER INFORMATION: Ceres CLONE ID no. 1276512

<400> SEQUENCE: 53

Met Ala Thr Ala Ala Ala Gln Gly Gly Ser Asp Lys Pro Ala Leu Arg
 1               5                  10                  15

Lys Pro Val Phe Thr Lys Val Asp Gln Leu Lys Pro Gly Thr Asn Gly
             20                  25                  30

His Thr Leu Thr Val Lys Val Val Ser Ala Thr Pro Val Pro Gly Arg
         35                  40                  45

Ala Arg Pro Gly Ala Pro Ala Ala Ser Ser Arg Ala Pro Arg Ile
     50                  55                  60

Ala Glu Cys Leu Val Gly Asp Glu Thr Gly Val Ile Val Phe Thr Ala
 65                  70                  75                  80

Arg Asn Asp Gln Val Asp Leu Leu Lys Pro Asp Ala Thr Val Ile Leu
                 85                  90                  95

Arg Asn Ala Lys Ile Asp Met Phe Lys Gly Ser Met Arg Leu Ala Val
            100                 105                 110

Asp Lys Trp Gly Arg Ile Glu Ala Thr Glu Pro Ala Ser Phe Thr Val
        115                 120                 125

Lys Glu Asp Asn Asn Leu Ser Leu Val Glu Tyr Glu Leu Val Asn Val
    130                 135                 140

Ala Glu
145

<210> SEQ ID NO 54
<211> LENGTH: 140
<212> TYPE: PRT
<213> ORGANISM: Oryza sativa subsp. japonica
<220> FEATURE:
<221> NAME/KEY: misc_feature
<222> LOCATION: (1)..(140)
<223> OTHER INFORMATION: Public GI no. 57900332

<400> SEQUENCE: 54

Met Ala Ala Ala Ala Ala Ala Ala Lys Arg Lys Pro Val Phe Val Lys
 1               5                  10                  15

Val Asp Gln Leu Lys Pro Gly Thr Gly Gly His Thr Leu Val Ala Lys

-continued

```
                20                  25                  30
Val Leu Ser Ser Lys Thr Val Val Gln Lys Gly Arg Ala Ala Gly
            35                  40                  45

Ala Gly Pro Ala Ala Arg Pro Thr Arg Ile Ala Glu Cys Leu Ile Gly
        50                  55                  60

Asp Glu Thr Gly Cys Ile Leu Phe Thr Ala Arg Asn Glu Gln Val Asp
65                  70                  75                  80

Leu Met Lys Ala Asp Ser Thr Val Ile Ile Arg Asn Ala Lys Ile Asp
                85                  90                  95

Met Phe Lys Gly Ser Met Arg Leu Ala Val Asp Lys Trp Gly Arg Ile
            100                 105                 110

Glu Val Thr Glu Pro Ala Ser Phe Asn Val Lys Glu Asp Asn Asn Leu
        115                 120                 125

Ser Leu Val Glu Tyr Glu Leu Val Asn Val Glu Gly
            130                 135                 140

<210> SEQ ID NO 55
<211> LENGTH: 139
<212> TYPE: PRT
<213> ORGANISM: Triticum aestivum
<220> FEATURE:
<221> NAME/KEY: misc_feature
<222> LOCATION: (1)..(139)
<223> OTHER INFORMATION: Ceres CLONE ID no. 678019

<400> SEQUENCE: 55

Met Ala Thr Ala Ala Ala Ala Lys Arg Lys Pro Val Phe Val Lys Val
1               5                   10                  15

Asp Gln Leu Lys Pro Val Thr Ser Gly His Thr Leu Val Ala Lys Val
            20                  25                  30

Leu Ser Ser Lys Thr Val Leu Gln Lys Ala Arg Ala Ala Gly Gly Pro
        35                  40                  45

Gly Pro Ala Ala Lys Pro Thr Arg Ile Ala Glu Cys Leu Ile Gly Asp
    50                  55                  60

Glu Thr Gly Cys Val Leu Phe Thr Ala Arg Asn Asp Gln Val Asp Val
65                  70                  75                  80

Leu Lys Pro Gly Asn Thr Val Ile Ile Arg Asn Ala Lys Ile Asp Met
                85                  90                  95

Phe Lys Gly Ser Met Arg Leu Ala Val Asp Lys Trp Gly Arg Val Glu
            100                 105                 110

Val Thr Glu Pro Ala Ser Phe Gly Val Lys Glu Asp Asn Asn Leu Ser
        115                 120                 125

Leu Val Glu Tyr Glu Leu Val Asn Val Glu Glu
    130                 135

<210> SEQ ID NO 56
<211> LENGTH: 127
<212> TYPE: PRT
<213> ORGANISM: Triticum aestivum
<220> FEATURE:
<221> NAME/KEY: misc_feature
<222> LOCATION: (1)..(127)
<223> OTHER INFORMATION: Ceres CLONE ID no. 569763

<400> SEQUENCE: 56

Met Thr Phe Asp Lys Val Glu Glu Leu Arg Pro Gly Thr Tyr Gly His
1               5                   10                  15

Asn Leu Gln Leu Arg Val Leu Ser Ser Lys Pro Val Val Leu His Arg
            20                  25                  30
```

```
Pro Gln Gly Gly Arg Ala Gly Gly Asn Met Arg Ile Ala Glu Cys Ile
        35                  40                  45

Val Gly Asp Asp Thr Gly Val Val Phe Thr Ala Arg Asn Glu Gln
 50                  55                  60

Val Asp Val Met Lys Pro Gly Ala Val Glu Ala Arg Lys Ala Arg
 65              70                  75                  80

Val Asp Met Tyr Lys Gly Ser Met Arg Leu Ala Val Asp Lys Trp Gly
             85                  90                  95

Thr Leu Lys Ala Ala Glu Ser Pro Ala Asp Phe Lys Val Lys Glu Asp
            100                 105                 110

Asn Asn Val Ser Leu Val Glu Phe Glu Leu Ile Thr Val Met Gln
            115                 120                 125

<210> SEQ ID NO 57
<211> LENGTH: 817
<212> TYPE: DNA
<213> ORGANISM: Arabidopsis thaliana
<220> FEATURE:
<221> NAME/KEY: misc_feature
<222> LOCATION: (1)..(817)
<223> OTHER INFORMATION: Ceres CLONE ID no. 15450
<220> FEATURE:
<221> NAME/KEY: misc_feature
<222> LOCATION: (1)..(137)
<223> OTHER INFORMATION: Also Known As Ceres CDNA ID no. 23368182
<220> FEATURE:
<221> NAME/KEY: misc_feature
<222> LOCATION: (1)..(162)
<223> OTHER INFORMATION: Also Known as Lead 94
<220> FEATURE:
<221> NAME/KEY: misc_feature
<222> LOCATION: (109)..(522)
<223> OTHER INFORMATION: CDS - REFERENCED BY SEQ ID NO: 58

<400> SEQUENCE: 57
gagaagggag aaaactttct ccgagctcga ttgttttcgg aaatcgtcaa tcagatattt      60
ctcgttcgtc tccgccttcg atttatccaa aggctcttgt tattgaaaat ggcagattcc     120
accaaagcag ggttgaagaa gccagctttc actaaggttg atcagctgcg tcctgggact     180
agcggacaca atgtcaatgt gaagattgtc agcacgaaaa tggtgttaca gaaaggtcgt     240
gctgatggtc ctcaagctcg ccagttgcgg atttctgaat gcattgttgg tgacgagaca     300
ggagtgatcg tctttaccgc aagaaatgac caagtggact aatgaaaga gggatcaact      360
gtaactctac gcaatgcgaa aatcgacatg tataaaggat caatgaggct agctgtagac     420
aagtggggtc gtgttgaagt cacagagcct gcgagcttca agtgaaaga agacaccaac     480
atgtccctta tcgagtatga gctcgtaaac gtcgttgaat gagtgacaaa ttcctcgaaa     540
taccactagg agaaacgccc tcaagaataa acaagtcaaa tccgtaaccg tttatgttag     600
cgtcaagaaa agagttaaac cctgatcagc tgatgtcttg cactaagcta tgtaagagtg     660
atgatggcta aagttgaatg cagagctttt ggcttaggtt atgacttcgt gatacctttt     720
cttttgtaat gtcatcatac acgctaaggc ttttgtgcta cattattact ctctttgtct     780
ttgcctcgtt tcaaaaaatc catattctta gtgaagc                              817

<210> SEQ ID NO 58
<211> LENGTH: 137
<212> TYPE: PRT
<213> ORGANISM: Arabidopsis thalia
<220> FEATURE:
<221> NAME/KEY: misc_feature
<222> LOCATION: (1)..(137)
<223> OTHER INFORMATION: Ceres CLONE ID no. 15450
<220> FEATURE:
```

```
<221> NAME/KEY: misc_feature
<222> LOCATION: (1)..(137)
<223> OTHER INFORMATION: Also Known As Ceres cDNA ID no. 23368182
<220> FEATURE:
<221> NAME/KEY: misc_feature
<222> LOCATION: (1)..(162)
<223> OTHER INFORMATION: Also Known as Lead 94

<400> SEQUENCE: 58

Met Ala Asp Ser Thr Lys Ala Gly Leu Lys Lys Pro Ala Phe Thr Lys
1               5                   10                  15

Val Asp Gln Leu Arg Pro Gly Thr Ser Gly His Asn Val Asn Val Lys
            20                  25                  30

Ile Val Ser Thr Lys Met Val Leu Gln Lys Gly Arg Ala Asp Gly Pro
        35                  40                  45

Gln Ala Arg Gln Leu Arg Ile Ser Glu Cys Ile Val Gly Asp Glu Thr
    50                  55                  60

Gly Val Ile Val Phe Thr Ala Arg Asn Asp Gln Val Asp Leu Met Lys
65                  70                  75                  80

Glu Gly Ser Thr Val Thr Leu Arg Asn Ala Lys Ile Asp Met Tyr Lys
                85                  90                  95

Gly Ser Met Arg Leu Ala Val Asp Lys Trp Gly Arg Val Glu Val Thr
            100                 105                 110

Glu Pro Ala Ser Phe Lys Val Lys Glu Asp Thr Asn Met Ser Leu Ile
        115                 120                 125

Glu Tyr Glu Leu Val Asn Val Val Glu
    130                 135

<210> SEQ ID NO 59
<211> LENGTH: 468
<212> TYPE: DNA
<213> ORGANISM: Populus balsamifera subsp. trichocarpa
<220> FEATURE:
<221> NAME/KEY: misc_feature
<222> LOCATION: (1)..(468)
<223> OTHER INFORMATION: Ceres GDNA ANNOT ID no. 1466677
<220> FEATURE:
<221> NAME/KEY: misc_feature
<222> LOCATION: (1)..(468)
<223> OTHER INFORMATION: CDS - REFERENCED BY SEQ ID NO: 60

<400> SEQUENCE: 59
atggcgacac aaacaccgat tgagcaacag gagagtagca gtgcgagtgc gagtgcgggt      60
gcaaaaccgg gacttagaaa gcctgtgttc atcaaagtgg accagcttaa gcctggaact     120
ggaggccaca cattgactgt caaggtcctt aatttcaata ctgtccctca aaaggaccgc     180
cgatcggtct ctctgcatgc ccgtcagaca cgaatagctg agtgtcttat tggggacgag     240
actggtacca tcattttcac cgcaagaaac gatcaagttg atctgatgaa gccagggaca     300
actgttattc tccgcaatgc aaagattgac atgtttaagg ggtctatgag gctagcagtt     360
gacaaatggg gtcgtgttga agtcactgag cctgcagaat ttgtagtcaa ggaagacaac     420
aatctctctc ttgttgaata tgagcttgtg aatgttgcag aagagtga                  468

<210> SEQ ID NO 60
<211> LENGTH: 155
<212> TYPE: PRT
<213> ORGANISM: Populus balsamifera subsp. trichocarpa
<220> FEATURE:
<221> NAME/KEY: misc_feature
<222> LOCATION: (1)..(155)
<223> OTHER INFORMATION: Ceres GDNA ANNOT ID no. 1466677

<400> SEQUENCE: 60
```

```
Met Ala Thr Gln Thr Pro Ile Glu Gln Glu Ser Ser Ala Ser
1               5                  10                 15

Ala Ser Ala Gly Ala Lys Pro Gly Leu Arg Lys Pro Val Phe Ile Lys
            20                  25                  30

Val Asp Gln Leu Lys Pro Gly Thr Gly His Thr Leu Thr Val Lys
        35                  40                  45

Val Leu Asn Phe Asn Thr Val Pro Gln Lys Arg Arg Ser Val Ser
    50                  55                  60

Leu His Ala Arg Gln Thr Arg Ile Ala Glu Cys Leu Ile Gly Asp Glu
65                  70                  75                  80

Thr Gly Thr Ile Ile Phe Thr Ala Arg Asn Asp Gln Val Asp Leu Met
                85                  90                  95

Lys Pro Gly Thr Thr Val Ile Leu Arg Asn Ala Lys Ile Asp Met Phe
                100                 105                 110

Lys Gly Ser Met Arg Leu Ala Val Asp Lys Trp Gly Arg Val Glu Val
            115                 120                 125

Thr Glu Pro Ala Glu Phe Val Val Lys Glu Asp Asn Asn Leu Ser Leu
        130                 135                 140

Val Glu Tyr Glu Leu Val Asn Val Ala Glu Glu
145                 150                 155

<210> SEQ ID NO 61
<211> LENGTH: 275
<212> TYPE: PRT
<213> ORGANISM: Arabidopsis thaliana
<220> FEATURE:
<221> NAME/KEY: misc_feature
<222> LOCATION: (1)..(275)
<223> OTHER INFORMATION: Ceres CLONE ID no. 26369
<220> FEATURE:
<221> NAME/KEY: misc_feature
<222> LOCATION: (1)..(275)
<223> OTHER INFORMATION: Also Known As Ceres CDNA ID no. 36516078
<220> FEATURE:
<221> NAME/KEY: misc_feature
<222> LOCATION: (1)..(162)
<223> OTHER INFORMATION: Also Known as Lead 95
<220> FEATURE:
<221> NAME/KEY: misc_feature
<222> LOCATION: (63)..(260)
<223> OTHER INFORMATION: Pfam Name: Chloroa_b-bind; Pfam Description:
      Chlorophyll A-B binding protein

<400> SEQUENCE: 61

Met Ala Thr Thr Thr Ala Ala Ala Ala Gly Ile Phe Gly Ile Arg Ile
1               5                  10                  15

Gln Asp Pro Arg Pro Gly Thr Gly Arg Val Gln Ala Arg Phe Gly Phe
            20                  25                  30

Ser Phe Gly Lys Lys Lys Pro Ala Pro Pro Lys Lys Ser Arg Gln
        35                  40                  45

Val Gln Asp Asp Gly Asp Arg Leu Val Trp Phe Pro Gly Ala Asn Pro
    50                  55                  60

Pro Glu Trp Leu Asp Gly Ser Met Ile Gly Asp Arg Gly Phe Asp Pro
65                  70                  75                  80

Phe Gly Leu Gly Lys Pro Ala Glu Tyr Leu Gln Tyr Asp Phe Asp Gly
                85                  90                  95

Leu Asp Gln Asn Leu Ala Lys Asn Val Ala Gly Asp Ile Ile Gly Ile
                100                 105                 110

Ile Gln Glu Ser Ser Glu Ile Lys Pro Thr Pro Phe Gln Pro Tyr Thr
            115                 120                 125
```

```
Glu Val Phe Gly Ile Gln Arg Phe Arg Glu Cys Glu Leu Ile His Gly
            130                 135                 140

Arg Trp Ala Met Leu Gly Thr Leu Gly Ala Ile Ala Val Glu Ala Leu
145                 150                 155                 160

Thr Gly Ile Ala Trp Gln Asp Ala Gly Lys Val Glu Leu Val Glu Gly
                165                 170                 175

Ser Ser Tyr Leu Gly Gln Pro Leu Pro Phe Ser Leu Thr Thr Leu Ile
            180                 185                 190

Trp Ile Glu Val Leu Val Val Gly Tyr Ile Glu Leu Gln Arg Asn Ser
        195                 200                 205

Glu Leu Asp Pro Glu Lys Arg Ile Tyr Pro Gly Gly Tyr Phe Asp Pro
    210                 215                 220

Leu Gly Leu Ala Ala Asp Pro Gly Lys Leu Asp Thr Leu Lys Leu Ala
225                 230                 235                 240

Glu Ile Lys His Ser Arg Leu Ala Met Val Ala Phe Leu Ile Phe Ala
                245                 250                 255

Leu Gln Ala Ala Phe Thr Gly Lys Gly Pro Val Ser Phe Leu Ala Thr
            260                 265                 270

Phe Asn Asn
        275

<210> SEQ ID NO 62
<211> LENGTH: 276
<212> TYPE: PRT
<213> ORGANISM: Brassica napus
<220> FEATURE:
<221> NAME/KEY: misc_feature
<222> LOCATION: (1)..(276)
<223> OTHER INFORMATION: Ceres CLONE ID no. 963170

<400> SEQUENCE: 62

Met Ala Thr Thr Thr Ala Ala Ala Ser Gly Ile Phe Gly Ile Arg
1               5                   10                  15

Ile Gln Asp Pro Ser Ser Gly Ala Gly Arg Val Gln Ala Lys Phe Asn
                20                  25                  30

Phe Ser Phe Gly Lys Lys Lys Pro Ala Pro Pro Lys Lys Thr Lys
            35                  40                  45

Gln Ile Gln Asn Asp Gly Asp Arg Leu Val Trp Phe Pro Gly Ala Asn
50                  55                  60

Pro Pro Glu Trp Leu Asp Gly Ser Met Ile Gly Asp Arg Gly Phe Asp
65                  70                  75                  80

Pro Phe Gly Leu Gly Lys Pro Ala Glu Tyr Leu Gln Tyr Asp Phe Asp
                85                  90                  95

Gly Leu Asp Gln Asn Leu Ala Lys Asn Val Ala Gly Leu Leu Gly
            100                 105                 110

Val Arg Gln Glu Ser Lys Glu Ile Asn Pro Thr Pro Phe Gln Pro Tyr
        115                 120                 125

Thr Glu Met Phe Gly Ile Glu Arg Phe Arg Glu Cys Glu Leu Ile His
    130                 135                 140

Gly Arg Trp Ala Met Leu Gly Thr Leu Gly Ala Leu Ala Val Glu Gly
145                 150                 155                 160

Leu Thr Gly Ile Ala Trp Gln Asp Ala Gly Lys Val Glu Leu Val Glu
                165                 170                 175

Gly Ser Ser Tyr Leu Gly Gln Pro Leu Pro Phe Ser Leu Thr Thr Leu
            180                 185                 190

Ile Trp Ile Glu Val Leu Val Val Gly Tyr Ile Glu Phe Gln Arg Asn
        195                 200                 205
```

```
Ala Glu Leu Asp Pro Glu Lys Arg Ile Tyr Pro Gly Gly Tyr Phe Asp
        210                 215                 220

Pro Leu Gly Leu Gly Ser Asp Pro Glu Lys Leu Asp Thr Leu Lys Leu
225                 230                 235                 240

Ala Glu Ile Lys His Ser Arg Leu Ala Met Ile Ala Phe Leu Ile Phe
                245                 250                 255

Ser Leu Gln Ala Ala Phe Thr Gly Lys Gly Pro Ile Ser Phe Leu Ala
                260                 265                 270

Thr Phe Ser Ser
        275

<210> SEQ ID NO 63
<211> LENGTH: 282
<212> TYPE: PRT
<213> ORGANISM: Glycine max
<220> FEATURE:
<221> NAME/KEY: misc_feature
<222> LOCATION: (1)..(282)
<223> OTHER INFORMATION: Ceres CLONE ID no. 481415
<220> FEATURE:
<221> NAME/KEY: misc_feature
<222> LOCATION: (200)..(200)
<223> OTHER INFORMATION: Xaa is any aa, unknown, or other
<220> FEATURE:
<221> NAME/KEY: misc_feature
<222> LOCATION: (203)..(203)
<223> OTHER INFORMATION: Xaa is any aa, unknown, or other
<220> FEATURE:
<221> NAME/KEY: misc_feature
<222> LOCATION: (209)..(209)
<223> OTHER INFORMATION: Xaa is any aa, unknown, or other
<220> FEATURE:
<221> NAME/KEY: misc_feature
<222> LOCATION: (211)..(211)
<223> OTHER INFORMATION: Xaa is any aa, unknown, or other

<400> SEQUENCE: 63

Met Ala Thr Ala Thr Ala Ala Ala Thr Ser Tyr Phe Phe Gly Thr
1               5                   10                  15

Arg Leu Asn Asn Val Asn Thr Thr Thr Leu Asn Asn Gly Arg Phe His
                20                  25                  30

Ala Leu Leu Asn Phe Gly Lys Lys Lys Thr Ala Pro Gln Pro Pro Pro
            35                  40                  45

Lys Lys Lys Glu Val Lys Val Lys Pro Ser Gly Asp Arg Leu Val Trp
    50                  55                  60

Phe Pro Asn Ala Glu Pro Pro Glu Trp Leu Asp Gly Ser Met Ile Gly
65                  70                  75                  80

Asp Arg Gly Phe Asp Pro Phe Gly Phe Ala Lys Pro Ala Glu Tyr Leu
                85                  90                  95

Gln Phe Asp Leu Asp Ser Leu Asp Gln Asn Leu Ala Lys Asn Ile Ala
                100                 105                 110

Gly Asp Val Ile Gly Thr Arg Val Glu Val Ala Glu Val Lys Pro Thr
            115                 120                 125

Pro Phe Gln Pro Tyr Ser Glu Val Phe Gly Ile Gln Arg Phe Arg Glu
    130                 135                 140

Cys Glu Leu Ile His Gly Arg Trp Ala Met Leu Gly Ser Leu Gly Ala
145                 150                 155                 160

Leu Ala Val Glu Ala Leu Thr Gly Val Ala Trp Gln Asp Ala Gly Lys
                165                 170                 175

Val Glu Leu Val Glu Gly Ser Ser Tyr Leu Gly Leu Pro Leu Pro Phe
                180                 185                 190
```

```
Ser Leu Thr Thr Leu Ile Trp Xaa Glu Val Xaa Val Ile Gly Tyr Ile
        195                 200                 205

Xaa Phe Xaa Arg Asn Ala Glu Leu Asp Pro Glu Lys Arg Leu Tyr Pro
    210                 215                 220

Gly Gly Arg Phe Phe Asp Pro Leu Gly Leu Ala Asn Asp Pro Glu Glu
225                 230                 235                 240

Lys Ala Arg Leu Gln Leu Ala Glu Ile Lys His Ser Arg Leu Ala Met
                245                 250                 255

Val Val Phe Leu Ile Phe Ala Ile Gln Ala Ala Val Thr Gly Lys Gly
                260                 265                 270

Pro Ile Ser Phe Leu Ala Thr Phe Asn Lys
                275                 280

<210> SEQ ID NO 64
<211> LENGTH: 286
<212> TYPE: PRT
<213> ORGANISM: Hordeum vulgare
<220> FEATURE:
<221> NAME/KEY: misc_feature
<222> LOCATION: (1)..(286)
<223> OTHER INFORMATION: Public GI no. 445116

<400> SEQUENCE: 64

Met Ala Ser Ser Val Ala Ala Ala Ser Thr Phe Leu Gly Thr Arg
1               5                   10                  15

Leu Ala Asp Pro Arg Pro Gln Asn Gly Arg Ile Val Ala Arg Phe Gly
                20                  25                  30

Phe Gly Lys Lys Lys Ala Pro Lys Lys Ala Lys Ala Pro Pro Thr
            35                  40                  45

Thr Asp Arg Pro Leu Trp Phe Pro Gly Ala Gln Ala Pro Glu Tyr Leu
50                  55                  60

Asp Gly Thr Leu Val Gly Asp Tyr Gly Phe Asp Pro Phe Gly Leu Gly
65                  70                  75                  80

Lys Pro Ala Glu Tyr Leu Gln Tyr Asp Val Asp Ser Leu Asp Gln Asn
                85                  90                  95

Leu Ala Gln Asn Leu Ala Gly Glu Ile Ile Gly Thr Arg Phe Glu Asp
            100                 105                 110

Ala Asp Val Lys Ser Thr Pro Phe Gln Pro Tyr Ala Glu Val Phe Gly
                115                 120                 125

Leu Gln Arg Phe Arg Glu Cys Glu Leu Ile His Gly Arg Trp Ala Met
    130                 135                 140

Leu Ala Thr Leu Gly Ala Leu Thr Val Glu Trp Leu Thr Gly Val Thr
145                 150                 155                 160

Trp Gln Asp Ala Gly Lys Val Glu Leu Val Asp Gly Ser Ser Tyr Leu
                165                 170                 175

Gly Gln Pro Leu Pro Phe Thr Ile Thr Thr Leu Ile Trp Ile Glu Val
            180                 185                 190

Leu Val Ile Gly Tyr Ile Glu Phe Gln Arg Asn Ala Glu Leu Asp Pro
        195                 200                 205

Glu Arg Arg Leu Tyr Pro Gly Gly Ser Tyr Phe Asp Pro Leu Gly Leu
    210                 215                 220

Ala Ala Asp Pro Glu Lys Lys Glu Thr Leu Gln Leu Ala Glu Ile Lys
225                 230                 235                 240

His Ala Arg Leu Ala Met Val Ala Phe Leu Gly Phe Ala Val Gln Ala
                245                 250                 255

Ala Ala Thr Gly Lys Gly Arg Leu Asn Asn Trp Ala Thr His Leu Ser
            260                 265                 270
```

```
Asp Pro Leu His Thr Thr Ile Phe Asp Thr Phe Gly Ser Ser
        275                 280                 285
```

<210> SEQ ID NO 65
<211> LENGTH: 290
<212> TYPE: PRT
<213> ORGANISM: Vigna radiata
<220> FEATURE:
<221> NAME/KEY: misc_feature
<222> LOCATION: (1)..(290)
<223> OTHER INFORMATION: Public GI no. 4689382

<400> SEQUENCE: 65

```
Met Ala Thr Ala Thr Ala Thr Ala Ala Thr Ser Ser Phe Met Gly
1               5                   10                  15

Thr Arg Leu Leu Asp Ala His Ser Gly Ser Gly Arg Ile Gln Ala Arg
                20                  25                  30

Phe Gly Phe Gly Ser Lys Lys Lys Ala Ala Pro Lys Lys Val Ser Lys
            35                  40                  45

Gly Pro Ser Thr Asp Arg Pro Leu Trp Tyr Pro Gly Ala Lys Ala Pro
    50                  55                  60

Glu Trp Leu Asp Gly Ser Leu Val Gly Asp Tyr Gly Phe Asp Pro Phe
65                  70                  75                  80

Gly Leu Gly Lys Pro Ala Glu Tyr Leu Gln Phe Glu Leu Asp Ser Leu
                85                  90                  95

Asp Gln Asn Leu Ala Lys Asn Glu Ala Gly Ile Ile Ile Gly Thr Arg
                100                 105                 110

Thr Glu Val Ala Asp Val Lys Ser Thr Pro Phe Gln Pro Tyr Ser Glu
            115                 120                 125

Val Phe Gly Leu Gln Arg Phe Arg Glu Cys Glu Leu Ile His Gly Arg
    130                 135                 140

Trp Ala Met Leu Ala Thr Leu Gly Ala Leu Ser Val Glu Trp Leu Thr
145                 150                 155                 160

Gly Val Thr Trp Gln Asp Ala Gly Lys Val Glu Leu Val Glu Gly Ser
                165                 170                 175

Ser Tyr Leu Gly Gln Pro Leu Pro Phe Ser Ile Thr Thr Leu Ile Trp
                180                 185                 190

Ile Glu Val Leu Val Ile Gly Tyr Ile Glu Phe Gln Arg Asn Ala Glu
            195                 200                 205

Leu Asp Pro Glu Lys Arg Leu Tyr Pro Gly Gly Ser Tyr Phe Asp Pro
    210                 215                 220

Leu Gly Leu Ala Ser Asp Pro Glu Lys Lys Ala Thr Leu Gln Leu Ala
225                 230                 235                 240

Glu Ile Lys His Ala Arg Leu Ala Met Val Gly Phe Leu Gly Phe Ala
                245                 250                 255

Val Gln Ala Ala Ala Thr Gly Lys Gly Pro Leu Asn Asn Trp Ala Thr
                260                 265                 270

His Leu Ser Asp Pro Leu His Thr Thr Ile Ile Asp Thr Phe Ser Ser
            275                 280                 285

Ser Ser
290
```

<210> SEQ ID NO 66
<211> LENGTH: 286
<212> TYPE: PRT
<213> ORGANISM: Triticum aestivum
<220> FEATURE:
<221> NAME/KEY: misc_feature

```
<222> LOCATION: (1)..(286)
<223> OTHER INFORMATION: Ceres CLONE ID no. 1047963

<400> SEQUENCE: 66
```

Met Ala Ser Ser Val Ala Ala Ala Ser Thr Phe Leu Gly Thr Arg
1               5                   10                  15

Leu Ala Asp Pro Ala Pro Gln Asn Gly Arg Ile Val Ala Arg Phe Gly
            20                  25                  30

Phe Gly Lys Lys Lys Ala Pro Lys Ala Lys Ala Pro Pro Thr
        35                  40                  45

Thr Asp Arg Pro Leu Trp Phe Pro Gly Ala Gln Ala Pro Glu Tyr Leu
    50                  55                  60

Asp Gly Thr Leu Val Gly Asp Tyr Gly Phe Asp Pro Phe Gly Leu Gly
65              70                  75                  80

Lys Pro Ala Glu Tyr Leu Gln Tyr Asp Val Asp Ser Leu Asp Gln Asn
                85                  90                  95

Leu Ala Gln Asn Leu Ala Gly Glu Ile Ile Gly Thr Arg Phe Glu Asp
            100                 105                 110

Ala Asp Val Lys Ser Thr Pro Phe Gln Pro Tyr Ala Glu Val Phe Gly
            115                 120                 125

Leu Gln Arg Phe Arg Glu Cys Glu Leu Ile His Gly Arg Trp Xaa Met
130                 135                 140

Leu Ala Thr Leu Gly Ala Leu Thr Val Glu Trp Leu Thr Gly Val Thr
145                 150                 155                 160

Trp Gln Asp Ala Xaa Lys Val Glu Leu Val Asp Gly Ser Ser Tyr Leu
                165                 170                 175

Gly Gln Pro Leu Pro Phe Thr Leu Thr Thr Leu Ile Trp Ile Glu Val
            180                 185                 190

Leu Val Ile Gly Tyr Ile Glu Phe Gln Arg Asn Ala Glu Leu Asp Pro
        195                 200                 205

Glu Arg Arg Leu Tyr Pro Gly Gly Ser Tyr Phe Asp Pro Leu Gly Leu
    210                 215                 220

Ala Ala Asp Pro Val Lys Lys Glu Thr Leu Gln Leu Ala Glu Ile Lys
225                 230                 235                 240

His Ala Arg Leu Ala Met Val Ala Phe Leu Gly Phe Ala Val Gln Ala
                245                 250                 255

Ala Ala Thr Gly Lys Gly Pro Leu Asn Asn Trp Ala Thr His Leu Ser
            260                 265                 270

Asp Pro Leu His Thr Thr Ile Phe Asp Thr Phe Gly Ser Ser
        275                 280                 285

```
<210> SEQ ID NO 67
<211> LENGTH: 291
<212> TYPE: PRT
<213> ORGANISM: Zea mays
<220> FEATURE:
<221> NAME/KEY: misc_feature
<222> LOCATION: (1)..(291)
<223> OTHER INFORMATION: Ceres CLONE ID no. 299035

<400> SEQUENCE: 67
```

Met Ala Ser Ser Val Ala Ala Ala Ser Thr Phe Leu Gly Thr Arg
1               5                   10                  15

Leu Ala Asp Pro Ala Pro Gln Asn Gly Arg Ile Val Ala Arg Phe Gly
            20                  25                  30

Phe Gly Leu Gly Gly Lys Ala Lys Pro Ala Pro Lys Lys Val Ala Lys
        35                  40                  45

```
Thr Ser Thr Ser Ser Asp Arg Pro Leu Trp Phe Pro Gly Ala Val Ala
     50                  55                  60

Pro Asp Tyr Leu Asp Gly Ser Leu Val Gly Asp Tyr Gly Phe Asp Pro
 65                  70                  75                  80

Phe Gly Leu Gly Lys Pro Val Glu Tyr Leu Gln Phe Glu Leu Asp Ser
                 85                  90                  95

Leu Asp Gln Asn Leu Ala Lys Asn Glu Ala Gly Gly Ile Ile Gly Thr
            100                 105                 110

Arg Phe Glu Ser Ser Glu Val Lys Ser Thr Pro Leu Gln Pro Tyr Ser
        115                 120                 125

Glu Val Phe Gly Leu Gln Arg Phe Arg Glu Cys Glu Leu Ile His Gly
    130                 135                 140

Arg Trp Ala Met Leu Ala Thr Leu Gly Ala Leu Ser Val Glu Trp Leu
145                 150                 155                 160

Thr Gly Val Thr Trp Gln Asp Ala Gly Lys Val Glu Leu Val Asp Gly
                165                 170                 175

Ser Ser Tyr Leu Gly Gln Pro Leu Pro Phe Ser Ile Ser Thr Leu Ile
            180                 185                 190

Trp Ile Glu Val Leu Val Ile Gly Tyr Ile Glu Phe Gln Arg Asn Ala
        195                 200                 205

Glu Leu Asp Pro Glu Lys Arg Leu Tyr Pro Gly Gly Ser Tyr Phe Asp
    210                 215                 220

Pro Leu Gly Leu Ala Ala Asp Pro Glu Lys Lys Glu Arg Leu Gln Leu
225                 230                 235                 240

Ala Glu Ile Lys His Ala Arg Leu Ala Met Val Ala Phe Leu Gly Phe
                245                 250                 255

Ala Val Gln Ala Ala Ala Thr Gly Lys Gly Pro Leu Asn Asn Trp Ala
            260                 265                 270

Thr His Leu Ser Asp Pro Leu His Thr Thr Ile Phe Asp Thr Phe Gly
        275                 280                 285

Gly Ser Ser
    290

<210> SEQ ID NO 68
<211> LENGTH: 272
<212> TYPE: PRT
<213> ORGANISM: Populus balsamifera subsp. trichocarpa
<220> FEATURE:
<221> NAME/KEY: misc_feature
<222> LOCATION: (1)..(272)
<223> OTHER INFORMATION: Ceres GDNA ANNOT ID no. 1454179

<400> SEQUENCE: 68

Met Gly Thr Arg Leu Pro Asp Ile Tyr Ser Asn Ser Gly Arg Ile Gln
1               5                   10                  15

Ala Arg Phe Gly Phe Gly Gly Lys Lys Ala Pro Lys Lys Ser Ile Lys
            20                  25                  30

Pro Ser Thr Pro Asp Arg Pro Leu Trp Tyr Pro Gly Ala Lys Ala Pro
        35                  40                  45

Glu Tyr Leu Asp Gly Ser Leu Val Gly Asp Tyr Gly Phe Asp Pro Phe
    50                  55                  60

Gly Leu Gly Lys Pro Ala Glu Tyr Leu Gln Phe Glu Leu Asp Ser Leu
65                  70                  75                  80

Asp Gln Asn Leu Ala Lys Asn Leu Ala Gly Asp Ile Ile Gly Thr Arg
                85                  90                  95

Thr Glu Phe Ala Asp Val Lys Ser Thr Pro Phe Gln Pro Tyr Ser Glu
            100                 105                 110
```

-continued

```
Val Phe Gly Leu Gln Arg Phe Arg Glu Cys Glu Leu Ile His Gly Arg
            115                 120                 125

Trp Ala Met Leu Ala Thr Leu Gly Ala Leu Ser Val Glu Trp Leu Thr
    130                 135                 140

Gly Val Thr Trp Gln Asp Ala Gly Lys Val Glu Leu Val Glu Gly Ser
145                 150                 155                 160

Ser Tyr Leu Gly Gln Pro Leu Pro Phe Ser Ile Thr Ala Leu Ile Trp
                165                 170                 175

Ile Glu Ala Val Ile Ile Gly Tyr Ile Glu Phe Gln Arg Asn Ala Glu
            180                 185                 190

Leu Asp Pro Glu Lys Arg Leu Tyr Pro Gly Gly Gln Phe Asp Pro
            195                 200                 205

Leu Gly Leu Ala Ser Asp Pro Glu Lys Lys Ala Thr Leu Gln Leu Ala
            210                 215                 220

Glu Ile Lys His Ala Arg Leu Ala Met Val Ala Phe Leu Gly Phe Ala
225                 230                 235                 240

Val Gln Ala Trp Val Thr Gly Lys Gly Pro Leu Asn Asn Trp Ala Thr
                245                 250                 255

His Leu Ser Asp Pro Leu His Thr Thr Ile Ile Asp Asn Leu Ser Ser
            260                 265                 270

<210> SEQ ID NO 69
<211> LENGTH: 290
<212> TYPE: PRT
<213> ORGANISM: Oryza sativa subsp. japonica
<220> FEATURE:
<221> NAME/KEY: misc_feature
<222> LOCATION: (1)..(290)
<223> OTHER INFORMATION: Public GI no. 51978982

<400> SEQUENCE: 69

Met Ala Ser Ser Val Ala Ala Ala Ser Thr Phe Leu Gly Thr Arg
1               5                   10                  15

Leu Ala Asp Pro Ala Pro Gln Ser Gly Arg Ile Val Ala Arg Phe Gly
            20                  25                  30

Phe Gly Gly Gly Lys Lys Ala Ala Lys Lys Ala Ala Arg Pro Ser
        35                  40                  45

Ala Pro Thr Thr Asp Arg Pro Leu Trp Phe Pro Gly Ala Val Ala Pro
    50                  55                  60

Asp Tyr Leu Asp Gly Ser Leu Val Gly Asp Tyr Gly Phe Asp Pro Phe
65                  70                  75                  80

Gly Leu Gly Lys Pro Ala Glu Tyr Leu Gln Phe Glu Leu Asp Ser Leu
                85                  90                  95

Asp Gln Asn Leu Ala Lys Asn Asn Ala Gly Glu Ile Ile Gly Thr Arg
            100                 105                 110

Phe Glu Thr Gly Glu Val Lys Ser Thr Pro Phe Gln Pro Tyr Thr Glu
        115                 120                 125

Val Phe Gly Leu Gln Arg Phe Arg Glu Cys Glu Leu Ile His Gly Arg
    130                 135                 140

Trp Ala Met Leu Ala Thr Leu Gly Ala Leu Ser Val Glu Trp Leu Thr
145                 150                 155                 160

Gly Val Thr Trp Gln Asp Ala Gly Lys Val Glu Leu Val Asp Gly Ser
                165                 170                 175

Ser Tyr Leu Gly Gln Pro Leu Pro Phe Ser Ile Ser Thr Leu Ile Trp
            180                 185                 190

Ile Glu Val Leu Val Ile Gly Tyr Ile Glu Phe Gln Arg Asn Ala Glu
```

-continued

```
                195                 200                 205
Leu Asp Pro Glu Lys Arg Leu Tyr Pro Gly Ser Tyr Phe Asp Pro
210                 215                 220

Leu Gly Leu Ala Ser Asp Pro Glu Lys Lys Glu Arg Leu Gln Leu Ala
225                 230                 235                 240

Glu Ile Lys His Ala Arg Leu Ala Met Val Ala Phe Leu Gly Phe Ala
                245                 250                 255

Val Gln Ala Ala Ala Thr Gly Lys Gly Pro Leu Asn Asn Trp Ala Thr
                260                 265                 270

His Leu Ser Asp Pro Leu His Thr Thr Ile Phe Asp Thr Phe Ser Ser
                275                 280                 285

Ser Ser
    290

<210> SEQ ID NO 70
<211> LENGTH: 275
<212> TYPE: PRT
<213> ORGANISM: Arabidopsis thalia
<220> FEATURE:
<221> NAME/KEY: misc_feature
<222> LOCATION: (1)..(275)
<223> OTHER INFORMATION: Ceres CLONE ID no.26369
<220> FEATURE:
<221> NAME/KEY: misc_feature
<222> LOCATION: (1)..(275)
<223> OTHER INFORMATION: Also Known As Ceres CDNA ID no. 36516078
<220> FEATURE:
<221> NAME/KEY: misc_feature
<222> LOCATION: (1)..(162)
<223> OTHER INFORMATION: Also Known as Lead 95
<220> FEATURE:
<221> NAME/KEY: misc_feature
<222> LOCATION: (63)..(260)
<223> OTHER INFORMATION: Pfam Name: Chloroa_b-bind; Pfam Description:
      Chlorophyll A-B binding protein

<400> SEQUENCE: 70

Met Ala Thr Thr Thr Ala Ala Ala Ala Gly Ile Phe Gly Ile Arg Ile
1               5                   10                  15

Gln Asp Pro Arg Pro Gly Thr Gly Arg Val Gln Ala Arg Phe Gly Phe
                20                  25                  30

Ser Phe Gly Lys Lys Lys Pro Ala Pro Pro Lys Lys Ser Arg Gln
            35                  40                  45

Val Gln Asp Asp Gly Asp Arg Leu Val Trp Phe Pro Gly Ala Asn Pro
50                  55                  60

Pro Glu Trp Leu Asp Gly Ser Met Ile Gly Asp Arg Gly Phe Asp Pro
65                  70                  75                  80

Phe Gly Leu Gly Lys Pro Ala Glu Tyr Leu Gln Tyr Asp Phe Asp Gly
                85                  90                  95

Leu Asp Gln Asn Leu Ala Lys Asn Val Ala Gly Asp Ile Ile Gly Ile
                100                 105                 110

Ile Gln Glu Ser Ser Glu Ile Lys Pro Thr Pro Phe Gln Pro Tyr Thr
            115                 120                 125

Glu Val Phe Gly Ile Gln Arg Phe Arg Glu Cys Glu Leu Ile His Gly
            130                 135                 140

Arg Trp Ala Met Leu Gly Thr Leu Gly Ala Ile Ala Val Glu Ala Leu
145                 150                 155                 160

Thr Gly Ile Ala Trp Gln Asp Ala Gly Lys Val Glu Leu Val Glu Gly
                165                 170                 175

Ser Ser Tyr Leu Gly Gln Pro Leu Pro Phe Ser Leu Thr Thr Leu Ile
                180                 185                 190
```

Trp Ile Glu Val Leu Val Val Gly Tyr Ile Glu Leu Gln Arg Asn Ser
            195                 200                 205

Glu Leu Asp Pro Glu Lys Arg Ile Tyr Pro Gly Gly Tyr Phe Asp Pro
        210                 215                 220

Leu Gly Leu Ala Ala Asp Pro Gly Lys Leu Asp Thr Leu Lys Leu Ala
225                 230                 235                 240

Glu Ile Lys His Ser Arg Leu Ala Met Val Ala Phe Leu Ile Phe Ala
                245                 250                 255

Leu Gln Ala Ala Phe Thr Gly Lys Gly Pro Val Ser Phe Leu Ala Thr
        260                 265                 270

Phe Asn Asn
        275

<210> SEQ ID NO 71
<211> LENGTH: 1003
<212> TYPE: DNA
<213> ORGANISM: Arabidopsis thalia
<220> FEATURE:
<221> NAME/KEY: misc_feature
<222> LOCATION: (1)..(1003)
<223> OTHER INFORMATION: Ceres CLONE ID no 26369
<220> FEATURE:
<221> NAME/KEY: misc_feature
<222> LOCATION: (1)..(1003)
<223> OTHER INFORMATION: Also Known As Ceres CDNA ID no. 36516078
<220> FEATURE:
<221> NAME/KEY: misc_feature
<222> LOCATION: (1)..(1003)
<223> OTHER INFORMATION: Also Known as Lead 95
<220> FEATURE:
<221> NAME/KEY: misc_feature
<222> LOCATION: (76)..(904)
<223> OTHER INFORMATION: REFERENCED BY SEQ ID NO: 72

<400> SEQUENCE: 71
attctaaaat ccaaaaaaac tatatgttat aacattggaa tcatcagtct ctaagcagta        60
tcacaccaac tcaatatggc taccaccact gcagcagcag cctcaggtat ttttgggatc       120
cggattcaag atcctagacc tggaaccggt agggtccaag cccggttcgg gttcagtttc       180
ggaaaaaaga aaccggctcc accgccaaag aaatcaaggc aggtccaaga cgatggagac       240
agactagttt ggttccccgg cgcaaacccg ccggaatggt tggacggatc gatgatcgga       300
gaccgtggat ttgatccgtt tggtttaggt aaaccggctg agtatcttca gtacgatttc       360
gatggacttg accaaaacct tgccaagaac gtggcgggtg acatcatcgg gatcatccaa       420
gaatcttcgg agatcaaacc gacgccgttt cagccgtaca ctgaagtctt tgggatccaa       480
cggttcagag aatgtgagct gatccatgga aggtgggcca tgcttggcac tctaggcgcc       540
atcgccgtag aggctcttac aggaattgca tggcaagacg ccggaaaggt ggaattggtg       600
gaaggatcat cgtatttggg acaaccattg ccgttctcgt tgacgacgtt gatatggata       660
gaagtgttag tggtcggata cattgagttc caacgtaact ctgaactgga tccagagaaa       720
cggatttacc cggtgggta ttttgacccg ttgggactcg cggctgatcc agagaagttg       780
gatactttga agctggctga gataaagcac tctcgtctcg ctatggtcgc atttctcatc       840
tttgctcttc aggcggcctt taccggcaaa ggccctgtca gcttccttgc cacctttaac       900
aattagttaa tgaacctttc tatctttatt ttatcaaaat aaaattatac ttcaaaaact       960
gtataatgca tgttacgcta tacttataaa gaagtctttt att                       1003

<210> SEQ ID NO 72
<211> LENGTH: 276

-continued

```
<212> TYPE: PRT
<213> ORGANISM: Arabidopsis thaliana
<220> FEATURE:
<221> NAME/KEY: misc_feature
<222> LOCATION: (1)..(276)
<223> OTHER INFORMATION: Public GI no. 21594018
<220> FEATURE:
<221> NAME/KEY: misc_feature
<222> LOCATION: (95)..(95)
<223> OTHER INFORMATION: Xaa is any aa, unknown, or other
<220> FEATURE:
<221> NAME/KEY: misc_feature
<222> LOCATION: (96)..(96)
<223> OTHER INFORMATION: Xaa is any aa, unknown, or other

<400> SEQUENCE: 72

Met Ala Thr Thr Thr Ala Ala Ala Ser Gly Ile Phe Gly Ile Arg
1               5                   10                  15

Ile Gln Asp Pro Arg Pro Gly Thr Gly Arg Val Gln Ala Arg Phe Gly
                20                  25                  30

Phe Ser Phe Gly Lys Lys Lys Pro Ala Pro Pro Lys Lys Ser Arg
        35                  40                  45

Gln Val Gln Asp Asp Gly Asp Arg Leu Val Trp Phe Pro Gly Ala Asn
50                  55                      60

Pro Pro Glu Trp Leu Asp Gly Ser Met Ile Gly Asp Arg Gly Phe Asp
65              70                  75                  80

Pro Phe Gly Leu Gly Lys Pro Ala Glu Tyr Leu Gln Tyr Asp Xaa Xaa
                85                  90                  95

Gly Leu Asp Gln Asn Leu Ala Lys Asn Val Ala Gly Asp Ile Ile Gly
                100                 105                 110

Ile Ile Gln Glu Ser Ser Glu Ile Lys Pro Thr Pro Phe Gln Pro Tyr
        115                 120                 125

Thr Glu Val Phe Gly Ile Gln Arg Phe Arg Glu Cys Glu Leu Ile His
130                 135                 140

Gly Arg Trp Ala Met Leu Gly Thr Leu Gly Ala Ile Ala Val Glu Ala
145                 150                 155                 160

Leu Thr Gly Ile Ala Trp Gln Asp Ala Gly Lys Val Glu Leu Val Glu
                165                 170                 175

Gly Ser Ser Tyr Leu Gly Gln Pro Leu Pro Phe Ser Leu Thr Thr Leu
            180                 185                 190

Ile Trp Ile Glu Val Leu Val Val Gly Tyr Ile Glu Phe Gln Arg Asn
        195                 200                 205

Ser Glu Leu Asp Pro Glu Lys Arg Ile Tyr Pro Gly Gly Tyr Phe Asp
    210                 215                 220

Pro Leu Gly Leu Ala Ala Asp Pro Glu Lys Leu Asp Thr Leu Lys Leu
225                 230                 235                 240

Ala Glu Ile Lys His Ser Arg Leu Ala Met Val Ala Phe Leu Ile Phe
                245                 250                 255

Ala Leu Gln Ala Ala Phe Thr Gly Lys Gly Pro Val Ser Phe Leu Ala
                260                 265                 270

Thr Phe Asn Asn
        275

<210> SEQ ID NO 73
<211> LENGTH: 204
<212> TYPE: PRT
<213> ORGANISM: Zea mays
<220> FEATURE:
<221> NAME/KEY: misc_feature
<222> LOCATION: (1)..(204)
<223> OTHER INFORMATION: Ceres CLONE ID no. 1376662
```

<400> SEQUENCE: 73

Met Ile Gly Asp Arg Gly Phe Asp Pro Phe Gly Leu Gly Lys Pro Ala
1               5                   10                  15

Glu Tyr Leu Gln Tyr Asp Phe Asp Gly Leu Asp Gln Asn Leu Ala Lys
            20                  25                  30

Asn Val Ala Gly Gly Leu Leu Gly Val Arg Gln Glu Ser Lys Glu Ile
        35                  40                  45

Asn Pro Thr Pro Phe Gln Pro Tyr Thr Glu Val Phe Gly Ile Glu Arg
    50                  55                  60

Phe Arg Glu Cys Glu Leu Ile His Gly Arg Trp Ala Met Leu Gly Thr
65                  70                  75                  80

Leu Gly Ala Leu Ala Val Glu Gly Leu Thr Gly Ile Ala Trp Gln Asp
                85                  90                  95

Ala Gly Lys Val Glu Leu Val Glu Gly Ser Ser Tyr Leu Gly Gln Pro
            100                 105                 110

Leu Pro Phe Ser Leu Thr Thr Leu Ile Trp Ile Glu Val Leu Val Val
        115                 120                 125

Gly Tyr Ile Glu Phe Gln Arg Asn Ala Glu Leu Asp Pro Glu Lys Arg
    130                 135                 140

Ile Tyr Pro Gly Gly Tyr Phe Asp Pro Leu Gly Leu Gly Ser Asp Pro
145                 150                 155                 160

Glu Lys Leu Asp Thr Leu Lys Leu Ala Glu Ile Lys His Ser Arg Leu
                165                 170                 175

Ala Met Ile Ala Phe Leu Ile Phe Ser Leu Gln Ala Ala Phe Thr Gly
            180                 185                 190

Lys Gly Pro Ile Ser Phe Leu Ala Thr Phe Ser Ser
        195                 200

<210> SEQ ID NO 74
<211> LENGTH: 276
<212> TYPE: PRT
<213> ORGANISM: Brassica napus
<220> FEATURE:
<221> NAME/KEY: misc_feature
<222> LOCATION: (1)..(276)
<223> OTHER INFORMATION: Ceres CLONE ID no. 963170

<400> SEQUENCE: 74

Met Ala Thr Thr Ala Ala Ala Ala Ser Gly Ile Phe Gly Ile Arg
1               5                   10                  15

Ile Gln Asp Pro Ser Ser Gly Ala Gly Arg Val Gln Ala Lys Phe Asn
            20                  25                  30

Phe Ser Phe Gly Lys Lys Lys Pro Ala Pro Pro Lys Lys Thr Lys
        35                  40                  45

Gln Ile Gln Asn Asp Gly Asp Arg Leu Val Trp Phe Pro Gly Ala Asn
    50                  55                  60

Pro Pro Glu Trp Leu Asp Gly Ser Met Ile Gly Asp Arg Gly Phe Asp
65                  70                  75                  80

Pro Phe Gly Leu Gly Lys Pro Ala Glu Tyr Leu Gln Tyr Asp Phe Asp
                85                  90                  95

Gly Leu Asp Gln Asn Leu Ala Lys Asn Val Ala Gly Leu Leu Gly
            100                 105                 110

Val Arg Gln Glu Ser Lys Glu Ile Asn Pro Thr Pro Phe Gln Pro Tyr
        115                 120                 125

Thr Glu Met Phe Gly Ile Glu Arg Phe Arg Glu Cys Glu Leu Ile His
    130                 135                 140

```
Gly Arg Trp Ala Met Leu Gly Thr Leu Gly Ala Leu Ala Val Glu Gly
145                 150                 155                 160

Leu Thr Gly Ile Ala Trp Gln Asp Ala Gly Lys Val Glu Leu Val Glu
                165                 170                 175

Gly Ser Ser Tyr Leu Gly Gln Pro Leu Pro Phe Ser Leu Thr Thr Leu
            180                 185                 190

Ile Trp Ile Glu Val Leu Val Val Gly Tyr Ile Glu Phe Gln Arg Asn
        195                 200                 205

Ala Glu Leu Asp Pro Glu Lys Arg Ile Tyr Pro Gly Gly Tyr Phe Asp
    210                 215                 220

Pro Leu Gly Leu Gly Ser Asp Pro Glu Lys Leu Asp Thr Leu Lys Leu
225                 230                 235                 240

Ala Glu Ile Lys His Ser Arg Leu Ala Met Ile Ala Phe Leu Ile Phe
                245                 250                 255

Ser Leu Gln Ala Ala Phe Thr Gly Lys Gly Pro Ile Ser Phe Leu Ala
            260                 265                 270

Thr Phe Ser Ser
        275
```

<210> SEQ ID NO 75
<211> LENGTH: 69
<212> TYPE: PRT
<213> ORGANISM: Brassica napus
<220> FEATURE:
<221> NAME/KEY: misc_feature
<222> LOCATION: (1)..(69)
<223> OTHER INFORMATION: Ceres CLONE ID no. 1309581

<400> SEQUENCE: 75

```
Met Ala Thr Thr Thr Ala Ala Ala Ser Gly Ile Phe Gly Ile Arg
1               5                   10                  15

Ile Gln Asp Pro Ser Ser Gly Ala Gly Arg Val Gln Ala Lys Phe Asn
        20                  25                  30

Phe Ser Phe Gly Lys Lys Lys Pro Ala Pro Pro Lys Lys Asn Glu
            35                  40                  45

Ala Gly Pro Lys Arg Arg Arg Pro Ala Cys Leu Val Pro Arg Arg Lys
    50                  55                  60

Pro Ala Gly Met Gly
65
```

<210> SEQ ID NO 76
<211> LENGTH: 204
<212> TYPE: PRT
<213> ORGANISM: Populus balsamifera subsp. trichocarpa
<220> FEATURE:
<221> NAME/KEY: misc_feature
<222> LOCATION: (1)..(204)
<223> OTHER INFORMATION: 1511507

<400> SEQUENCE: 76

```
Met Val Gly Asp Arg Gly Phe Asp Pro Phe Ala Leu Gly Lys Pro Ala
1               5                   10                  15

Glu Tyr Leu Gln Phe Asp Leu Asp Ser Leu Asp Gln Asn Leu Ala Lys
            20                  25                  30

Asn Leu Ala Gly Asp Val Ile Gly Val Arg Val Asp Ala Thr Glu Val
        35                  40                  45

Lys Pro Thr Pro Phe Gln Pro Tyr Ser Glu Val Phe Gly Leu Gln Arg
    50                  55                  60

Phe Arg Glu Cys Glu Leu Ile His Gly Arg Trp Ala Met Leu Gly Thr
```

```
                65                  70                  75                  80
Leu Gly Ala Ile Ala Val Glu Ala Leu Thr Gly Val Ala Trp Gln Asp
                    85                  90                  95

Ala Gly Lys Val Glu Leu Ile Glu Gly Ser Ser Tyr Leu Gly Gln Pro
                100                 105                 110

Leu Pro Phe Ser Leu Thr Thr Leu Ile Trp Ile Glu Val Ile Val Val
            115                 120                 125

Gly Tyr Ile Glu Phe Gln Arg Asn Ala Glu Leu Asp Pro Glu Lys Arg
        130                 135                 140

Leu Tyr Pro Gly Gly Tyr Phe Asp Pro Leu Gly Leu Ala Ser Asp Pro
145                 150                 155                 160

Glu Lys Ile Glu Asn Leu Gln Leu Ala Glu Ile Lys His Ala Arg Leu
                165                 170                 175

Ala Met Val Ala Phe Leu Ile Phe Gly Ile Gln Ala Ala Phe Thr Gly
                180                 185                 190

Lys Gly Pro Ile Ser Phe Val Ala Thr Phe Asn Asn
            195                 200

<210> SEQ ID NO 77
<211> LENGTH: 228
<212> TYPE: PRT
<213> ORGANISM: Oryza sativa subsp. indica
<220> FEATURE:
<221> NAME/KEY: misc_feature
<222> LOCATION: (1)..(228)
<223> OTHER INFORMATION: Ceres GDNA ANNOT ID no. 1458261

<400> SEQUENCE: 77

Met Val Gly Asp Arg Gly Phe Asp Pro Phe Ala Leu Gly Lys Pro Ala
1               5                   10                  15

Glu Tyr Leu Gln Phe Asp Leu Asp Ser Leu Asp Gln Asn Leu Ala Lys
                20                  25                  30

Asn Leu Ala Gly Asp Val Ile Gly Val Arg Val Asp Ala Thr Glu Val
            35                  40                  45

Lys Pro Thr Pro Phe Gln Pro Tyr Ser Glu Val Phe Gly Leu Gln Arg
        50                  55                  60

Phe Arg Glu Cys Glu Leu Ile His Gly Arg Trp Ala Met Leu Gly Thr
65                  70                  75                  80

Leu Gly Ala Ile Ala Val Glu Ala Leu Thr Gly Val Ala Trp Gln Asp
                    85                  90                  95

Ala Gly Lys Ser Leu Asp Asn Gln Ala Val Thr Ser Ser Ser Leu Thr
                100                 105                 110

Ile Ser Ile Tyr Leu Ile Lys Ile Lys His Lys Val Glu Leu Ile Glu
            115                 120                 125

Gly Ser Ser Tyr Leu Gly Gln Pro Leu Pro Phe Ser Leu Thr Thr Leu
        130                 135                 140

Ile Trp Ile Glu Val Ile Val Val Gly Tyr Ile Glu Phe Gln Arg Asn
145                 150                 155                 160

Ala Glu Leu Asp Pro Glu Lys Arg Leu Tyr Pro Gly Gly Tyr Phe Asp
                165                 170                 175

Pro Leu Gly Leu Ala Ser Asp Pro Glu Lys Ile Glu Asn Leu Gln Leu
            180                 185                 190

Ala Glu Ile Lys His Ala Arg Leu Ala Met Val Ala Phe Leu Ile Phe
        195                 200                 205

Gly Ile Gln Ala Ala Phe Thr Gly Lys Gly Pro Ile Ser Phe Val Ala
    210                 215                 220
```

Thr Phe Asn Asn
225

<210> SEQ ID NO 78
<211> LENGTH: 107
<212> TYPE: PRT
<213> ORGANISM: Arabidopsis thaliana
<220> FEATURE:
<221> NAME/KEY: misc_feature
<222> LOCATION: (1)..(107)
<223> OTHER INFORMATION: Ceres CLONE ID no. 1333427
<220> FEATURE:
<221> NAME/KEY: misc_feature
<222> LOCATION: (100)..(100)
<223> OTHER INFORMATION: Xaa is any aa, unknown, or other

<400> SEQUENCE: 78

Met Gly Thr Arg Val Val Ser Asp Ile Ser Ser Asn Ser Ser Arg Phe
1               5                   10                  15

Thr Ala Arg Phe Gly Phe Gly Thr Lys Lys Ala Ser Pro Lys Lys Ala
            20                  25                  30

Lys Thr Val Ile Ser Glu Leu Val Asp Gly Ser Ser Tyr Leu Gly Gln
        35                  40                  45

Xaa Leu Pro Phe Ser Ile Ser Thr Leu Ile Trp Ile Glu Val Leu Val
50                  55                  60

Val Gly Tyr Ile Glu Phe Gln Arg Asn Ala Glu Leu Asp Ser Glu Lys
65                  70                  75                  80

Arg Leu Tyr Pro Gly Gly Lys Phe Phe Asp Pro Leu Gly Leu Ala Ser
                85                  90                  95

Asp Pro Gly Xaa Lys Gly Ser Ala Ser Ala Ser
            100                 105

<210> SEQ ID NO 79
<211> LENGTH: 129
<212> TYPE: PRT
<213> ORGANISM: Glycine max
<220> FEATURE:
<221> NAME/KEY: misc_feature
<222> LOCATION: (1)..(129)
<223> OTHER INFORMATION: Ceres CLONE ID no. 519218

<400> SEQUENCE: 79

Met Asn Leu Val Phe Asp Phe Xaa Val Glu Leu Val Glu Gly Ser Ser
1               5                   10                  15

Tyr Leu Gly Gln Pro Leu Pro Phe Ser Ile Thr Thr Leu Ile Trp Ile
            20                  25                  30

Glu Val Leu Val Ile Gly Tyr Ile Glu Phe Gln Arg Asn Ala Glu Leu
        35                  40                  45

Asp Pro Glu Lys Arg Leu Tyr Pro Gly Gly Ser Tyr Phe Asp Pro Leu
50                  55                  60

Gly Leu Ala Ser Asp Pro Glu Lys Lys Ala Thr Leu Gln Leu Ala Glu
65                  70                  75                  80

Ile Lys His Ala Arg Leu Ala Met Val Gly Phe Leu Gly Phe Ala Val
                85                  90                  95

Gln Ala Ala Ala Thr Gly Lys Gly Pro Leu Asn Asn Trp Ala Thr His
            100                 105                 110

Leu Ser Asp Pro Leu His Thr Thr Ile Ile Asp Thr Phe Ser Ser Ser
            115                 120                 125

Ser

<210> SEQ ID NO 80

```
<211> LENGTH: 142
<212> TYPE: PRT
<213> ORGANISM: Populus balsamifera subsp. trichocarpa
<220> FEATURE:
<221> NAME/KEY: misc_feature
<222> LOCATION: (1)..(142)
<223> OTHER INFORMATION: Ceres GDNA 1475895

<400> SEQUENCE: 80
```

Met Leu Ala Thr Leu Gly Ala Leu Ser Val Glu Trp Leu Thr Gly Val
1               5                   10                  15

Thr Trp Gln Asp Ala Gly Lys Val Glu Leu Val Glu Gly Ser Ser Tyr
            20                  25                  30

Leu Gly Gln Pro Leu Pro Phe Ser Ile Thr Thr Leu Ile Leu Ile Glu
        35                  40                  45

Val Leu Val Ile Gly Tyr Ile Glu Phe Gln Arg Asn Ala Glu Leu Asp
50                  55                  60

Pro Glu Lys Arg Leu Tyr Pro Gly Gly Asn Phe Phe Asp Pro Leu Gly
65                  70                  75                  80

Leu Ala Ala Asp Pro Glu Lys Lys Ala Thr Leu Gln Leu Ala Glu Ile
                85                  90                  95

Lys His Ala Arg Leu Ala Met Val Ala Phe Leu Gly Phe Ala Val Gln
            100                 105                 110

Ala Trp Val Thr Gly Lys Gly Pro Leu Asn Asn Trp Ala Thr His Leu
        115                 120                 125

Ser Asp Pro Leu His Thr Thr Ile Ile Asp Thr Leu Ser Ser
    130                 135                 140

```
<210> SEQ ID NO 81
<211> LENGTH: 282
<212> TYPE: PRT
<213> ORGANISM: Glycine max
<220> FEATURE:
<221> NAME/KEY: misc_feature
<222> LOCATION: (1)..(282)
<223> OTHER INFORMATION: Ceres CLONE ID no. 481415
<220> FEATURE:
<221> NAME/KEY: misc_feature
<222> LOCATION: (200)..(200)
<223> OTHER INFORMATION: Xaa is any aa, unknown, or other
<220> FEATURE:
<221> NAME/KEY: misc_feature
<222> LOCATION: (203)..(203)
<223> OTHER INFORMATION: Xaa is any aa, unknown, or other
<220> FEATURE:
<221> NAME/KEY: misc_feature
<222> LOCATION: (209)..(209)
<223> OTHER INFORMATION: Xaa is any aa, unknown, or other
<220> FEATURE:
<221> NAME/KEY: misc_feature
<222> LOCATION: (211)..(211)
<223> OTHER INFORMATION: Xaa is any aa, unknown, or other

<400> SEQUENCE: 81
```

Met Ala Thr Ala Thr Ala Ala Ala Thr Ser Tyr Phe Phe Gly Thr
1               5                   10                  15

Arg Leu Asn Asn Val Asn Thr Thr Thr Leu Asn Asn Gly Arg Phe His
            20                  25                  30

Ala Leu Leu Asn Phe Gly Lys Lys Lys Thr Ala Pro Gln Pro Pro Pro
        35                  40                  45

Lys Lys Lys Glu Val Lys Val Lys Pro Ser Gly Asp Arg Leu Val Trp
50                  55                  60

Phe Pro Asn Ala Glu Pro Pro Glu Trp Leu Asp Gly Ser Met Ile Gly
65                  70                  75                  80

```
Asp Arg Gly Phe Asp Pro Gly Phe Ala Lys Pro Ala Glu Tyr Leu
            85                  90                  95

Gln Phe Asp Leu Asp Ser Leu Asp Gln Asn Leu Ala Lys Asn Ile Ala
            100                 105                 110

Gly Asp Val Ile Gly Thr Arg Val Glu Val Ala Glu Val Lys Pro Thr
            115                 120                 125

Pro Phe Gln Pro Tyr Ser Glu Val Phe Gly Ile Gln Arg Phe Arg Glu
            130                 135                 140

Cys Glu Leu Ile His Gly Arg Trp Ala Met Leu Gly Ser Leu Gly Ala
145                 150                 155                 160

Leu Ala Val Glu Ala Leu Thr Gly Val Ala Trp Gln Asp Ala Gly Lys
            165                 170                 175

Val Glu Leu Val Glu Gly Ser Ser Tyr Leu Gly Leu Pro Leu Pro Phe
            180                 185                 190

Ser Leu Thr Thr Leu Ile Trp Xaa Glu Val Xaa Val Ile Gly Tyr Ile
            195                 200                 205

Xaa Phe Xaa Arg Asn Ala Glu Leu Asp Pro Glu Lys Arg Leu Tyr Pro
            210                 215                 220

Gly Gly Arg Phe Asp Pro Leu Gly Leu Ala Asn Asp Pro Glu Glu
225                 230                 235                 240

Lys Ala Arg Leu Gln Leu Ala Glu Ile Lys His Ser Arg Leu Ala Met
            245                 250                 255

Val Val Phe Leu Ile Phe Ala Ile Gln Ala Ala Val Thr Gly Lys Gly
            260                 265                 270

Pro Ile Ser Phe Leu Ala Thr Phe Asn Lys
            275                 280

<210> SEQ ID NO 82
<211> LENGTH: 286
<212> TYPE: PRT
<213> ORGANISM: Hordeum vulgare
<220> FEATURE:
<221> NAME/KEY: misc_feature
<222> LOCATION: (1)..(286)
<223> OTHER INFORMATION: Public GI no. 445116

<400> SEQUENCE: 82

Met Ala Ser Ser Val Ala Ala Ala Ser Thr Phe Leu Gly Thr Arg
1               5                   10                  15

Leu Ala Asp Pro Arg Pro Gln Asn Gly Arg Ile Val Ala Arg Phe Gly
            20                  25                  30

Phe Gly Lys Lys Lys Ala Pro Lys Lys Ala Lys Ala Pro Pro Thr
            35                  40                  45

Thr Asp Arg Pro Leu Trp Phe Pro Gly Ala Gln Ala Pro Glu Tyr Leu
            50                  55                  60

Asp Gly Thr Leu Val Gly Asp Tyr Gly Phe Asp Pro Phe Gly Leu Gly
65                  70                  75                  80

Lys Pro Ala Glu Tyr Leu Gln Tyr Asp Val Asp Ser Leu Asp Gln Asn
            85                  90                  95

Leu Ala Gln Asn Leu Ala Gly Glu Ile Ile Gly Thr Arg Phe Glu Asp
            100                 105                 110

Ala Asp Val Lys Ser Thr Pro Phe Gln Pro Tyr Ala Glu Val Phe Gly
            115                 120                 125

Leu Gln Arg Phe Arg Glu Cys Glu Leu Ile His Gly Arg Trp Ala Met
            130                 135                 140

Leu Ala Thr Leu Gly Ala Leu Thr Val Glu Trp Leu Thr Gly Val Thr
145                 150                 155                 160
```

```
Trp Gln Asp Ala Gly Lys Val Glu Leu Val Asp Gly Ser Ser Tyr Leu
                165                 170                 175
Gly Gln Pro Leu Pro Phe Thr Ile Thr Thr Leu Ile Trp Ile Glu Val
            180                 185                 190
Leu Val Ile Gly Tyr Ile Glu Phe Gln Arg Asn Ala Glu Leu Asp Pro
        195                 200                 205
Glu Arg Arg Leu Tyr Pro Gly Gly Ser Tyr Phe Asp Pro Leu Gly Leu
210                 215                 220
Ala Ala Asp Pro Glu Lys Lys Glu Thr Leu Gln Leu Ala Glu Ile Lys
225                 230                 235                 240
His Ala Arg Leu Ala Met Val Ala Phe Leu Gly Phe Ala Val Gln Ala
                245                 250                 255
Ala Ala Thr Gly Lys Gly Arg Leu Asn Asn Trp Ala Thr His Leu Ser
                260                 265                 270
Asp Pro Leu His Thr Thr Ile Phe Asp Thr Phe Gly Ser Ser
                275                 280                 285

<210> SEQ ID NO 83
<211> LENGTH: 290
<212> TYPE: PRT
<213> ORGANISM: Vigna radiata
<220> FEATURE:
<221> NAME/KEY: misc_feature
<222> LOCATION: (1)..(290)
<223> OTHER INFORMATION: Public GI no. 4689382

<400> SEQUENCE: 83

Met Ala Thr Ala Thr Ala Thr Ala Ala Thr Ser Ser Phe Met Gly
1               5                   10                  15
Thr Arg Leu Leu Asp Ala His Ser Gly Ser Gly Arg Ile Gln Ala Arg
                20                  25                  30
Phe Gly Phe Gly Ser Lys Lys Lys Ala Ala Pro Lys Lys Val Ser Lys
            35                  40                  45
Gly Pro Ser Thr Asp Arg Pro Leu Trp Tyr Pro Gly Ala Lys Ala Pro
        50                  55                  60
Glu Trp Leu Asp Gly Ser Leu Val Gly Asp Tyr Gly Phe Asp Pro Phe
65                  70                  75                  80
Gly Leu Gly Lys Pro Ala Glu Tyr Leu Gln Phe Glu Leu Asp Ser Leu
                85                  90                  95
Asp Gln Asn Leu Ala Lys Asn Glu Ala Gly Ile Ile Ile Gly Thr Arg
                100                 105                 110
Thr Glu Val Ala Asp Val Lys Ser Thr Pro Phe Gln Pro Tyr Ser Glu
            115                 120                 125
Val Phe Gly Leu Gln Arg Phe Arg Glu Cys Glu Leu Ile His Gly Arg
        130                 135                 140
Trp Ala Met Leu Ala Thr Leu Gly Ala Leu Ser Val Glu Trp Leu Thr
145                 150                 155                 160
Gly Val Thr Trp Gln Asp Ala Gly Lys Val Glu Leu Val Glu Gly Ser
                165                 170                 175
Ser Tyr Leu Gly Gln Pro Leu Pro Phe Ser Ile Thr Thr Leu Ile Trp
                180                 185                 190
Ile Glu Val Leu Val Ile Gly Tyr Ile Glu Phe Gln Arg Asn Ala Glu
            195                 200                 205
Leu Asp Pro Glu Lys Arg Leu Tyr Pro Gly Gly Ser Tyr Phe Asp Pro
        210                 215                 220
Leu Gly Leu Ala Ser Asp Pro Glu Lys Lys Ala Thr Leu Gln Leu Ala
```

```
225                 230                 235                 240
Glu Ile Lys His Ala Arg Leu Ala Met Val Gly Phe Leu Gly Phe Ala
                245                 250                 255

Val Gln Ala Ala Ala Thr Gly Lys Gly Pro Leu Asn Asn Trp Ala Thr
                260                 265                 270

His Leu Ser Asp Pro Leu His Thr Thr Ile Ile Asp Thr Phe Ser Ser
                275                 280                 285

Ser Ser
    290

<210> SEQ ID NO 84
<211> LENGTH: 286
<212> TYPE: PRT
<213> ORGANISM: Triticum aestivum
<220> FEATURE:
<221> NAME/KEY: misc_feature
<222> LOCATION: (1)..(286)
<223> OTHER INFORMATION: Ceres CLONE ID no. 1047963

<400> SEQUENCE: 84

Met Ala Ser Ser Val Ala Ala Ala Ser Thr Phe Leu Gly Thr Arg
1               5                   10                  15

Leu Ala Asp Pro Ala Pro Gln Asn Gly Arg Ile Val Ala Arg Phe Gly
                20                  25                  30

Phe Gly Lys Lys Lys Ala Pro Pro Lys Lys Ala Lys Ala Pro Pro Thr
            35                  40                  45

Thr Asp Arg Pro Leu Trp Phe Pro Gly Ala Gln Ala Pro Glu Tyr Leu
        50                  55                  60

Asp Gly Thr Leu Val Gly Asp Tyr Gly Phe Asp Pro Phe Gly Leu Gly
65                  70                  75                  80

Lys Pro Ala Glu Tyr Leu Gln Tyr Asp Val Asp Ser Leu Asp Gln Asn
                85                  90                  95

Leu Ala Gln Asn Leu Ala Gly Glu Ile Ile Gly Thr Arg Phe Glu Asp
                100                 105                 110

Ala Asp Val Lys Ser Thr Pro Phe Gln Pro Tyr Ala Glu Val Phe Gly
            115                 120                 125

Leu Gln Arg Phe Arg Glu Cys Glu Leu Ile His Gly Arg Trp Xaa Met
        130                 135                 140

Leu Ala Thr Leu Gly Ala Leu Thr Val Glu Trp Leu Thr Gly Val Thr
145                 150                 155                 160

Trp Gln Asp Ala Xaa Lys Val Glu Leu Val Asp Gly Ser Ser Tyr Leu
                165                 170                 175

Gly Gln Pro Leu Pro Phe Thr Leu Thr Thr Leu Ile Trp Ile Glu Val
                180                 185                 190

Leu Val Ile Gly Tyr Ile Glu Phe Gln Arg Asn Ala Glu Leu Asp Pro
            195                 200                 205

Glu Arg Arg Leu Tyr Pro Gly Gly Ser Tyr Phe Asp Pro Leu Gly Leu
        210                 215                 220

Ala Ala Asp Pro Val Lys Lys Glu Thr Leu Gln Leu Ala Glu Ile Lys
225                 230                 235                 240

His Ala Arg Leu Ala Met Val Ala Phe Leu Gly Phe Ala Val Gln Ala
                245                 250                 255

Ala Ala Thr Gly Lys Gly Pro Leu Asn Asn Trp Ala Thr His Leu Ser
                260                 265                 270

Asp Pro Leu His Thr Thr Ile Phe Asp Thr Phe Gly Ser Ser
            275                 280                 285
```

-continued

<210> SEQ ID NO 85
<211> LENGTH: 287
<212> TYPE: PRT
<213> ORGANISM: Zea mays
<220> FEATURE:
<221> NAME/KEY: misc_feature
<222> LOCATION: (1)..(287)
<223> OTHER INFORMATION: Ceres CLONE ID no. 1444714

<400> SEQUENCE: 85

Met Ala Ser Ser Val Ala Ala Ala Ser Ala Phe Leu Gly Thr Arg
1               5                   10                  15

Leu Ala Asp Pro Ala Pro Gln Asn Gly Arg Ile Val Ala Arg Phe Gly
            20                  25                  30

Phe Gly Lys Lys Lys Ala Pro Pro Lys Lys Ala Lys Ala Pro Pro Thr
        35                  40                  45

Thr Asp Arg Pro Leu Trp Phe Pro Gly Ala Gln Ala Pro Glu Tyr Leu
    50                  55                  60

Asp Gly Thr Leu Val Gly Asp Tyr Gly Phe Asp Pro Phe Gly Leu Gly
65                  70                  75                  80

Lys Pro Ala Glu Tyr Leu Gln Tyr Asp Val Asp Ser Leu Asp Gln Asn
                85                  90                  95

Leu Ala Gln Asn Leu Ala Gly Glu Ile Ile Gly Thr Arg Phe Glu Ser
            100                 105                 110

Ser Asp Val Lys Ser Pro Pro Leu Gln Pro Tyr Ser Glu Val Phe Gly
        115                 120                 125

Leu Gln Arg Phe Arg Glu Cys Glu Leu Ile His Gly Arg Trp Ala Met
    130                 135                 140

Leu Ala Thr Leu Gly Ala Leu Thr Val Glu Trp Leu Thr Gly Val Thr
145                 150                 155                 160

Trp Gln Asp Ala Gly Lys Val Glu Leu Val Asp Gly Ser Ser Tyr Leu
                165                 170                 175

Gly Gln Pro Leu Pro Phe Thr Ile Ser Thr Leu Ile Trp Ile Glu Val
            180                 185                 190

Leu Val Ile Gly Tyr Ile Glu Phe Gln Arg Asn Ala Glu Leu Asp Pro
        195                 200                 205

Glu Lys Arg Leu Tyr Pro Gly Gly Ser Tyr Phe Asp Pro Leu Ala Leu
    210                 215                 220

Ala Ala Asp Pro Glu Lys Lys Glu Arg Leu Gln Leu Ala Glu Ile Lys
225                 230                 235                 240

His Ala Arg Leu Ala Met Val Ala Phe Leu Gly Phe Ala Val Gln Ala
                245                 250                 255

Ala Ala Thr Gly Lys Gly Pro Leu Asn Asn Trp Ala Thr His Leu Ser
            260                 265                 270

Asp Pro Leu His Thr Thr Ile Phe Asp Thr Phe Gly Gly Ser Ser
        275                 280                 285

<210> SEQ ID NO 86
<211> LENGTH: 291
<212> TYPE: PRT
<213> ORGANISM: Zea mays
<220> FEATURE:
<221> NAME/KEY: misc_feature
<222> LOCATION: (1)..(291)
<223> OTHER INFORMATION: Ceres CLONE ID no. 299035

<400> SEQUENCE: 86

Met Ala Ser Ser Val Ala Ala Ala Ser Thr Phe Leu Gly Thr Arg
1               5                   10                  15

Leu Ala Asp Pro Ala Pro Gln Asn Gly Arg Ile Val Ala Arg Phe Gly
            20                  25                  30

Phe Gly Leu Gly Gly Lys Ala Lys Pro Ala Pro Lys Lys Val Ala Lys
        35                  40                  45

Thr Ser Thr Ser Ser Asp Arg Pro Leu Trp Phe Pro Gly Ala Val Ala
    50                  55                  60

Pro Asp Tyr Leu Asp Gly Ser Leu Val Gly Asp Tyr Gly Phe Asp Pro
65                  70                  75                  80

Phe Gly Leu Gly Lys Pro Val Glu Tyr Leu Gln Phe Glu Leu Asp Ser
                85                  90                  95

Leu Asp Gln Asn Leu Ala Lys Asn Glu Ala Gly Ile Ile Gly Thr
            100                 105                 110

Arg Phe Glu Ser Ser Glu Val Lys Ser Thr Pro Leu Gln Pro Tyr Ser
        115                 120                 125

Glu Val Phe Gly Leu Gln Arg Phe Arg Glu Cys Glu Leu Ile His Gly
    130                 135                 140

Arg Trp Ala Met Leu Ala Thr Leu Gly Ala Leu Ser Val Glu Trp Leu
145                 150                 155                 160

Thr Gly Val Thr Trp Gln Asp Ala Gly Lys Val Glu Leu Val Asp Gly
                165                 170                 175

Ser Ser Tyr Leu Gly Gln Pro Leu Pro Phe Ser Ile Ser Thr Leu Ile
            180                 185                 190

Trp Ile Glu Val Leu Val Ile Gly Tyr Ile Glu Phe Gln Arg Asn Ala
        195                 200                 205

Glu Leu Asp Pro Glu Lys Arg Leu Tyr Pro Gly Gly Ser Tyr Phe Asp
    210                 215                 220

Pro Leu Gly Leu Ala Ala Asp Pro Glu Lys Lys Glu Arg Leu Gln Leu
225                 230                 235                 240

Ala Glu Ile Lys His Ala Arg Leu Ala Met Val Ala Phe Leu Gly Phe
                245                 250                 255

Ala Val Gln Ala Ala Ala Thr Gly Lys Gly Pro Leu Asn Asn Trp Ala
            260                 265                 270

Thr His Leu Ser Asp Pro Leu His Thr Thr Ile Phe Asp Thr Phe Gly
        275                 280                 285

Gly Ser Ser
    290

<210> SEQ ID NO 87
<211> LENGTH: 291
<212> TYPE: PRT
<213> ORGANISM: Zea mays
<220> FEATURE:
<221> NAME/KEY: misc_feature
<222> LOCATION: (1)..(291)
<223> OTHER INFORMATION: Public GI no. 2326947

<400> SEQUENCE: 87

Met Ala Ser Ser Val Ala Ala Ala Ser Thr Phe Leu Gly Thr Arg
1               5                   10                  15

Leu Ala Asp Pro Ala Pro Gln Asn Gly Arg Ile Val Ala Arg Phe Gly
            20                  25                  30

Phe Gly Leu Gly Gly Lys Ala Lys Pro Ala Pro Lys Lys Val Ala Lys
        35                  40                  45

Thr Ser Thr Ser Ser Asp Arg Pro Leu Trp Phe Pro Gly Ala Val Ala
    50                  55                  60

Pro Asp Tyr Leu Asp Gly Ser Leu Val Gly Asp Tyr Gly Phe Asp Pro

```
                65                  70                  75                  80
Phe Gly Leu Gly Lys Pro Val Glu Tyr Leu Gln Phe Glu Leu Asp Ser
                    85                  90                  95

Leu Asp Gln Asn Leu Ala Lys Asn Glu Ala Gly Gly Ile Ile Gly Thr
                100                 105                 110

Arg Phe Glu Ser Ser Glu Val Lys Ser Thr Pro Leu Gln Pro Tyr Ser
                115                 120                 125

Glu Val Phe Gly Leu Gln Arg Phe Arg Glu Cys Glu Leu Ile His Gly
    130                 135                 140

Arg Trp Ala Met Leu Ala Thr Leu Gly Ala Leu Ser Val Glu Trp Leu
145                 150                 155                 160

Thr Gly Val Thr Trp Gln Asp Ala Gly Lys Val Glu Leu Val Asp Gly
                    165                 170                 175

Ser Ser Tyr Leu Gly Gln Pro Leu Pro Phe Ser Ile Ser Thr Leu Ile
                180                 185                 190

Trp Ile Glu Val Leu Val Ile Gly Tyr Ile Glu Phe Gln Arg Asn Ala
                195                 200                 205

Glu Leu Asp Pro Glu Lys Arg Leu Tyr Pro Gly Gly Ser Tyr Phe Asp
    210                 215                 220

Pro Leu Gly Leu Ala Ala Asp Pro Glu Lys Lys Glu Arg Leu Gln Leu
225                 230                 235                 240

Ala Glu Ile Lys His Ala Arg Leu Ala Met Val Ala Phe Leu Gly Phe
                    245                 250                 255

Ala Val Gln Ala Ala Ala Thr Gly Lys Gly Pro Leu Asn Asn Trp Ala
                260                 265                 270

Thr His Leu Ser Asp Pro Leu His Thr Thr Ile Phe Asp Thr Phe Gly
            275                 280                 285

Gly Ser Ser
    290

<210> SEQ ID NO 88
<211> LENGTH: 291
<212> TYPE: PRT
<213> ORGANISM: Zea mays
<220> FEATURE:
<221> NAME/KEY: misc_feature
<222> LOCATION: (1)..(291)
<223> OTHER INFORMATION: Ceres CLONE ID no. 1544777

<400> SEQUENCE: 88

Met Ala Ser Ser Val Ala Ala Ala Ser Thr Phe Leu Gly Thr Arg
1               5                   10                  15

Leu Ala Asp Pro Ala Pro Gln Asn Gly Arg Ile Val Ala Arg Phe Gly
                20                  25                  30

Phe Gly Leu Gly Gly Lys Ala Lys Pro Ala Pro Lys Lys Val Ala Lys
                35                  40                  45

Thr Ser Thr Ser Ser Asp Arg Pro Leu Trp Phe Pro Gly Ala Val Ala
50                  55                  60

Pro Asp Tyr Leu Asp Gly Ser Leu Val Gly Asp Tyr Gly Phe Asp Pro
65                  70                  75                  80

Phe Gly Leu Gly Lys Pro Val Glu Tyr Leu Gln Phe Glu Leu Asp Ser
                    85                  90                  95

Leu Asp Gln Asn Leu Ala Lys Asn Glu Ala Gly Gly Ile Ile Gly Thr
                100                 105                 110

Arg Phe Glu Ser Ser Glu Val Lys Ser Thr Pro Leu Gln Pro Tyr Ser
                115                 120                 125
```

```
Glu Val Phe Gly Leu Gln Arg Phe Arg Glu Cys Glu Leu Ile His Gly
        130                 135                 140

Arg Trp Ala Met Leu Ala Thr Leu Gly Ala Leu Ser Val Glu Trp Leu
145                 150                 155                 160

Thr Gly Val Thr Trp Gln Asp Ala Gly Lys Val Glu Leu Val Asp Gly
                165                 170                 175

Ser Ser Tyr Leu Gly Gln Pro Leu Pro Phe Ser Ile Ser Thr Leu Ile
            180                 185                 190

Trp Ile Glu Val Leu Val Ile Gly Tyr Ile Glu Phe Gln Arg Asn Ala
        195                 200                 205

Glu Leu Asp Pro Glu Lys Arg Leu Tyr Pro Gly Gly Ser Tyr Phe Asp
    210                 215                 220

Pro Leu Gly Leu Ala Ala Asp Pro Glu Lys Lys Glu Arg Leu Gln Leu
225                 230                 235                 240

Ala Glu Ile Lys His Ala Arg Leu Ala Met Val Ala Phe Leu Gly Phe
                245                 250                 255

Ala Val Gln Ala Ala Thr Gly Lys Gly Pro Leu Asn Asn Trp Ala
                260                 265                 270

Thr His Leu Ser Asp Pro Leu His Thr Thr Ile Phe Asp Thr Phe Gly
        275                 280                 285

Gly Ser Ser
    290

<210> SEQ ID NO 89
<211> LENGTH: 288
<212> TYPE: PRT
<213> ORGANISM: Zea mays
<220> FEATURE:
<221> NAME/KEY: misc_feature
<222> LOCATION: (1)..(288)
<223> OTHER INFORMATION: Ceres CLONE ID no. 1064222

<400> SEQUENCE: 89

Met Ala Ala Thr Ser Thr Ala Ala Ala Ser Ser Ile Met Gly Thr
1               5                   10                  15

Arg Val Val Ser Asp Ile Asn Ser Gly Ser Ser Arg Phe Thr Ala Arg
            20                  25                  30

Phe Gly Phe Gly Thr Lys Lys Ala Ala Ala Pro Lys Lys Ala Lys Thr
        35                  40                  45

Val Ile Ser Asp Arg Pro Leu Trp Phe Pro Gly Ala Lys Ser Pro Glu
50                  55                  60

Tyr Leu Asp Gly Ser Leu Val Gly Asp Tyr Gly Phe Asp Pro Phe Gly
65                  70                  75                  80

Leu Gly Lys Pro Ala Glu Tyr Leu Gln Phe Asp Leu Asp Ser Leu Asp
                85                  90                  95

Gln Asn Leu Ala Lys Asn Ile Ala Gly Asp Val Ile Gly Thr Arg Thr
            100                 105                 110

Glu Ala Ala Asp Pro Lys Ser Thr Pro Phe Gln Pro Tyr Ser Glu Val
        115                 120                 125

Phe Gly Leu Gln Arg Phe Arg Glu Cys Glu Leu Ile His Gly Arg Trp
    130                 135                 140

Ala Met Leu Ala Thr Leu Gly Ala Leu Ser Val Glu Trp Leu Thr Gly
145                 150                 155                 160

Val Thr Trp Gln Asp Ala Gly Lys Val Glu Leu Val Asp Gly Ser Ser
                165                 170                 175

Tyr Leu Gly Gln Pro Leu Pro Phe Ser Ile Ser Thr Leu Ile Trp Ile
            180                 185                 190
```

```
Glu Val Leu Val Ile Gly Tyr Ile Glu Phe Gln Arg Asn Ala Glu Leu
            195                 200                 205

Asp Ser Glu Lys Arg Leu Tyr Pro Gly Gly Lys Phe Phe Asp Pro Leu
        210                 215                 220

Gly Leu Ala Ser Asp Pro Glu Lys Lys Ala Gln Leu Gln Leu Ala Glu
225                 230                 235                 240

Ile Lys His Ala Arg Leu Ala Met Val Ala Phe Leu Gly Phe Ala Val
                245                 250                 255

Gln Ala Ala Ala Thr Gly Lys Gly Pro Leu Asn Asn Trp Ala Thr His
            260                 265                 270

Leu Ser Asp Pro Leu His Thr Thr Ile Ile Asp Thr Phe Ser Ser Ser
        275                 280                 285

<210> SEQ ID NO 90
<211> LENGTH: 289
<212> TYPE: PRT
<213> ORGANISM: Zea mays
<220> FEATURE:
<221> NAME/KEY: misc_feature
<222> LOCATION: (1)..(289)
<223> OTHER INFORMATION: Ceres CLONE ID no. 1364336

<400> SEQUENCE: 90

Met Ala Ala Thr Ser Thr Ala Ala Ala Ala Ser Xaa Ile Met Gly
1               5                   10                  15

Thr Arg Val Val Ser Asp Ile Asn Ser Gly Ser Xaa Arg Phe Thr Ala
            20                  25                  30

Arg Phe Gly Phe Gly Thr Lys Lys Ala Ala Pro Lys Lys Ala Lys
        35                  40                  45

Thr Val Ile Ser Asp Arg Pro Leu Trp Phe Pro Gly Ala Lys Ser Pro
50                  55                  60

Glu Tyr Leu Asp Gly Ser Leu Val Gly Asp Tyr Gly Phe Asp Pro Phe
65                  70                  75                  80

Gly Leu Gly Lys Pro Ala Glu Tyr Leu Gln Phe Asp Leu Asp Ser Leu
                85                  90                  95

Asp Gln Asn Leu Ala Lys Asn Ile Ala Gly Asp Val Ile Gly Thr Arg
            100                 105                 110

Thr Glu Ala Ala Asp Pro Lys Ser Thr Pro Phe Gln Pro Tyr Ser Glu
        115                 120                 125

Val Phe Gly Leu Gln Arg Phe Arg Glu Cys Glu Leu Ile His Gly Arg
    130                 135                 140

Trp Ala Met Leu Ala Thr Leu Gly Ala Leu Ser Val Glu Trp Leu Thr
145                 150                 155                 160

Gly Val Thr Trp Gln Asp Ala Gly Lys Val Glu Leu Val Asp Gly Ser
                165                 170                 175

Ser Tyr Leu Gly Gln Pro Leu Pro Phe Ser Ile Ser Thr Leu Ile Trp
            180                 185                 190

Ile Glu Val Leu Val Ile Gly Tyr Ile Glu Phe Gln Arg Asn Ala Glu
        195                 200                 205

Leu Asp Ser Glu Lys Arg Leu Tyr Pro Gly Gly Lys Phe Phe Asp Pro
    210                 215                 220

Leu Gly Leu Ala Ser Asp Pro Glu Lys Lys Ala Gln Leu Gln Leu Ala
225                 230                 235                 240

Glu Ile Lys His Ala Arg Leu Ala Met Val Ala Phe Leu Gly Phe Ala
                245                 250                 255

Val Gln Ala Ala Ala Thr Gly Lys Gly Pro Leu Asn Asn Trp Ala Thr
```

-continued

```
                   260                 265                 270
His Leu Ser Asp Pro Leu His Thr Thr Ile Ile Asp Thr Phe Ser Ser
            275                 280                 285

Ser

<210> SEQ ID NO 91
<211> LENGTH: 289
<212> TYPE: PRT
<213> ORGANISM: Zea mays
<220> FEATURE:
<221> NAME/KEY: misc_feature
<222> LOCATION: (1)..(289)
<223> OTHER INFORMATION: Ceres CLONE ID no. 1440675

<400> SEQUENCE: 91

Met Ala Ala Thr Ser Thr Ala Ala Ala Ala Ser Ser Ile Met Gly
1               5                   10                  15

Thr Arg Val Val Ser Asp Ile Asn Ser Gly Ser Gly Arg Phe Thr Ala
            20                  25                  30

Arg Phe Gly Phe Gly Thr Lys Lys Ala Ala Ala Leu Lys Lys Ala Lys
        35                  40                  45

Thr Val Ile Ser Asp Arg Pro Leu Trp Phe Pro Gly Ala Lys Ser Pro
    50                  55                  60

Glu Tyr Leu Asp Gly Ser Leu Val Gly Asp Tyr Gly Phe Asp Pro Phe
65                  70                  75                  80

Gly Leu Gly Lys Pro Ala Glu Tyr Leu Gln Phe Asp Leu Asp Ser Leu
                85                  90                  95

Asp Gln Asn Leu Ala Lys Asn Ile Ala Gly Asp Val Ile Gly Thr Arg
            100                 105                 110

Thr Glu Ala Val Asp Pro Lys Ser Thr Pro Phe Gln Pro Tyr Ser Glu
        115                 120                 125

Val Phe Gly Leu Gln Arg Phe Arg Glu Cys Glu Leu Ile His Gly Arg
    130                 135                 140

Trp Ala Met Leu Ala Thr Leu Gly Ala Leu Ser Val Glu Trp Leu Thr
145                 150                 155                 160

Gly Val Thr Trp Gln Asp Ala Gly Lys Val Glu Leu Val Asp Gly Ser
                165                 170                 175

Ser Tyr Leu Gly Gln Pro Leu Pro Phe Ser Ile Ser Thr Leu Ile Trp
            180                 185                 190

Ile Glu Val Leu Val Ile Gly Tyr Ile Glu Phe Gln Arg Asn Ala Glu
        195                 200                 205

Leu Asp Ser Glu Lys Arg Leu Tyr Pro Gly Gly Lys Phe Phe Asp Pro
    210                 215                 220

Leu Gly Leu Ala Ser Asp Pro Glu Lys Lys Ala Gln Leu Gln Leu Ala
225                 230                 235                 240

Glu Ile Lys His Ala Arg Leu Ala Met Val Ala Phe Leu Gly Phe Ala
                245                 250                 255

Val Gln Ala Ala Ala Thr Gly Lys Gly Pro Leu Asn Asn Trp Ala Thr
            260                 265                 270

His Leu Ser Asp Pro Leu His Thr Thr Ile Ile Asp Thr Phe Ser Ser
        275                 280                 285

Ser

<210> SEQ ID NO 92
<211> LENGTH: 858
<212> TYPE: DNA
<213> ORGANISM: Populus balsamifera subsp. trichocarpa
```

```
<220> FEATURE:
<221> NAME/KEY: misc_feature
<222> LOCATION: (1)..(858)
<223> OTHER INFORMATION: Ceres GDNA ANNOT ID no. 1454179
<220> FEATURE:
<221> NAME/KEY: misc_feature
<222> LOCATION: (1)..(858)
<223> OTHER INFORMATION: CDS - REFERENCED BY SEQ ID NO: 92

<400> SEQUENCE: 92
atggctgcca ccacagctgc tgccgctaca tcttccttca tgggaacacg tctgcccgat    60
atctattcaa actcgggtag gatccaagcc aggttcggat ttgggggcaa gaaagcaccc   120
aagaagtcta taaagcctag tactccagac cgcccacttt ggtatccagg agccaaggca   180
cctgagtacc tagatggcag cttggttggt gattacggat ttgacccatt tgggttgggc   240
aaaccagctg agtacttgca gttcgagctt gactcttttgg accaaaactt ggctaagaat   300
ctggctggag atattattgg gacacgtact gagtttgctg atgtgaagtc aactccattt   360
cagccttaca gtgaggtttt tgggttgcaa aggttcaggg agtgtgagct cattcatgga   420
aggtgggcta tgttggctac tcttggtgca ctctctgttg agtggctcac tggagttacc   480
tggcaagatg ctggaaaggt ggagttggtt gaaggctcat catccttgg tcagccacta   540 ccattctcca ttacagcatt gatctggatc gaggctgtca ttattggata cattgaattc   600
caaaggaacg cagagcttga cccagagaaa aggctctacc caggaggcca gttctttgat   660
cctctaggcc tagcttccga cccagaaaag aaggctaccc ttcaattggc agagatcaag   720
cacgctcgcc ttgccatggt agccttcctt ggcttcgcag ttcaagcttg ggttactgga   780
aaaggtcccc tcaacaactg ggctactcac ttgagcgatc ctctccacac aaccattatt   840
gacaacttgt cctcttaa                                                 858

<210> SEQ ID NO 93
<211> LENGTH: 272
<212> TYPE: PRT
<213> ORGANISM: Populus balsamifera subsp. trichocarpa
<220> FEATURE:
<221> NAME/KEY: misc_feature
<222> LOCATION: (1)..(272)
<223> OTHER INFORMATION: Ceres GDNA ANNOT ID no. 1454179

<400> SEQUENCE: 93

Met Gly Thr Arg Leu Pro Asp Ile Tyr Ser Asn Ser Gly Arg Ile Gln
1               5                   10                  15

Ala Arg Phe Gly Phe Gly Gly Lys Lys Ala Pro Lys Lys Ser Ile Lys
            20                  25                  30

Pro Ser Thr Pro Asp Arg Pro Leu Trp Tyr Pro Gly Ala Lys Ala Pro
        35                  40                  45

Glu Tyr Leu Asp Gly Ser Leu Val Gly Asp Tyr Gly Phe Asp Pro Phe
    50                  55                  60

Gly Leu Gly Lys Pro Ala Glu Tyr Leu Gln Phe Glu Leu Asp Ser Leu
65                  70                  75                  80

Asp Gln Asn Leu Ala Lys Asn Leu Ala Gly Asp Ile Ile Gly Thr Arg
                85                  90                  95

Thr Glu Phe Ala Asp Val Lys Ser Thr Pro Phe Gln Pro Tyr Ser Glu
            100                 105                 110

Val Phe Gly Leu Gln Arg Phe Arg Glu Cys Glu Leu Ile His Gly Arg
        115                 120                 125

Trp Ala Met Leu Ala Thr Leu Gly Ala Leu Ser Val Glu Trp Leu Thr
    130                 135                 140
```

| Gly | Val | Thr | Trp | Gln | Asp | Ala | Gly | Lys | Val | Glu | Leu | Val | Glu | Gly | Ser |
| --- | --- | --- | --- | --- | --- | --- | --- | --- | --- | --- | --- | --- | --- | --- | --- |
| 145 | | | | 150 | | | | 155 | | | | | | 160 | |

| Ser | Tyr | Leu | Gly | Gln | Pro | Leu | Pro | Phe | Ser | Ile | Thr | Ala | Leu | Ile | Trp |
| --- | --- | --- | --- | --- | --- | --- | --- | --- | --- | --- | --- | --- | --- | --- | --- |
| | | | | 165 | | | | | 170 | | | | | 175 | |

| Ile | Glu | Ala | Val | Ile | Ile | Gly | Tyr | Ile | Glu | Phe | Gln | Arg | Asn | Ala | Glu |
| --- | --- | --- | --- | --- | --- | --- | --- | --- | --- | --- | --- | --- | --- | --- | --- |
| | | | 180 | | | | | 185 | | | | | 190 | | |

| Leu | Asp | Pro | Glu | Lys | Arg | Leu | Tyr | Pro | Gly | Gly | Gln | Phe | Phe | Asp | Pro |
| --- | --- | --- | --- | --- | --- | --- | --- | --- | --- | --- | --- | --- | --- | --- | --- |
| | | | 195 | | | | | 200 | | | | | 205 | | |

| Leu | Gly | Leu | Ala | Ser | Asp | Pro | Glu | Lys | Lys | Ala | Thr | Leu | Gln | Leu | Ala |
| --- | --- | --- | --- | --- | --- | --- | --- | --- | --- | --- | --- | --- | --- | --- | --- |
| | 210 | | | | | 215 | | | | 220 | | | | | |

| Glu | Ile | Lys | His | Ala | Arg | Leu | Ala | Met | Val | Ala | Phe | Leu | Gly | Phe | Ala |
| --- | --- | --- | --- | --- | --- | --- | --- | --- | --- | --- | --- | --- | --- | --- | --- |
| 225 | | | | | 230 | | | | | 235 | | | | | 240 |

| Val | Gln | Ala | Trp | Val | Thr | Gly | Lys | Gly | Pro | Leu | Asn | Asn | Trp | Ala | Thr |
| --- | --- | --- | --- | --- | --- | --- | --- | --- | --- | --- | --- | --- | --- | --- | --- |
| | | | | 245 | | | | | 250 | | | | | 255 | |

| His | Leu | Ser | Asp | Pro | Leu | His | Thr | Thr | Ile | Ile | Asp | Asn | Leu | Ser | Ser |
| --- | --- | --- | --- | --- | --- | --- | --- | --- | --- | --- | --- | --- | --- | --- | --- |
| | | | 260 | | | | | 265 | | | | | 270 | | |

<210> SEQ ID NO 94
<211> LENGTH: 1823
<212> TYPE: DNA
<213> ORGANISM: Arabidopsis thaliana
<220> FEATURE:
<221> NAME/KEY: misc_feature
<222> LOCATION: (1)..(1823)
<223> OTHER INFORMATION: Ceres Promoter 21876

<400> SEQUENCE: 94

```
gtctcttaaa aaggatgaac aaacacgaaa ctggtggatt atacaaatgt cgccttatac      60
atatatcggt tattggccaa aagagctatt ttaccttatg gataatggtg ctactatggt     120
tggagttgga ggtgtagttc aggcttcacc ttctggttta agccctccaa tgggtaatgg     180
taaatttccg gcaaaaggtc ctttgagatc agccatgttt ccaatgttga aggtcttata     240
ttccaagtat gagaaaggta aaataaatgc gtttcctata gtggagttgc tagatagtag     300
tagatgttat gggctacgaa ttggtaagag agttcgattt tggactagtc cactcggata     360 cttttttcaat tatggtggtc ctggaggaat ctcttgtgga gtttgatatt tgcgagtata     420
atctttgaac ttgtgtagat tgtacccaaa accgaaaaca tatcctatat aaatttcatt     480
atgagagtaa aattgtttgt tttatgtatc atttctcaac tgtgattgag ttgactattg     540
aaaacatatc ttagataagt ttcgttatga gagttaatga tgattgatga catacacact     600
cctttatgat ggtgattcaa cgttttggag aaaattttatt tataatctct cataaattct     660
ccgttattag ttgaataaaa tcttaaatgt ctcctttaac catagcaaac caacttaaaa     720
atttagattt taaagttaag atggatattg tgattcaacg attaattatc gtaatgcata     780
ttgattatgt aaaataaaat ctaactaccg gaatttattc ataactcca ttgtgtgact      840 gcatttaaat atatgtttta tgtcccatta attaggctgt aatttcgatt tatcaattta     900
tatactagta ttaatttaat tccatagatt tatcaaagcc aactcatgac ggctagggtt     960
ttccgtcacc ttttcgatca tcaagagagt tttttttataa aaaatttat acaattatac    1020 aatttcttaa ccaaacaaca cataattata agctatttaa catttcaaat tgaaaaaaaa    1080
aatgtatgag aattttgtgg atccattttt gtaattcttt gttgggtaaa ttcacaacca    1140
aaaaaataga aaggcccaaa acgcgtaagg gcaaattagt aaaagtagaa ccacaaagag    1200
aaagcgaaaa ccctagacac ctcgtagcta taagtaccct cgagtcgacc aggattaggg    1260
tgcgctctca tatttctcac attttcgtag ccgcaagact cctttcagat tcttacttgc    1320
```

|  |  |  |  |  |
|---|---|---|---|---|
| aggttagata | ttttctctct | ttagtgtctc | cgatcttcat | cttcttatga ttattgtagc | 1380 |
| tgtttagggt | ttagattctt | agttttagct | ctatattgac | tgtgattatc gcttattctt | 1440 |
| tgctgttgtt | atactgcttt | tgattctcta | gctttagatc | cgtttactcg tcgatcaata | 1500 |
| ttgttcctat | tgagtctgat | gtataatcct | ctgattaatt | gatagcgttt agttttgata | 1560 |
| tcgtcttcgc | atgtttttta | tcatgtcgat | ctgtatctgc | tctggttata gttgattctg | 1620 |
| atgtatttgg | ttggtgatgt | tccttagatt | tgatatacct | gttgtctcgt ggtttgatat | 1680 |
| gatagctcaa | ctggtgatat | gtggttttgt | ttcagtggat | ctgtgtttga ttatattgtt | 1740 |
| gacgttttgg | ttgttgtatg | gttgatggtt | gatgtatttt | tgttgattct gatgtttcga | 1800 |
| ttttgttttt | tgttttgaca | gct |  |  | 1823 |

<210> SEQ ID NO 95
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0668

<400> SEQUENCE: 95

|  |  |  |  |  |
|---|---|---|---|---|
| atagagtttt | actatgctt | tggaatcttt | cttctaatgt | gccaactaca gagaaataca | 60 |
| tgtattacca | ctaggaatcg | gaccatatca | tagatatcag | gattagataa ctagttctcg | 120 |
| tcgctatcac | ttcgcattaa | gttctagtaa | ttgttaaaga | ttctaatttt ttactaaaca | 180 |
| aaaactaaat | caacatcaaa | tatgcaaagt | gtgtgttgtc | cacacaagtg actcaaagta | 240 |
| tacgcaggtg | ggattggacc | atattattgc | aaatcgtttc | cgaaccactc atatttcttt | 300 |
| ttttctctcc | ttttttatc | cggagaatta | tggaaccact | tcatttcaac ttcaaaacta | 360 |
| atttttggt | tcagtgatca | aatacaaaaa | aaaaaaaaaa | gttatagata ttaaatagaa | 420 |
| aactattcca | atcttaaaaa | tacaaatgaa | accataattt | taatttatac aaaactattt | 480 |
| aattagctaa | gggttgtctt | aacgtttaga | aaataaaaaa | ttatgattgt ctgtttaaaa | 540 |
| ttacaatgaa | tgaataaaaa | aaatatgcaa | tgaatgaaag | aataaattt gtacatccga | 600 |
| tagaatgaga | aaatgaattt | tgtacaaacc | actcaagaat | tcaaaacaat tgtcaaagtt | 660 |
| ttcttctcag | ccgtgtgtcc | tcctctccta | gccgccacat | ctcacacact aatgctaacc | 720 |
| acgcgatgta | accgtaagcg | ctgagttttt | gcatttcaga | tttcacttcc accaaacaaa | 780 |
| actcgccacg | tcatcaatac | gaatcattcc | gtataaacgt | ctagattctt tacagcctac | 840 |
| aatgttctct | tctttggtcg | gccattattt | aacgctttga | acctaaatct agcccagcca | 900 |
| acgaagaaga | cgaagcaaat | ccaaaccaaa | gttctccatt | ttcgtagctt ctttaagctt | 960 |
| tttcagtatc | atagagacac | ttttttttt | ttgattagaa |  | 1000 |

<210> SEQ ID NO 96
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0535

<400> SEQUENCE: 96

|  |  |  |  |  |
|---|---|---|---|---|
| ttagtgaaat | tatgcactta | agtaaggttt | tcttagttag | ctaatgtatg gctattcaat | 60 |
| tgttatgtta | ggctattta | gttagtatat | gaatttaggc | agtctatgca aatgatttcg | 120 |

```
ttttcatttt ttcatatgta aacatcaaga tcaagtaacg ccattcgagt tgatatttt      180 tttttaaatt agtgtgtgta aattttggac cgcttatttg agtttgctaa tgaagttgca      240
tatatattac gttaaaccat aggcaaacta atttgaaaca tccgattcga tttcctgtaa      300
tttttcttgg ttaattgacc aaaatcaaga tcttcagaaa taaaataaaa gacgaaagaa      360
agctgtcgca aagcagattg tgttaaaaaa aagtggattg ggctcaaacg caacttgtcc      420
agcccgtgac aattacccta tacgcaagta agagtaacgt atcactggca aaagttggta      480
ttagttacga tatctttgtc atgggggcat gcatgggcat ggcttaagag ttaagcctta      540
agaagagtcc cacactcgtg actctcatga tcacttgttg tttcttacgg gcaaatacat      600
ttaactttat tcttcattta ttcacctata ttcttttgga taataacttt tctctatata      660
aaataacaaa catcgtacgt ttcatttatt tacaacaagc gatgagaatt aaaaggagac      720
cttaattgat gatactcttc ttttctctcg gttacaacgg gattattaca gataatgata      780
atctatatgg atgctgacgt ggaaaaacaa aatttggtga aacacgtcaa ttaagcacga      840
cttttccatg gctagtggct aagatcgttt catcacatgg ctatatcata taatacttgg      900
atgaattcaa aataaacgac tgagaaaatg tccacgtcac ggcgcaccgc tttggactta      960
agtctcctat aataaataca acaccaaaca ttgcattcca                           1000
```

<210> SEQ ID NO 97
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter PT0585

<400> SEQUENCE: 97

```
tgaagtcatt taatatgagt ttgacattag gtaaacctaa tctatgagat tatagaatgt       60
agcaaaacta tcaatgtttc ttttccaaaa tattttgtgg ttttttcttt tggttcatta      120
tgttttgtta tttgtgaatt attttaatat gaagtaatta tattgatttt atatgatata      180
catattattt tgatatataaaa tttaacactt atccattaaa atagcatggg cataatcaaa      240
atcgggacta ttacgatgaa aaagatagtt aaattgtatg ataaaataaa atgtgtaaga      300
ttaaaatttt gggttttaga aaattactaa acaaaatata gacaaagtat gttgactatt      360
atttaaaatt taaatatcat caataagata tagttaaagt cattaagtgt atagcaaaat      420
gaaaattcta agattaaaat tcgattaaaa tttttttac taaattaaat atttaaaaat       480
agggattatc atttactatt tacaattcta atatcatggg taaaaattga taacttttttt      540 taaacccgcc tatctaggtg ggcctaacct agttttactaa ttactatatg attaacttat      600
taccactttt acttcttctt ttttggtcaa attactttat tgtttttttat aaagtcaaat      660 tactctttgc attgtaaata atagtagtaa ctaaaatctt aaaacaaaat attcaacctt      720
tcccattatt ggaatggtaa tgtcttcaac accattgacc aacgttaagg aatgtcttt      780 aatattttg gaacctaaat gctaatactg tataccacaa tcacttatga gtattgaagt      840
tgagatagag gaggtacaag gagaccttat ctgcagaaga caaaaagcca ttttttagcaa      900 aactaaagaa agaaaaaaga ttgaaacaca aatatgcgcc actcgtagtc cacccctatc      960
tctttggcaa aagccacttc actcttttttc ccttttttat                            999
```

<210> SEQ ID NO 98
<211> LENGTH: 1000
<212> TYPE: DNA

<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0613

<400> SEQUENCE: 98

| | | | | | |
|---|---|---|---|---|---|
| ttaatactaa | cattgtagaa | agccacaaaa | aagaaattga | aatgtgagta | gatgctgagt | 60 |
| cagaggtttg | gtcaatacac | aacagctaat | tgagataata | ttatacacgt | cacgatgact | 120 |
| tgttttttct | cctcccaact | tgttaatttc | tttattctta | aaattaaacc | atcgcaaaaa | 180 |
| cagaagaaca | cagctgtttt | tctcgactcc | caatttctat | tttgctgcta | aggacatttc | 240 |
| atttcattat | ttcccaattc | aggactcctt | agattttcct | aaatttgttt | tcctaacttg | 300 |
| ctctctctca | ttctaacatt | ttctcatttt | tttagattat | cttgtacttt | ttagtagatt | 360 |
| attttatcag | gttttacaaa | catacattga | cattctaaaa | agggcttcta | aaaattcagt | 420 |
| gtggaatgct | gatatactaa | aaaaaggtca | tgcaaaatta | tctacgattt | atctaaaatt | 480 |
| agataatttg | ccatatataa | ctattaacta | ataatcgatc | ctttgatttt | ttgtttagat | 540 |
| aaaacgaaac | agctatatct | tttttttttg | ttatcggatt | ttaatcgaat | aaaagctgaa | 600 |
| aaataacagt | tatatcttct | tctttttttaa | ctaatgaaac | agttatatct | taaacaaaca | 660 |
| acagaaacag | taaatatta | atgcaaatcc | gcgtcaagag | ataaattta | acaaactaat | 720 |
| aacaattgag | ataagattag | cgcaaaagaa | actctaattt | tagagcgtgt | aaacacaaac | 780 |
| acgtcttgaa | agtaaacgtg | aattacacgc | ttctaaaacg | agcgtgagtt | ttggttataa | 840 |
| cgaagatacg | gtgaagtgtg | acacctttct | acgttaattt | cagtttgagg | acacaactca | 900 |
| agttatgttt | gatatctaag | gacttgcact | gtctccaaat | ctgcaggaag | gactttttga | 960 |
| ttggatcaat | ataatacca | tctccattct | cgtctccttc | | | 1000 |

<210> SEQ ID NO 99
<211> LENGTH: 351
<212> TYPE: DNA
<213> ORGANISM: Arabidopsis thaliana
<220> FEATURE:
<221> NAME/KEY: misc_feature
<222> LOCATION: (1)..(351)
<223> OTHER INFORMATION: Ceres Promoter PT0625

<400> SEQUENCE: 99

| | | | | | |
|---|---|---|---|---|---|
| gatcatgatc | agtttcaact | cgctgtgccc | acgtgtcgag | agatcggcac | gtgcctgagc | 60 |
| tctcagccgc | tcataaatac | acttgtttag | tagcaacagt | atactatagt | agtcctctcc | 120 |
| tgtttggctt | ttagcttgca | tcgatggatg | gatggatgga | tcgcatgaga | gggcttcgcg | 180 |
| aaggtacgga | accttacaca | acgcgtgtcc | tttctacgtg | gccatcgtgt | aggcgtctcg | 240 |
| ccatgctacg | tgtcccggag | gatgtctcga | tgccaaccct | tataaatact | gttccattcc | 300 |
| aatcccatcg | ccacagccag | tgcaaatctg | atcgatcaag | ataatcgagc | a | 351 |

<210> SEQ ID NO 100
<211> LENGTH: 1022
<212> TYPE: DNA
<213> ORGANISM: Arabidopsis thaliana
<220> FEATURE:
<221> NAME/KEY: misc_feature
<222> LOCATION: (1)..(1022)
<223> OTHER INFORMATION: Ceres Promoter PT0633

<400> SEQUENCE: 100

| | | | | | |
|---|---|---|---|---|---|
| cccgatcggc | cttaatctga | gtcctaaaaa | ctgttatact | taacagttaa | cgcatgattt | 60 |

-continued

| | |
|---|---|
| gatggaggag ccatagatgc aattcaatca aactgaaatt tctgcaagaa tctcaaacac | 120 |
| ggagatctca aagtttgaaa gaaaatttat ttcttcgact caaaacaaac ttacgaaatt | 180 |
| taggtagaac ttatatacat tatattgtaa ttttttgtaa caaaatgttt ttattattat | 240 |
| tatagaattt tactggttaa attaaaaatg aatagaaaag gtgaattaag aggagagagg | 300 |
| aggtaaacat tttcttctat tttttcatat tttcaggata aattattgta aaagtttaca | 360 |
| agatttccat ttgactagtg taaatgagga atattctcta gtaagatcat tatttcatct | 420 |
| acttctttta tcttctacca gtagaggaat aaacaatatt tagctccttt gtaaatacaa | 480 |
| attaattttc gttcttgaca tcattcaatt ttaattttac gtataaaata aaagatcata | 540 |
| cctattagaa cgattaagga gaaatacaat tcgaatgaga aggatgtgcc gtttgttata | 600 |
| ataaacagcc acacgacgta aacgtaaaat gaccacatga tgggccaata gacatggacc | 660 |
| gactactaat aatagtaagt tacatttttag gatggaataa atatcatacc gacatcagtt | 720 |
| tgaaagaaaa gggaaaaaaa gaaaaaataa ataaaagata tactaccgac atgagttcca | 780 |
| aaaagcaaaa aaaaagatca agccgacaca gacacgcgta gagagcaaaa tgactttgac | 840 |
| gtcacaccac gaaaacagac gcttcatacg tgtccctta tctctctcag tctctctata | 900 |
| aacttagtga gaccctcctc tgttttactc acaaatatgc aaactagaaa acaatcatca | 960 |
| ggaataaagg gtttgattac ttctattgga aagaaaaaaa tctttggaaa aggcctgcag | 1020 |
| gg | 1022 |

<210> SEQ ID NO 101
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0650

<400> SEQUENCE: 101

| | |
|---|---|
| catacttaat tctaaaaaaa caacacttat agtttataag cagctcttat gataaaaatc | 60 |
| tttctgagtt atagctctgt taaacttgta ttcaccccaa aaacggatgt ttcatttctt | 120 |
| attttttact tggagtattt tattgtaatt tgtaaaaaaa aatgtaaagt gggggatatc | 180 |
| atgaaaaaca acgtcacttt gtttggtcac aatatacatt tgataaaata atggtcgtcg | 240 |
| cgtgatttag ttgattttttg tttttatcaac cacgtgtttc acttgatgag tagtttatat | 300 |
| agttaacatg attcggccac ttcagatttg ggtttgccca catatgacat accgacatag | 360 |
| aaggttaaat ccacgtggga aatgccaata ttcaatgttt ggttttcaaa agagaatcat | 420 |
| ttctttatat gatctcaaaa gtatggaatt gaaatgacta atgagcacat gcaattggtg | 480 |
| ctatcttaaa aaccgaacgt ctttgaattt aatttgtttt tcaccaaagg tacctaatga | 540 |
| aacccttttca ttaaaaaata aaggtaacaa acaaaatttt gtattggaaa aaacattttt | 600 |
| tggaatatat aatttggtaa tagaattatg agcaaaaaag aaaagaaaa gaaagaataa | 660 |
| tgagcataat aaagccttta cagtattact aattgggccg agcagttttg ggctcttgat | 720 |
| catgtctagt aatcttaaac agacgataaa gttaactgca atttagttgg ttcaggtgag | 780 |
| ctaccaaatc caaaaatacg cagattaggt tcaccgtacc ggaacaaacc ggatttatca | 840 |
| aaatccttaa gttatacgaa atcacgcttt tccttcgatt tctccgctct tctccactct | 900 |
| tcttctctgt tctatcgcag acattttgt ttatatgcat acataataat aatacactct | 960 |
| tgtcaggatt tttgattctc tctttggttt tctcggaaaa | 1000 |

<210> SEQ ID NO 102
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter PT0660

<400> SEQUENCE: 102

```
caagtcaagt tccaatattc taaggagaaa taatagtata ctaaacatac attagagagg      60
ttaaacttct ttttggattt aagtgtgtat gcataggcta tttattctta agtataacta     120
ttaactgtag ctagatttat acaagaaata cataaaactt tatgcatgtg aggtagccat     180
gaatatacgt acatgttgca atcgattata catgttgtat ttggatttct ctatacatgt     240
tttaacttgt cattctctaa gtatatacat accattaata ctgtgggcat gagtttatga     300
taagactttt cttttggaga ccagttttgt tttccttttcc acctatattt gtctataggc    360
ttcacggtac actagtttac aagtgttttt atatgttcta aataaaattg agattttccg     420
gaacggtatg atctgtttgc aaataaggac gtatatataa cagtatcaaa tatatttgtt     480
gttataaggc aataatatat tttctgagat attgcgtgtt acaaaaaaga aatatttgtt     540
aagaaaaaaa aagatggtcg aaaaagggga gtaggtgggg gcggtcggct tttgattagt     600
aataaaagaa accacacgag tgacctaccg attcgactca acgagtctac cgagctaaca     660
cagattcaac tcgctcgagc ttcgttttat gacaagttgg ttttttttttt tttttttaat   720
tttttcatct tcttgggttt ggttgggtca ctcttcaggt caggtgtgta aaaagaaag     780
aaagaaaaga gagattgttg tgttgtaacc cctttgacta aaatctaatg aacttttttta   840
acacaacaaa actccttcag atctgaaagg gttcttcttc tctcttagtc tcttcgtcct    900
tttattctcc gtcgtcgttt catgatctga ctctctggtc ttctcttctt cttcttcttc   960
ttctatttttt tcttacttcg tcactgttgt gtctgaac                           998
```

<210> SEQ ID NO 103
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0665

<400> SEQUENCE: 103

```
aaaaaggatg ggtaatggga cctatttttcc ccaacatccc acatgcacac ttccctctcc    60
attctctcac atttatttct ttcattctaa tttatccatt ccgtgtgtaa catattcact    120
aataatctca tctcactaac tcattcattg attgtgatat gtttatctag aattagtgtt   180
ttaacactgt gtctacatat gatttccttt tcattgtatg tgaacatgtt aactcactaa    240
tcattttgta ttttcgagtt aacatgagtc tccacttcgg tagactaaag taaagatagg    300
tttgagtata ataagtttta aaatttgctt taaaatcaat atttataaat aagttttat    360
cataagtgat ttttgtatgt tatattggac cttgtataaa cagactacag aagaaaatta    420
tttatgagaa cttgtaatgt tagagtggac ctcgtataaa ctaattatgt gggcttttac    480
cataaactat ttatgaaaat tattatggcc cacaccacta taactaaagc ccacatattt   540
agcagcccag tttcattgta agagacatgt tcgctctgga actagaattt tctggttttt   600
gggtatttgt tttcttatgt gtagagaaat gatggtaacg attaaatgtt gtgtattaca   660
```

-continued

| | |
|---|---|
| atttacaatg gtaagacgat taatatattt acacacaatt ttgttgttgc tgtaacacgt | 720 |
| tagtgtgtgt gatgatagaa tttcataaag ctttaactac gaggggcaaa atgttaattc | 780 |
| taaatagttg acagcagaaa aagatatgta tacataatat aaggattaaa acgtaaataa | 840 |
| taataaataa ggcgagttaa attaaaaccc tgttaaaacc ctagcttgaa acacatgtat | 900 |
| aaaaacactt gcgagcgcag cttcatcgcc atcgccattc tctctctcat caaaagcttt | 960 |
| tctccttgat tttcgcattc tttagagtct taacgcaaag | 1000 |

<210> SEQ ID NO 104
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter PT0672

<400> SEQUENCE: 104

| | |
|---|---|
| cagccgtaaa tcctccataa atttattttg caagttttgc tcattatata atgagcggaa | 60 |
| tttatgatat aatcgtttgt aataatgtta tgttttgatc aaaatttgaa attaaaagta | 120 |
| ggtgagaact tgttatacag tgtagataag gtggatcttg aatataaaaa taaaatttat | 180 |
| aagatgtatt taaagcagaa aagcataaaa ctttagataa aataatgtaa aaatgtgtta | 240 |
| gcatcaatgt tgggatattg gccgacccga acttaatcaa tgtcggaagc cattacttct | 300 |
| ctcccaaaag acctttttcc ttcggagaac taggaacttc ctcactacct ttcgcttaac | 360 |
| gtgaaagcca taaatttcat atattcataa aaatcagaaa atctaaaact gtttagtatc | 420 |
| acctgttttt ggtatagact attggttttg tgttacttcc taaactatat gatttcgtac | 480 |
| ttcattggat cttatagaga tgaatattcg taaaaagata agttatctgg tgaaacgtta | 540 |
| cttcagtcat gttgggtcta gatttacata ctactatgaa acatttttaag ataataatta | 600 |
| tcctagccaa ctatatgttc tatattatgg gccaagaaga tatagaacta aaagttcaga | 660 |
| atttaacgat ataaattact agtatattct aatacttgaa tgattactgt tttagttgtt | 720 |
| tagaataaat agtagcgtgt tggttaagat accatctatc cacatctata tttgtgtggg | 780 |
| ttacataaaa tgtacataat attatataca tatatatgta tattttgat aaagccatat | 840 |
| attactcctt gacctctgcc cccatttcct tttactataa ataggaatac tcatgatcct | 900 |
| ctaattcagc aatcaacacc aacgaacaca accttttcca aagccaataa taaaagaaca | 960 |
| aaagctttta gtttcatcaa agacgaagct gccttagaa | 999 |

<210> SEQ ID NO 105
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0676

<400> SEQUENCE: 105

| | |
|---|---|
| aagatagtac agtttcagtg ttttgagaaa aaaagctgaa ctaaaactaa aatgtttaag | 60 |
| gacacaatat ttagtttcaa ttagataatt caacagtttg aacaattttt tttttttttt | 120 |
| tttgaagtca tttatttata caatgttttta aaacgcatta agcatttagg cagccgacaa | 180 |
| acgcctattg tctaactgta aataggcgct tccactiagg ttcatattgc atatttacta | 240 |
| tatgtgtata gtgacaaaaa ccaatatttc tcttatttttg gatgaaggta tagtagttgt | 300 |

```
taaatgttca atataattaa gcattaatga caaataaaat aaaattaatt tagttgataa        360
aaagataatc ttataaaaag atcgatgaat agatataatg gtttactgaa ttctatagct        420
cttaccttgc acgactatgt cccaaggaga ggaagtacct taactataat tctgaacata        480
attttgtcta tcttggtgag tattatatga cctaaaccct ttaataagaa aaagtataat        540
actggcgtaa cgtaataaat taacacaatc ataagttgtt gacaagcaaa aaaacataca        600
taatttgttt aatgagatat attagttata gttcttatgt caaagtacaa ttatgcctac        660
caaaattaat taatgatttc aacaggaagt ctgagatgat gggccgacgt gtagttacgt        720
ttcttgaatt gtgagagatg gtatttatta tactgaagaa acattatttt actaaataaa        780
ttttcatttc acatcttctg taatcaatgc gggtagatga agaagttgtt aatacgatgg        840
ccaaccatat ggatctcttt tttggcgttt ctatatatag taacctcgac tccaaaggca        900
ttacgtgact caataaaatc aagtcttttg tttccttttta tccaaaaaaa aaaaaaagtc        960
ttgtgtttct cttaggttgg ttgagaatca tttcatttca                             1000

<210> SEQ ID NO 106
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter PT0678

<400> SEQUENCE: 106
aattaaatga aaccgcccct aaattaggag ggatttgggt aagtggtaac acattcactg         60
gaaacatgtg aagaaaggag gatgtcaagt agctgaaaac tcagtatagt aaccaacggc        120
ttctcaccaa cctttcatta ataatttggt catccctata ttttattca acattttgtt         180 tttcaatagc ttagagcacc ttaatacctt tcagtgtttt tttataaaaa aaacaaaaat        240
tgggattaat catcaatccc caaatgtaac gtttacttag attatgttca ttttctata         300 cacacaaatc atattctttt gttttaatct tcgaaaaacg agaggacatt aaatacccct        360
aaaaaaggag gggacattac taccaacgta cattaacatg tttgatagca aacgattat        420 tttgttcgtt ttgaaaaggg gaaagtaatg tgtaaattat gtaaagatta ataaactttt        480
atggtatagt aacattttcg aataataaga gagggaaaac actcgccatt gtcggcaatt        540
tagaaccaat attagaaggg tttttttaga gaaaaaggac ttaaaagttt agagaccta         600 acaacaactt atttagaaat agacatgctt aagttgacaa cagcgagttt attttctata        660
tcgaagaaaa atacgaactt tttcttaatt agatttcgaa tgcatgcact atcgagaatc        720
gaccgtcaca agaaaaaact aatatacata ctgtacatat ctatattcaa tattggtggg        780
gatgggttta atgtgtattt ataattcatg gataaattca cacaataagg tccatgaaac        840
tagaaggtac caaaaataag cattaatgac tcttgccac ttatatatat gattctctca        900
tagtaccatt ttattctccc aaacctatct tcttcttcct ctcttgtctc tctcgctctc        960
tctcttctac attgtttctt gaggtcaatc tattaaaa                               998

<210> SEQ ID NO 107
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0683
```

-continued

```
<400> SEQUENCE: 107
gattgaatga tgagtgtgca cccttgtatt actaataaaa aatttagcaa cagttataag      60
ctaacgtcat ccatgagtca ttcattagat tcactatttg cgttctcaaa aatcgaattg     120
ttaaaatttg agaagctcta atatacgagt caatgagatg tggcaaaagc atgtccttga     180
ccataaaatt tcgaggggtc aactcattag ataaggacaa gaatcaacca attgaaggcg     240
tcttctataa caagtttctt tattactaat attaaagtcc aatggggtga ggggagaag      300 aacttaaata aaaggaaata attggtaagt gaataaaatc taaatacgat actagatgat     360
tgatttgtgc tagtgcatgg tattagatca gatatgtgtt actattcgaa ttcaaattgg     420
catattccat gttgttgata agaaaattgt agaagtgtaa aagctgagtt actatattca     480
aactagtggt ttacataaag tgagacaaca actgtttcac aaaaatgact ataaaatagt     540
aagtagtatt aggtcaattg atttttaaaat tttaatcaaa ttcaaatttg tgatataatc     600
aaatttgttt atagaaaatg ttaagaaatc aattttggca gaactaattc agtgagaaac     660
aatcatttac aaaaacaatt ttaacattat ttaacagtaa gatttgacat ttaacccgtt     720
cgtgtgaacc catcatatct aacatggctc tacccatgac gcctccatgc catggacaat     780
tttgacagat cagaagttct gaacgtggac gaggtaagaa caccatgatg atacgattgg     840
agttagttat gtcgccaccg acatcactgc caatctcatt aataaaagtg gtactaaatc     900
tctaatctct attaactata aatataacaa agaaccaaaa gaaagtttct tatctctctt     960
atctttcata atttccaaga aacacaaacc ttttctacta                          1000

<210> SEQ ID NO 108
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0688

<400> SEQUENCE: 108
acgttcagag gcatcgcttt tgtacaaatt gaagcgggtt tgttcaatat ttaaaataac      60
acaggaaaca ttcaaatgta ttattgatgt tgcttaggtt tgtgaaatga tatgaaccat     120
atcgtatata ttactagatt tttcttatat gttttaaggg tagtggggct gacctatcat     180
tctgtttggc attaccaatc agactatcag agtattcacc attcaggatt ccataactag     240
aaaaagaagg ggtttacatt ttctcatact gtataatttt ctactatcag agattttatc     300
gattacatta atctcatagt gattattctg atttataaaa aagttgacaa ataattaaa      360 accagtattt tataacaaga ttgtctctct cccatggcca ttattttgac ctctgactta     420
tttaaatctt aattaacagc ataatactgt attaagcgta tttaaatgaa acaaaataaa     480
agaaaaaaag aacaaaacga aagagtggac cacatgcgtg tcaagaaagg ccggtcgtta     540
ccgttaaggt gtgtcgaact gtgattgggc cacgttaacg gcgtatccaa aagaaagaaa     600
gggcacgtgt atagatctag gaaaaaagaa agaatggacg gtttagattg tatctaggta     660
ccaggaaatg gaacgtcaca ccaaacggta cgtgtcggat cctgcccgtt gatgctgacg     720
gtcagcaact tccccttatt catgcccccc tgccgttaa ttacgtgtaa cccttccatg     780
cgaaaatcaa acccttttt tttttgcgt tcttcttcaa cttttcttt taaatcaaac     840 cttttctttt taaatcaca ttgcatttcc taacgctcaa caaaatctct ctctactaat     900
atctctctct ctctctctct attgttgaag aagactcata atcggagatt gtttgttttt     960
```

<210> SEQ ID NO 109
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0695

<400> SEQUENCE: 109

```
aacatttttct ttaacttact cttaaatttt aatagtaagt tgatgcatgt tatgttgatc      60
cgtcttgatc acaaatattg ttttatggac gaattctttg acagtaaatg gctatagtga     120
ctcagcttgg agcatcccga tatgaaaaca aagtgcagta ttgtgtcgtg gtcatcacta     180
acgcactttc ctagaactat cgcgcgtgtt tgacctatgc aacacaccag atgtcatgaa     240
cgtatactta aatagaaaca atgatataga caattggcta tattctgtca tggaacgcaa     300
accggataac atgtctatta gattcatcgg acttgatcat ggttatgtct aatagacga      360
attctttgtt aacgattggt taaaacggct cacgttagag catcctacta tgacttcaaa     420
attgataaat attacatgga aatcacttta attttagtta gaaggtagtt aatttagata     480
ttcttattta ataaattaaa aaatagaaga aaaaagatg agaagagttt ttgtttataa      540
aataagaaat atctttttatt gtaattttaa aattaaacaa atttaattta tattaaaatt    600
atctttgttt tattgttaag gcaataatta ttttttttggt gggaattgtt aaaacaataa    660
ttagtatact gttaagtggt cctttaataa taagataacg tgatttaaaa aagaacgaga    720
caggctaata tagtagagag gaaaaaatac aatttaggcc caataaagcc caatatagag    780
ttgtgctcaa acacaggtct cgccagatt tcctatgacg ccgtgtgtca atcatgacgc     840
caagtgtcat tcaagaccgt cacgtggcgt tgtttctaca cataggcgat ccatacaaat    900
cagtaacaaa cacgaaaaga gcattcatat gtacgaaagt agaaaagaag agactctttg    960
tgataaaact aagtaagaaa tagcataaaa gtaaaaggga                         1000
```

<210> SEQ ID NO 110
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0708

<400> SEQUENCE: 110

```
gtttccaaaa ctagtattct ttatttgctc tattcattat atttttatat ttgtaacgtc      60
ccgaccgtct ttattaggtt tcgacaatca cttctcggaa ggtcgtccat cctgaaatta     120
ctctatccta aacatgttta actataaaat tctctcgaaa cttttgtaac gtatataacc     180
acataaattc tcttaaactt atttgcatac accattatat ttctgaaatc gatatgttac     240
aatattattt aatatttaga ttacttttac tgaatcgaat taaatatcaa atcgaaacaa     300
atctaatcta ccaaaaataa ttttgttata aacatttctt gcctagttct acctcatata     360
cattttagtt aaagaaagaa atcacaacaa ttcccataat tcaataatta aatccacaaa    420
atcttggagt aagtaagaga aataaaaaga tagtatctta acataaacaa ttcaaagatg    480
ctctctcaca caattcacac acacttacaa aacaaaagac agaaacaatg ttttcattca    540
aatcaaaaga agttataaca ctagtacaaa aaaagctcaa attctaatag taactctttt    600
```

-continued

```
tatttcccaa ttacccaaag attctctctc acttcacaaa actagctttg agagtcgtgt      660
tccacaaaat ccattaaagc tgaaacggtt ttgctcacca ttcaaacaaa tacaaaattg      720
caaaacccca aattataaca aaataatata aaaattaaac cgctaaaaag agtgaaccaa      780
caaaaatcgc cgaatgtgtg tgtaatgaga aaaccgaccc atcatcccaa tcatctcttc      840
ccgtgtcact ctcttcctct cccacgtttc ttctctcttc cctttatggg ttttaacttc      900
tccttcttct tcttcttcaa tcttcagttt tcaaattcaa caacaattca cattttgatt      960
tcttcatcat ctctctctct ctcgcttctc tctcaaatcg                           1000
```

<210> SEQ ID NO 111
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0710

<400> SEQUENCE: 111

```
tagtgcgcgt ggggagaggg aatggtgaaa ccttagtggt taagttatga ggaaaatgat       60
aaaaggataa aacaatcaaa tgcagcttga aacggccata acataaagta ccttatggtg      120
gtgcgaatat ttttgtgttt ctttcactct tttattgctg aaagctacga cacttgtctt      180
aatatattgt ttccgcaagt cacatgatct actttttatt taacgtctag aaacgccgag      240
atatatgatg attagtatat cacgtctatg caaattgtta gttcgtgttt ggccaaaaga      300
tatcgagaca tgtctgaaga accgagtctg gttttgagat atttcttcaa gcattactat      360
acaatagaaa aaggagacac gcgaatatga taatagcaaa aggcataaaa aggcgaaaat      420
taaagaaaaa cgtaaagtga tttggcctca atcaacggga acgtatctta atttagagg      480 ttcttcttt actttgaga cgagagagtt tgcgtctttg cgagctgctt tggttgacta       540
aacattatca tattgaaaac caaaatacaa cggaggaata tttgtcacag tttcactttc      600
acattgtttc cttaacgttt aatcaaacct gttcaaaatt tctatagttg taatcatcat      660
tgtttacaaa attttcgttc aaagatgatt ttaaataaaa ttgtgaaaga aaacctttc      720 tgaaataagg attggatgat agtgttaaaa gaaaaatatg aactgaggca aaaagaggag      780
tggtccccgg aagattgtga aatgtgtcat ctaaaccagc cagacgtagt cacgtgttct      840
ctctagcttt atgaacttcc ttagccagca ccatcattgt gattgtagta tatatgtaac      900
cctaccttca tctctcccat tttccattct ccatatagac tcctttacaa tacaaaaac      960 ctatccaaaa gcgaagaagc caagcaaaca tattataaaa                          1000
```

<210> SEQ ID NO 112
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter PT0723

<400> SEQUENCE: 112

```
gtcatatctt atcaacacgt caacgatcaa aacctttagc ctattaaatt caacggctta       60
gatcaaaacg aaactaggtg ggtcccactt ttaatatcgt ggctgcataa catttcctcg      120
ataactgaag ccgttgtggt ctttctcaga atctggtgct taaacactct ggtgagttct      180
agtacttctg ctatgatcga tctcattacc atttcttaaa tttctctccc taaatattcc      240
```

-continued

| | |
|---|---|
| gagttcttga tttttgataa cttcaggttt tctcttttg ataaatctgg tctttccatt | 300 |
| ttttttttt tgtggttaat ttagtttcct atgttcttcg attgtattat gcatgatctg | 360 |
| tgtttggatt ctgttagatt atgttattgg tgaatatgta tgtgttttg catgtctggt | 420 |
| tttggtctta aaaatgttca aatctgatga tttgattgaa gcttttttag tgttggtttg | 480 |
| attcttctca aaactactgt taatttacta tcatgtttc caactttgat tcatgatgac | 540 |
| acttttgttc tgctttgtta taaaattttg gttggtttga ttttgtaatt atagtgtaat | 600 |
| tttgttagga atgaacatgt tttaatactc tgttttrcga tttgtcacac attcgaatta | 660 |
| ttaatcgata atttaactga aaattcatgg ttctagatct tgttgtcatc agattatttg | 720 |
| tttcgataat tcatcaaata tgtagtcctt ttgctgattt gcgactgttt cattttttct | 780 |
| caaaattgtt ttttgttaag tttatctaac agttatcgtt gtcaaaagtc tctttcattt | 840 |
| tgcaaaatct tctttttttt tttgtttgta actttgtttt ttaagctaca catttagtct | 900 |
| gtaaaatagc atcgaggaac agttgtctta gtagacttgc atgttcttgt aacttctatt | 960 |
| tgtttcagtt tgttgatgac tgctttgatt ttgtaggtca aa | 1002 |

<210> SEQ ID NO 113
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter PT0740

<400> SEQUENCE: 113

| | |
|---|---|
| tgtggccact aaagatttac ccttaaccgg gcccatataa gcccacgtca agtggcgctt | 60 |
| atacgctctc cgtaagagag ccaacatttg gtatgtaatg ttgcaaatta ttcttcaaga | 120 |
| caataaattc aaatataatt caatattgtc caaatatagt gatgtacttc agttgtgcac | 180 |
| atagaaactc cactaaaacca acttttagat agatgcattc acaaattttc aacaatgtcg | 240 |
| cgaaagtcta atccatcacc agattctaac attttaatta ttatatttaa ctatacatac | 300 |
| tctaatcagc atgagtcaaa cgtgtacaat agcccaagca tataataaga ccaaagtcaa | 360 |
| actcaaataa atgtctccaa actcaaaact tgaaaaagac ctaattatta catggtagat | 420 |
| atgactttgt cgacaagtaa accaactaat cctcgaagct accttctctt cccagttatt | 480 |
| atgtgtgatc gatttataaa tctcttcttc taataacacc tatatttttc ttatgatgtg | 540 |
| aataaatata aaacttttaa cttaaaaca tatttatccg aaatattgca cttagatttc | 600 |
| aaatagataa ataatagtac tatctaactg atattgaaaa gacctaacac ggaaaacagt | 660 |
| tttataaaaa atcccaaatg tgggtaatta tcttgatttc ttgggggaaa cagaaaatgg | 720 |
| attaagatta atcggagtcg tgtcaagcag ctcgttaata actgtagcaa gttgactgag | 780 |
| taagcatcaa cgtgtcatct ccgtaaagcc cattatttct agtctcgccg cgtcttctct | 840 |
| tccacgtagc acttcactt ttctctcctt ttgtttcctt tggaacacaa acgtttctat | 900 |
| ttataggaat aattacgtcg tccgtatctg tgtcggaaca tagatccaaa ttaaaagcga | 960 |
| cttacttaat tacatatcgt tcgtgttttt ttcttcaaaa a | 1001 |

<210> SEQ ID NO 114
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)

<223> OTHER INFORMATION: Ceres Promoter PT0743

<400> SEQUENCE: 114

| | | | | | |
|---|---|---|---|---|---|
| tcgattggcc | cgatcggccc | caaaatcaag | ctgagccgct | tcaaacttca | gcttttgaaa | 60 |
| tcaccccaa | actcatgtcc | tcttatcatt | ataactaaag | gatctttcat | tttatttaac | 120 |
| tcatcgtctt | gcactaccca | acccaaaggt | tccaactata | cccgaagctt | tctaaaggtc | 180 |
| caaagacttt | tttttttcgag | ccagactatt | caagccaaga | aaagccaaac | cccacaagcc | 240 |
| agtactttc | aattccatat | tataaactta | tctgtcttgt | tttagtccca | ctaaaaacaa | 300 |
| cagaatttaa | tttaggttga | gctaaaaccc | ttgacaaaag | tgtatagtcg | tcgattcagt | 360 |
| agcacactca | tcactcatca | gatttgatag | ttgacctaaa | gtatgactac | tccatttcaa | 420 |
| ctaacaaatg | aaaataaaag | agacctaagg | gttagaggat | tgaaactata | ctctcaagtc | 480 |
| ttttatcact | aggctactac | cagctagtta | acttgatgga | tttaagcaag | aaaacgtaga | 540 |
| atttatattc | gagcagattg | tttagctaaa | aaagcttggg | tttgaaattg | ccttttctcc | 600 |
| catataagca | cgtcggttcc | taaataactc | tttctagcgg | agagtgtctt | tccaataatt | 660 |
| taataaaaat | ggtgtttgta | tatcaaaaaa | aaagaaaaa | agaaactgat | cgagatagaa | 720 |
| cgtttgcagt | tttataaaca | atttaaaaaa | caaaaaaat | taaactcaat | gtattttta | 780 |
| ttaattcaca | aacaataata | aatcatagga | tcgaatattt | acacggtatc | aaaacctact | 840 |
| cgccgctact | atataaaaat | tgaagtcaaa | tatcaaccgc | aattattaaa | ccagcaagac | 900 |
| aataattcat | aaacttaata | taaacataaa | taaattaatg | ttacacaacg | atatatggtg | 960 |
| agggttatta | ctatcttctt | cctctcaaaa | cacatctcct | aaccttaagc | tttagacggc | 1020 |
| ctgc | | | | | | 1024 |

<210> SEQ ID NO 115
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0758

<400> SEQUENCE: 115

| | | | | | |
|---|---|---|---|---|---|
| agctagccac | atcagtgacc | aaaaaagata | attaacaaac | caaataaaat | aacaaatttt | 60 |
| gatcatttgg | aataaaattt | ataaaggaa | cgaaagcgcc | ttctcacggg | tcccatccat | 120 |
| tgaaatatat | tctctctttt | tgctctatat | aataataacg | cgtactaatt | tgtagtatat | 180 |
| attattacaa | agtcgatatt | tgattgtttt | gtgaacgttg | atatattaat | tttcttggat | 240 |
| gatgacaaaa | aaagtcatag | aaagtaacgt | gtgaacatag | cattaacaaa | atacaaacat | 300 |
| aatatataac | caaatatatg | aaaataggat | aaaatctcat | tgaatagatc | ttcttctatt | 360 |
| caaatatata | aatatttgtt | tgtctataaa | attaacagag | cattcacatt | atctaaaata | 420 |
| atagtaaaat | caaaataaaa | ctaaataaaa | ataactctgg | ttttataacg | attgatttta | 480 |
| aatattagtt | tttgttgtaa | agagatcatt | atatatgtct | gtaatatttt | tatactgagt | 540 |
| tacatgatat | ttagttatta | tagcgtaatt | aactaagata | agaaattaac | taaagtgata | 600 |
| ttctgattat | tattatttttt | gttaggacac | gtacgtggaa | aaactaaaca | ctataggtta | 660 |
| caaaacggta | taataaactc | accattactg | gaaaatgttt | gcatttgact | caataagtaa | 720 |
| cttattataa | gttactgata | taatgcatag | ttttgaaatt | cttaaataaa | ttattttggt | 780 |
| ttcgcatgaa | aatatgaaag | gagagaaatt | tattattgtc | acttatatat | atacacatcg | 840 |

```
taatcatttt ttcgtgaata attctctctc ccattccatt atttctcagt atctctcttt    900
ctttcccttc ctttattgtt gcttttaaac cttcaatttg ctcataaacc aaatatataa    960
tatcaaaaca aacaaacaaa aaatcagaat tcccctaata                          1000
```

<210> SEQ ID NO 116
<211> LENGTH: 921
<212> TYPE: DNA
<213> ORGANISM: Arabidopsis thaliana
<220> FEATURE:
<221> NAME/KEY: misc_feature
<222> LOCATION: (1)..(921)
<223> OTHER INFORMATION: Ceres Promoter PT0829

<400> SEQUENCE: 116

```
aaagttttga attattggga atcaatttcg aagttttgta attctttggg ggctaatagg     60
atattttatt ttcttggttt cgtctattgt tgttttttcta tttatggttg ggcttttaga   120
actctggaca ggcccatgtc atatgttttc ccttctcctt atattttca tttttcattt    180 tgttaaatta atgcataata tccaaaaaca atttaaattt ttgaaggaac cctttagtta    240
cggctccgaa gctttcacaa gtgagaatgt gagatcaaag aaggcaaatg gaggatttta    300
aaagttaaaa tcatctttta tctgcaaaag ttgacaattt ttttgtatca aatctaaatc    360
atcaaactct cttaaactac aagagcataa caacctctat gtaatccatg aaataatctg    420
cttgaaggac ataacataaa tcattatggc tagagtgact aacttcaatc aaatcctctt    480
aactctagct cccttacaat ggtatcgtaa aacattatgc attagggatt gttgtcctag    540
gaaaataaaa taaaatccc cacagaccaa ctaccatttt aacttaaaaa taagcttcgt    600
ccgcgacgaa ttgttttcca tcctaaaaat agaatggtgt aatctgctaa tggtttagtt    660
ccattaactt gcaagttcta ttgaaagcct aaatgtcaat aaagatatta aaattcggag    720
tcaaagacaa aatgaatcaa aagcaacaag acaagtcagc tccattcttc actacccatc    780
ttttacaata aatcatctct cttttcacaa atttcaaact actctcattg cccttttagct    840 ttgttataga gccaacacta cagagagact cacacacttg tttcaataat taaatctgaa    900
tttggctctt cttataaact a                                              921
```

<210> SEQ ID NO 117
<211> LENGTH: 763
<212> TYPE: DNA
<213> ORGANISM: Arabidopsis thaliana
<220> FEATURE:
<221> NAME/KEY: misc_feature
<222> LOCATION: (1)..(763)
<223> OTHER INFORMATION: Ceres Promoter PT0837

<400> SEQUENCE: 117

```
aactacaagg gagacataat atcaccatct ggttcctgtt atcatctgaa gatttcttgt     60
tttaccttcc agtgataaaa tgatccttat aatacatata gatatattaa attgctgtat    120
tttaagatta tagatatata aggtacatga gagtgtttat ttaaaaaaat tcacttggaa    180
ttcatgtttt gtgatacgtt agattggaat ccatttggga aaagaagaat catctgttct    240
tatgtctcaa attttgactt cattcacttt tcttcttgtc ttttaagaaa gcttccacaa    300
tctaactgtt cgatgtgaaa actgagattc gagtaagaaa atgtgaactg tgttatactg    360
ttttttaatt agataattta gattgcactc agataaatta ataacattcc tcgaatactt    420
ttatgtgatt ggatatatta ggtatatctg ccaaccaacc aataaactgc tatgtttaaa    480
caaattaaat aaattagtat atgtttactc aagaataaag aagatagaaa agaaaattct    540
```

```
atatgagcta aatttgctgg aggaggcatc ggacgtgggt accagacctt ccaagcaca      600 cgagtagtgc ttagccatgt catgctaaca tacaccattt ggttcataca aaatccaaat     660
caaaatctat ttttaaaatc ttttgcacac gtctttgaaa aacacctctc atactatagc    720 tacgaagct tcaatttcaa ggtttgtcta aaagctaacg att                        763
```

<210> SEQ ID NO 118
<211> LENGTH: 751
<212> TYPE: DNA
<213> ORGANISM: Arabidopsis thaliana
<220> FEATURE:
<221> NAME/KEY: misc_feature
<222> LOCATION: (1)..(751)
<223> OTHER INFORMATION: Ceres Promoter PT0838

<400> SEQUENCE: 118

```
atactggtat gcttaaggtt gaagccaaga tctctgtctt acccaagtaa ccactttcta      60
ttagaaggga tcaacactaa gaatatggag atttaagcct aagggctaag gcggttctca    120
acaatacatg atgtgaatac aatcacagac gatttactga ggtttgttga taagatcttg    180
atcagtctct gcatcatctg ttcaacaatc tcaatctttg actgtttgct ttcggagcca    240
taaacagagg aatcccttat tccctgttat aggagcaata caccaagtat tatttccatg    300
gctgaaattc tcttatggaa acctaattgt tccattgaag ctgtaaaatc gaatctggtg    360
aatattctcg agcaaagccg catgctaatt atgtcaattc agaagagttt gattaggaga    420
ctcgaagcga gtttgatgat cttcttgat gttcaactcc gattgtaagg gtataattga     480
cttttcatgt attacggctc caccacctga cactaaggca ctctttgtcc atctcgttgg    540
tatcatcgga ttcggatggt aaaaataaaa agagcgagag gaaacttgtta ctcatgcaag   600 cttctcaggt gccacgtcac tccattacgt gtcatcttca cacaccatct cgctcaaaac    660
cgatctcatt tttcaaacct taaggcaga agcaactgat taagttaaca ctcttgagaa     720
gctctcgatt aagcttgaac ttggaggatc a                                    751
```

<210> SEQ ID NO 119
<211> LENGTH: 669
<212> TYPE: DNA
<213> ORGANISM: Arabidopsis thaliana
<220> FEATURE:
<221> NAME/KEY: misc_feature
<222> LOCATION: (1)..(669)
<223> OTHER INFORMATION: Ceres Promoter PT0848

<400> SEQUENCE: 119

```
tctctttaaa tcagttaact aaccgtttat atatttacga taaggtttga agagattatt      60
gataaaataa tacatttcat aatcccgcgt tcaaccgttt aaagtaacat ttaagttgac    120
tatatctaat ttttttttcca ttaaatatgg agctggtaaa ctttatcaac ttctaaaaag   180
tgtaacaaca aaaattaggt caatcacaat tctgttttttt ttattatttt ggattgactt   240
ccaattgcaa atagtcttag tgatcaccat tatcatacat atatacatca agtaggtttc    300
atcatgatat accacaaagt atttgacaag ccatatggtt ttggatcaaa aagtcggtcc    360
aaaattaatg ttttatgtgc aagaaccgac ccattgtaca cacgtgttaa catcttcaag    420
actttcatct ctatttttct tttggtcatt aagatacca ttgatccgaa tctgttacat     480
tcccacctac ttttttaatt tttactatcc actccaaatt aaacacaacc gatgatttta    540
ataattggaa gcttttaaaa atatttcaaa acaagcctct ttgtgtttgt ctatatatat    600
acacgtaata agaaggtgaa tgaatctcac agcttacttg ttctaaggct tccaataacg    660
``` aaaacagta                                                              669

<210> SEQ ID NO 120
<211> LENGTH: 702
<212> TYPE: DNA
<213> ORGANISM: Arabidopsis thaliana
<220> FEATURE:
<221> NAME/KEY: misc_feature
<222> LOCATION: (1)..(702)
<223> OTHER INFORMATION: Ceres Promoter PT0863

<400> SEQUENCE: 120
cgggaaacga caatctgatc tctagtccag tcgattggcc cgatcggccg attataaact      60
tacatgagac aagtataaat aattattata aacttattaa gtttaagatc aaggcttttg     120
tgcaatgtat caatgaatgt tagatgtgat atgatgaaag caatgtttta aacacataca     180
tagtcattga tcggaatgtg tgttattaga aatgcatgcc taagccgata gggttatcta     240
tgtttggtct tggacattat agccaaattt cgaatctaat tcttccaata tatattttt      300 ttttttgct tagggccact actagtattg cttatcaatt ttaagagctc atgaaaatgc      360
aacaatatag tagttgcaaa tccttgtttc aagagaaatc aaagggccac ttgtgaattg     420
aataataata atatttgcaa ataacctttc actaaaccat accaacaaaa ccacacagat     480
ttggcaaaga cataaccttt gggagacgtg aaaaggctca aaatttgaca attgtcctta     540
caaattcgct cattagtgca attgtgagat ttgtttgcat ccaaatccaa ttcataactc     600
acactcgtct caaattcgaa aaggcctgca gggccagtgc actgggatcc aacaatgtcc     660
tccgactcgt ccaagatcaa gaggaagcgg aaccgcaccg cg                        702

<210> SEQ ID NO 121
<211> LENGTH: 435
<212> TYPE: DNA
<213> ORGANISM: Arabidopsis thaliana
<220> FEATURE:
<221> NAME/KEY: misc_feature
<222> LOCATION: (1)..(435)
<223> OTHER INFORMATION: Ceres Promoter PT0879

<400> SEQUENCE: 121
ttctaggaag actggtcaag ctaagctgtt tctgtttttt gttttgtac tttacttttt       60 gtttgctagt gggaactggg tttattgggc cttgaagttg ataaaagatg aataaaagac     120
atatcgccta aagcccatat gagaagcaga agacaaaaac ctccaacttt gggcataaat     180
tttgattata gttaaaagtc cagacccaat ttggcacctg gcttagttac gattctaagg     240
catgacacct gcctaatatg tttattacag aaaataaaga gaatcagcta ggtgtccctt     300
attgaacaca ttaacaaact ccaacgacac tacgtgtctt cgtgactctt actatatcca     360
aaaacctata gctaaagctg aattttccat gattagtata gtcccaacca aaaaaatact     420
gaagaaggca taagc                                                      435

<210> SEQ ID NO 122
<211> LENGTH: 397
<212> TYPE: DNA
<213> ORGANISM: Arabidopsis thaliana
<220> FEATURE:
<221> NAME/KEY: misc_feature
<222> LOCATION: (1)..(397)
<223> OTHER INFORMATION: Ceres Promoter PT0886

<400> SEQUENCE: 122
agtgtatttg aaaacgacat tgaagaatta atatattttt ttttaatttt agttttttat      60

-continued

| | | |
|---|---|---|
| agtacaaata ttaaaacaaa caatcctacc atatcataac atttgtaaat aacattttaa | 120 | |
| gttttgtttt gagttttaat taattttcta tgacaaaaaa atgaagtcaa tagactaagt | 180 | |
| gaatcatata gtataaataa acacaattta aatagtttca aataaattta gaaagaataa | 240 | |
| aacaaataga aatcagaagg tgtctgtttc ctcctcgcaa catacgatca aagagaaaca | 300 | |
| acttgaccct ttacattgct caagagctca tctcttccct ctacaaaaat ggccgcacgt | 360 | |
| ctccaacctt ctcccaactc cttcttccgc catcatc | 397 | |

<210> SEQ ID NO 123
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0007

<400> SEQUENCE: 123

| | | |
|---|---|---|
| agcagaacaa ctatatttat tgtgtcacat aaatctgaga tcatttataa ccaccaaaga | 60 | |
| acctatacac agtaaatgac aaatgtatct ccctctatct ctattgccca tatgtagatg | 120 | |
| ctaaagtaag atttctcttt tttttaatgt acttttttt gtataaagta tattccataa | 180 | |
| gaaaaaggaa aagcttgttt atggatcaat tgaccccaaa aaaagttttt agatcaaagc | 240 | |
| ccaatataaa aaaaaaacac agtagtgaca caaaggaact taaataaacc atgaattgat | 300 | |
| ctataaacag tagagatcga taaggcgaac attttccatg tgaagtgtct tctttcatct | 360 | |
| ataatatttt tgacatccaa taatttcctc tataatatca ttcacataat tgatagaaac | 420 | |
| attatgttag aattgtccac atcatttgag ctgtaatata ttctgtttta acaaattata | 480 | |
| tggtagttgc ttaatcttat gtccatcttc ttctatgcat cgttttcgcg cctagttgtc | 540 | |
| cagtccattt caactaccta cctctaattc ttatcttaaa acaacatttt ttaatttaag | 600 | |
| tattatgctc aaagactaac tagatagaaa accgttatta acattaaaac gaattaaaag | 660 | |
| tcttacatgg aaaatgtagg tttataaacc acgagttatg attgacaata aaaaaaatgc | 720 | |
| aaatcatcaa tcaaaagaga cttgagtgcg actctatatc aaccattgca attaaaatta | 780 | |
| tctatcacaa aaattttaga cagattaagt taatttagtc taaattcact aatttatttt | 840 | |
| ctataattag taattaacta tatttatttta tttacacatt ttctgataat ttagaaattt | 900 | |
| gcatgaataa caaatataag attttggaaa ttagtagcaa atttaattaa taattatttt | 960 | |
| tgcctaaatg aaccaaacta taaaacctcc acatacacca gtcatcaaat ttacagagac | 1020 | |
| aaca | 1024 | |

<210> SEQ ID NO 124
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0008

<400> SEQUENCE: 124

| | | |
|---|---|---|
| ctcgagagat gaagtcttag taatgtttga acaaacaata atcacgtttt ccatcaaatt | 60 | |
| cgagcattta aagtttatat tactacatgc cccaagatga taccgtccat ctcatccgaa | 120 | |
| aatatttctg aaattgcgct aagacaacaa tgtttgctca aattcgatca tttaaagttt | 180 | |
| acaaatctct catcaatctt acaaacttct cacactaaac agaggtacat attttcttat | 240 | |

```
aaagacaaaa ggttcgaaca gctggcttct caactcgagt tgtttgtcag ggcctctctt      300
cactaactac aagttggtac ttcaaatatt ggtggctagc ttcacgtgat attgtctaca      360
aattaaaccc atgaaaaagc tgcattaatt gttccaagtg aaccctgagg agtgtcaata      420
gtctttgctt tagtgtgatc attaaaccaa atctctaaat tcctaatttg tactaacatt      480
tggaacgtat ttcctactct tctccctgct ccaactccca aaaataagat tagttagatt      540
tctataacta atatacatgt atactcccaa aaacagtaaa accatattaa taaagctaat      600
tttgcataga tttatttcgg taaaccggcg gttcaagttg gggaaaaaaa agacaaacgg      660
tctaaagtca tccaaagaca aaaaaccaaa gacaagttga gagagacgag accaatcaca      720
acattgcttc gtagattgcg tgacatcatc cttgacggct actttcattt gtgtcttatt      780
tggataaaac gcacgtgttt aattcacgaa ccttcatagc aataagaaat ttccattact      840
ttcatatttt caactttttt tattacccat tacatgctta aaatattaat tcacaagtct      900
ttgtcaaaat tcaatatttt ccaggttcat gaacccttt tatctcaatc tactctataa      960
tatctcccta taaattacaa caaaacctct ttattttca                           1000

<210> SEQ ID NO 125
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0019

<400> SEQUENCE: 125
gatataagta gaatcatttt ttgccgccgt ttctcgctaa cacaccgaaa actgaatcaa       60
atctcctagc tcttctacgc aaaatcgagt gcatcgacaa tggcggaacg tggtgtcgaa      120
cgtggtggag atcgcggcga tttcggacgt ggattcggtg gtcgcggcgg tggaagaggt      180
ggtccgagag gtcgtggtcg ccgtgcaggt cgtgctccag aggaggagaa atgggtgcca      240
gtgactaagc ttggtcgtct cgtaaaggaa ggtaagatca caaagattga gcagatctac      300
ctccattctc tcccagtcaa ggagtaccag atcatagatt tactcgtcgg tccttcattg      360
aaagacgaag tgatgaaaat catgccggtt caaaacaaa ccagagccgg tcagagaacg      420
agattcaagg ccttcatcgt cgtcggagat agtaacggtc acgtcggatt aggagtcaaa      480
tgctccaagg aagttgcgac ggcgatcaga ggcgcgatca ttctcgcgaa attgtctgtg      540
gttccgatac gaagaggtta ttggggtaac aagattggaa aaccacatac ggttccgtgt      600
aaggtaaccg ggaaatgtgg atctgttact gtacgtatgg ttccagctcc gagaggttct      660
ggtattgtgg cggctagagt tcctaagaag gttcttcaat tcgctggaat tgatgatgtc      720
tttacttctt ctagaggatc caccaaaact cttggaaact tcgtcaaggt atgtactttc      780
acaatggctg ttttggtttg atgaactctg aattaggcag tgaaaagta atcattacca       840 gttaagtgaa tttatattga agattaggat ttagctgatt gtattggttt gagcatgtga      900
gtttgtgttt aagattgctt gaattgaaat gctttaggtt gtttgattac gctaaattct      960
gactaatgta attcaaattg ttgttgtttt tttttggtc                            999

<210> SEQ ID NO 126
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
```

<223> OTHER INFORMATION: Ceres Promoter YP0028

<400> SEQUENCE: 126

| | |
|---|---|
| gtcagtgaag tcgattggta gtacttgaaa cacttggttg gtttcatgta tttggcctat | 60 |
| atataaacaa acatcgtaat tatatacgga ttttttcgg aattttacgc catatctgta | 120 |
| agtatatata acatgcatgt cgttttcaaa ttcatatgat gaacgatcca cgtaagtgct | 180 |
| actactccta caatattgca tgagagagat atgtatttat aaatttattt ttgaagaaga | 240 |
| aataagaggg aaggttactt gggtggatcg atgtgaaaac aaaagaagaa aaagcgaaac | 300 |
| ccactaagcc attacatgat atcgaccttc ttatcttttt cctctttatt ttatttttct | 360 |
| catcttcttt ttgtcaggac ttttttctac ttaatgaaac ctccaaacta tctaactaat | 420 |
| acactcccat gtagaataaa gaaaattata aagatattg ttgatatttt gtaactagaa | 480 |
| aatatatttg ctctgtaatt tttcgtaagt taaatcaaca ttttaaagta gaaacaaata | 540 |
| ttactgcaaa aagtaggatc attattttg tccaaaatct cagttagcta tagggttgta | 600 |
| gtaaaaacaa aacacattct tgatttgccc caaaaaataa agagagagaa gaatattgtt | 660 |
| caaaagtggt ctcttctctc tctaattatg ttttcactaa acccaattag attcaaacag | 720 |
| tctacaaagt ccaaaagata aacatgggac aacaattcga tgcaaaaaat cctcttttca | 780 |
| tgctcttttt ttattctcta gtcttttaaa ttactaataa aaactcacaa atccaccaaa | 840 |
| cccattctct acaactcacc ttcatctaga tttacccact cccaccgaga aacacaagaa | 900 |
| aaaaaatata catatataaa tatacaagac aacacatgat gctgatgcaa tatacacaac | 960 |
| aaagtattaa atcttagata ttgtgggtct cccttctc tattcatttt cttattcatt | 1020 |
| aaaa | 1024 |

<210> SEQ ID NO 127
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0039

<400> SEQUENCE: 127

| | |
|---|---|
| ccgttcgagt atttgaaaat ttcgggtaca cccgcctaaa taggcggacc ttatctagta | 60 |
| tatatataca tttgaactat attgtttact ttttagttga tttaggctat gtcatgacat | 120 |
| tgacataaat ctacctgtta tttatcacgt gtaattcgtg taaagtgtaa actagaaagt | 180 |
| tcaaatacgt atttgttttt gttctgttat ataggattgt catagttgta aatctacaat | 240 |
| ttattacaac atgaataagt acacaagcaa tgtaattgga tttaattgct aaactctta | 300 |
| catggtcaat ctaaatttga taagaaatac gtcacatatt actaagactg atagttttt | 360 |
| tgttgtcacc aattattttt gttaaattga cgaaaacaat tccaaaaact caaatgtaca | 420 |
| aaatcataca gtctcacaaa catctcatag agaaagatat aaatctccca tatgggaacg | 480 |
| ataacacgag gtcgaaatac tattcgtaaa actaaaacgc cttagttata aatcgttagt | 540 |
| tgtaaccgcg gtcgagaata catacagatc cacgaaacta ctactacaca tgctgctgaa | 600 |
| ttggaatttg gaaaagacca tcttctttag gaagagctca cccaatgagt gacaaaggtg | 660 |
| tcggtggctt gttttctacc catatgtata catcaaatgg tagtttcatt aacgtttggt | 720 |
| tttgagaaaa gtaagacttt ggctagtagc taggttcgta tataataaac tcttttgaga | 780 |
| aagttcatca ctggtggaaa atgttaaacc ggttttttct catttttcc gccatgttaa | 840 |

```
ccaccggttt aaaaagaccg taacacattg aaagattaat aagggtatat ttgtaattac    900
ggtttgctgg caatttttaa ttattatttt aattagagaa aatagagaag ccctatcaat    960
gtacatggta tatatataaa aggcaaaacc ctagaaaacg atactattcg actcagccgt   1020
cctt                                                                1024

<210> SEQ ID NO 128
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0050

<400> SEQUENCE: 128
aatctgatct ctagtccagt cgattggtac ttagggaaa catcatattt ttaaaccttg      60
tctcagtaag ctaacacaca ccccttgtga ttacttatcc atgtttatcc acaagaatgc    120
agttggattg agatattttc ttctttgttg aaatcaggcc tcaaggtgtt catgtggtct    180
gcaaaaaaat tcccaaaaat aaagatagtg acatctgaaa tcgataatgg attagacgaa    240
gagtttcgtg ttattccttg gtatgggcgg gtttgggac agatattttg gcacagacga    300
ggactaggcc actgtggtcc tgcagcatta ggtgtcccett ccatgtcctg cattacattt    360
tattgatgga ttcatcaccc tatctactac aacggctaca caaactatga agagttttgt    420
ttactaataa atgcccaagt gaggggtcga tcgaacccgg gacacgtttt tcagtttacc    480
atatagaatt atccttggaa cccttgatac tccatagaac atcaccacct ctgttgtcat    540
ctcaggaatc caggttcaaa cctagtctct ctctccctag tgggaggtat atggccactg    600
ggccaatgat gacaaaatgc aaaaaaaata aaatacattt gggttcatta tctaaaatat    660
ctcttgtgtt tgtaagtttt ggttgcacac tcgtgtggtt gaagtgtgtg tgagaggtac    720 tatacaaatac actctgcttt tgttttgtac ctatctcttt ctcttctcca catatccaag    780
actttgggga taaagctgag atcattggtt gccatttggt tgtgtagaag caatcaccca    840 tttgcttttat ccgaggttga taaatttcct cgggttctcc ttctgacacg tatgacaaat    900
tctaatagta tattcctcgt agatattacc tatatattct caatagttgc aggtacttaa    960
ggctttgtct tggcatcctc gtcctcttca gcaaaactcg tctctcttgc actccaaaaa   1020
gcaa                                                                1024

<210> SEQ ID NO 129
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0086

<400> SEQUENCE: 129
cttatccttt aacaatgaac aggttttag aggtagcttg atgattcctg cacatgtgat      60
cttggcttca ggcttaattt tccaggtaaa gcattatgag atactcttat atctcttaca    120
tacttttgag ataatgcaca agaacttcat aactatatgc tttagtttct gcatttgaca    180
ctgccaaatt cattaatctc taatatcttt gttgttgatc tttggtagac atgggtacta    240
gaaaaagcaa actacaccaa ggtaaaatac ttttgtacaa acataaactc gttatcacgg    300
aacatcaatg gagtgtatat ctaacggagt gtagaaacat ttgattattg caggaagcta    360
```

```
tctcaggata ttatcggttt atatggaatc tcttctacgc agagtatctg ttattcccct      420
tcctctagct ttcaatttca tggtgaggat atgcagtttt ctttgtatat cattcttctt      480
cttctttgta gcttggagtc aaaatcggtt ccttcatgta catacatcaa ggatatgtcc      540
ttctgaattt ttatatcttg caataaaaat gcttgtacca attgaaacac cagcttttg       600 agttctatga tcactgactt ggttctaacc aaaaaaaaaa aaatgtttaa tttacatatc      660
taaaagtagg tttagggaaa cctaaacagt aaaatatttg tatattattc gaatttcact      720
catcataaaa acttaaattg caccataaaa ttttgtttta ctattaatga tgtaatttgt      780
gtaacttaag ataaaaataa tattccgtaa gttaaccggc taaaaccacg tataaaccag      840
ggaacctgtt aaaccggttc tttactggat aaagaaatga aagcccatgt agacagctcc      900
attagagccc aaaccctaaa tttctcatct atataaaagg agtgacatta gggttttgt       960 tcgtcctctt aaagcttctc gttttctctg ccgtctctc                             999

<210> SEQ ID NO 130
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0088

<400> SEQUENCE: 130
tcgattggga ttactacttc atctagtaag gttctgaaaa cgtttgttgt tgataaggaa       60
gattcgtctc aggttattac tgttgatctt caaggtttgt gattgtgacg cttatacatg      120
tgctgaaact gtggtgttta tttattgaaa acaaaaaaaa agtctctctt gtagtttcat      180
tgtactaaat agaaaacaag aaacgttttt ttctttaatc ttctacattg ataatattgg      240
atcaaaggat tgtttctgca agacacaaca caaacatact tatactagtt tacttctact      300
aagtactaac tacatacccca tacacacact tgcacctaga cttttacttct agacatcatt      360 accctaaggt agaaccaagc ttacaagcaa gttttaccga caactcttac attacaactc      420
tagtctgtag tctttaacgt agacttacta actagtcatt agtggtttaa ttttttaaat      480
tttcatccat atgttttgt tgtagatata aactaaagtc ggtcacattt aataattgtc       540
attatgtccg cgtaaaagtc aattcagcta ttggacattt atgaaatgta agattttctc      600
tctcatttcc ccgtgcgtga agacatgcat tggttttct gtaataatca acaaatccaa       660
accccttttc gatctttatt tggacattgt tagagacaaa atttctctat agtctttttc      720
ctaatttgat accatgtttt tgtttctgca caaatttact cactggttta actaactatc      780
cacttattta tgattttacc attaggcgtc agctagccct agtcaaattt gtaaacaagc      840
caagctatct acataaatcg agatgtcatt aacgttaatc gtcgttaatt cgaatttgaa      900
aacatagata gctttagcag tacaatgggc aatggtaaga agaatagcaa aaggcccaat      960
atttggtttg cagaaattaa agccttaaaa aaaagcccac agatatttgt caaagaaccc     1020
taat                                                                  1024

<210> SEQ ID NO 131
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0092
```

```
<400> SEQUENCE: 131
aaagattgag ttgagagaga tggtggagac gcagaacaga caaagggagt ttaccatata      60
gtgctctaaa gggcaatgag attgcagtga tgtggctatc cggggaatca tcgcaggtta     120
ttccttccca tgagcaacaa tcaatggatg ggttccaatt cagaggagaa acagaagaag     180
aaacgtttcc agagaaccac agtagggatt ctcgatcttg cgagttgcag agagcctctg     240
aaactgcaat agaaaggaca ctgatgaaaa gaacacactg aaggagtatg ccaatcatgt     300
gaaaactcag agcttgtatt ggtcttgtgg ttgatgaagt tctcacaaaa cctttggctt     360
tgaatctccc ctcattagtc atggtgagaa caagaacaag acgagaaaca gacaaagaag     420
atgaaaaaac ttgttggcca gtgttgacta aggggggaata gccccagaca taacaaaatt     480
agacttgtcg tacatcttta atattttttt atctgtttct ttgtcctgac gctttcatta     540
ttcctgtgat caattttctc ataccattgg tccatcgtta atcctttctt aatttcattt     600
tctacgtaac atgagaggag accaagtcct atgagaacag ttgacgtaac agtggttgtt     660
aagttaagtt aaaaagagga agctagtgag agtgaccgtt aggtagagaa gtgagatctt     720
taaccactct tctttctctc tctctctgct tttttcgtcg tctttcacat ctactgttcg     780
caaactctct tatgcttcca ataatggtga taccaattga gacttgcagg agaatctcct     840
cttctccaca ctctatcaac tggtcagcca tggaatggtc gtttcagttt caatattcct     900
ggattctttt taaggattcc tgtttctctt ctgttcctgg tatattctta acgacgaaat     960
tagtatcgga tcctggtaat acattttgaa gcttttaagt accattgcac tgggatccaa    1020
caat                                                                 1024

<210> SEQ ID NO 132
<211> LENGTH: 1020
<212> TYPE: DNA
<213> ORGANISM: Arabidopsis thaliana
<220> FEATURE:
<221> NAME/KEY: misc_feature
<222> LOCATION: (1)..(1020)
<223> OTHER INFORMATION: Ceres Promoter YP0096

<400> SEQUENCE: 132
gaggtcagtg agtcgattgg tgcaaaattg aaaaattgaa gggtgaaaca aatttaaaga      60
taatatctat taaatcctct aattttaaaa atttagcaaa aattgtattt tcttatggat     120
ctgttagttc acacgtatct taattagtac caaatcatat ctaatgatta gtgataaaac     180
tagttagata tctatatgtg tctttaccat ttaacttgaa tccttcttct ttttttttacg     240 taaacaactt gaatccttcg ttaatacata aatttaaagc attttttctt taattctatt     300
gatcggtata tatttactat aagttttagc tcatatgcaa tttcaaatga tatgctttta     360
aattttgtct aggtgtgata gttgtatctt aacataaat cttatagcaa aattatactt     420
gatattctaa atttatctat ttgctcttgt gaacctcata ttagtctaga gaaactttga     480
aatcctttca attagttgta tgtccaatac attttttacta acatttatta gtcttttttaa     540 ttaagattat tgttagaaaa aaaaagattt tttaaaaata aataatatgt tttagataca     600
atgtgagtta ggcttcttat atttttaaaaa ataaatttat ttcatactta aaaatagttt     660
ggaatttcaa tttatttggc tgaataccat aaaaatatgtc aatttgaacc ttatacccat     720
tgactatttg gtgttagaaa cccttttaaca aaaaaaaact atttggtgtt agatatcaaa     780
ataaaaaaag tttaaccatt ggtttcttat attgaattgg atattgttac atgtattaaa     840 gttttttttgg tttaattttg aaacgttgat agaaactatt aagtttaagt ttggtagtat     900
```

-continued

| | |
|---|---|
| atttatttgt ggaaaattta attgccatta aatataacgt caactttttt tggttttttt | 960 |
| tgagaagtta cgttgtgatt ttgatttcct atataaaagt tagattacgt cattttttaa | 1020 |

<210> SEQ ID NO 133
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0097

<400> SEQUENCE: 133

| | |
|---|---|
| ttcatcttta tatttaagag tttaaaaact gcaacttttg ttttcttttc actaagtctt | 60 |
| atggccacag ttaattaaaa gcagatgaaa ggtggtccaa tggaaaagga gaatgtgatt | 120 |
| gggctagttg ggagagttct gatgtctagt gttgggtaca cgtgtccgtc agttacacat | 180 |
| agcattaaat cagacggcat gtcattattc aaatctagtt cacatagtac gactaatagc | 240 |
| tgataaatta atgattatac agcatatgaa ttatgaattc aaaaaaaaaa aaaaattgaa | 300 |
| aatgttaagg agatgctata ttttacaaaa ttcatcgcaa tgctttctac taatttgcta | 360 |
| agtggtcttc tccagttagt cttgtcgatt ccaagcgata ttattaaatc ttgaagcatc | 420 |
| gctcaaagca ttatagctta agataaccaa attgttatta aaacaccta gtgaaatttt | 480 |
| taaattaaaa caattttgat atctttgtaa tatctaatac tactcttct gtgtctaaaa | 540 |
| ggattaattt tcaaaaattt cacacatatt aaaaaaaaaa aaaaattact agctaaacaa | 600 |
| ttttcaataa tcataaaaca atagtaactt ataattttt ttttattttc aaaatagtcc | 660 |
| ttcaagttta caattcattt tagtattata atcaacaaaa tttgtattaa aaagttggaa | 720 |
| aattaatctt tgtggaacaa aaaaatctag aaatcatttt ttagaattag agagaggttt | 780 |
| gataaaaaaa aataaaaaaa aatagagaga ggtagtacat actaaacgat gtgatactac | 840 |
| tattgacaaa atcttaattc tcagtttagt agaataaact agaaggaatg aatgaagtaa | 900 |
| atgcgaatcc aactactaac aaaccctact tagtcatcat attttcccat atgaaatccc | 960 |
| tatataaacc catcatcatc tcccactttt ttcatatcca | 1000 |

<210> SEQ ID NO 134
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0101

<400> SEQUENCE: 134

| | |
|---|---|
| ttctcgttct ctagaatatt gctggaccgg attaggtcaa tattattggg ccagattaga | 60 |
| tattgaattg tcgacgttgc ttacgttacg ttatatcttg tttaagaatt aaacctatcg | 120 |
| acttagtctt aattaagaaa acattgcctt aaattctctg gtctgcgacc gtttttttga | 180 |
| ccgttaaccc ctaattaaag aaacaaaata attatagaaa gagcactgaa atgtgattat | 240 |
| tttaacagta ctcttatgag aaaattcgta cttttttagtt ttttttttgt acaaatctct | 300 |
| aagaaaaaca ctactactaa ttaagaaacg tttcaaacaa ttttattttc gttggctcat | 360 |
| aatctttctt tctcggtccg ggactaaccg ttggcaaaaa aaaaaaaaaa gttgacaata | 420 |
| attattaaag cgtaaatcat acctctcaaa taaaaacttg aatttggaaa caaagacaac | 480 |
| taaaaaactc gaatttaaga gaattcctaa aatcaagtga agtatcatca cttggtaaaa | 540 |

```
tttcataacc gttggcttct atttctatgt gtgccttggt ttgcaggaga taatatttca      600
tttccaacca atgatattcg tacacatagt caaacaaatg tttgtctttg ttattatatt      660
gagaaagaaa caagaaagag agagagagat agataagacg aaggaagtga agcttccaag      720
cgcccaccgt taaaatctc gtgtgcaagt ttcaaataca agtggccggt ggtctccata       780
atttgatcgt catccaatta aaaggaaga aaaagcgtgt tttatacaag aaaactcatt       840
aaaatagcaa gtctagaaat atctcaacac taatctacca cgtctattac acacacacac     900
acacacactt gatcttaatt tattttcaag attcaagaaa atacccattc cattaccaca     960
acttgaccac acgcctatat ataaaacata aagccctttt cccc                     1004

<210> SEQ ID NO 135
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0102

<400> SEQUENCE: 135
atttggttga taacgttttc actcgactaa ttatatactt cagaaggata gtaatagaat       60
accaaaataa ttaatgatt ggttagtgcc ttagtggaga cttttaacc gattctaata        120 gactaatgat gtagctaagc atttatttgg gatcatcact gtttgaaaac gtgaaatgtg      180 ataaagtta tgaaacgatt aaaatataaa ataaccgtac aaaacattat gtaccgtttt       240
tttctctgtt cttttggcga tttggtttag ttcgttacac tctaaatgtt attgcagata     300
tatatataat gatgcatttg catctgagga acatataatt ccggttaaca cttccaaatc     360
ttatatccgt ctaggtaggg attttataaa tcatttgtgt catcatgcgt tatgcttgtc     420
ggctttgacc ataacgcaga gatatagaac tagcttttac ttaactttta gatttattat     480
ttgatctaga gttaagtgga gatatatagt gttttttgtta gattattggt ggatgtgaga    540
gtttgtcttt agtttcaagt tgagaatata aggcaagagg agactctgag gcaatcagag     600
gttttgattg gcaaaatatc caaaaggccc aaaccaagtc gaagcccatc tcgtacaaaa      660
aaagaaagag atctgtaaga aaaaatattc tttgatattc ttacaaaaat aagtgtaaaa      720
cttttattag tcaaaatctt caatctttaa aaactctcat cactcctacg aaagcgcgtg     780
agagttatga gacattcctt aatagcatta ctcacaagtc acaagttcaa aacgtctgac     840
tgaaacagaa acaagccttt gttgaagtct tgaagaagag acattagtac tcgtcgtata     900
gccataaaag gtaatatacg aaatttcttc gctaatctct tcaccttcct ctacgcgttt     960
cactttcact ttataaatcc aaatctccct tcgaaaacat                          1000

<210> SEQ ID NO 136
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0103

<400> SEQUENCE: 136
gttttgaaga acaatctgga tcgaaatcta acataaggtc atcgtattca agttacgcag        60
tcaaggactt gacatcatcc tactctggtc tgaggttacc acttccaaag atgggatttt       120
tcgactcggt atgcttccta agaaattcgt tttattgaac ctagcaaata tcttgtaatg      180
```

```
taagattcct gagatgatga agaaaaaaca aacttttgtt acagcaggag aacggagaga       240
aagaaaacag agaaccaaat gctcttgaag caaacagaag aagaagacac aaatccaaac       300
ttgagacttc ttctacacca gaaaaccgca gcattctggg acaacgcaaa acacgaaagt       360
gaaacgggca atgatatata tgtcttgggt gcgttacaag gcatcgtttg caactgttga       420
gttggataag tcaactgtct tctttttcctt tggttgtagt agctgccttt ttttccttt        480 gttgctttaa gaaatagccc gaaaaaaaga atgttctaca tttcggagca gaaaactaac       540
cgaatgagtt tttggtcgga tcatcggatc gatcagatat attttgagtt acgaactgtt       600
ataaaaaaag ccataatttt gtgttgagtt tgcaaaatac cttataactt gttatttgag       660
attgcacctc catatatatt aattcgtaag agtatttatt aagtaagctt tagtataaat       720 cctttttttcc tttaaagtaa gttaatgttc tactaaataa tagtaaagtt gaagaaccgc       780
tccgttttta caccatgcac gtgttatcta acaaagaaaa tatggtacac ctaatggcta       840
atgcaaagga caacacaatg aaactaactt gactctgtgt tatagaaacc catagacatc       900
tgcatacatc ctagtatttg tataaattgg actcaaattc ctgaggacaa tcatagcaaa       960
caatcacatc atcgcaatat acataaacaa aagaggaaga aaaa                      1004

<210> SEQ ID NO 137
<211> LENGTH: 1003
<212> TYPE: DNA
<213> ORGANISM: Arabidopsis thaliana
<220> FEATURE:
<221> NAME/KEY: misc_feature
<222> LOCATION: (1)..(1003)
<223> OTHER INFORMATION: Ceres Promoter YP0107

<400> SEQUENCE: 137
taacaatcct tgggaacatt gcatccatag atatccggtt aagatcgatc tttgaactca        60
taaaaactag tagattggtt ggttggtttc catgtaccag aaggcttacc ctattagttg       120
aaagttgaaa ctttgttccc tactcaattc ctagttgtgt aaatgtatgt atatgtaatg       180
tgtataaaac gtagtactta aatgactagg agtggttctt gagaccgatg agagatggga       240
gcagaactaa agatgatgac ataattaaga acgaatttga aaggctctta ggtttgaatc       300
ctattcgaga atgttttttgt caaagatagt ggcgattttg aaccaaagaa aacatttaaa       360
aaatcagtat ccggttacgt tcatgcaaat agaaagtggg ctaggatctg attgtaattt       420
tagacttaaa gagtctctta agattcaatc ctggctgtgt acaaaactac aaataatcta       480
ttttagacta tttgggcctt aactaaactt ccactccatt atttactgag gttagagaat       540
agacttgcga ataaacacat tccccgagaa atactcatga tcccataatt agtcggaggg       600
tatgccaatc agatctaaga acacacattc cctcaaattt taatgcacat gtaatcatag       660
tttagcacaa ttcaaaaata atgtagtatt aaagacagaa atttgtagac ttttttttgg       720
cgttaaaaga agactaagtt tatacgtaca ttttattttta agtggaaaac cgaaattttc       780
catcgaaata tatgaattta gtatatatat ttctgcaatg tactattttg ctattttggc       840
aactttcagt ggactactac tttattacaa tgtgtatgga tgcatgagtt tgagtataca       900
catgtctaaa tgcatgcttt gtaaaacgta acggaccaca aaagaggatc catacaaata       960
catctcatag cttcctccat tattttccga cacaaacaga gca                       1003

<210> SEQ ID NO 138
<211> LENGTH: 1024
<212> TYPE: DNA
<213> ORGANISM: Arabidopsis thaliana
<220> FEATURE:
```

```
<221> NAME/KEY: misc_feature
<222> LOCATION: (1)..(1024)
<223> OTHER INFORMATION: Ceres Promoter YP0110

<400> SEQUENCE: 138
gggatgcggt tccgcttcct cttgatcttg gacgagtcgg aggacattgt tggatcccag      60
tgcaatggta atataaaaca agaaaacaag agattttata ggacaatcac taaatgacat     120
ttaattgatt aaacatttat tcattaataa ttgtatgtta ctaacttcaa catttaataa     180
ttttgtttaa gatacgttta catcagagac tattaatatt tttacaggtt gtaactttaa     240
actttgtctt gaatcgaaca tgactataga ttttgggcaa acttaaagat aacaacattt     300
ccgttttttt tcaaattatt acaaatcaaa ctgatatatt agacacaaca cgattacacg     360
taatgaaaaa agaaaagat aaaaagataa agaagggat cgattctgtt tggtctggtt       420
tagtgagatt caaagttaag ctcttccttt caagacatgc cttcttaaac cgggaatgtg     480
aacgtttgta atgtagtccg tccagttaat gcttccaaca tcaaatccaa attctctctt     540
ctcgtcctct gacatattct ccattaatct ctggggtatt gctgttatca aatctgtaaa     600
agaaaccaaa aaaaaagat gaaactttg cgggtaccgg ttttgtctgc tctaagaatt       660
agaatgttaa tgagttctgt cttaccttcc accatagaaa gtgtatggct cataaatagt     720
agcaaggtgt ttggcttgtt caacagattt cttgcatata aactttagct tctgcatcat     780
cttactatcc actgaactca taccactcat caacccactc cgttcttgag catctctcca     840
caaatgatcc gagaaatcat caacggaatt gaaaagtttc atcaaacgca cataatagg     900 atcacctta gagtccatgc atggagatgt tttgtagtgg ttataaagaa gctccgctaa     960
gtcttcgaaa accagcgggt ttatcgccga agaagcgatc tgatacacgt ttatttcagg    1020
ttcc                                                                  1024

<210> SEQ ID NO 139
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0111

<400> SEQUENCE: 139
cgattggatt tagtctatac attatagggc gcaagtttgt ggatttaaga attatataaa      60
aacttgaaat atatagtttt tatgcattct cctcttgtgt aatacataaa ccaaatatga     120
gataggttaa tctgtatttc agataatatt aaattccaaa caatattttt acttgttata     180
agaaggcaat taatatctct ctgttaatgg caagtggtac caagtagtat taaactatta     240
atgcaatgga agagtactgt tggaaattat aatcctctat cacacattca aacagatctc     300
ctgaaatctt ctcttccaaa cttgtacttc tctgatccaa atgtaggctc caaaatatag     360
acatttacca tttactaagt ccacaactcc tttcttgtct ccttcaaaaa tgactcttgt     420
gtaaccacca tatgactccg acagttcggc attgccatga tgagagctta aaaattcacc     480
ttcctgagca tttcaagtct tcactccctt agcttgacct gaaccaagat aaaatgcctt     540
tgtcgtcccg taatatccat cctgctttgg acggcatcat agttacattc gatccatcct     600
atttacaatg ttattttagt attaaaaaca tgacaataaa tttgttgtta aacatattca     660
aatacaatat gattggattt ataagtaatt gtaaatgaa atgtccttag taatatgtta      720
aaaaatacat agatacacac acgtactaaa agaggcaacg cggagatgt cattagagga     780
```

| | |
|---|---|
| agaactagga agcagagcgt tcatgcaaaa tgctaccaaa acgttaatg caatatctca | 840 |
| actaatcagc acagtccatt tcatactgag aatgtaaaaa ccaatcagca tcgtccattt | 900 |
| tttcatctaa ttatttgtta actcttaatt ggccacaact tccaaccaca tgacgctctt | 960 |
| tctattccct ttatatattc ccatctcaaa tgttcttgga gacacaaaat atcataaaca | 1020 |
| tata | 1024 |

```
<210> SEQ ID NO 140
<211> LENGTH: 996
<212> TYPE: DNA
<213> ORGANISM: Arabidopsis thaliana
<220> FEATURE:
<221> NAME/KEY: misc_feature
<222> LOCATION: (1)..(996)
<223> OTHER INFORMATION: Ceres Promoter YP0115

<400> SEQUENCE: 140
```

| | |
|---|---|
| gtcgattgga tgatgaacat tctacatata taattattat gtttaagcac ttagacagca | 60 |
| taaattcttt ctaattatat aaatctaacc ttgttacatt gtacatctat aaattacttg | 120 |
| aagaaataac gagttctatt tcttttttaaa aattaaaaat actataccat atctcagtga | 180 |
| ttaagttgaa ccaaaaggta cggaggagaa acaagcattt gattcttcct tattttattt | 240 |
| tattcatctc tcactaatga tggtggagaa aaaagaaaaa tacctaacaa acaaatatat | 300 |
| attgtcatac aaaaatattt ctatattttt agttaattag tttatattcc tcacttttca | 360 |
| gggcttatat aagaaagtga gcaaacacaa atcaaaatgc agcagcaaat actatcatca | 420 |
| cccatctcct tagttctatt ttataattcc tcttcttttt gttcatagct ttgtaattat | 480 |
| agtcttattt ctctttaagg ctcaataaga ggaggtacta ttactacact tctctctact | 540 |
| tttacttgta ttttagcatt aaaatcctaa aatccgtttt aaattcaaaa ataaacttag | 600 |
| agatgtttaa tctcgattcg ttttttcggc tttaggagaa taattatatg aaattagtat | 660 |
| ggatatcttt actagtttcc attcaaatga ttctgatttc aatctaatac tctcactctt | 720 |
| taattaaact atatgtagtg taatttcaca ctgttaaatt tctaccatgt catgtatatt | 780 |
| agagttgcat agaaaattgt aaaacatcca tttgaattcg aatgaaacaa atgttttaa | 840 |
| aataaaattt tggttttttaa aagaaaaatc taaaactgaa ttatatcgtt taaccaagtt | 900 |
| gtaaaagtca taaaacgtag tatcttgtaa atcgctcttc cacggtccaa atagacttct | 960 |
| agtaataaac aagtaaaact aattttggtt tcttac | 996 |

```
<210> SEQ ID NO 141
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0117

<400> SEQUENCE: 141
```

| | |
|---|---|
| gtcagtgagt cgattggatc acagtccttt atgataaaac aaactcataa ttattccacc | 60 |
| gacaacatgc gttttaaatt attttttctt aaattatatt atattatatt gatatcaacc | 120 |
| tagctaaaat aattcggatg gcgaaatcgg acaattttta atagaaaaaa tgggtatgaa | 180 |
| gatagtctat gattccgttc ttagcgacta gagggacctg ctcaaatctc cgggtgata | 240 |
| cgcgatgtca agctcaatag aaccccacaa ccgacgagac cgagaaatcc ttgatttggg | 300 |
| ctagaagatt ttgaaataaa tttaatatat tctaagtaac ttgcttaaat ttttttttcaa | 360 |

```
actctaaaga cataactaac ataaagtaaa aaaaaaaaag ttaatacatg ggaagaaaaa      420
aattaaacta atgattagct ctctaacgtg tttaatctcg tatcaagttt ttttttaaaa      480
attatattgc tattaaaaca ttgtactatt gtttctattt tgtttagcta ttattcttgt      540
gaaatgaaaa gttgtgttta ttcaattact aaatggcaat atttatcttg gaaaactata      600
cctctaattg gattaggccc tagacatcct ctttagctta ttgacgttaa aattattccc      660
aaaactatta agtttagta gtttgaaaga tgcatcaaga cctactcaga taggtaaaag       720
tagaaaacta cagttagtgt gattatattt taaaatatat aaaacaatct tattaaacta      780
aatattcaag atatatactc aaatggaaga taaaaacatt tagtctgtta ccactaccag      840
cctagctagt cactaatagt cactttggaa ctgagtagat atttgcatct tgagttacca      900
tggactcaaa agtccaaaaa gagaccccga gtgaaaatgc taccaactta ataacaaaga     960
agcatttaca gcggtcaaaa agtatctata aatgtttaca caacagtagt cataagcacc    1020
attg                                                                 1024

<210> SEQ ID NO 142
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0119

<400> SEQUENCE: 142
taccaaaaat aaggagtttc caaaagatgg ttctgatgag aaacagagcc catccctctc       60
cttttcccct tcccatgaaa gaaatcggat ggtcctcctt caatgtcctc cacctactct     120
tctcttcttt cttttttcct ttcttattat taaccattta attaatttcc ccttcaattt     180
cagtttctag ttctgtaaaa agaaaataca catctcactt atagatatcc atatctattt     240
atatgcatgt atagagaata aaaaagtgtg agtttctagg tatgttgagt atgtgctgtt     300
tggacaattg ttagatgatc tgtccatttt ttctttttt cttctgtgta taaatatatt      360
tgagcacaaa gaaaaactaa taaccttctg ttttcagcaa gtagggtctt ataaccttca     420
aagaaatatt ccttcaattg aaaacccata aaccaaaata gatattacaa aaggaaagag    480
agatattttc aagaacaaca taattagaaa agcagaagca gcagttaagt ggtactgaga     540
taaatgatat agtttctctt caagaacagt ttctcattac ccaccttctc ctttttgctg     600
atctatcgta atcttgagaa ctcaggtaag gttgtgaata ttatgcacca ttcattaacc     660
ctaaaaataa gagatttaaa ataaatgttt cttctttctc tgattcttgt gtaaccaatt     720
catgggtttg atatgttct tggttattgc ttatcaacaa agagatttga tcattataaa      780
gtagattaat aactcttaaa cacacaaagt ttctttattt tttagttaca tccctaattc     840
tagaccagaa catggatttg atctatttct tggttatgta ttcttgatca ggaaaaggga    900
tttgatcatc aagattagcc ttctctctct ctctctagat atctttcttg aatttagaaa    960 tcttttattta attatttggt gatgtcatat ataggatcaa                        1000

<210> SEQ ID NO 143
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0120
```

-continued

<400> SEQUENCE: 143

```
tagttttttga tttaatctac gtttttctta atcataaatg ggtaattatt agttttttgca      60
aaatcaaaat ccaaaaattg ttctaaacac tgcaaccatt taaggcctat atcactcaga     120
aaatttctgg tgggagaact aatcgtttgt cctttctaaa tctcacatat tagaatttag     180
aattagtgtg ctacataaga atattagttc agctcggaac aactattttt tggtaaaaca     240
gagaacttaa acaaatgcat tatttttatca acatgcattt tgaattgaat ataaaatttc     300
ataattgtaa agacataaat tacataaaat tttacatgaa aaaatagata tagaaagaaa     360
atgaaactaa ctgatgatat gctctctaaa ttttttaatc tcataacaag aattcaaatt     420
aattagttca tattttttggt aatataaca tttacctgtc taagttggaa ctttcatttt     480
tttctgtttt gtttagtcag tattcttaat gtgaaacgga aagttgaatt tattcaaact     540
taaattcaat agcattaatt aaaggcgaaa gctattatct ctacatgtgg ttcaaactag     600
acatccaatt taattagctt attgacgttg aaatgttttc caaaactact atagtttggc     660
aatttgaaag atgcatcaga actactcaga caggtaaaag tagaacctct agctgtgtga     720
attgtatgtt agtccataaa gaacatcttg taaacttcat acttaagata tatattacaa     780
tatatacttg aatggtagat aaaaacgatt agtctgattg ctagcatact cacaactatt     840
tggaaatgag taagatattg gcattctaga gttactacta tggagacaaa agtcgaataa     900
aagagacctc acgtgaaaat gttacgagct agtaaaaaaa gcatttacac taacggtaaa     960
aaaagtatct ataaatgttt acacaaggta gtagtcatt                            999
```

<210> SEQ ID NO 144
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0121

<400> SEQUENCE: 144

```
ttggattttt ttttttgttga gtcagcagac catctaatct ctctttttcc accacagcct      60
gctttctatg aagcatttgg gcttacggtt gtggaatcaa tgacttgtgc actcccaacg     120
tttgctacct gtcatggtgg acccgcagag attatcgaaa acggagtttc tgggttccac     180
attgacccat atcatccaga ccaggttgca gctaccttgg tcagcttctt tgagacctgt     240
aacaccaatc caaatcattg ggttaaaatc tctgaaggag ggctcaagcg aatctatgaa     300
aggttggccc attctccttg acaggcttaa caatacaact tgtatcgctt caacaagatg     360
atggcttaat aaggattttt gcatgtatag gtacacatgg aagaagtact cagagagact     420
gcttaccctg gctggagtct atgcattctg gaaacatgtg tctaagctcg aaaggagaga     480
aacacgacgt tacctagaga tgttttactc attgaaattt cgtgatttgg ttagtgtaac     540
ccactgttat tcttttgatg tctacatcta ctttacttac attattcttt tcttcggttt     600
gcaggccaat tcaatcccgc tggcaacaga tgagaactga tcatgacagg gtaggatttt     660
atttcctgca ctttctttag atcttttgtt tgtgttatct tgaataaaaa ttgttgggtt     720
ttgtttcctt cagtggtttg atttttggact tattttgtgtt aatgttgttt tggctgttct     780
cttaatatca ataacaaata aatttactgg ttggtatcta agatctaaca atagttacta     840
tttttagagg taaagacacc aaccttgtta tattggtcag agagctaaaa ccttgacttg     900
ttgggaaaac aaaactctaa tgacagaaaa tctgacatga tgccttataa ttcacagcct     960
```

| | | |
|---|---|---|
| catgttctac ataaatccta acaatagcac tttgtttct | | 999 |

<210> SEQ ID NO 145
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0128

<400> SEQUENCE: 145

| | | |
|---|---|---|
| gataaactga taatggaaaa gaacaaagaa accagttttt aactatttgc atatgtaatt | | 60 |
| tatttgttgc aaattatatt tagttaaaat gtttcctcta tttatatata tatatatcag | | 120 |
| tcaagcacta tgtataagaa atgtcaattt ataaattttt acatgtcctt aacagaaag | | 180 |
| aaaatgaatt tttacatgtc attcatagag agtcactcgt ttatttctta tatagagaat | | 240 |
| aacacactca catgcatatg catgcaatat gatacatttt atgacaaaga taatcaacgg | | 300 |
| aaacggtcaa gacataattt gataaacaac ttgcacgatg cacagatctg atcaaatata | | 360 |
| taactcttta acatatccaa aatattcaaa aagaaaaact cgatccaaac tagcaacatc | | 420 |
| acgctcacgc ggtaggctaa aaatttatta atctccaaaa gtctttctta tgaacactgc | | 480 |
| aaacacaaca acttgaaaag tcatataggt ttagatgatg acgcgtattg gctatcgctt | | 540 |
| accggagtgg ctcataaata caataaacaa tacgtaaaag tcaaagtcaa atatatttag | | 600 |
| tcaactataa ccattaatcg ggcaaaacct ttagctgtca aaacaacgtg aaaacgatat | | 660 |
| ttgtatatat catcaagaat cagtagataa gagaatgatt taatcccctg actattacaa | | 720 |
| ttttggtgta ataaacagtc tctattggtt tttattcttt gttttaattt ctcatgacct | | 780 |
| atagagagaa ttaggtagtt tcgaaaattg gctaatcaac ttttgaaaac tactgtctac | | 840 |
| tttgcttaaa ttctctacac ttagtttcgg ataagataat tgtcggacta atagttaatc | | 900 |
| ccttgacaat ctttgatatt ataaaggtt tagttaatct cttctctata taaatattca | | 960 |
| tacaccagct ttcaaaaata tataatccaa acaccaaaaa caaa | | 1004 |

<210> SEQ ID NO 146
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter YP0137

<400> SEQUENCE: 146

| | | |
|---|---|---|
| gtggcacatg ctgaaacccc gagcatctct ccggaagaca cgcgtcgttc gctccaaaga | | 60 |
| aaacagtcac agctgccgga gaatctccgc cgtcttcttc tgccaccgga aaaactctct | | 120 |
| ccaccacttt cagtgcccac ctcgtgttat atccactgta tcctcgtagc accatatcag | | 180 |
| cctaataaaa ttttatgtat caaatttta gacatagccg aaactacact atactagaca | | 240 |
| ataataatat gatttgtttc ctgaaaaatt atggttcat gagaaacatt aatcatctat | | 300 |
| aaaacaaatt agctatggca tcgaagagtt atcaatcaaa actgatgaat ctttacttaa | | 360 |
| tatatacaac atatctttac cttgcggcgg agaagatcgg cgagagaagc acccagcca | | 420 |
| ccgtcactaa aggattcttc agtgatggaa tcaccaaaga gaaaaacctt ccgtctcatc | | 480 |
| atcttccaca caatcttctt gagaaaatct gagagataag aaaggtgtag tggttttgct | | 540 |
| gaagtgatcg tgtttgattt agtaaagaaa tgctttattt attgttgggg gaaacataaa | | 600 |

```
taaataaagt aaaagtggat gcactaaatg ctttcaccca ctaatcaccg acctttcatg    660
gtttattgtg aaatacactc atagatagac atacaatacc ttatgtacgt aaataacatt    720
ttatttgtcg acacttatgt aagtaacgca tagattattt tctatgtgat tgccactctc    780
agactctcag tttcaaccaa taataacaat aactacaaca acattaatca taaacatatg    840
ctctggttta caattaaagc ttagattaag aaactgtaac aacgttacag aaaaaaaatg    900
ttatttacgt tttgtaagat tagtctctag aatcatcacc gttttttata tattaatgat    960
tctttcttat atataaaacc tttctcgaaa tacccatgaa a                       1001
```

<210> SEQ ID NO 147
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter YP0143

<400> SEQUENCE: 147

```
atacaacaga tggcagatat cgagttaaat acgtgaatca gccgttacga tattttaaaa     60
ctagaaaatt atttaaaaat attgcaaaat accatttaat ttcattgttc ataaaaaaaa    120
gaaattcaaa aacttaaaaa ctgattcaaa aatttggatt aattctcatt aacagtcttc    180
aacactacaa caacatgttt ctaatttatt ttatatttta ataattaaac aatatatacg    240
tctgcacatt gttgctccga cataatctag tataaaaata gttgcagcat atgtgaaaag    300
caagcagcat ttatcactca atactttaa ttttatctgt tgtatgtatt aaggttttgt    360
agctttaaga aaacgcttat aatataaaat aacttctaaa agatatttca tgcgtataca    420
ataaatattt gtgaaaaaac atttcgaaaa cgtgtacaat atataaacta ttgtgttatc    480
ttttgacatt caaacaaatg ttgacaatgt aattttatcc atgatatgat tggccaatta    540
gctgcgaggt aaaaatccgt atacgagtaa aagtaagata aaatttcgca agaagatttt    600
tagcaggaaa tctaagacaa gtgtcatgaa cgtgtcaatc aacaaacgaa aaggagaatt    660
atagaatcca gattcgacgt accacattaa taaaatcaa aacatttat gttattttat    720 ttttgctctg gcagttacac tcttttttcat tgctccaata aaaaaatcac tcgcatgcat    780
gcatatatat acaccatagt aaactccgcc tcttcttcat tttaaaagta tcagtttaca    840
ctgacacaat ccttaactat tttcctttgt tcttcttcat ctttattaca cattttttc    900 aaggtaacaa ataatctttt taagtcactt ttatactctt taaatcttag attgatatat    960
gaatgcatgt taatatttca agatttatag gtctaccaaa c                      1001
```

<210> SEQ ID NO 148
<211> LENGTH: 1003
<212> TYPE: DNA
<213> ORGANISM: Arabidopsis thaliana
<220> FEATURE:
<221> NAME/KEY: misc_feature
<222> LOCATION: (1)..(1003)
<223> OTHER INFORMATION: Ceres Promoter YP0144

<400> SEQUENCE: 148

```
aaacgttgca agattattga ttgtgagaaa gagtgctcaa ggtagtactg atttctgtaa     60
agctcacggt ggtgggaaac gatgttcttg gggagatggg aaatgtgaga aaatttgcta    120
gaggaaagaa gcggtttatg cgctgcgcat aacactatta tgtctcggga gaacaaagat    180
ggaagcaaga gcggtttgat tggaccggga ctctttagtg gccttgtttt tggctctact    240
```

```
tctgatcatt ctcagtctgg agctagcgct gtctctgatt gtactgattc tgttgaacga        300
atacagtttg agaataggca gaagaacaag aagatgatga taccgatgca ggttctagta        360
ccttcatcaa tgaaatctcc aagtaattca catgaaggag aaacaaacat ctatgacttc        420
atggttccgg aggagagagt tcacggcggt gggctagtaa tgtctttact tggtggctcc        480
attgatcgaa actgaaagcc atttatggta aaagtgtcac attctcagca aaaacctgtg        540
taaagctgta aaatgtgtgg gaatctccga atctgtttgt agccggttac gttatgctgg        600
atcaaaaact caagatttgt tggatattgt tatgctggat cggtggtgaa accacttccc        660
ggttgctaaa taaataaacg ttttgtttt ataatctttt tcactaaacg gcagtatggg        720
cctttagtgg gcttccttta agcgaccaat acaatcgtcg caccggaatc tactaccatt        780
tataggttta ttcatgtaaa acctcggaaa atttgagagc cacaacggtc aagagacaaa        840
aacaacttga agataaaggg ataaggaagg cttcctacat gatggacaac atttctttcc        900
acacaaattc tcataataaa aatcttataa tacaaatact tacgtcataa tcattcaatc        960
tagtccccat gttttaaggt cctgtttctt gtctgataca aat                         1003
```

```
<210> SEQ ID NO 149
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0156

<400> SEQUENCE: 149
```

```
ttggtttgca ttgtgaagat ttgtattaac tatagaacat tgaattgatg gtgttaagtt         60
cttacacaag cgtgcttctc ggtttgaact gtttcttttg tatgttgaat cagagcttag        120
tttataggaa ccagagtatc tacttagtca ttctctgatg ctaagtgcta aggttctacc        180
tagttgccct ctaggccctt atgttattga taacttatga agctatttga acacttgatt        240
cttaggagac ctaagttggt acagccagat agagtgtatg ttcttgttct ctatgtgaca        300
ggatcaagct gccacacata gttcaagggt atgctctgtg tgggtttgct cagattgagg        360
acaaatctat acaaggaagt agagtctttg acattttgat gttgtatgat aagaagaaga        420
aaggagagta ataagaaag agaaaaggga aacagaaaca cgtgggagaa catcccaaag        480
aggaagcaca cgcggatctt catgcaaagc tccccgattc tcccatgtgg tccctttctc        540
cctttgtccc cctcctcttt cttctttct cattttactc ctttttttac cattatacaa        600
cgaatctttt ttatcataat ttttggttt tggtttattt tccaataaca ctttcttggt        660
tacttcccat tctcactttt tcatataaga aactcacttt gggaaactta tgtttgagaa        720
tgacaagtct ttttagagaa agtgatgtaa caaatctaaa gtgattatat aataaccttg        780
cacaatgttt ttgatttttt gtaagattcg aatattaggt ttattattcg tagggaataa        840
acttactttc aaaagcgttc ataagttaat actttcatat atgatcataa gtacggacac        900
tattgttttt tgtttgtttg tgtttattct aaaagaaagt agcttttaat tgaaatgtcc        960
tcggaggcac agtttaaagt tcgagtgtaa cagtttctaa ggca                        1004
```

```
<210> SEQ ID NO 150
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
```

<223> OTHER INFORMATION: Ceres Promoter YP0158

<400> SEQUENCE: 150

```
ttattagatt aatagattgc attgcattgc ttgtgctttc aatttacaaa ttgtctccca        60
actccatcga cacatctctt tttgtgtata taagattcag acttgttata ttttttttat       120
aaatatgtta ttagcatctt aagttaaatt gattttttat atctgcatta aggattacac       180
gactatattt gcgattgtgt gttggttaaa atataattta ggattgtctt taactacatt       240
taggattata tgactatatt tggttaaata taaaatctag ctgtgattat tagtattcaa       300
aaataagtag cctaaccaat taaaacaacg gctattgggg caaattagaa cattttagtg       360
tgtccaaaat ataatggtca ttaggtcata ttcctcctag cttcatcgca gcataattga       420
atgattgcct tatttagaag agcttttcca ctttcccaaa atctaggtgg gatcttttg        480
ttttgacctt cattttttctt gtttaccatt tttagctaaa ttatttacga ttacaaaaga      540
tatcaaaagt tggatcataa tacaatttat agacttactg tagaaaattc gtatgtacaa      600
gtacaacaaa ttcttcataa taaattttga aaattctatt acaaatgttg taagaaatag      660
aatttgaaat atatataaac taaggagaaa aaaaagaga acatgcattg ctctagtcag        720
agtggaccaa catcaacgag ataagataac ataaaaacca actcaccata actaaaaaca      780
tcccaagaga tccaacgatt catatcaaac acaaaaacat cgaacgatca gatttaaacc      840
atctctggta tctccaaaac acaaacactt ttttttttct tttgtctgaa tggaacaaaa      900
gcatgcgaca tctctgtgtc tttatcttct ctctcctctt cttgaaaaac tgaacctta       960
attctttctt cacatctcct ttagctttct gaagctgcta                           1000
```

<210> SEQ ID NO 151
<211> LENGTH: 1005
<212> TYPE: DNA
<213> ORGANISM: Arabidopsis thaliana
<220> FEATURE:
<221> NAME/KEY: misc_feature
<222> LOCATION: (1)..(1005)
<223> OTHER INFORMATION: Ceres Promoter YP0188

<400> SEQUENCE: 151

```
gattggtatg aaatttcgga gaccaacaaa aaaaacttta ttgagcttgg agtgaagcta        60
tatatatggg gcaagatcat aatatgttta tatcggcctt ttcgttaact gaaaataata       120
gttttgagaa atatatcaaa tggtaaacag acatcatctt tgaaaaatac catcaatgaa       180
gttaatattg ttattggcat atggtttacc catcttaatt ttaatgcaac caaacaaaca       240
agaaacaaaa actgtataag atacaaggtg ttttacgatt ttccgtctta aaaccgaaat       300
attttttgttc ctacgacttt aaacggactt tgcttaagtt gtgtgcatgt aagctcgtcg      360
tccctcgatt gtcatcaaca ttcaccaata tcagcctcta tcacacgagt gaaggtggtg       420
attcggctta atgaaaacag agaaatattt caatatgatt cctattaaat tttaaatctt       480
ttttctcaat ctctagattt tcattaaaag catcatgatt tttttccact atgttcatat      540
atctctatca cagttttagg tacattgtag aaattggata agatacgtca tacgtctaac       600
atgaatttgg tctagcaagg aaggtttgag ataataagtg aaaagaaaac acaagataat       660
aaattataat ttataaatgc tttatagtat tgaaaaataa gatgatttt tttttttta         720
ataccggatt ggctgatcca cttatgatga ctcaaatgtt attaagtttc aagacaattt       780
atgatgacac aaatcacaat gagtcaatag tagccacgaa gccagaaaaa aaaaatgtac      840
tacaaaaaga taatgatagt acaaaatgat acgtcgtact gccacatgta cgacacaact      900
```

```
cgattaccaa aaagcagagc catccaacca taaaactcaa aacacacaga ttccactggc    960
gtgtgctctc ctcacttcac tcgtccttga aacttgaggt actga                  1005
```

<210> SEQ ID NO 152
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter YP0190

<400> SEQUENCE: 152

```
taaatagtga cattggtaag aagaaaaaaa acactattaa atagtgaaaa aatggtttat     60
aactctctta attaacatta cttattattg ctagcaccta aaatctccca caaaatattt    120
gttgtaaaac acaaatttac aaaatgattt tgttttttaaa ttagtaacac atgttcatat    180
atacgttaat aagaacatac cctatatgat tttatataaa aaaatttctt tgagacgtct    240
tattcttttt tctttaataa tatgcaattg tgagagtttg gatttgaatg gtagcattag    300
aagcaaactt gaaccaaaca tatttcatga agtcaaactt gaaccaatgt gatcactaat    360
cacagtgttc gcagtgtaag gcatcagaaa atagaagaag ggacatagct atgaatcata    420
taatcttgac acatgtttta taggttttag gtgtgtatgc taacaaaaaa tgagacagct    480
ttcttctaat agacttaata tttgggctaa atgtaccaca gttgtgaatt cttacaaaa     540 atgggccgag ctacaaaaaa ctacaggccc actctcaact cttatcaaac gacagcgttt    600 tacttttta aaagcacaca cttttgttt ggtgtcggtg acggtgagtt tcgtccgctc     660
ttcctttaaa ttgaagcaac ggttttgatc cgatcaaatc caacggtgct gattacacaa    720
agcccgagac gaaaacgttg actattaagt taggttttaa tctcagccgt taatctacaa    780
atcaacggtt ccctgtaaaa cgaatcttcc ttccttcttc acttccgcgt cttctctctc    840
aatcacctca aaaaaatcga tttcatcaaa atattcaccc gcccgaattt gactctccga    900
tcatcgtctc cgaatctaga tcgacgagat caaaacccta gaaatctaaa tcggaatgag    960
aaattgattt tgatacgaat tagggatctg tgtgttgagg ac                     1002
```

<210> SEQ ID NO 153
<211> LENGTH: 995
<212> TYPE: DNA
<213> ORGANISM: Arabidopsis thaliana
<220> FEATURE:
<221> NAME/KEY: misc_feature
<222> LOCATION: (1)..(995)
<223> OTHER INFORMATION: Ceres Promoter YP0212

<400> SEQUENCE: 153

```
agtcgattgg tacactctta atttaattag agtaagagat caacaaaaat atagaatttt     60
ctttatatcg aagtgctacg accttatata tatagaaaaa aaagcatagg tgaatctcta    120
aattgagatt gtgctgtagt aaacatatta agttttagt ttttttaaga aatgaatctt     180
tttgttgatt aattcaaact agtagtcatt aagattccgg agattccaat ttagaaaagt    240
caaagattca agaacaagt ccaggtccac atgttgaatc cgattcatca tccactcatc     300
cttcatatct tcctccaccg tctccgccca aaaatcaat aacaataaaa atcctaaaa      360 aaacatattt gattttgaaa aaactttatc atatattata ttaattaaat agttatccga    420
tgactcatcc tatggtcagg gccttgctgt ctctgacgtc cttaattatc attattttta    480
aatttgtctc tctcagaaaa ttacgccaca atcttcctct ttccctttc cgaaaacagc    540
```

```
taatatttgt ggacctaaac taaataacgt agcctctaga ttttatataa ttactaatac    600
tatatgctac tacttgttat tatttactcc aatcatatat gataccaatc aagaatcact    660
acataagtag aaaactttgc aatgagtcca ttaattaaaa ttaagaataa acttaaaatt    720
ttatggtatt ttaagattcc ctttggattg taatgacaag aaatcagcaa attagtcgta    780
actcgtaaga ataaacaaga tcaattttta ctttctttac aaagattccg ttgtaatttt    840 agaaatttt ttttgtcact gtttttttat agattaattt atctgcatca atccgattaa    900
gaagtgtaca catgggcatc tatatatatc taacaggtaa aacgtgtatg tacatgcata    960
aggttttacg tgcttctata aatatatgtg gcagt                               995

<210> SEQ ID NO 154
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0214

<400> SEQUENCE: 154
ccagtcgatt ggcgcctcgc atgcctatca tatttaaccg tcaataatgg atttggcggt     60
tttggtaggc cgggtcaacc ggattaaaag aaaacggttt ggagtccttc cttgcaattg    120
aattttcaca cattcgggtt ttgtgatttc tctgtcataa tgggcccggc acatatggtt    180
cataacccat gtgggcctat ggtataattt ttccaattaa aactattgtt aggtcgataa    240
aacaaaaaac aataaaaacg agtggaatac acataccaaa aagaatgtga tgaacattag    300
taattttatt ttgatggtta atgaaaaaca aaataaatgc atcttggcat cttccgttgg    360
aaagcgcaaa tagggcagat tttcagacag atatcactat gatgggggt gagagaaaga    420 aaacgaggcg tacctaatgt aacactactt aattagtcgt tagttatagg acttttttt     480 tgtttgggcc tagttatagg atcataaggt aaaaatgaag aatgaatatt agattagtag    540
gagctaatga tggagttaag tatgcacgtg taagaactgg gaagtgaaac ctcctgtatg    600
gtgaagaaac tatacaacaa agcccttgtg tggtgtatac gtattaattt ttattctttt    660
atcacaagcg atacgtatct taagacataa taaatatata tcttactcat aataaatatc    720
ttaagatata tatacagtat acacctgtat atatataata aataggcata tagtagaaat    780
taatatgagt tgttgttgtt gcaaatatat aaatcaatca aaagatttaa aacccaccat    840
tcaatcttgg taagtaacga aaaaaaggg aagcaagaag aaccacagaa aagggggcta    900
acaactagac acgtagatct tcatctgccc gtccatctaa cctaccacac tctcatcttc    960
tttttcccgt gtcagtttgt tatataagct ctcactctcc ggtatatttc cccattgcac   1020
tgga                                                                1024

<210> SEQ ID NO 155
<211> LENGTH: 911
<212> TYPE: DNA
<213> ORGANISM: Arabidopsis thaliana
<220> FEATURE:
<221> NAME/KEY: misc_feature
<222> LOCATION: (1)..(911)
<223> OTHER INFORMATION: Ceres Promoter YP0263

<400> SEQUENCE: 155
atctagctgt ggattccacc aaaattctgg cagggccatg atctaaaaac tgagactgcg     60
cgtgttgttt tgcagtgatt tgtatttcat atttgcacca tcctacacag tccacttggt    120
```

| | |
|---|---|
| atcgtaaccaa aacataagga gaacctaatt acattattgt tttaatttcg tcaaactggt | 180 |
| ttttacctttt tagttacata gttgattctt catttgtttt agtagttatg gagcacaata | 240 |
| atgtgcaaca aagaaagatc atagtggatt aatatgttga gaggtcagaa attcttggtt | 300 |
| aacaaaaaaa agttacaagg actgagattt tgggtgggag aaagccatag cttttaaaac | 360 |
| atgattgaac ttaaaagtga tgttatggtt tgagggggaaa aaggttgatg tcaactaaga | 420 |
| tagttgaagt aatgtcttaa actaaagtaa accaccggtc caaccgtggt ccggaagcat | 480 |
| ctctggtatg atttatccta aaaatcaaaa tagtagaaac atactttaaa tatatacatt | 540 |
| gatcggacga aaattgtaaa ctagtatagt ttcaaaaact agttgaacag gttatgtacc | 600 |
| ttaaacattt atttcaaact taaacactaa agaacatata tgaatagaag tttatataaa | 660 |
| ttactatata tctaccataa atctcttata attatgatgt cacgatgagg aagtgttgaa | 720 |
| acgttaaaat gccaaaatat aagcatgcga cggaattttg gcagaagatt gtagagttgt | 780 |
| aatctgtcgc aatcattact cgtgctagca ttttttcattt tcccttcatt tgtggataac | 840 |
| gcacgatata acattctaca caccaacaag attctataaa aacgcaaagg ttgtctccat | 900 |
| agaatatcgt c | 911 |

<210> SEQ ID NO 156
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0275

<400> SEQUENCE: 156

| | |
|---|---|
| aaacattaat atgtagtaac tatgggcgta tgctttactt tttaaaatgg gcctatgcta | 60 |
| taattgaatg acaaggatta acaactaat aaaattgtag atgggttaag atgacttatt | 120 |
| tttttactta ccaatttata aatgggcttc gatgtactga aatatatcgc gcctattaac | 180 |
| gaggccattc aacgaatgtt ttaagggccc tatttcgaca ttttaaagaa cacctaggtc | 240 |
| atcattccag aaatggatat tataggattt agataatttc ccacgtttgg tttatttatc | 300 |
| tatttttga cgttgaccaa cataatcgtg cccaaccgtt tcacgcaacg aatttatata | 360 |
| cgaaatatat atatttttca aattaagata ccacaatcaa aacagctgtt gattaacaaa | 420 |
| gagatttttt tttttggtt ttgagttaca ataacgttag aggataaggt ttcttgcaac | 480 |
| gattaggaaa tcgtataaaa taaaatatgt tataattaag tgttttattt tataatgagt | 540 |
| attaatataa ataaaacctg caaaaggata gggatattga ataataaaga gaaacgaaag | 600 |
| agcaatttta cttctttata attgaaatta tgtgaatgtt atgttacaa tgaatgattc | 660 |
| atcgttctat atattgaagt aaagaatgag tttattgtgc ttgcataatg acgttaactt | 720 |
| cacatataca cttattacat aacatttatc acatgtgcgt cttttttttt ttttactttg | 780 |
| taaaatttcc tcacttttaa gacttttata acaattacta gtaaaataaa gttgcttggg | 840 |
| gctacaccct ttctccctcc aacaactcta tttatagata acattatatc aaatcaaaa | 900 |
| catagtccct ttcttctata aaggtttttt cacaaccaaa tttccattat aaatcaaaaa | 960 |
| ataaaaactt aattagtttt tacagaagaa aagaaaaca | 999 |

<210> SEQ ID NO 157
<211> LENGTH: 981
<212> TYPE: DNA
<213> ORGANISM: Arabidopsis thaliana
<220> FEATURE:

```
<221> NAME/KEY: misc_feature
<222> LOCATION: (1)..(981)
<223> OTHER INFORMATION: Ceres Promoter YP0285

<400> SEQUENCE: 157
gggattatat atgatagacg attgtatttg cgggacattg agatgtttcc gaaaatagtc    60
atcaaatatc aaaccagaat ttgatgtgaa acactaatt aaaacatata attgacaact   120
agactatatc atttgttaag ttgagcgttg aagaaaatg aaagagtgta gactgtagta   180
cgtatgagtt tcccaaaaga tggtgcttga atattattgg gaagagactt tggttggttc   240
ggttgaatga agattttac ctgccatgtt gatagagaaa ggcaaataaa tgtaggggtc    300
gatgtctaac gtaaagactg gatcaaccaa gagtcctcct cctcgtcttc accaaaaaaa   360
aagagtcctc ctcgtggaaa cttatttctt ctccagccaa gatctcatct catctcttca   420
ctctatgaaa tataaaggaa tcttatggtt tttctaaaaa ctatagtacg tctatatacc   480
aaaggaaaca atataaaatc agttaatctg ataaattttg agtaaataat aaagttaact   540
ttgtacttac ctatatcaaa ctaattcaca aaataaagta ataataacaa agaattttta   600
gtagatccac aatatacaca cacactatga gaaatcataa tagagaattt taatgatttt   660
gtctaactca tagcaacaag tcgctttggc cgagtggtta aggcgtgtgc ctgctaagta   720
catgggctct gcccgcgaga gttcgaatct ctcaggcgac gtttcttttg ttttcggcca   780
taaaggaaaa agcccaatta acacgtctcg cttataagcc cataaagcaa acaatgggct   840
gtctctgtct cactcacaca cgcgttttcc tactttttga ctatttttat aaccggcggg   900
tctgacttaa ttagggtttt ctttaataat cagacactct ctcactcgtt tcgtcaacat   960
tgaacacaga caaaaccgcg t                                             981

<210> SEQ ID NO 158
<211> LENGTH: 996
<212> TYPE: DNA
<213> ORGANISM: Arabidopsis thaliana
<220> FEATURE:
<221> NAME/KEY: misc_feature
<222> LOCATION: (1)..(996)
<223> OTHER INFORMATION: Ceres Promoter YP0286

<400> SEQUENCE: 158
gaaaacaatc ataggttacg ctattatcat cgaaaggtat gtgatgcata ttcccattga    60
accagatttc catatatttt atttgtaaag tgataatgaa tcacaagatg attcaatatt   120
aaaaatgggt aactcacttt gacgtgtagt acgtggaaga atagttagct atcacgcata   180
catatatcta tgaataagtg tgtatgacat aagaaactaa aatatttacc taaagtccag   240
ttactcatac tgatttcatg catatatgta ttatttattt attttaata aagaagcgat   300
tggtgttttc atagaaatca tgatagattg ataggtattt cagttccaca aatctagatc   360
tgtgtgctat acatgcatgt attaatttt tccccttaaa tcatttcagt tgataatatt   420
gctctttgtt ccaactttag aaaaggtatg aaccaacctg acgattaaca agtaaacatt   480
aattaatctt tatatgagat aaaaccgagg atatatatga ttgtgttgct gtctattgat   540
gatgtgtcga tattatgctt gttgtaccaa tgctcgagcc gagcgtgatc gatgccttga   600
caaactatat atgtttcccg aattaattaa gttttgtatc ttaattagaa taacatttc    660
atacaatgta atttctcaag cagacaagat atgtatccta tattaattac tatatatgaa   720
ttgccgggca cctaccagga tgtttcaaat acgagagccc attagtttcc acgtaaatca   780
caatgacgcg acaaaatcta gaatcgtgtc aaaactctat caatacaata atatatattt   840
```

```
caagggcaat tcgacttct cctcaactca atgattcaac gccatgaatc tctatataaa      900
ggctacaaca ccacaaagga tcatcagtca tcacaaccac attaactctt caccactatc      960
tctcaatctc tcgtttcatt tcttgacgcg tgaaaa                                996
```

<210> SEQ ID NO 159
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0337

<400> SEQUENCE: 159

```
taattttttt attttggaa ctaacactta ttagtttagg tttccatcac ctatttaatt       60
cgtaattctt atacatgcat ataatagaga tacatatata caaatttatg atcattttg      120 cacaacatgt gatctcattc attagtatgc attatgcgaa aacctcgacg cgcaaaagac     180
acgtaatagc taataatgtt actcatttat aatgattgaa gcaagacgaa acaacaaca      240 tatatatcaa attgtaaact agatatttct taaaagtgaa aaaaaacaaa gaaatataaa     300
ggacaatttt gagtcagtct cttaatatta aaacatatat acataaataa gcacaaacgt    360
ggttacctgt cttcatgcaa tgtggacttt agtttatcta atcaaaatca aaataaaagg    420
tgtaatagtt ctcgtcattt tcaaattttt aaaaatcaga accaagtgat ttttgtttga   480
gtattgatcc attgtttaaa caatttaaca cagtatatac gtctcttgag atgttgacat    540
gatgataaaa tacgagatcg tctcttggtt ttcgaatttt gaactttaat agttttcttt    600
tttagggaaa ctttaatagt tgtttatcat aagattagtc acctaatggt tacgttgcag    660
taccgaacca atttttacc cttttttcta aatgtggtcg tggcataatt tccaaaagag    720
atccaaaacc cggtttgctc aactgataag ccggtcggtt ctggtttgaa aaacaagaaa    780
taatctgaaa gtgtgaaaca gcaacgtgtc tcggtgtttc atgagccacc tgccacctca    840
ttcacgtcgg tcattttgtc gtttcacggt tcacgctcta gacacgtgct ctgtccccac    900
catgactttc gctgccgact cgcttcgctt tgcaaactca aacatgtgtg tatatgtaag    960
tttcatccta ataagcatct cttaccacat taattaaaaa                         1000
```

<210> SEQ ID NO 160
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0356

<400> SEQUENCE: 160

```
ttagttcatt gaaacgtcaa ctttttactt gcaaccactt tgtaggacca ttaactgcaa       60
aataagaatt ctctaagctt cacaaggggt tcgtttggtg ctataaaaac attgttttaa     120
gaactggttt actggttcta taaatctata aatccaaata tgaagtatgg caataataat    180
aacatgttag cacaaaaaat actcattaaa ttcctaccca aaaaaaatct ttatatgaaa    240
ctaaaactta tatacacaat aatagtgata caaagtaggt cttgatattc aactattcgg    300
gattttctgg tttcgagtaa ttcgtataaa aggtttaaga tctattatgt tcactgaaat    360
cttaactttg ttttgtttcc agttttaact agtagaaatt gaattttta aaaattgtta    420 cttacaataa aatttgaatc aatatccatta atcaaaggat cttaagacta gcacaattaa   480
```

| | | |
|---|---|---|
| aacatataac gtagaatatc tgaaataact cgaaaatatc tgaactaagt tagtagtttt | 540 | |
| aaaatataat cccggtttgg accgggcagt atgtacttca atacttgtgg gttttgacga | 600 | |
| ttttggatcg gattgggcgg gccagccaga ttgatctatt acaaatttca cctgtcaacg | 660 | |
| ctaactccga acttaatcaa agattttgag ctaaggaaaa ctaatcagtg atcacccaaa | 720 | |
| gaaaacattc gtgaataatt gtttgctttc catggcagca aaacaaatag gacccaaata | 780 | |
| ggaatgtcaa aaaaagaaa gacacgaaac gaagtagtat aacgtaacac acaaaaataa | 840 | |
| actagagata ttaaaaacac atgtccacac atggatacaa gagcatttaa ggagcagaag | 900 | |
| gcacgtagtg gttagaaggt atgtgatata attaatcggc ccaaatagat tggtaagtag | 960 | |
| tagccgtcta tatcatccat actcatcata acttcaacct | 1000 | |

<210> SEQ ID NO 161
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0374

<400> SEQUENCE: 161

| | | |
|---|---|---|
| aagcacccg taaatgttgt catgtagaag aaactagaaa cgttaaacgc atcaaatcaa | 60 | |
| gaaattaaat tgaaggtaat ttttaacgcc gcctttcaaa tattcttcct aggagaggct | 120 | |
| acaagacgcg tatttctttc gaattctcca accattacc attttgatat ataataccga | 180 | |
| catgccgttg ataaagtttg tatgcaaatc gttcattggg tatgagcaaa tgccatccat | 240 | |
| tggttcttgt aattaaatgg tccaaaaata gtttgttccc actactagtt actaatttgt | 300 | |
| atcactctgc aaaataatca tgatataaac gtatgtgcta tttctaatta aaactcaaaa | 360 | |
| gtaatcaatg tacaatgcag agatgaccat aaaagaacat taaaacacta cttccactaa | 420 | |
| atctatgggg tgccttggca aggcaattga ataaggagaa tgcatcaaga tgatatagaa | 480 | |
| aatgctattc agtttataac attaatgttt tggcggaaaa ttttctatat attagacctt | 540 | |
| tctgtaaaaa aaaaaaaatg atgtagaaaa tgctattatg tttcaaaaat ttcgcactag | 600 | |
| tataatacgg aacattgtag tttacactgc tcattaccat gaaaaccaag gcagtatata | 660 | |
| ccaacattaa taaactaaat cgcgatttct agcaccccca ttaattaatt ttactattat | 720 | |
| acattctctt tgcttctcga ataataaaac ttctctatat cattctacat aataaataag | 780 | |
| aaagaaatcg acaagatcta aatttagatc tattcagctt tttcgcctga gaagccaaaa | 840 | |
| ttgtgaatag aagaaagcag tcgtcatctt cccacgtttg gacgaaataa aacataacaa | 900 | |
| taataaaata ataatcaaa tatataaatc cctaatttgt ctttattact ccacaatttt | 960 | |
| ctatgtgtat atatataccc acctctctct tgtgtatttg | 1000 | |

<210> SEQ ID NO 162
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter YP0377

<400> SEQUENCE: 162

| | | |
|---|---|---|
| tataaaccat tcctataaca ccatatttaa acataacaat gaattgcttg gatttcaaac | 60 | |
| tttattaaat ttggatttta aattttaatt tgattgaatt ataccccctt aattggataa | 120 | |

```
attcaaatat gtcaactttt tttttgtaag atttttttat ggaaaaaaaa attgattatt        180
cactaaaaag atgacaggtt acttataatt taatatatgt aaaccctaaa aagaagaaaa        240
tagtttctgt tttcacttta ggtcttatta tctaaacttc tttaagaaaa tcgcaataaa        300
ttggtttgag ttctaacttt aaacacatta atatttgtgt gctatttaaa aaataattta        360
caaaaaaaaa aacaaattga cagaaaatat caggttttgt aataagatat ttcctgataa        420
atatttaggg aatataacat atcaaaagat tcaaattctg aaaatcaaga atggtagaca        480
tgtgaaagtt gtcatcaata tggtccactt ttctttgctc tataacccaa aattgaccct        540
gacagtcaac ttgtacacgc ggccaaacct ttttataatc atgctattta tttccttcat        600
ttttattcta tttgctatct aactgatttt tcattaacat gataccagaa atgaatttag        660
atggattaat tcttttccat ccacgacatc tggaaacact tatctcctaa ttaaccttac        720
ttttttttta gtttgtgtgc tccttcataa aatctatatt gtttaaaaca aaggtcaata        780
aatataaata tggataagta taataaatct ttattggata tttctttttt taaaaaagaa        840
ataaatcttt tttggatatt ttcgtggcag catcataatg agagactacg tcgaaaccgc        900
tggcaaccac ttttgccgcg tttaatttct ttctgaggct tatataaata gatcaaaggg        960
gaaagtgaga tataatacag acaaaacaag agaaaaga                                998
```

<210> SEQ ID NO 163
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0380

<400> SEQUENCE: 163

```
acaagtacca ttcactttt tacttttcaa tgtatacaat catcatgtga taaaaaaaaa         60
aatgtaacca atcaacacac tgagatacgg ccaaaaaatg gtaatacata aatgtttgta        120
ggttttgtaa tttaaatact ttagttaagt tatgatttta ttattttgc ttatcactta        180 tacgaaatca tcaatctatt ggtatctctt aatcccgctt tttaatttcc accgcacacg        240
caaatcagca aatggttcca gccacgtgca tgtgaccaca tattgtggtc acagtactcg        300
tccttttttt ttcttttgta atcaataaat ttcaatccta aaacttcaca cattgagcac        360
gtcggcaacg ttagctccta aatcataacg agcaaaaaag ttcaaattag ggtatatgat        420
caattgatca tcactacatg tctacataat taatatgtat tcaaccggtc ggtttgttga        480
tactcatagt taagtatata tgtgctaatt agaattagga tgaatcagtt cttgcaaaca        540
actacggttt catataatat gggagtgtta tgtacaaaat gaaagaggat ggatcattct        600
gagatgttat gggctcccag tcaatcatgt tttgctcgca tatgctatct tttgagtctc        660
ttcctaaact catagaataa gcacgttggt tttttccacc gtcctcctcg tgaacaaaag        720
tacaattaca ttttagcaaa ttgaaaataa ccacgtggat ggaccatatt atatgtgatc        780
atattgcttg tcgtcttcgt tttctttttaa atgtttacac cactacttcc tgacacgtgt        840
ccctattcac atcatccttg ttatatcgtt ttacttataa aggatcacga acaccaaaac        900
atcaatgtgt acgtcttttg cataagaaga aacagagagc attatcaatt attaacaatt        960
acacaagaca gcgagattgt aaaagagtaa gagagagag                               999
```

<210> SEQ ID NO 164
<211> LENGTH: 1000
<212> TYPE: DNA

<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0381

<400> SEQUENCE: 164

| | | | | | |
|---|---|---|---|---|---|
| cacggtcaaa | gtattgctaa | catggtcatt | acattgaaaa | agaaaattaa | ttgtctttac | 60 |
| tcatgtttat | tctatacaaa | taaaaatatt | aaccaaccat | cgcactaaca | aaatagaaat | 120 |
| cttattctaa | tcacttaatt | gttgacaatt | aaatcattga | aaatacact | taaatgtcaa | 180 |
| atattcgttt | tgcatacttt | tcaatttaaa | tacatttaaa | gttcgacaag | ttgcgtttac | 240 |
| tatcatagaa | aactaaatct | cctaccaaag | cgaaatgaaa | ctactaaagc | gacaggcagg | 300 |
| ttacataacc | taacaaatct | ccacgtgtca | attaccaaga | gaaaaaaga | gaagataagc | 360 |
| ggaacacgtg | gtagcacaaa | aaagataatg | tgatttaaat | taaaaaacaa | aaacaaagac | 420 |
| acgtgacgac | ctgacgctgc | aacatcccac | cttacaacgt | aataaccact | gaacataaga | 480 |
| cacgtgtacg | atcttgtctt | tgttttctcg | atgaaaacca | cgtgggtgct | caaagtcctt | 540 |
| gggtcagagt | cttccatgat | tccacgtgtc | gttaatgcac | caaacaaggg | tactttcggt | 600 |
| attttggctt | ccgcaaatta | gacaaaacag | cttttttgttt | gattgatttt | tctcttctct | 660 |
| ttttccatct | aaattctctt | tgggctctta | atttctttt | gagtgttcgt | tcgagatttg | 720 |
| tcggagattt | tttcggtaaa | tgttgaaatt | ttgtgggatt | ttttttatt | tctttattaa | 780 |
| acttttttt | attgaattta | taaaaaggga | aggtcgtcat | taatcgaaga | aatggaatct | 840 |
| tccaaaattt | gatattttgc | tgttttcttg | ggatttgaat | tgctctttat | catcaagaat | 900 |
| ctgttaaaat | ttctaatcta | aaatctaagt | tgagaaaaag | agagatctct | aatttaaccg | 960 |
| gaattaatat | tctccgaccg | aagttattat | gttgcaggct | | | 1000 |

<210> SEQ ID NO 165
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0384

<400> SEQUENCE: 165

| | | | | | |
|---|---|---|---|---|---|
| tttaaaaaat | tggataaaac | accgataaaa | attcacattt | gcaaatttta | ttcagtcgga | 60 |
| atatatattt | gaaacaagtt | ttgaaatcca | ttggacgatt | aaaattcatt | gttgagagga | 120 |
| taaatatgga | tttgttcatc | tgaaccatgt | cgttgattag | tgattgacta | ccatgaaaaa | 180 |
| tatgttatga | aaagtataac | aacttttgat | aaatcacatt | tattaacaat | aaatcaagac | 240 |
| aaaatatgtc | aacaataata | gtagtagaag | atattaattc | aaattcatcc | gtaacaacaa | 300 |
| aaaatcatac | cacaattaag | tgtacagaaa | aaccttttgg | atatatttat | tgtcgctttt | 360 |
| caatgatttt | cgtgaaaagg | atatatttgt | gtaaaataag | aaggatcttg | acgggtgtaa | 420 |
| aaacatgcac | aattcttaat | ttagaccaat | cagaagacaa | cacgaacact | tctttattat | 480 |
| aagctattaa | acaaaatctt | gcctatttg | cttagaataa | tatgaagagt | gactcatcag | 540 |
| ggagtggaaa | atatctcagg | atttgctttt | agctctaaca | tgtcaaacta | tctagatgcc | 600 |
| aacaacacaa | agtgcaaatt | cttttaatat | gaaaacaaca | ataatatttc | taatagaaaa | 660 |
| ttaaaagggg | aaataaaata | tttttttaaa | atatacaaaa | gaagaaggaa | tccatcatca | 720 |
| aagttttata | aaattgtaat | ataatacaaa | cttgtttgct | tccttgtctc | tccctctgtc | 780 |

| | | |
|---|---|---|
| tctctcatct ctcctatctt ctccatatat acttcatctt cacacccaaa actccacaca | 840 | |
| aaatatctct ccctctatct gcaaattttc caaagttgca tcctttcaat ttccactcct | 900 | |
| ctctaatata attcacattt tcccactatt gctgattcat tttttttgt gaattatttc | 960 | |
| aaacccacat aaaaaaatct ttgtttaaat ttaaaacca | 999 | |

```
<210> SEQ ID NO 166
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter YP0385
```

<400> SEQUENCE: 166

| | | |
|---|---|---|
| actcaacaat aggacaagcc aaaaaaattc caattattgt gttactctat tcttctaaat | 60 | |
| ttgaacacta atagactatg acatatgagt atataatgtg aagtcttaag atattttcat | 120 | |
| gtgggagatg aataggccaa gttggagtct gcaaacaaga agctcttgag ccacgacata | 180 | |
| agccaagttg atgaccgtaa ttaatgaaac taaatgtgtg tggttatata ttagggaccc | 240 | |
| atggccatat acacaatttt tgtttctgtc gatagcatgc gtttatatat atttctaaaa | 300 | |
| aaactaacat atttactgga tttgagttcg aatattgaca ctaatataaa ctacgtacca | 360 | |
| aactacatat gtttatctat atttgattga tcgaagaatt ctgaactgtt ttagaaaatt | 420 | |
| tcaatacact taacttcatc ttacaacggt aaaagaaatc accactagac aaacaatgcc | 480 | |
| tcataatgtc tcgaaccctc aaactcaaga gtatacattt tactagatta gagaatttga | 540 | |
| tatcctcaag ttgccaaaga attggaagct tttgttacca aacttagaaa cagaagaagc | 600 | |
| cacaaaaaaa gacaaaggga gttaaagatt gaagtgatgc atttgtctaa gtgtgaaagg | 660 | |
| tctcaagtct caactttgaa ccataataac attactcaca ctccctttttt ttttcttttt | 720 | |
| ttttcccaaa gtacccttt taattccctc tataacccac tcactccatt ccctctttct | 780 | |
| gtcactgatt caacacgtgg ccacactgat gggatccacc tttcctctta cccacctccc | 840 | |
| ggtttatata aacccttcac aacacttcat cgctctcaaa ccaactctct cttctctctt | 900 | |
| ctctcctctc ttctacaaga agaaaaaaaa cagagccttt acacatctca aaatcgaact | 960 | |
| tactttaacc accaaatact gattgaacac acttgaaa | 998 | |

```
<210> SEQ ID NO 167
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0396
```

<400> SEQUENCE: 167

| | | |
|---|---|---|
| catagtaaaa gtgaatttaa tcatactaag taaaataaga taaacatgt tatttgaatt | 60 | |
| tgaatatcgt gggatgcgta tttcggtatt tgattaaagg tctggaaacc ggagctccta | 120 | |
| taacccgaat aaaaatgcat aacatgttct tccccaacga ggcgagcggg tcagggcact | 180 | |
| agggtcattg caggcagctc ataaagtcat gatcatctag gagatcaaat tgtatgtcgg | 240 | |
| ccttctcaaa attacctcta agaatctcaa acccaatcat agaacctcta aaagacaaa | 300 | |
| gtcgtcgctt tagaatgggt tcggttttg gaaccatatt tcacgtcaat ttaatgttta | 360 | |
| gtataatttc tgaacaacag aatttggat ttatttgcac gtatacaaat atctaattaa | 420 | |

| | |
|---|---|
| taaggacgac tcgtgactat ccttacatta agtttcactg tcgaaataac atagtacaat | 480 |
| acttgtcgtt aatttccacg tctcaagtct ataccgtcat ttacggagaa agaacatctc | 540 |
| tgtttttcat ccaaactact attctcactt tgtctatata tttaaaatta agtaaaaaag | 600 |
| actcaatagt ccaataaaat gatgaccaaa tgagaagatg gttttgtgcc agattttagg | 660 |
| aaaagtgagt caaggtttca catctcaaat ttgactgcat aatcttcgcc attaacaacg | 720 |
| gcattatata tgtcaagcca attttccatg ttgcgtactt ttctattgag gtgaaaatat | 780 |
| gggtttgttg attaatcaaa gagtttgcct aactaatata actacgactt tttcagtgac | 840 |
| cattccatgt aaactctgct tagtgtttca tttgtcaaca atattgtcgt tactcattaa | 900 |
| atcaaggaaa aatatacaat tgtataattt tcttatattt taaaattaat tttgatgtat | 960 |
| taccccttta taaataggct atcgctacaa caccaataac | 1000 |

<210> SEQ ID NO 168
<211> LENGTH: 1514
<212> TYPE: DNA
<213> ORGANISM: Arabidopsis thaliana
<220> FEATURE:
<221> NAME/KEY: misc_feature
<222> LOCATION: (1)..(1514)
<223> OTHER INFORMATION: Ceres Promoter p13879

<400> SEQUENCE: 168

| | |
|---|---|
| tttcgatcct cttctttttt aggtttcttg atttgatgat cgccgccagt agagccgtcg | 60 |
| tcggaagttt cagagattaa aaccatcacc gtgtgagttg gtagcgaatt aacggaaagt | 120 |
| ctaagtcaag attttttaaa aagaaattta tgtgtgaaaa gaagccgttg tgtatattta | 180 |
| tataatttag aaaatgtttc atcattttaa ttaaaaaatt ataaatttgt agaagaaaga | 240 |
| agcatttttt atacataaat catttacctt ctttactgtg ttttttcttca cttacttcat | 300 |
| ttttactttt ttacaaaaaa gtgaaaagta aattacgtaa ttggtaacat aaattcactt | 360 |
| taaatttgca tatgttttgt tttcttcgga aactatatcg aaaagcaaac ggaaagaact | 420 |
| tcacaaaaaa ccctagctaa ctaaagacgc atgtgttctt cttattcttc atatatcctc | 480 |
| tgtttcttgt gttctgtttt gagtcttaca ttttcaatat ctgactctga ttactatatc | 540 |
| taaaagggaa catgaagaac ttgagaccat gttaaactgt acaatgcctt caaacatggc | 600 |
| taactaaaga tacattagat ggctttacag tgtgtaatgc ttattatctt taggtttttt | 660 |
| aaatcccttg tattaagtta tttaccaaat tatgttcttg tactgcttat tggcttggtt | 720 |
| gttgtgtgct ttgtaaacaa caccttttggc tttatttcat cctttgtaaa cctactggtc | 780 |
| tttgttcagc tcctcttgga agtgagtttg tatgcctgga acgggtttta atggagtgtt | 840 |
| tatcgacaaa aaaaaaatgt agcttttgaa atcacagaga gtagttttat attcaaatta | 900 |
| catgcatgca actaagtagc aacaaagttg atatggccga gttggtctaa ggcgccagat | 960 |
| taaggttctg gtccgaaagg gcgtgggttc aaatcccact gtcaacattc tcttttctc | 1020 |
| aaattaatat ttttctgcct caatggttca ggcccaatta tactagacta ctatcgcgac | 1080 |
| taaaataggg actagccgaa ttgatccggc ccagtatcag ttgtgtatca ccacgttatt | 1140 |
| tcaaatttca aactaaggga taaagatgtc atttgacata tgagatattt ttttgctcca | 1200 |
| ctgagatatt tttctttgtc ccaagataaa atatctttc tcgcatcgtc gtctttccat | 1260 |
| ttgcgcatta aaccaaaaag tgtcacgtga tatgtcccca accactacga atttaacta | 1320 |
| cagatttaac catggttaaa ccagaattca cgtaaaccga ctctaaacct agaaaatatc | 1380 |
| taaaccttgg ttaatatctc agcccccctta taaataacga gacttcgtct acatcgttct | 1440 |

| | |
|---|---:|
| acacatctca ctgctcacta ctctcactgt aatcccttag atcttctttt caaatttcac | 1500 |
| cattgcactg gatg | 1514 |

<210> SEQ ID NO 169
<211> LENGTH: 1954
<212> TYPE: DNA
<213> ORGANISM: Arabidopsis thaliana
<220> FEATURE:
<221> NAME/KEY: misc_feature
<222> LOCATION: (1)..(1954)
<223> OTHER INFORMATION: Ceres Promoter p326

<400> SEQUENCE: 169

| | |
|---|---:|
| gtgggtaaaa gtatccttct ttgtgcattt ggtattttta agcatgtaat aagaaaaacc | 60 |
| aaaatagacg gctggtattt aataaaagga gactaatgta tgtatagtat atgatttgtg | 120 |
| tggaatataa taaagttgta aaatatagat gtgaagcgag tatctatctt ttgactttca | 180 |
| aaggtgatcg atcgtgttct ttgtgatagt tttggtcgtc ggtctacaag tcaacaacca | 240 |
| ccttgaagtt ttcgcgtctc ggtttcctct tcgcatctgg tatccaatag catacatata | 300 |
| ccagtgcgga aaatggcgaa gactagtggg cttgaaccat aaggtttggc cccaatacgg | 360 |
| attccaaaca acaagcctag cgcagtcttt tgggatgcat aagactaaac tgtcgcagtg | 420 |
| atagacgtaa gatatatcga cttgattgga atcgtctaag ctaataagtt taccttgacc | 480 |
| gtttatagtt gcgtcaacgt ccttatggag attgatgccc atcaaataaa cctgaaaatc | 540 |
| catcaccatg accaccataa actcccttgc tgccgctgct ttggcttgag caaggtgttt | 600 |
| ccttgtaaag ctccgatctt tggataaagt gttccacttt ttgcaagtag ctctgacccc | 660 |
| tctcagagat gtcaccggaa tcttagacag aacctcctct gccaaatcac ttggaagatc | 720 |
| ggacaatgtc atcattttg caggtaattt ctccttcgtt gctgctttgg cttgagcacg | 780 |
| gtgcttcttt gtaaagctcc gatctttgga taagagcgga tcggaatcct ctaggaggtg | 840 |
| ccagtccctt gacctattaa tttatagaag gttttagtgt attttgttcc aatttcttct | 900 |
| ctaacttaac aaataacaac tgcctcatag tcatgggctt caaatttat cgcttggtgt | 960 |
| atttcgttat ttgcaaggcc ttggcccatt ttgagcccaa taactaaatc tagccttttc | 1020 |
| agaccggaca tgaacttcgc atattggcgt aactgtgcag ttttacctttt tcggatcag | 1080 |
| acaagatcag atttagacca cccaacaata gtcagtcata tttgacaacc taagctagcc | 1140 |
| gacactacta aaagcaaac aaaagaagaa ttctatgttg tcattttacc ggtggcaagt | 1200 |
| ggacccttct ataaaagagt aaagagacag cctgtgtgtg tataatctct aattatgttc | 1260 |
| accgacacaa tcacacaaac ccttctctaa tcacacaact tcttcatgat ttacgacatt | 1320 |
| aattatcatt aactctttaa attcacttta catgctcaaa aatatctaat ttgcagcatt | 1380 |
| aatttgagta ccgataacta ttattataat cgtcgtgatt cgcaatcttc ttcattagat | 1440 |
| gctgtcaagt tgtactcgca cgcggtggtc cagtgaagca aatccaacgg tttaaaacct | 1500 |
| tcttacattt ctagatctaa tctgaaccgt cagatatcta gatctcattg tctgaacaca | 1560 |
| gttagatgaa actgggaatg aatctggacg aaattacgat cttacaccaa cccctcgac | 1620 |
| gagctcgtat atataaagct tatacgctcc tccttcacct tcgtactact actaccacca | 1680 |
| catttcttta gctcaacctt cattactaat ctcctttaa ggtatgttca cttttcttcg | 1740 |
| attcatactt tctccaagatt cctgcatttc tgtagaattt gaaccaagtg tcgatttttg | 1800 |
| tttgagagaa gtgttgattt atagatctgg ttattgaatc tagattccaa tttttaattg | 1860 |
| attcgagttt gttatgtgtg tttatactac ttctccattga tcttgtttga tttctctgct | 1920 |

```
ctgtattagg tttctttcgt gaatcagatc ggaa                         1954
```

<210> SEQ ID NO 170
<211> LENGTH: 2016
<212> TYPE: DNA
<213> ORGANISM: Arabidopsis thaliana
<220> FEATURE:
<221> NAME/KEY: misc_feature
<222> LOCATION: (1)..(2016)
<223> OTHER INFORMATION: Ceres Promoter p32449

<400> SEQUENCE: 170

```
gatcggcctt cttcaggtct tctctgtagc tctgttactt ctatcacagt tatcgggtat     60
ttgagaaaaa agagttagct aaaatgaatt tctccatata atcatggttt actacaggtt    120
tacttgattc gcgttagctt tatctgcatc caaagttttt tccatgatgt tatgtcatat    180
gtgataccgt tactatgttt ataactttat acagtctggt tcactggagt ttctgtgatt    240
atgttgagta catactcatt catccttttgg taactctcaa gtttaggttg tttgaattgc    300
ctctgttgtg atacttattg tctattgcat caatcttcta atgcaccacc ctagactatt    360
tgaacaaaga gctgtttcat tcttaaacct ctgtgtctcc ttgctaaatg gtcatgcttt    420
aatgtcttca cctgtctttc tcttctatag atatgtagtc ttgctagata gttagttcta    480
cagctctctt ttgtagtctt gttagagagt tagttgagat attacctctt aaaagtatcc    540
ttgaacgctt tccggttatg accaatttgt tgtagctcct tgtaagtaga acttactggg    600
accagcgaga cagtttatgt gaatgttcat gcttaagtgt cgaacgtatc tatctctact    660
atagctctgt agtcttgtta gacagttagt tttatatctc cattttttttg tagtcttgct    720
agttgagata ttacctcttc tcttcaaagt atccttgaac gctcaccggt tatgaaatct    780
ctacactata gctctgtagt cttgctagat agttagttct ttagctctct ttttgtagcc    840
tagttcttta gctctccttt tgtagccttg ctacagagta agatgggata ttacctcctt    900
gaacgctctc cggttatgac caatttgttg tagctccttg taagtagaac ttaggataga    960
gtgagtcaac tttaagaaag aacctagtat gtggcataac cagattgcag gctctgtctc   1020
ggctacagta acgtaactct atagctcttt gttttgttca gaaagaacca gtgattggat   1080
gattcgtcct tagaaactgg acctaacaac agtcattggc tttgaaatca agccacaaca   1140
atgcctatat gaaccgtcca tttcatttat ccgtttcaaa ccagcccatt acatttcgtc   1200
ccattgataa ccaaaagcgg ttcaatcaga ttatgtttta attttaccaa attctttatg   1260
aagtttaaat tatactcaca ttaaaaggat tattggataa tgtaaaaatt ctgaacaatt   1320
actgattttg gaaaattaac aaatattctt tgaaatagaa gaaaaagcct ttttccttt     1380
gacaacaaca tataaaatca tactcccatt aaaaagattt taatgtaaaa ttctgaatat   1440
aagatatttt ttacaacaac aaccaaaaat atttatttttt ttccttttttt acagcaacaa   1500
gaaggaaaaa cttttttttt tgtcaagaaa agggagagatt atgtaaacag ataaaacagg   1560
gaaaataact aaccgaactc tcttaattaa catcttcaaa taaggaaaat tatgatccgc   1620
atatttagga agatcaatgc attaaaacaa cttgcacgtg gaaagagaga ctatacgctc   1680
cacacaagtt gcactaatgg tacctctcac aaaccaatca aaatactgaa taatgccaac   1740
gtgtacaaat tagggtttta cctcacaacc atcgaacatt tcgaaacat tttaaacagc    1800
ctggcgccat agatctaaac tctcatcgac caattttttga ccgtccgatg gaaactctag   1860
cctcaaccca aaactctata taagaaaatc ttttccttcg ttattgctta ccaaatacaa    1920
accctagccg ccttattcgt cttcttcgtt ctctagttttt ttcctcagtc tctgttctta   1980
```

```
gatcccttgt agtttccaaa tcttccgata aggcct                              2016
```

<210> SEQ ID NO 171
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter PR0924

<400> SEQUENCE: 171

```
atctataacg agttaacatg ttgccagttt gaatcaagaa gcttggatga tgaatgaatg     60
gatcggtttg tggtacaatt cttaaaattg tagtagagga gacagagaaa aaacatgata    120
agactttggt atttacaact tgacggagac aagacagtaa gccaaatctg tcacaaaaac    180
actcaaactc ttttctcagt gttttgagtt taaagagaga cttattcact tcccctttcg    240
taacacttat ttgtctccca accaaacagt ttctgtcctt tcccttgtcc tcccacgtgc    300
atctttatat ctcatgactt ttcgtttcta gatcttgaat aatgtcttag tggattaggt    360
ttgttgtcgg taaattaggt gaccgttttt ttcttatatt tggaagatcg cgggatgaag    420
cagatactga gtttcagggc atacacacct aatttgaaaa tcattgttag tccaatttca    480
ctttaatctt gtttacaaaa aaattgatct gaaaatgttg atgggataag taaaaatgta    540
agttttgcta gtagtcatga tataataata gcaaaccag atcaattttg agcaaaagga    600
agaaacaaaa aacagatcga tcccacgagc aagactaagt gtaaagtggt tcccacaaga    660
gccatatgga tatggtcctt caacttttaa agcccattac ttcagtggtc gacccgacat    720
tacgccacga gtagtcacgc acgcacgact ccgttcacgt gacattcacg ttgatatttc    780
cccctctact ctcttctgct tggttgatct aaaaaacatg aagagaccaa cctaatttca    840
tattaatata tgatatagac ttcatactca acagtcactt tcgtaatcca aatccatatc    900
ttacgaaatt agttcttaat aaaggttgtg gattaagtta taatattgtg ttaagagtta    960
agacacagca tataaccttg taccaacagt gctttattct taaatggaaa caaaacatat   1020
gtca                                                               1024
```

<210> SEQ ID NO 172
<211> LENGTH: 857
<212> TYPE: DNA
<213> ORGANISM: Arabidopsis thaliana
<220> FEATURE:
<221> NAME/KEY: misc_feature
<222> LOCATION: (1)..(857)
<223> OTHER INFORMATION: Ceres Promoter PD1367
<220> FEATURE:
<221> NAME/KEY: misc_feature
<222> LOCATION: (116)..(116)
<223> OTHER INFORMATION: n is a, c, t, g, unknown, or other
<220> FEATURE:
<221> NAME/KEY: misc_feature
<222> LOCATION: (136)..(136)
<223> OTHER INFORMATION: n is a, c, t, g, unknown, or other
<220> FEATURE:
<221> NAME/KEY: misc_feature
<222> LOCATION: (154)..(154)
<223> OTHER INFORMATION: n is a, c, t, g, unknown, or other
<220> FEATURE:
<221> NAME/KEY: misc_feature
<222> LOCATION: (159)..(159)
<223> OTHER INFORMATION: n is a, c, t, g, unknown, or other
<220> FEATURE:
<221> NAME/KEY: misc_feature
<222> LOCATION: (168)..(168)
<223> OTHER INFORMATION: n is a, c, t, g, unknown, or other
<220> FEATURE:

```
<221> NAME/KEY: misc_feature
<222> LOCATION: (172)..(172)
<223> OTHER INFORMATION: n is a, c, t, g, unknown, or other
<220> FEATURE:
<221> NAME/KEY: misc_feature
<222> LOCATION: (175)..(175)
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<222> LOCATION: (680)..(680)
<223> OTHER INFORMATION: n is a, c, t, g, unknown, or other
<220> FEATURE:
<221> NAME/KEY: misc_feature
<222> LOCATION: (686)..(686)
<223> OTHER INFORMATION: n is a, c, t, g, unknown, or other
<220> FEATURE:
<221> NAME/KEY: misc_feature
<222> LOCATION: (724)..(724)
<223> OTHER INFORMATION: n is a, c, t, g, unknown, or other
<220> FEATURE:
<221> NAME/KEY: misc_feature
<222> LOCATION: (737)..(737)
<223> OTHER INFORMATION: n is a, c, t, g, unknown, or other

<400> SEQUENCE: 172
ttggaattaa ttctgcggcc atggggctgc aggaattcga tggcccgatc ggccacagtt      60
ttcttttctc atcttacaac aagtttccag gaggatagag acataaacga agctcngat     120 tgtatcgttc tttttnagct tttattcaca tccngaaang tcctgtangt tntangattc    180
tgttatcttg cggttttgag ttaatcagaa acagagtaat caatgtaatg ttgcaggcta    240
gatctttcat ctttggaaat ttgttttttt ctcatgcaat ttctttagct tgaccatgag    300
tgactaaaag atcaatcagt agcaatgatt tgatttggct aagagacatt tgtccacttg    360
gcatcttgat ttgatggtt acaacttgca agacccaatt ggatacttgc tatgacaact    420
ccaactcaag agtgtcgtgt aactaagaac cttgactaat ttgtaatttc aatcccaagt    480
catgttacta tatgttttt tgtttgtatt attttctctc ctacaattaa gctctttgac    540
gtacgtaatc tccggaacca actcctatat ccaccattta ctccacgttg tctccaatta    600
ttggacgttg aaacttgaca caacgtaaac gtatctacgt ggttgattgt atgtacatat    660
gtacaaacgt acacctttnn ctcctnctt cacttcatca cttggcttgt gaattcatta    720
attncctgcg aaggccntgc agggccatca ccactgcagt ggaacaatga agactaatct    780
ttttctcttt ctcatctttt cacttctcct atcattatcc tcggccgaat tcagtaaagg    840
agaagaactt ttcactg                                                     857

<210> SEQ ID NO 173
<211> LENGTH: 852
<212> TYPE: DNA
<213> ORGANISM: Populus balsamifera subsp. trichocarpa
<220> FEATURE:
<221> NAME/KEY: misc_feature
<222> LOCATION: (1)..(852)
<223> OTHER INFORMATION: Ceres gDNA:1454179

<400> SEQUENCE: 173
atggctgcca ccacagctgc tgccgctaca tcctccttta ttggaacacg tgtgcccgac      60
gtctattcaa acgcgggtag gatccaagcc aggttcggat ttggcaagaa agcacccaag    120
aaatctatta agaccattcc agaccgccca ctttggtatc caggagccaa ggcacctgag    180
tacctagatg gcagtttggt tggtgattac gggtttgacc catttgggtt gggcagacca    240
```

```
gctgagtact tgcagttcga gcttgactct ttggatcaaa acttggctaa gaatctggct    300
ggagatatta tttgggacccg tactgaggtt tctgatgtga agtcaactcc gttccagcct    360
tacagtgagg ttttcgggtt gcaaaggttc agggagtgtg agctcattca tggaaggtgg    420
gctatgttgg ctactctcgg tgctctctca gtcgagtggc tcactggagt tacctggcaa    480
gatgctggaa aggtggaatt agttgaagga tcatcatacc ttggtcagcc actaccattt    540
tccattacaa cattgatctt gattgaggtt ttggtgattg gatacattga attccaaagg    600
aacgcagagc ttgacccaga gaaaaggctc tacccaggag gcaatttctt tgatcctctt    660
ggcttagctg ctgacccaga aaagaaggct acccttcaat ggcagagat caagcacgct    720 cgccttgcca tggttgcctt ccttggcttt gcagttcaag cttgggttac aggaaaaggc    780
cccctcaaca actgggctac tcacttaagt gatcctctcc acacgaccat tattgacacc    840
ttatcctctt aa                                                         852

<210> SEQ ID NO 174
<211> LENGTH: 828
<212> TYPE: DNA
<213> ORGANISM: Populus balsamifera subsp. trichocarpa
<220> FEATURE:
<221> NAME/KEY: misc_feature
<222> LOCATION: (1)..(828)
<223> OTHER INFORMATION: CeresGdna:1511507
<220> FEATURE:
<221> NAME/KEY: misc_feature
<222> LOCATION: (1)..(828)
<223> OTHER INFORMATION: REFERENCED BY SEQ ID NO: 76

<400> SEQUENCE: 174
atggctgcaa cgactgctgt tgccgcgtcc tatttttcgg ggacccgaac tcaatacaca     60
aaacaaaatc caggaaaaat tcaagccctg tttggatttg gaaccaagaa atcgcctcct    120
cctcctccac caaagaaatc ctccccaaaa caatttgaag atcggcttgt atggttccct    180
ggtgcatccc cacctgaatg gcttgatgga accatggttg gagaccgcgg ttttgaccca    240
ttcgctcttg gtaagcccgc agagtacttg caatttgatt tggattcgtt ggaccagaac    300
ttggcaaaga atttggccgg tgatgttatt ggagtccgag tagatgccac ggaggtgaaa    360
ccaacaccct tccagccata ctctgaggtt tttgggctgc agaggtttag agaatgcgaa    420
cttattcatg gacggtgggc aatgttgggt actcttggtg ccattgctgt ggaggctctc    480
accggtgttg catggcaaga tgcaggaaag gtggagctga ttgaggggtc atcctacctt    540
ggccagccac ttcctttctc cttgaccacg ttgatatgga ttgaggtgat agtagttggg    600
tacattgagt tccaaagaaa tgcagaacta gacccagaga aaggctata tcctggtggc    660 tactttgatc ctcttggctt agcatctgat cctgaaaaga tagagaacct tcaactggca    720
gagattaagc atgctaggct agctatggtg gccttcctta tatttggtat tcaagctgct    780
tttacaggaa aaggtcccat tagctttgtg gctacccttca acaattga               828

<210> SEQ ID NO 175
<211> LENGTH: 900
<212> TYPE: DNA
<213> ORGANISM: Populus balsamifera subsp. trichocarpa
<220> FEATURE:
<221> NAME/KEY: misc_feature
<222> LOCATION: (1)..(900)
<223> OTHER INFORMATION: CeresGdna:1511507
<220> FEATURE:
<221> NAME/KEY: misc_feature
<222> LOCATION: (1)..(900)
<223> OTHER INFORMATION: CDS - REFERENCED BY SEQ ID NO:
```

<400> SEQUENCE: 175

```
atggctgcaa cgactgctgt tgccgcgtcc tattttttcgg ggacccgaac tcaatacaca    60
aaacaaaatc caggaaaaat tcaagccctg tttggatttg aaccaagaa atcgcctcct    120
cctcctccac caaagaaatc ctccccaaaa caatttgaag atcggcttgt atggttccct    180
ggtgcatccc cacctgaatg gcttgatgga accatggttg agaccgcgg ttttgaccca    240
ttcgctcttg gtaagcccgc agagtacttg caatttgatt tggattcgtt ggaccagaac    300
ttggcaaaga atttggccgg tgatgttatt ggagtccgag tagatgccac ggaggtgaaa    360
ccaacaccct tccagccata ctctgaggtt tttgggctgc agaggtttag agaatgcgaa    420
cttattcatg gacggtgggc aatgttgggt actcttggtg ccattgctgt ggaggctctc    480
accggtgttg catggcaaga tgcaggaaag agccttgata tcaagcagt cacgagttcg    540
agtctcacca tctctatttta tttgataaaa attaagcata aggtggagct gattgagggg    600
tcatcctacc ttggccagcc acttcctttc tccttgacca cgttgatatg gattgaggtg    660
atagtagttg ggtacattga gttccaaaga aatgcagaac tagacccaga gaaaaggcta    720
tatcctggtg gctactttga tcctcttggc ttagcatctg atcctgaaaa gatagagaac    780
cttcaactgg cagagattaa gcatgctagg ctagctatgg tggccttcct tatatttggt    840
attcaagctg cttttacagg aaaaggtccc attagctttg tggctacctt caacaattga    900
```

<210> SEQ ID NO 176
<211> LENGTH: 852
<212> TYPE: DNA
<213> ORGANISM: Populus balsamifera subsp. trichocarpa
<220> FEATURE:
<221> NAME/KEY: misc_feature
<222> LOCATION: (1)..(852)
<223> OTHER INFORMATION: CeresGdna:1475895
<220> FEATURE:
<221> NAME/KEY: misc_feature
<222> LOCATION: (1)..(852)
<223> OTHER INFORMATION: CDS - REFERENCED BY SEQ ID NO: 80

<400> SEQUENCE: 176

```
atggctgcca ccacagctgc tgccgctaca tcctccttta ttggaacacg tgtgcccgac    60
gtctattcaa cgcgggtag gatccaagcc aggttcggat ttggcaagaa agcacccaag    120
aaatctatta agaccattcc agaccgccca ctttggtatc caggagccaa ggcacctgag    180
tacctagatg gcagtttggt tggtgattac gggtttgacc catttgggtt gggcagacca    240
gctgagtact tgcagttcga gcttgactct ttggatcaaa acttggctaa gaatctggct    300
ggagatatta ttgggacccg tactgaggtt tctgatgtga agtcaactcc gttccagcct    360
tacagtgagg ttttcgggtt gcaaaggttc agggagtgtg agctcattca tggaaggtgg    420
gctatgttgg ctactctcgg tgctctctca gtcgagtggc tcactggagt tacctggcaa    480
gatgctggaa aggtggaatt agttgaagga tcatcatacc ttggtcagcc actaccattt    540
tccattacaa cattgatctt gattgaggtt ttggtgattg atacattga attccaaagg    600
aacgcagagc ttgacccaga gaaaaggctc tacccaggag gcaatttctt tgatcctctt    660
ggcttagctg ctgacccaga aaagaaggct acccttcaat tggcagagat caagcacgct    720
cgccttgcca tggttgcctt ccttggcttt gcagttcaag cttgggttac aggaaaaggc    780
cccctcaaca actgggctac tcacttaagt gatcctctcc acacgaccat tattgacacc    840
ttatcctctt aa                                                         852
```

<210> SEQ ID NO 177

-continued

```
<211> LENGTH: 144
<212> TYPE: PRT
<213> ORGANISM: Unknown
<220> FEATURE:
<223> OTHER INFORMATION: Figure 1 consensus sequence derived from
      various organisms

<400> SEQUENCE: 177

Met Leu Arg Phe Pro Gln Ala Arg Arg Leu Leu Arg Arg Met Gly Leu
1               5                   10                  15

Asp Lys Glu Asp Ala Tyr Phe Trp Lys Gln Gly Lys Ala Met Leu Cys
            20                  25                  30

Thr Tyr Thr Leu Phe Gly Val Ala Trp Leu Trp Asn Glu Thr Ser Pro
        35                  40                  45

Leu Gly Trp Trp Thr Leu Lys Pro Arg Pro Lys Glu Glu Arg Glu Met
50                  55                  60

Ala His Leu Tyr Glu Arg Arg Glu Phe Pro Tyr Pro Gly Asp Glu Glu
65                  70                  75                  80

Ala Val Glu Glu Phe Val Lys Ser Gly Gly Ala Leu Gly Thr Thr Ile
                85                  90                  95

Gly Pro Lys Gly Phe Ala Asp Asn Met Asp Ser Asp Asn Met Gln Lys
            100                 105                 110

Gln Leu Gln Ser Lys Lys Phe Asp Gln Glu Ala Gln Lys Leu Trp Phe
        115                 120                 125

Arg Met Arg Asn Glu Val Val Glu Leu Gln Glu Lys Gly Asp Val Glu
130                 135                 140

<210> SEQ ID NO 178
<211> LENGTH: 84
<212> TYPE: PRT
<213> ORGANISM: Unknown
<220> FEATURE:
<223> OTHER INFORMATION: Figure 2 consensus sequence derived from
      various organisms

<400> SEQUENCE: 178

Met Glu Glu Leu Val Ser Val Glu Leu Pro Ala Pro Ser Ser Trp Lys
1               5                   10                  15

Lys Leu Phe Tyr Pro Lys Lys Gly Thr Pro Lys Thr Glu Ile Val Phe
            20                  25                  30

Val Ala Pro Thr Gly Glu Glu Ile Ser Asn Arg Lys Gln Leu Glu Gln
        35                  40                  45

Tyr Leu Lys Ala His Pro Gly Asn Pro Ile Ser Glu Phe Asp Trp Thr
50                  55                  60

Thr Gly Glu Thr Pro Arg Arg Ser Ala Arg Ile Ser Glu Lys Val Thr
65                  70                  75                  80

Lys Ser Pro Ser

<210> SEQ ID NO 179
<211> LENGTH: 121
<212> TYPE: PRT
<213> ORGANISM: Unknown
<220> FEATURE:
<223> OTHER INFORMATION: Figure 3 consensus sequence derived from
      various organisms

<400> SEQUENCE: 179

Ser Lys Leu Arg Lys Pro Val Phe Lys Val Asp Gln Leu Lys Pro Gly
1               5                   10                  15

Thr Asn Gly His Thr Leu Val Lys Val Ser Lys Val Gln Lys Gly Arg
            20                  25                  30
```

Ala Gly Pro Ala Arg Gln Met Arg Ile Ala Glu Cys Leu Val Gly Asp
            35                  40                  45

Glu Thr Gly Val Ile Phe Thr Ala Arg Asn Asp Gln Val Asp Leu Met
 50                  55                  60

Lys Pro Gly Ala Thr Val Ile Leu Arg Asn Ala Lys Ile Asp Met Phe
 65                  70                  75                  80

Lys Gly Ser Met Arg Leu Ala Val Asp Lys Trp Gly Arg Val Glu Val
                 85                  90                  95

Thr Glu Pro Ala Ser Phe Thr Val Lys Glu Asp Asn Asn Leu Ser Leu
            100                 105                 110

Ile Glu Tyr Glu Leu Val Asn Val Glu
            115                 120

Figure 4B:
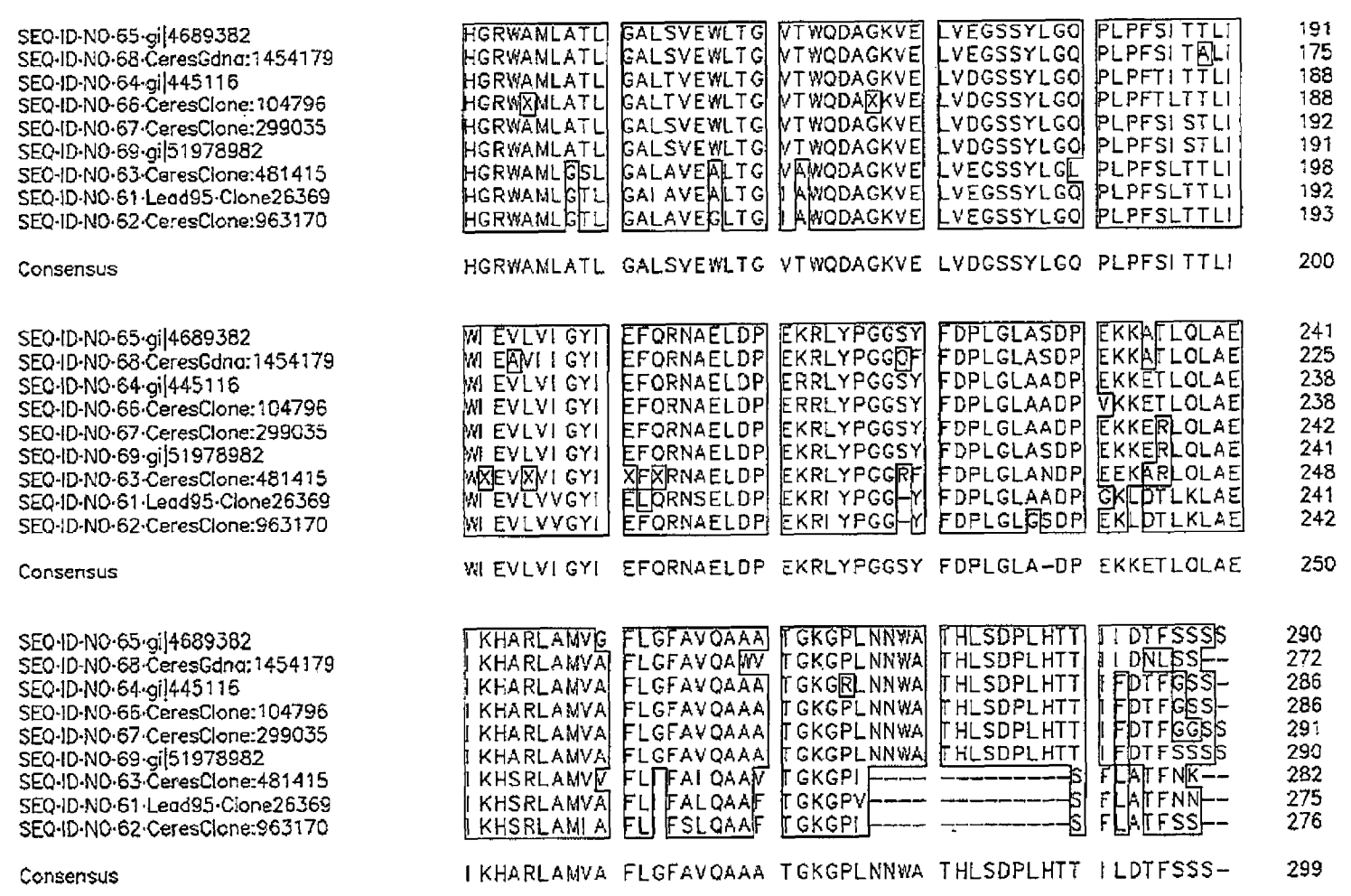

<210> SEQ ID NO 180
<211> LENGTH: 269
<212> TYPE: PRT
<213> ORGANISM: Unknown
<220> FEATURE:
<223> OTHER INFORMATION: Figure 4 consensus sequence derived from
      various organisms

<400> SEQUENCE: 180

Met Ala Ser Ala Ala Ala Ser Thr Phe Leu Gly Thr Arg Leu Asp
 1               5                  10                  15

Pro Pro Gly Arg Ile Ala Arg Phe Gly Phe Gly Lys Lys Pro Pro Lys
                 20                  25                  30

Lys Lys Pro Thr Thr Asp Arg Pro Leu Trp Phe Pro Gly Ala Ala Pro
             35                  40                  45

Glu Trp Leu Asp Gly Ser Leu Val Gly Asp Tyr Gly Phe Asp Pro Phe
 50                  55                  60

Gly Leu Gly Lys Pro Ala Glu Tyr Leu Gln Tyr Asp Leu Asp Ser Leu
 65                  70                  75                  80

Asp Gln Asn Leu Ala Lys Asn Leu Ala Gly Ile Ile Gly Thr Arg Glu
                 85                  90                  95

Ala Asp Val Lys Ser Thr Pro Phe Gln Pro Tyr Ser Glu Val Phe Gly
            100                 105                 110

Leu Gln Arg Phe Arg Glu Cys Glu Leu Ile His Gly Arg Trp Ala Met
            115                 120                 125

Leu Ala Thr Leu Gly Ala Leu Ser Val Glu Trp Leu Thr Gly Val Thr
 130                 135                 140

Trp Gln Asp Ala Gly Lys Val Glu Leu Val Asp Gly Ser Ser Tyr Leu
 145                 150                 155                 160

Gly Gln Pro Leu Pro Phe Ser Ile Thr Thr Leu Ile Trp Ile Glu Val
                 165                 170                 175

Leu Val Ile Gly Tyr Ile Glu Phe Gln Arg Asn Ala Glu Leu Asp Pro
            180                 185                 190

Glu Lys Arg Leu Tyr Pro Gly Gly Ser Tyr Phe Asp Pro Leu Gly Leu
            195                 200                 205

Ala Asp Pro Glu Lys Lys Glu Thr Leu Gln Leu Ala Glu Ile Lys His
 210                 215                 220

Ala Arg Leu Ala Met Val Ala Phe Leu Gly Phe Ala Val Gln Ala Ala
 225                 230                 235                 240

```
Ala Thr Gly Lys Gly Pro Leu Asn Asn Trp Ala Thr His Leu Ser Asp
            245                 250                 255

Pro Leu His Thr Thr Ile Leu Asp Thr Phe Ser Ser Ser
            260                 265
```